US008835603B2

(12) United States Patent
Anderson et al.

(10) Patent No.: US 8,835,603 B2
(45) Date of Patent: Sep. 16, 2014

(54) AGENTS FOR THE TREATMENT OF CELIAC DISEASE

(75) Inventors: Robert P. Anderson, Ivanhoe (AU);
Jessica A. Stewart, Flemington (AU);
James A. Dromey, West Footscray (AU); Jason A. Tye-Din, Collingwood (AU)

(73) Assignee: ImmusanT, Inc., Cambridge, MA (US)

( * ) Notice: Subject to any disclaimer, the term of this patent is extended or adjusted under 35 U.S.C. 154(b) by 0 days.

(21) Appl. No.: 13/131,787

(22) PCT Filed: Nov. 30, 2009

(86) PCT No.: PCT/AU2009/001556
§ 371 (c)(1),
(2), (4) Date: Aug. 15, 2011

(87) PCT Pub. No.: WO2010/060155
PCT Pub. Date: Jun. 3, 2010

(65) Prior Publication Data
US 2011/0293644 A1    Dec. 1, 2011

Related U.S. Application Data

(60) Provisional application No. 61/118,643, filed on Nov. 30, 2008.

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)
*A61K 39/00* (2006.01)
*A61K 39/38* (2006.01)
*C07K 14/415* (2006.01)
*A61K 38/10* (2006.01)

(52) U.S. Cl.
CPC ............... *C07K 14/415* (2013.01); *A61K 38/10* (2013.01)
USPC ........................................ 530/326; 424/184.1

(58) Field of Classification Search
None
See application file for complete search history.

(56) References Cited

U.S. PATENT DOCUMENTS

| | | | |
|---|---|---|---|
| 4,740,371 A | 4/1988 | St. Remy et al. | |
| 5,128,270 A | 7/1992 | Delacroix et al. | |
| 5,334,504 A | 8/1994 | Wood et al. | |
| 5,494,799 A | 2/1996 | Wood et al. | |
| 5,547,669 A | 8/1996 | Rogers et al. | |
| 5,750,356 A | 5/1998 | Spack et al. | |
| 6,218,132 B1 | 4/2001 | Spack et al. | |
| 6,300,308 B1 | 10/2001 | Schroit | |
| 6,759,234 B1 | 7/2004 | Gefter et al. | |
| 6,806,354 B2 | 10/2004 | Schroit | |
| 7,094,555 B2 | 8/2006 | Kwok et al. | |
| 7,144,569 B1 | 12/2006 | Anderson et al. | |
| 7,202,216 B2 | 4/2007 | Sollid et al. | |
| 7,303,871 B2 | 12/2007 | Hausch et al. | |
| 7,361,480 B2 | 4/2008 | Maki et al. | |
| 7,462,688 B2 | 12/2008 | Khosla et al. | |
| 7,563,864 B2 | 7/2009 | Marti et al. | |
| 7,604,957 B2 | 10/2009 | Fine | |
| 7,608,392 B2 | 10/2009 | Rothel et al. | |
| 7,888,460 B2 | 2/2011 | Anderson et al. | |
| 8,053,235 B2 | 11/2011 | Buckner et al. | |
| 8,329,144 B2 | 12/2012 | Anderson et al. | |
| 2003/0215438 A1 | 11/2003 | Hausch et al. | |
| 2005/0014205 A1 | 1/2005 | Rothel et al. | |
| 2005/0249719 A1 | 11/2005 | Shan et al. | |
| 2005/0256054 A1 | 11/2005 | Sollid et al. | |
| 2006/0024334 A1 | 2/2006 | Larche et al. | |
| 2006/0154853 A1 | 7/2006 | Steptoe et al. | |
| 2006/0178299 A1 | 8/2006 | Anderson et al. | |
| 2006/0189540 A1 | 8/2006 | Khosla et al. | |
| 2006/0240475 A1 | 10/2006 | Khosla et al. | |
| 2006/0286601 A1 | 12/2006 | Marti et al. | |
| 2008/0145837 A1 | 6/2008 | Paulie et al. | |
| 2008/0175971 A1 | 7/2008 | Anderson et al. | |
| 2008/0318852 A1* | 12/2008 | Anderson et al. ............... 514/12 |
| 2009/0053297 A1 | 2/2009 | Balu-Iyer et al. | |
| 2009/0156490 A1 | 6/2009 | Khosla et al. | |
| 2009/0226471 A1 | 9/2009 | Kwok et al. | |
| 2009/0269285 A1 | 10/2009 | Anderson et al. | |
| 2010/0221712 A1 | 9/2010 | Radford et al. | |
| 2011/0311536 A1 | 12/2011 | von Boehmer et al. | |
| 2013/0078267 A1 | 3/2013 | Anderson et al. | |

FOREIGN PATENT DOCUMENTS

| | | |
|---|---|---|
| AU | 2003277989 B2 | 6/2004 |
| CA | 1299099 C | 4/1992 |
| CN | 1703505 A | 11/2005 |

(Continued)

OTHER PUBLICATIONS

[No Author Listed], ImmusanT Initiates Clinical Trials of Nexvax2 Therapeutic Vaccine for Celiac Disease. ImmusanT Press Release. Cambridge, MA. Sep. 4, 2012. 2 pgs.

[No Author Listed], ImmusanT Names Patrick Griffin as Chief Medical Officer, Expands Management Team. ImmusanT Press Release. Cambridge, MA. Mar. 19, 2012. 2 pgs.

[No Author Listed], ImmusanT Raises $20 Million in Series A Financing to Advance Immunotherapeutic and Diagnostic for Celiac Disease. ImmusanT Press Release. Cambridge, MA. Dec. 13, 2011. 2 pgs.

(Continued)

*Primary Examiner* — Robert Landsman
(74) *Attorney, Agent, or Firm* — Wolf, Greenfield & Sacks, P.C.

(57) ABSTRACT

The invention provides agents and vaccines for treating and diagnosing celiac disease. In particular, the present invention provides a combination of three peptides that are useful for treating and diagnosing celiac disease in a large proportion of patients.

11 Claims, 21 Drawing Sheets

(56) References Cited

FOREIGN PATENT DOCUMENTS

| EP | 0 296 158 B1 | 6/1992 |
|---|---|---|
| EP | 1 332 760 A1 | 8/2003 |
| EP | 1 453 539 B1 | 9/2004 |
| EP | 1 393 070 B1 | 8/2007 |
| EP | 1 561 106 B1 | 4/2009 |
| EP | 1 740 949 B1 | 11/2011 |
| IT | 2007FE003 | 2/2007 |
| WO | WO 93/19178 A2 | 9/1993 |
| WO | WO 96/06630 A1 | 3/1996 |
| WO | WO 96/07428 A1 | 3/1996 |
| WO | WO 01/25793 A2 | 4/2001 |
| WO | WO 02/083722 A2 | 10/2002 |
| WO | WO 03/066079 A2 | 8/2003 |
| WO | WO 03/096979 A2 | 11/2003 |
| WO | WO 03/096984 A2 | 11/2003 |
| WO | WO 03/104273 A2 | 12/2003 |
| WO | WO 2004/042396 A1 | 5/2004 |
| WO | WO 2004/045392 A2 | 6/2004 |
| WO | WO 2005/105129 A2 | 11/2005 |
| WO | WO 2007/019411 A2 | 2/2007 |
| WO | WO 2007/022477 A2 | 2/2007 |
| WO | WO 2008/090223 A2 | 7/2008 |
| WO | WO 2008/113119 A1 | 9/2008 |
| WO | WO 2009/131909 A2 | 10/2009 |
| WO | WO 2010/009494 A1 | 1/2010 |
| WO | WO 2010/060155 A1 | 6/2010 |
| WO | WO 2011/000773 A1 | 1/2011 |
| WO | WO 2011/075773 A1 | 6/2011 |
| WO | WO 2011/146968 A1 | 12/2011 |
| WO | WO 2013/000021 A1 | 1/2013 |
| WO | WO 2013/085851 A2 | 6/2013 |

OTHER PUBLICATIONS

[No Author Listed], ImmusanT Reports Positive Results from Nexvax2 Phase 1 Study in Celiac Disease: Data Featured in Poster of Distinction and Symposia on Advances in Celiac Disease at Digestive Disease Week. Chicago, Illinois, May 9, 2011. 3 pgs.

[No Author Listed], Link Between Gluten and Immune Reaction Revealed for HLA DQ8 Celiac Disease. ImmusanT Press Release. Cambridge, MA. Oct. 11, 2012. 2 pgs.

[No Author Listed], Start-Up ImmunsanT Seeks to Restore Tolerance to Gluten in Celiac Disease with Immunotherapy. PR Newswire. Mar. 3, 2011. Last Accessed on Nov. 13, 2012 from http://www.prnewswire.com/news-releases/start-up-immusant-seeks-to-restore-tolerance-to-gluten-in-celiac-disease-with-immunotherapy-117996359.html.

Anderson et al., Antagonists and non-toxic variants of the dominant wheat gliadin T cell epitope in coeliac disease. Gut. Apr. 2006;55(4):485-91. Epub Nov. 18, 2005.

Anderson et al., Bioactivity of peptides homologous to the coeliac disease-specific dominant A-gliadin T cell epitope. 2001. Abstract 3694.

Anderson et al., Bioactivity of peptides homologous to the coeliac disease-specific dominant T-cell epitope. DDW Poster. 2001. 1 page.

Anderson et al., Bioactivity of peptides homologous to the coeliac disease-specific dominant T-cell epitope. British Soc Gast Poster. 2001. 1 page.

Anderson et al., Celiac disease associated with HLA-DQ8 and DQ2 have different T-cell repertoires in vivo. 2003. Abstract 130.

Anderson et al., Celiac Disease. Chapter 22 in Evidence-Based Gastroenterology. Eds Irvine et al. 2000. BC Decker Inc. Ontario, Canada. pp. 307-322.

Anderson et al., Definitive T cell epitope mapping for a human disease: gluten challenge in coeliac disease identifies a dominant transglutaminase-deamidated T cell epitope. 2001 Kiel Conference Proceedings. 13 pgs.

Anderson et al., In vivo antigen challenge in celiac disease identifies a single transglutaminase-modified peptide as the dominant A-gliadin T-cell epitope. Nat Med. Mar. 2000;6(3):337-42.

Anderson et al., In vivo cross-reactivity of wheat and rye T-cell epitopes in celiac disease. AGA Abstracts 2003. Abstract W1364.

Anderson et al., Peripheral blood T cells induced by gluten challenge in coeliac disease target a specific molecular motif and express a gut-homing integrin. 2001 Abstract 3695.

Anderson et al., Peripheral blood T cells induced by gluten challenge in coeliac disease target a specific motif and express a gut-homing integrin. DDW Poster. 2001. 1 page.

Anderson et al., Screening for coeliac disease: integration of technology and stakeholders. eliA™ J. 2004;1:1-1 1.

Anderson et al.,T cells in peripheral blood after gluten challenge in coeliac disease. Gut. Sep. 2005;54(9):1217-23.

Anderson, Coeliac disease. Aust Fam Physician. Apr. 2005;34(4):239-42.

Anderson. Coeliac disease is on the rise. Med J Aust. Mar. 21, 2011;194(6):278-9.

Anderson. Coeliac disease: current approach and future prospects. Intern Med J. Oct. 2008;38(10):790-9.

Anderson. Coeliac disease: new tests, new genes and rising prevalence. MedicineToday. Jun. 2011;12(6):69-71.

Anderson. Development of a vaccine for celiac disease. Frontiers in Celiac Disease. 2008;12:172-180.

Arentz-Hansen et al., The intestinal T cell response to alpha-gliadin in adult celiac disease is focused on a single deamidated glutamine targeted by tissue transglutaminase. J Exp Med. Feb. 21, 2000;191(4):603-12.

Bateman et al., IgA antibodies of coeliac disease patients recognise a dominant T cell epitope of A-gliadin. Gut. Sep. 2004;53(9):1274-8.

Beissbarth et al., A systematic approach for comprehensive T-cell epitope discovery using peptide libraries.Bioinformatics. Jun. 2005;21 Suppl I:i29-37.

Broughton et al., Biased T Cell Receptor Usage Directed against Human Leukocyte Antigen DQ8-Restricted Gliadin Peptides Is Associated with Celiac Disease. Immunity. Oct. 19, 2012;37(4):611-21. Epub Oct. 11, 2012.

Brown et al., A phase I study to determine safety, tolerability and bioactivity of nexvax2 in HLA DQ2+ volunteers with celiac disease following a long-term, strict gluten free diet . AGA Abstracts. 2011; p. S-437-8: Abstract Su1235.

Brown et al., A phase I study to determine safety, tolerability and bioactivity of Nexvax2® in HLA DQ2+ volunteers with celiac disease following long-term, strict gluten-free diet. DDW Poster. 2011. 1 page.

Camarca et al., Short wheat challenge is a reproducible in-vivo assay to detect immune response to gluten. Clin Exp Immunol. Aug. 2012;169(2):129-36.

Camarca et al., Intestinal T cell responses to gluten peptides are largely heterogeneous: implications for a peptide-based therapy in celiac disease. J Immunol. Apr. 1, 2009;182(7):4158-66.

Camarca et al., Intestinal T-cell responses to gluten-derived peptides reveal a large repertoire and a hierarchy of gluten epitopes in adult HLA-DQ2-positive celiac patients. AGA Abstracts. 2006; p. A-94: Abstract 657.

Catassi et al. (eds), Primary Prevention for Coeliac Disease the Utopia of the New Millennium? vol. I: Perspectives on Coeliac Disease. Proceedings of the Meeting on Coeliac Disease held in Pavia on Oct. 12, 2001. Published in 2003. AIC Press. Italian Coeliac Society. Pisa, Italy. pp. 1-112.

Catassi et al., World Perspective on Celiac Disease. J Pediatr Gastroenterol Nutr. Nov. 2012;55(5):494-499.

Costa et al., A population study to optimize the role of serology and genetics in the diagnosis of celiac disease (CD). DDW Poster. 2011. 1 page.

Costa et al., A population study to optimize the role of serology and genetics in the diagnosis of celiac disease . AGA Abstracts. 2011; p. S-440: Abstract Su1246.

Daveson et al., Effect of hookworm infection on wheat challenge in celiac disease—a randomised double-blinded placebo controlled trial. PLoS One. Mar. 8, 2011;6(3):1-9.

Daveson et al., Small bowel endoscopy and coeliac disease. Best Pract Res Clin Gastroenterol. Jun. 2012;26(3):315-23.

De Kauwe et al., Resistance to celiac disease in humanized HLA-DR3-DQ2-transgenic mice expressing specific anti-gliadin CD4+ T cells. J Immunol. Jun. 15, 2009;182(12):7440-50.

(56) References Cited

OTHER PUBLICATIONS

Erickson, 10 Promising Therapeutic Vaccines. Fierce Vaccines. Oct. 27, 2011. Last Accessed on Nov. 13, 2012 from http://www.fiercevaccines.com/story/10-promising-therapeutic-vaccines/2011-10-27.
Hagan, The vaccine that means coeliacs can eat wheat. Good Health. Tuesday, Oct. 9, 2012. 1 pg.
Haines et al., Systematic review: The evidence base for long-term management of coeliac disease. Aliment Pharmacol Ther. Nov. 1, 2008;28(9):1042-66. Epub Jul. 30, 2008.
Henderson et al., A structural and immunological basis for the role of human leukocyte antigen DQ8 in celiac disease. Immunity. Jul. 2007;27:1-12.
Henderson et al., Supplemental Data: A structural and immunological basis for the role of human leukocyte antigen DQ8 in celiac disease. Immunity. Jul. 2007;27:1-9.
Henderson et al., The production and crystallization of the human leukocyte antigen class II molecules HLA-DQ2 and HLA-DQ8 complexed with deamidated gliadin peptides implicated in coeliac disease. Acta Crystallogr Sect F Struct Biol Cryst Commun. Dec. 1, 2007;63(Pt 12):1021-5. Epub Nov. 21, 2007.
Huan et al., Single-chain recombinant HLA-DQ2.5/peptide molecules block α2-gliadin-specific pathogenic CD4+ T-cell proliferation and attenuate production of inflammatory cytokines: a potential therapy for celiac disease. Mucosal Immunol. Jan. 2011;4(1):112-20. Epub Aug. 25, 2010.
Keech et al., Immune tolerance induced by peptide immunotherapy in an HLA Dq2-dependent mouse model of gluten immunity. Gastroenterology May 2009;136(5):A57. Abstract 355.
McSorley et al., Suppression of inflammatory immune responses in celiac disease by experimental hookworm infection. PLoS One. 2011;6(9):1-7. Epub Sep. 16, 2011.
Oldfield et al., Effect of T-cell peptides derived from Fel d 1 on allergic reactions and cytokine production in patients sensitive to cats: a randomised controlled trial. Lancet. Jul. 6, 2002;360(9326):47-53.
Ontiveros et al., A whole blood cytokine release assay employing short-term gluten challenge identifies patients with celiac disease on a gluten free diet . AGA Abstracts. 2012; p. S-271: Abstract Sa1317.
Ontiveros et al., A whole blood cytokine release assay employing short-term gluten challenge identifies patients with celiac disease on a gluten free diet. DDW ePoster. And Poster. 2012. 1 page.
Pincus, Coeliac vaccine trials world first. 12 Weekend Professional Health. The Weekend Australian. Mar. 21-22, 2009. 1 page.
Potkin et al., Wheat gluten challenge in schizophrenic patients. Am J Psychiatry. Sep. 1981;138(9):1208-11.
Saxby et al., A study of IgA antibodies to a T cell epitope of α-gliadin in coeliac disease. British Soc Immunol Poster. 2002. 1 page.
Scibilia et al., Wheat allergy: a double-blind, placebo-controlled study in adults. J Allergy Clin Immunol. Feb. 2006;117(2):433-9.
Sollid et al., Nomenclature and listing of celiac disease relevant gluten T-cell epitopes restricted by HLA-DQ molecules. Immunogenetics. Jun. 2012;64(6):455-60. doi: 10.1007/s00251-012-0599-z. Epub Feb. 10, 2012.
Stewart et al., Dominance, hierarchy and redundancy of T cell stimulatory peptides in celiac disease. AGA Abstracts. 2009; p. A-57: Abstract 354.
Tan et al., Non-axial bone fracture but not depression as a risk factor for coeliac disease. Intern Med J. Mar. 2010;40(3):225-7.
Tanner et al., Dissecting the T-cell response to hordeins in coeliac disease can develop barley with reduced immunotoxicity. Aliment Pharmacol Ther. Nov. 2010;32(9):1184-91. Epub Sep. 15, 2010.
Tarlac et al., HLA-DR3-DQ2 Mice Do Not Develop Ataxia in the Presence of High Titre Anti-gliadin Antibodies. Cerebellum. Oct. 20, 2012.
Tye-Din et al., A 35mer peptide with T cell stimulatory activity comparable to whole gliadin: a lead compound for peptide immunotherapy in celiac disease. AGA Abstracts. 2006; p. A-95: Abstract 661.
Tye-Din et al., A comprehensive bioinformatic and functional screen of wheat gluten T-cell epitopes in HLA-DQ2 celiac disease in vivo. AGA Abstracts. 2005; p. A-2: Abstract 13.
Tye-Din et al., A third celiac disease: genotyping reveals a functionally distinct subtype. AGA Abstracts. 2006; p. A-664: Abstract W1238.
Tye-Din et al., Comprehensive T-cell epitope characterization in HLA-DQ8 celiac disease. AGA Abstracts. 2005; p. A-2: Abstract 14.
Tye-Din et al., Comprehensive, quantitative mapping of T cell epitopes in gluten in celiac disease. Sci Transl Med. Jul. 21, 2010;2(41):1-14.
Tye-Din et al., Comprehensive, quantitative mapping of T cell epitopes in gluten in celiac disease. Sci Transl Med. Jul. 21, 2010;2(41):41ra51.
Tye-Din et al., HLA-DQ genotype reverses incorrect diagnosis of celiac disease. AGA Abstracts.2005; p. A-259: Abstract S1805.
Tye-Din et al., Immunopathogenesis of celiac disease. CurrGastroenterol Rep. Oct. 2008;10(5):458-65.
Tye-Din et al., Oats induce avenin specific T-cells in celiac disease. AGA Abstracts. 2005; pp. A-259: Abstract S1804.
Tye-Din et al., T-cell epitope hierarchy after rye and barley ingestion in celiac disease. AGA Abstracts. 2005; p. A-259: Abstract S1803.
Tye-Din et al., The effects of ALV003 pre-digestion of gluten on immune response and symptoms in celiac disease in vivo. Clin Immunol. Mar. 2009;134(3):1-7.
Tye-Din et al., Universal and grain-specific T cell epitopes in celiac disease. AGA Abstracts.2007; p. A-108: Abstract 760.
Vader et al., Characterization of cereal toxicity for celiac disease patients based on protein homology in grains. Gastroenterology. Oct. 2003;125(4):1105-13.
Walker-Smith et al., Revised criteria for diagnosis of coeliac disease. Report of Working Group of European Society of Paediatric Gastroenterology and Nutrition. Arch Dis Child. Aug. 1990;65(8):909-11.
WPI Database Submission, Accession No. AED68481; Shan et al..; Jan. 12, 2006. 2 pages.
GENBANK Submission; NIH/NCBI, Accession No. ABS72146; Chen et al.; Aug. 5, 2007. 1 page.
GENBANK Submission; NIH/NCBI, Accession No. AAB28161;Sainova et al.; Jan. 19, 1994. 1 page.
GENBANK Submission; NIH/NCBI, Accession No. AA276368.1; Han et al.; Mar. 20, 2008.. 1 page.
[No Author Listed] Diagnosis and treatment of coeliac disease targeting gluten-specific T cells. Presentation. Burnet Institute. Melbourne, Australia. May 29, 2011. 48 pages.
[No Author Listed] Vaccination for celiac disease: utopia or concrete hope for celiac disease recovery. AIC Presentation. Florence, Italy. Mar. 30, 2012. 23 pages.
Anderson et al., Acrocyanosis due to imipramine. Arch Dis Child. Feb. 1988;63(2):204-5.
Anderson et al., Coeliac disease. Check Program of Self Assessment. 2005. The Royal Australian College of General Practitioners. Victoria, Australia. pp. 1-32.
Anderson, Translating discovery of toxic gluten peptides to a peptide immunotherapy for coeliac disease. Presentation given in Wellington, New Zealand. 2010. 77 pages.
Anderson, A blueprint for the future of coeliac disease. Presentation for NZ Coeliac Society. 2011. 37 pages.
Anderson, A phase I study to determine safety, tolerability and bioactivity of Nexvax2® in HLA DQ2+ volunteers with celiac disease following long-term, strict gluten-free diet. Presentation. Kiama NSW. 2011. 15 pages.
Anderson, Coeliac disease in a select population: optimizing serogenetic testing. Presentation. The George Institute. Sydney, Australia. 2010. 43 pages.
Anderson, Coeliac Disease: Diagnosis without biopsy, and therapy without dietary changes. Swiss Coeliac Day Presentation. Zurich, Switzerland. 2011. 53 pages.
Anderson, Coeliac T cell epitopes in cereals: What are they and why do they matter? AOECS Presentation. Helsinki, Finland. Sep. 6, 2012. 26 pages.
Anderson, Future Therapies. University Chicago Presentation. 2011. 60 pages.

(56) References Cited

OTHER PUBLICATIONS

Anderson, Genetic susceptibility and regulation of the immune response in celiac disease. DDW Presentation. 2011. 30 pages.
Anderson, Harnessing gluten toxicity to make a drug for coeliac disease. Presentation for The Garvan Institute. Sydney, Australia. 2010. 38 pages.
Anderson, Overcoming gluten toxicity: additions or replacements to diet? ICDS Presentation. Oslo, Norway. Jun. 22, 2011. 49 pages.
Anderson, Sunrise Session: Basic science celiac disease. DDW Presentation. 2011. 29 pages.
Anderson., Update in coeliac disease: from food to molecular therapeutics and diagnostics. ASCIA Presentation. 2011. 46 pages.
Attwood, Genomics. The Babel of bioinformatics. Science. Oct. 20, 2000;290(5491):471-3. 5 pages.
Biagi et al., A non-toxic analogue of a coeliac-activating gliadin peptide: a basis for immunomodulation? Aliment Pharmacol Ther. Jul. 1999;13(7):945-50.
Brown et al., A phase I study to determine safety, tolerability and bioactivity of Nexvax2® in HLA DQ2+ volunteers with celiac disease following long-term, strict gluten-free diet. DDW Presentation. 2011. 6 pages.
Cornell et al., In vitro mucosal digestion of synthetic gliadin-derived peptides in celiac disease. J Protein Chem. Jul. 1995;14(5):335-9.
Costa et al., Quantifying community need and potential impact of rational testing for Coeliac Disease: A basis for disciplinary guidelines in Australia. Presentation. St. Georges, Sydney, Australia. 2011. 34 pages.
De Kauwe et al., Resistance to celiac disease in humanized HLA-DR3-DQ2-transgenic mice expressing specific anti-gliadin CD4+ T cells. J Immunol. Jun. 15, 2009;182(12):7440-50. Doi: 10.4049/jimmunol.0900233.
Fleckenstein et al., Gliadin T cell epitope selection by tissue transglutaminase in celiac disease. Role of enzyme specificity and pH influence on the transamidation versus deamidation process. J Biol Chem. Sep. 13, 2002;277(37):34109-16. Epub Jul. 1, 2002.
Fraser et al., Coeliac disease: in vivo toxicity of the putative immunodominant epitope. Gut. Dec. 2003;52(12):1698-702.
Hirahara et al., New specific immunotherapies for Japanese cedar pollinosis. Biolog Eng. 2002;80(4): 152-55.
Marylia et al., A population study to optimize the role of serology and genetics in the diagnosis of celiac disease (CD). DDW Poster. 2011. 1 page.
Ngo et al., Computational Complexity, Protein Structure Prediction, and the Levinthal Paradox. The Protein Folding Problem and tertiary Structure Prediction. Merz et al., Eds. 1994:14,492-5.
Ontiveros et al., A whole blood cytokine release assay employing short-term gluten challenge identifies patients with celiac disease on a gluten free diet. DDW ePoster. And Poster. 2012. 9 pages.
Raki et al., Tetramer visualization of gut-homing gluten-specific T cells in the peripheral blood of celiac disease patients. Proc Natl Acad Sci U S A. Feb. 20, 2007;104(8):2831-6. Epub Feb. 16, 2007.

Saito, New Immunotherapy—Peptide therapy & DNA vaccine therapy. Clinical of Allergy. Nov. 2003; 23(12):26-30.
Skerritt et al., Antigenecity of wheat prloamins: detailed epitope analysis using a panel of monoclonal antibodies. J Cereal Sci. 2000;32:259-79.
Skolnick et al., From genes to protein structure and function: novel applications of computational approaches in the genomic era. Trends Biotechnol. Jan. 2000;18(1):34-9.
Van De Wal et al., Small intestinal T cells of celiac disease patients recognize a natural pepsin fragment of gliadin. Proc Natl Acad Sci U S A. Aug. 18, 1998;95(17):10050-4.
Cornell et al., Studies of in vitro gamma-interferon production in coeliac disease as a response to gliadin peptides. Biochim Biophys Acta. May 25, 1994;1226(2):126-30.
Anderson et al., Vaccine against autoimmune disease: antigen-specific immunotherapy. Curr Opin Immunol. Jun. 2013;25(3):410-7. doi: 10.1016/j.coi.2013.02.004. Epub Mar. 13, 2013.
Brottveit et al., Absence of somatization in non-coeliac gluten sensitivity. Scand J Gastroenterol. Jul. 2012;47(7):770-7.
Brottveit et al., Assessing possible celiac disease by an HLA-DQ2-gliadin Tetramer Test. Am J Gastroenterol. Jul. 2011;106(7):1318-24. doi: 10.1038/ajg.2011.23. Epub Mar. 1, 2011. Erratum in: Am J Gastroenterol, Apr. 2012;107(4):638.
Brottveit et al., Mucosal cytokine response after short-term gluten challenge in celiac disease and non-celiac gluten sensitivity. Am J Gastroenterol. May 2013;108(5):842-50. doi: 10.1038/ajg.2013.91. Epub Apr. 16, 2013.
Brottveit, Gluten challenge in coeliac disease and non-coeliac gluten sensitivity. Oslo University Hospital. 2012:2-74.
Cheng et al., CD4+, but not CD8+, T cells from mammary tumor-bearing mice have a down-regulated production of IFN-gamma: role of phosphatidyl serine. J Immunol. Mar. 15, 1998;160(6):2735-41.
Goldman, Best thing since sliced bread? Stanford Medicine. A (potential) new diagnostic for celiac disease. Scope. Stanford Medicine. Jun. 22, 2013. http://scopeblog.stanford.edu/2013/07/22/best-thing-since-sliced-bread-a-potential-new-diagnostic-for-celiac-disease/ [last accessed Nov. 19, 2013].
Han et al., Dietary gluten triggers concomitant activation of CD4+ and CD8+ αβ T cells and γδ T cells in celiac disease. Proc Natl Acad Sci U S A. Aug. 6, 2013;110(32):13073-8.
Norman et al., Treatment of Cat Allergy with T-cell Reactive Peptides. Am J Respir Crit Care Med. 1996;154:1623-8.
Oberhuber et al., The histopathology of coeliac disease: time for a standardized report scheme for pathologists. Eur J Gastroenterol Hepatol. Oct. 1999;11(10):1185-94. Review.
Quarsten et al., Staining of celiac disease-relevant T cells by peptide-DQ2 multimers. J Immunol. Nov. 1, 2001;167(9):4861-8.
Rubio-Tapia et al., ACG clinical guidelines: diagnosis and management of celiac disease. Am J Gastroenterol. May 2013;108(5):656-76.

\* cited by examiner

| Fraction | Pool no. | Peptide no. | Peptide | ξ-I | ξ-II | III | ξ-IV | ξ-V | VI | VII | Wheat Day 6 n=5 DQ2 Pools | Wheat Day 6 n=5 DQ2 Peptides | Wheat Day 7 n=5 DQ2 Peptides | Wheat Day 6/7 n=4 DQ2,8 Peptides | Wheat Day 6 n=13 DQ2 Peptides | Rye Day 6 n=4 DQ2 Peptides |
|---|---|---|---|---|---|---|---|---|---|---|---|---|---|---|---|---|
| Gliadin 0.5mg/ml | | | | | | | | | | | 135 | | | | | |
| Alpha | 12 | 89 | PQLPYPQPQLPYPQPQLPYP | ■ | ■ | | | | | | | 70 | 89 | 23 | 57 | 0 |
| Alpha | 12 | 91 | PQPFPPQLPYPQPQLPYPQP | ■ | ■ | | | | | | | 70 | 85 | 61 | 59 | 0 |
| Alpha | 10 | 74 | MQLQPFPQPQLPYPQPQLPY | | ■ | ■ | | | | | | 68 | 83 | 55 | 55 | 2 |
| Alpha | 12 | 90 | PQLPYPQPQLPYPQPQPFRP | ■ | ■ | | | | | | | 70 | 81 | 33 | 54 | 0 |
| Alpha | 10 | 76 | LQLQPFPQPQLPYPQPQPFR | | ■ | ■ | | | | | | 68 | 79 | 20 | 65 | 6 |
| Omega | 80 | 626 | PQQPQQPFPQPQQPFPQPFPW | | | | | | ■ | | | 46 | 58 | 14 | 27 | 35 |
| Omega | 81 | 631 | FPQQPQQPFPQPQLPFPQQS | | | | | | | | | 90 | 57 | 13 | 25 | 7 |
| Omega | 80 | 627 | QPFPQPQQPFPWQQQPFPQ | | | | | | ■ | | | 46 | 50 | 10 | 20 | 34 |
| Omega | 81 | 636 | PQQPQQPFPQPQQPIPVQPQ | | | | | | | | | 90 | 47 | 14 | 27 | 56 |
| Alpha | 10 | 73 | LQLQPFPQPQLPYPQPQLPY | ■ | ■ | ■ | | | | | | 68 | 45 | 12 | 31 | 4 |

*DQ2-restricted epitopes: GLIA-20, ξ-I, ξ-II, ξ-III, ξ-IV, ξ-V, GLT-156, GLT-17 not present

Figure 4

| Core identifier[7] | 1st round 20mer [2nd round core] | 1st round score | 2nd round Score | 2nd round Res[4] | 2nd round Dom[5] | TCC, % IFN-γ ELISpot SFU to cognate ligand[6] 1 | 2 | 3 | 4 | 5 | 6 | 7 | 8 | 9 | 10 | 11 | 12 | Defined or *predicted* gluten epitopes[3] |
|---|---|---|---|---|---|---|---|---|---|---|---|---|---|---|---|---|---|---|
| W01 | PQPFPQLPYPQPQLPYPQP | 60 | 75 | 96 | 69 | | | | | | | | | | | | | α-II, α-III |
| W02 | MQLQPFFQPQLPYPQPQLPY | 55 | 74 | 88 | 58 | | | | | | | | | | | | | α-I, α-II |
| W03 | QPFFQPQQPFFWQPQPQLPY | 53 | 65 | 81 | 35 | | | | | | | | | | | | | ω-I ω-II |
| W04 | PQQPQQPFFQPQQPIPVQPQ | 31 | 53 | 77 | 31 | | | | | | | | | | | | | *PFPQPQQPI, PQPQQPIPV* |
| W05 | PQQQQPFFQPQQPFFSQQPQQ | 19 | 39 | 69 | 15 | | | | | | | | | | | | | ω-I |
| W06 | QQPQQPFFQPQLPFFQQSEQ | 25 | 34 | 69 | 15 | | | | | | | | | | | | | *PFPQPQLPF, PQPQLPFFQ* |
| W07 | WPQQPFPQQPFCQQPQQ | 15 | 27 | 62 | 8 | | | | | | | | | | | | | ω-I |
| W08 | LQLQPFPQLPYSQPQPER | 15 | 24 | 65 | 8 | | | | | | | | | | | | | α-I |
| W09 | LQPFPQPQLPFLPQLPYPQQ | 34 | 23 | 54 | 0 | | | | | | | | | | | | | |
| W10 | SQQPQQQFSQPQQQFPQPQQ | 6 | 20 | 42 | 0 | | | | | | | | | | | | | γ-VII |
| W11 | QAFPQPQQTFPHQPEQQQFPQ | 6 | 18 | 50 | 0 | | | | | | | | | | | | | |
| W12 | CKVFLQQQCSPVAMPQRLAR | 12 | 16 | 54 | 4 | | | | | | | | | | | | | |
| W13 | LQLQPFPQLPYLQPQPFR | 20 | 15 | 54 | 4 | | | | | | | | | | | | | α-I |
| W14 | QQFIQPQQLPYPQQPFRP | 10 | 15 | 46 | 4 | | | | | | | | | | | | | |
| W15 LMW | SHIPGLERPWQQQPLPPQQT | 9 | 13 | 17 | 11 | | | | | | | | | | | | | |
| W16 | SQQPQQPFPQQQFPQPQQ | 15 | 13 | 50 | 0 | | | | | | | | | | | | | γ-VIIa *PQQQFPQPQ* |
| W17 | QQPFFPQQPQLPFFQQFQQ | 12 | 10 | 35 | 0 | | | | | | | | | | | | | *PFPQPQQPQ* |
| W18 | PQLPYPQLPYPQPQPFRP | 54 | 10 | 39 | 0 | | | | | | | | | | | | | α-II |
| W19 | QPFPQPQQPFPWQPQQPFFQ | 53 | 10 | 35 | 0 | | | | | | | | | | | | | |
| W20 | FPELQPIPQPQQPFPLQP | 6 | 10 | 31 | 4 | | | | | | | | | | | | | *QQPQQPFPL* |
| W21 HMW | QGQQGYYPISPQQSGQGQQP | 7 | 10 | 22 | 6 | | | | | | | | | | | | | |
| W22 HMW | LQPGGQQPFYPTSPQQIGQ | 11 | 9 | 17 | 6 | | | | | | | | | | | | | |
| W23 | QQFLQPQQPFPQQQPFPQ | 15 | 9 | 33 | 0 | | | | | | | | | | | | | γ-III |
| W24 HMW | PGQGQSGYYPTSPQQSGQKQ | 5 | 9 | 17 | 6 | | | | | | | | | | | | | |
| W25 | TPIQPQPFPQQPQQPFPF | 15 | 8 | 35 | 0 | | | | | | | | | | | | | |
| W26 | PQGQQPFFLQPQQPFPQP | 10 | 8 | 35 | 0 | | | | | | | | | | | | | |
| W27 | PFTQPQPFPIQPQQPFPQQ | 12 | 7 | 23 | 0 | | | | | | | | | | | | | |
| W28 | QQPFFPQPQQTFPQQPQLPF | 7 | 7 | 22 | 6 | | | | | | | | | | | | | *QQTFPQQPQ* |
| W29 HMW | GQGQSGYYPTSPQQSGQEAT | 6 | 7 | 17 | 6 | | | | | | | | | | | | | |
| W30 | PLQPQQPFPQQPLPQPQPQ | 19 | 6 | 19 | 0 | | | | | | | | | | | | | γ-VIa |
| W31 | QPFFQLQQPQQPFPQPQ | 9 | 6 | 4 | 0 | | | | | | | | | | | | | |
| W32 | QQPFFPQQPQPFPQQPIP | 37 | 6 | 23 | 0 | | | | | | | | | | | | | γ-VIIb, *PFPQQPQQPF** |
| W33 | PQQPFFQPQQTFPQQPQLPF | 7 | 5 | 17 | 0 | | | | | | | | | | | | | *PFPQPQQTF* |
| W34 | VAHAIIMHQQQQQQQEQKQQ | 6 | 5 | 22 | 0 | | | | | | | | | | | | | |
| W35 | PQQPFPQQPQQPFPQPFQPQ | 11 | 5 | 19 | 0 | | | | | | | | | | | | | *PFPQQPQQQ, QQPQQQFPPQ* |
| W36 | QQPAQTEVIRSLVLRTLPRM | 9 | 2 | 11 | 4 | | | | | | | | | | | | | |
| W37 | ATANMQVDSGQVQWFPQQQ | 0 | 6 | 6 | 6 | | | | | | | | | | | | | |

Figure 7A

| Core identifier[?] | 1st round 20mer [2nd round core] | 1st round score | 2nd round Score | 2nd round Res[4] | 2nd round Dom[5] | TCC, % IFN-γ ELISpot SFU to cognate ligand[a] 1 | 2 | 3 | 4 | 5 | 6 | 7 | 8 | 9 | 10 | 11 | 12 | Defined or *predicted* gluten epitopes[3] |
|---|---|---|---|---|---|---|---|---|---|---|---|---|---|---|---|---|---|---|
| B01 | QPFFQPQQPFFWQPQQPFPQ | 50 | 66 | 88 | 50 | - | - | - | - | - | - | - | - | ■ | - | - | - | ω-I ω-II |
| B02 | WQPQPFQPQQPFFLQPFQQ | 53 | 64 | 75 | 50 | - | - | - | - | - | - | - | - | - | - | - | - | ω-I |
| B03 | QPQQPFPQFQQPIPYQPQQP | 32 | 55 | 75 | 38 | - | - | - | - | - | - | - | - | - | - | - | - | QFPQPQQPF |
| B04 | QPQQPFPQQPVPQQPQPY | 38 | 45 | 63 | 25 | - | - | - | - | - | - | - | - | - | ■ | - | - | |
| B05 | PQPFPQQPIFQQPQPYPQQP | 38 | 43 | 50 | 25 | - | - | - | - | - | - | - | - | - | ■ | - | - | Hor-I *PQPFPQQPI, PFPQQPIPQ, QQPIPQQPQ* |
| B06 | QQPQFFSQQPIPQQPQPYPQ | 63 | 40 | 50 | 25 | - | - | - | - | - | - | - | - | - | - | - | - | Hor-I *QQPIPQQPQ* |
| B07 | QSQQFFQFQQPFFQQPYPQQP | 8 | 37 | 63 | 13 | - | - | - | - | - | - | - | ■ | - | - | - | - | Hα2/Sα2 QFPQPQQPF |
| B08 | QQPFPQQPIFQQPQPYFQQP | 38 | 33 | 38 | 25 | - | - | - | - | - | - | - | - | - | - | - | - | Hor-I *QQPIPQQPQ* |
| B09 | QQPFFPQQPQPYPQQP | 26 | 32 | 50 | 13 | - | - | - | - | - | - | - | - | - | - | - | - | γ-VIa QQPFPQQPF, *PFPQQPFPQ, PFPQQPQPY* |
| B10 | PQQPFFQPQQPYFQQPFPQP | 39 | 27 | 50 | 13 | - | - | - | - | - | ■ | - | - | - | - | - | - | Hα9/Sα9 (ω-I) |
| B11 | QPQPYQQPFFQQPFQPQ | 39 | 26 | 50 | 0 | - | - | - | - | - | - | - | - | - | - | - | - | *PQPYPQQPQ, PYPQQPQPY* |
| B12 | QQPFPQQPFFQQPYPQQPP | 26 | 23 | 50 | 13 | - | - | - | - | - | - | - | - | - | - | - | - | γ-VIa *PFPQQPQPY* |
| B13 | PQFYPQQPFFQQPPFCQQ | 19 | 21 | 50 | 0 | - | - | - | - | - | - | - | - | - | - | - | - | *PQPYPQQPQ* |
| B14 | FQQPQQSIFVQPQQPFFQPQ | 22 | 19 | 38 | 0 | - | - | - | - | - | ■ | - | - | - | - | - | - | |
| B15 | YPQQPQPFFPQQPIPQQPQPY | 41 | 19 | 38 | 0 | - | - | - | - | - | ■ | - | - | - | - | - | - | *PQPFPQQPI, PFPQQPIPQ* |
| B16 | QQPFPQQPIFQQPQPYQQ | 41 | 16 | 38 | 0 | - | - | - | - | - | ■ | - | - | - | - | - | - | *QQPFPQQPI, PFPQQPIPQ* |
| B17 | QPQQPFPQQPVPQQPQPY | 38 | 15 | 38 | 0 | - | - | - | - | - | - | - | - | - | - | - | - | *PQPFPQQPI* |
| B18 | QPQPFFQQPIPLQPHQPYTQ | 7 | 14 | 38 | 0 | - | - | - | - | - | - | - | - | - | - | - | - | |
| B19 | LPRFQQPFFWQPQQPFFPQ | 14 | 13 | 25 | 0 | - | - | - | - | - | - | - | - | - | - | - | - | |
| B20 | QQPFPLQPQPFFPQPQPFPQ | 13 | 12 | 25 | 0 | - | - | - | - | - | - | - | - | - | - | - | - | Hα9/Sα9 (ω-I) |
| B21 | PFPQPQQPFFQPQPFRQQ | 19 | 10 | 25 | 0 | - | - | - | - | - | - | - | - | - | - | - | - | |
| B22 | PQQPFQPQQPFFQQTIPQQP | 8 | 10 | 25 | 0 | - | - | - | - | - | - | - | - | - | - | - | - | |
| B23 | NFLQPQPFPLQPQPPQQPF | 9 | 10 | 25 | 0 | - | - | - | - | - | - | - | - | - | - | - | - | |
| B24 | NPFLQPQPFFLQPQPPQQPF | 9 | 9 | 25 | 0 | - | - | - | - | - | - | - | - | - | - | - | - | |
| B25 | PFPQQPFFLQPQQPFRQQ | 19 | 8 | 25 | 0 | - | - | - | - | - | - | - | - | - | - | ▤ | - | γ-VIIb |
| B26 | QPQQPFFLQPQQPFFWQFQQ | 7 | 7 | 13 | 0 | - | - | - | - | - | - | - | - | - | - | - | - | |
| B27 | TFPPSQQFNFLQPQPPFFLQ | 18 | 7 | 13 | 0 | - | - | - | - | - | - | - | - | - | - | - | - | |
| B28 | PQQTIPQQPQPFFLQPQQP | 10 | 6 | 25 | 0 | - | - | - | - | - | - | - | - | - | - | - | - | |
| B29 | QPQQPFSFSQQPQPFFLQP | 9 | 6 | 25 | 0 | - | - | - | - | - | - | - | - | - | - | - | - | |
| B30 | QQPFFPQQPFFQQPQPYPQQP | 26 | 5 | 25 | 0 | - | - | - | - | - | - | - | - | - | - | - | - | γ-VIa *QQPFPQQPF* |

Figure 7B

| Core identifier[7] | 1st round 20mer [2nd round core] | 1st round score | 2nd round Score | 2nd round Res[4] | 2nd round Dom[5] | TCC, % IFN-γ ELISpot SFU to cognate ligand[6] 1 | 2 | 3 | 4 | 5 | 6 | 7 | 8 | 9 | 10 | 11 | 12 | Defined or predicted gluten epitopes[3] |
|---|---|---|---|---|---|---|---|---|---|---|---|---|---|---|---|---|---|---|
| R01 | QQLPLQPQQPFPQQPIPQ | 48 | 67 | 82 | 64 | - | - | - | - | - | - | - | - | - | - | - | - | PQPQQPIPQ |
| R02 | SIPQPQQPFPQPQQPFPQSQ | 30 | 64 | 82 | 55 | - | - | - | - | - | - | - | ■ | ■ | - | - | - | Hα2/Sα2, Hα9/Sα9 (ω-I) |
| R03 | QPFPQPQQFTIQPQQPFPQ | 51 | 62 | 91 | 55 | - | - | - | - | - | - | - | - | - | - | - | - | PFPQPQQPT, PQPQQPTPI |
| R04 | QPFPQPQQPTPIQPQQPFPQ | 51 | 29 | 73 | 0 | - | - | - | - | - | - | - | - | - | - | - | - | IQPQQPFPQ |
| R05 | PAPIQPQQPFPQCPQQPFPQ | 18 | 23 | 55 | 9 | - | - | - | - | - | - | - | - | - | - | - | - | IQPQQPFPQ |
| R06 | PQQPFPQQPEQIIPQQPQQP | 42 | 34 | 82 | 27 | - | - | - | - | - | - | - | - | - | - | - | - | |
| R07 | QYSPYQPQQPFPQPQQPTPI | 19 | 27 | 64 | 0 | - | - | - | - | - | - | - | - | - | - | - | - | |
| R08 | SQQPQRPQQPFPQQPQQIIP | 14 | 32 | 70 | 10 | - | - | - | - | - | - | - | ■ | ■ | - | ■ | - | γ-VIa, PFQQPQQI |
| R09 | QQLPLQPQQPFPQPQQPIPQ | 48 | 23 | 73 | 0 | - | - | - | - | - | - | - | - | - | - | ■ | - | |
| R10 | FPLQPQQPFPQPEQIISQQ | 29 | 26 | 45 | 18 | - | - | - | - | - | - | - | - | - | - | ■ | - | |
| R11 | PQQPFPQQPEQIIPQPQQP | 42 | 24 | 55 | 9 | - | - | - | - | - | - | - | - | ■ | - | ■ | - | |
| R12 | FPQQPQQPFPQQQLPLQP | 29 | 47 | 80 | 40 | - | - | - | - | - | - | - | - | - | - | ■ | - | PQPQQQLPL |
| R13 | SPQPQQPYPQQPFPQQPQQP | 11 | 18 | 64 | 0 | - | - | - | - | - | - | - | ■ | ■ | - | - | - | PYPQQPFPQ, QQPYPQQPF |
| R14 | QQPQQPFPLQPQQPVPQPQ | 33 | 17 | 64 | 0 | - | - | - | - | - | - | - | - | ■ | - | - | - | |
| R15 | QPQQIIPQPQQPFPLQPQQ | 25 | 15 | 64 | 0 | - | - | - | - | - | - | - | - | ■ | - | - | - | |
| R16 | PQQPFPQQPEQIIPQPQQP | 42 | 14 | 55 | 0 | - | - | - | - | - | - | - | ■ | ■ | - | - | - | |
| R17 | QTQQSIPQPQQPFPQPQQPF | 24 | 14 | 55 | 0 | - | - | - | - | - | - | - | - | ■ | - | ■ | - | Hα2/Sα2 |
| R18 | QQPFPLQPQQPFSQPQQPFL | 9 | 13 | 55 | 0 | - | - | - | - | - | - | - | - | - | - | - | - | |
| R19 | QQPQQPFPLQPQQPVPQPQ | 33 | 13 | 55 | 0 | - | - | - | - | - | - | - | - | ■ | - | - | - | |
| R20 | EQIISQQPFPLQPQQPFSQP | 10 | 12 | 45 | 0 | - | - | - | - | - | - | - | - | ■ | - | - | - | |
| R21 | NMQVGPSGQVEWPQQQPLPQ | 10 | 11 | 36 | 0 | - | - | - | - | - | - | - | - | - | - | - | - | |
| R22 | PQQLFPLPQQPFPQPQQPFP | 64 | 13 | 36 | 9 | - | - | - | - | - | - | - | - | - | - | - | - | |
| R23 | PQTQQPQQPFPQPQQPQLF | 49 | 11 | 55 | 0 | - | - | - | - | - | - | - | - | - | - | - | - | γ-VIIb |
| R24 | SPQQPQLPFPQPQQPFVVV | 21 | 11 | 64 | 0 | - | - | - | - | - | - | - | ■ | ■ | - | ■ | - | Hα9/Sα9 (ω-I) |
| R25 | FPQQPEQIISQPQQPPPLQ | 6 | 9 | 45 | 0 | - | - | - | - | - | - | - | - | - | - | ■ | - | |
| R26 | PAPIQPQQPFPQPQQPFPQ | 18 | 9 | 55 | 9 | - | - | - | - | - | - | - | - | ■ | - | ■ | - | γ-VIIb |
| R27 | PQEPQDLFPSQQPFPQQPFPQ | 7 | 6 | 27 | 0 | - | - | - | - | - | - | - | - | ■ | - | - | - | γ-VIIb |
| R28 | SPQQPYFQQPFPQQPQQP | 11 | 6 | 36 | 0 | - | - | - | - | - | - | ■ | - | - | - | - | - | γ-VIa |
| R29 | PTPIQPQPFFQRPQQPFPQ | 8 | 5 | 40 | 0 | - | - | - | - | - | - | - | - | - | - | - | - | |

Figure 7C

Legend for Figures 7A-C 1. 1st round library 20mer with a "score" of >5 confirmed by 2nd-round 16mer (core 12mer in bold) with score >5 using Day-6 PBMC after gluten challenge.
2. Recognition determined by T-cell clones raised to cognate ligand and incubated with 2nd-round peptides and "Verification" Library (2µg/ml).
3. Established epitopes α-I PFPQPQLPY, α-II PQPQLPYPQ, γVIa QQPFPQQPQ, Hα2/Sα2 PQPQQPFPQ, Hα9/Sα9 PFPQPQQPF or predicted and confirmed by Vader et al (*), or epitopes predicted by Shan et al (italics).
4. "Res" is % of 2nd-round donors responding to tTG-treated 16mer >4X medium alone and at least 10 SFU/well
5. "Dom" is % of 2nd-round donors with response to tTG-treated 16mer >70% of maximal response to any 2nd-round tTG-treated 16mer
6. Colour coding represents a clone's IFN-g response to 2nd round peptide, expressed as a percentage of the response to cognate ligand.
   ▫ 6-10%   ▨ 11-20%   ▩ 21-40%   ▦ 41-70%   ■ 71-100%
7. Duplicate core sequences: W03 and B01; W19 and B19; W25 and R04; W26 and B20; W30 and R28; W32, B25 and R26. W (Wheat gliadin, unless LMW or HMW indicated), B (Barley), R (Rye). Epitopes:α-I PFPQPELPY, α-II PQPELPYPQ, α-I PFPQPEQPF, ω-II PQPEQPFPW, Hor-I PIPEQPQPY Figure 14A
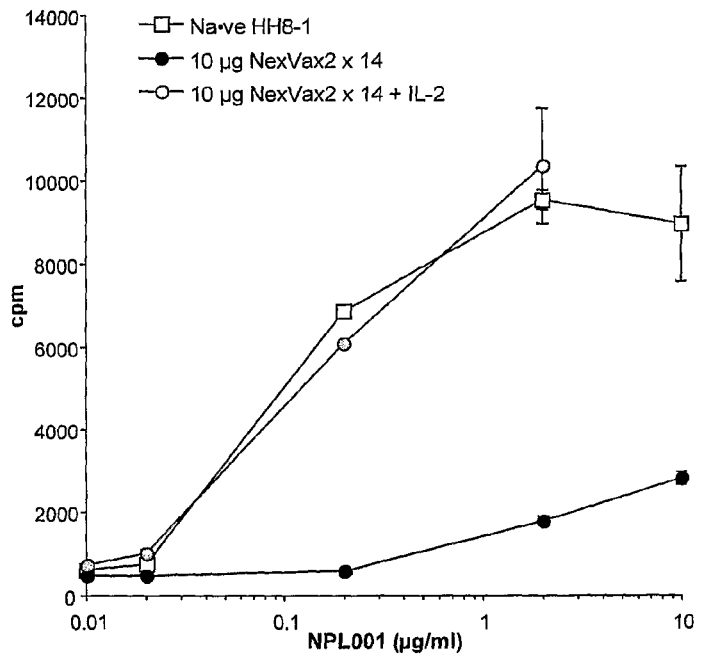
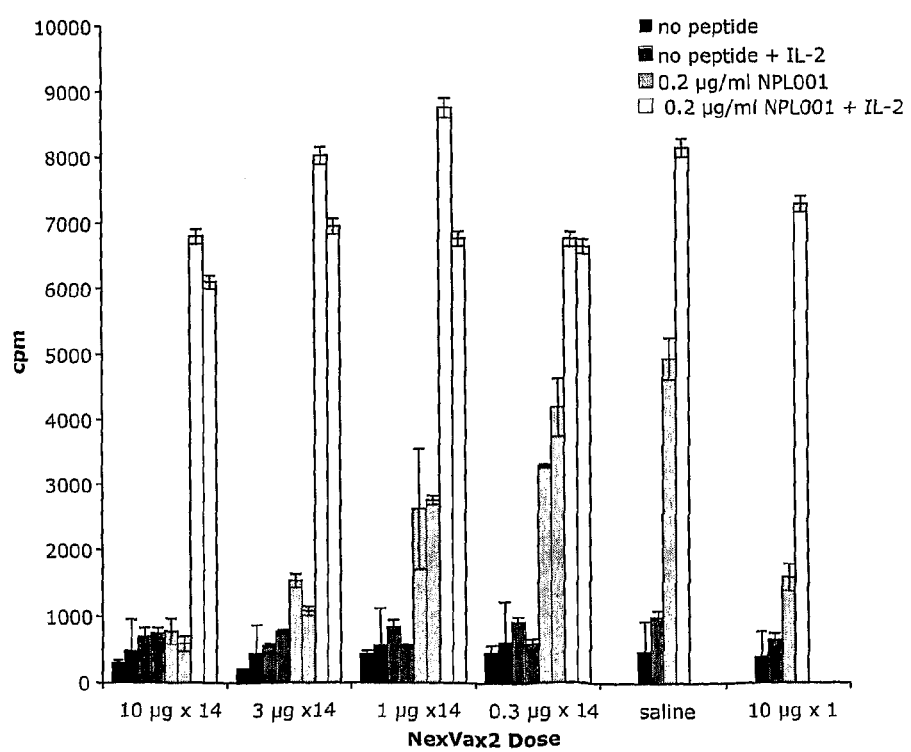

| Day | Time (24 hour notation) | Treatment Administration | Meals & Fluid + Gluten Challenge | ELISpot/ Bioplex SAMPLE | Serum antibody sample | PK Blood Sample (10 mL) | Vital Signs | ECG | Time (relative to dosing) |
|---|---|---|---|---|---|---|---|---|---|
| 1 | 0700 | | | 1 | 1 | | X | X | pre-dose (-60 min) |
| | 0800 | Administer Dose | | | | | | | 0 minutes |
| | 1200 | | Lunch# | | | | X | X | 4 hours |
| 6 | 0800 | | | 2 | | | X | X | 24 hours |
| 8 | 0700 | | | | | | X | X | pre-dose (-60 min) |
| | 0800 | Administer Dose | | | | | | | 0 minutes |
| | 1200 | | Lunch# | | | | X | X | 4 hours |
| 15 | 0700 | | | 3 | | 1 | X | X | pre-dose (-60 min) |
| | 0800 | Administer Dose | | | | | | | 0 minutes |
| | 0815 | | | | | 2 | | | 15 minutes |
| | 0830 | | | | | 3 | | | 30 minutes |
| | 0845 | | | | | 4 | | | 45 minutes |
| | 0900 | | | | | 5 | | | 1 hour |
| | 0915 | | | | | 6 | | | 1.25 hour |
| | 0930 | | | | | 7 | | | 1.5 hour |
| | 1000 | | | | | 8 | | | 2 hour |
| | 1100 | | | | | 9 | | | 3 hour |

Figure 17A

| Day | Time | Lunch# | | | | 4 hours |
|---|---|---|---|---|---|---|
| 20 | 1200 | | | | | |
| | 0800 | Gluten Challenge | 4 | | X | X | - |
| | 1200 | Gluten Challenge | 2 | | X | X | - |
| 21 | 0800 | Gluten Challenge | | | X | X | - |
| | 1200 | Gluten Challenge | | | X | X | - |
| 22 | 0800 | Gluten Challenge | | | X | X | - |
| | 1200 | Gluten Challenge | | | X | X | - |
| 25 | 0800 | | 5 | | X | X | - |

Note: Meals served 5-10 minutes after blood collection.
Subjects were released from the clinical facility 6 to 8 hours after dosing with NexVax2. ECGs were performed in triplicate approximately 1 minute apart.

Figure 17B

SEQUENCE LISTING

<160> NUMBER OF SEQ ID NOS: 486

<210> SEQ ID NO 1

-continued

```
<211> LENGTH: 33
<212> TYPE: PRT
<213> ORGANISM: Artificial Sequence
<220> FEATURE:
<223> OTHER INFORMATION: alpha2-gliadin 56-88

<400> SEQUENCE: 1

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 2
<211> LENGTH: 33
<212> TYPE: PRT
<213> ORGANISM: Artificial Sequence
<220> FEATURE:
<223> OTHER INFORMATION: deamidated alpha2-gliadin 56-88

<400> SEQUENCE: 2

Leu Gln Leu Gln Pro Phe Pro Gln Pro Glu Leu Pro Tyr Pro Gln Pro
1               5                   10                  15

Glu Leu Pro Tyr Pro Gln Pro Glu Leu Pro Tyr Pro Gln Pro Gln Pro
            20                  25                  30

Phe

<210> SEQ ID NO 3
<211> LENGTH: 9
<212> TYPE: PRT
<213> ORGANISM: Artificial Sequence
<220> FEATURE:
<223> OTHER INFORMATION: DQ2-alpha-I

<400> SEQUENCE: 3

Pro Phe Pro Gln Pro Glu Leu Pro Tyr
1               5

<210> SEQ ID NO 4
<211> LENGTH: 9
<212> TYPE: PRT
<213> ORGANISM: Artificial Sequence
<220> FEATURE:
<223> OTHER INFORMATION: DQ2-alpha-II

<400> SEQUENCE: 4

Pro Gln Pro Glu Leu Pro Tyr Pro Gln
1               5

<210> SEQ ID NO 5
<211> LENGTH: 9
<212> TYPE: PRT
<213> ORGANISM: Artificial Sequence
<220> FEATURE:
<223> OTHER INFORMATION: DQ2-alpha-III

<400> SEQUENCE: 5

Pro Tyr Pro Gln Pro Glu Leu Pro Tyr
1               5

<210> SEQ ID NO 6
<211> LENGTH: 11
<212> TYPE: PRT
<213> ORGANISM: Artificial Sequence
<220> FEATURE:
```

```
<223> OTHER INFORMATION: alpha-gliadin p60-70

<400> SEQUENCE: 6

Pro Phe Pro Gln Pro Gln Leu Pro Tyr Pro Gln
1               5                   10

<210> SEQ ID NO 7
<211> LENGTH: 17
<212> TYPE: PRT
<213> ORGANISM: Artificial Sequence
<220> FEATURE:
<223> OTHER INFORMATION: alpha-gliadin p57-73

<400> SEQUENCE: 7

Gln Leu Gln Pro Phe Pro Gln Pro Gln Leu Pro Tyr Pro Gln Pro Gln
1               5                   10                  15

Ser

<210> SEQ ID NO 8
<211> LENGTH: 17
<212> TYPE: PRT
<213> ORGANISM: Artificial Sequence
<220> FEATURE:
<223> OTHER INFORMATION: alpha-gliadin p57-73 QE65

<400> SEQUENCE: 8

Gln Leu Gln Pro Phe Pro Gln Pro Glu Leu Pro Tyr Pro Gln Pro Gln
1               5                   10                  15

Ser

<210> SEQ ID NO 9
<211> LENGTH: 9
<212> TYPE: PRT
<213> ORGANISM: Artificial Sequence
<220> FEATURE:
<223> OTHER INFORMATION: gluten derived peptide

<400> SEQUENCE: 9

Pro Phe Pro Gln Pro Gln Gln Pro Phe
1               5

<210> SEQ ID NO 10
<211> LENGTH: 9
<212> TYPE: PRT
<213> ORGANISM: Artificial Sequence
<220> FEATURE:
<223> OTHER INFORMATION: Halpha9/Salpha9, DQ2-omega-I

<400> SEQUENCE: 10

Pro Phe Pro Gln Pro Glu Gln Pro Phe
1               5

<210> SEQ ID NO 11
<211> LENGTH: 9
<212> TYPE: PRT
<213> ORGANISM: Artificial Sequence
<220> FEATURE:
<223> OTHER INFORMATION: gluten derived peptide

<400> SEQUENCE: 11

Pro Gln Pro Gln Gln Pro Phe Pro Gln
1               5

<210> SEQ ID NO 12
<211> LENGTH: 9
```

-continued

```
<212> TYPE: PRT
<213> ORGANISM: Artificial Sequence
<220> FEATURE:
<223> OTHER INFORMATION: Halpha2/Salpha2

<400> SEQUENCE: 12

Pro Gln Pro Glu Gln Pro Phe Pro Gln
1               5

<210> SEQ ID NO 13
<211> LENGTH: 15
<212> TYPE: PRT
<213> ORGANISM: Artificial Sequence
<220> FEATURE:
<223> OTHER INFORMATION: NPL033

<400> SEQUENCE: 13

Leu Gln Pro Phe Pro Gln Pro Glu Leu Pro Tyr Pro Gln Pro Gln
1               5                   10                  15

<210> SEQ ID NO 14
<211> LENGTH: 14
<212> TYPE: PRT
<213> ORGANISM: Artificial Sequence
<220> FEATURE:
<223> OTHER INFORMATION: NPL038

<400> SEQUENCE: 14

Gln Pro Phe Pro Gln Pro Glu Gln Pro Phe Pro Trp Gln Pro
1               5                   10

<210> SEQ ID NO 15
<211> LENGTH: 9
<212> TYPE: PRT
<213> ORGANISM: Artificial Sequence
<220> FEATURE:
<223> OTHER INFORMATION: DQ2-omega-II

<400> SEQUENCE: 15

Pro Gln Pro Glu Gln Pro Phe Pro Trp
1               5

<210> SEQ ID NO 16
<211> LENGTH: 15
<212> TYPE: PRT
<213> ORGANISM: Artificial Sequence
<220> FEATURE:
<223> OTHER INFORMATION: NPL034

<400> SEQUENCE: 16

Pro Glu Gln Pro Ile Pro Glu Gln Pro Gln Pro Tyr Pro Gln Gln
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: DQ2-Hor-I

<400> SEQUENCE: 17

Pro Ile Pro Glu Gln Pro Gln Pro Tyr
1               5

<210> SEQ ID NO 18
<211> LENGTH: 9
<212> TYPE: PRT
```

```
<213> ORGANISM: Artificial Sequence
<220> FEATURE:
<223> OTHER INFORMATION: gluten derived peptide

<400> SEQUENCE: 18

Glu Gln Pro Ile Pro Glu Gln Pro Gln
1               5

<210> SEQ ID NO 19
<211> LENGTH: 9
<212> TYPE: PRT
<213> ORGANISM: Artificial Sequence
<220> FEATURE:
<223> OTHER INFORMATION: gluten derived peptide

<400> SEQUENCE: 19

Gln Gln Pro Ile Pro Glu Gln Pro Gln
1               5

<210> SEQ ID NO 20
<211> LENGTH: 22
<212> TYPE: PRT
<213> ORGANISM: Artificial Sequence
<220> FEATURE:
<223> OTHER INFORMATION: gluten derived peptide

<400> SEQUENCE: 20

Pro Gln Gln Pro Gln Gln Pro Gln Gln Pro Phe Pro Gln Pro Gln Gln
1               5                   10                  15

Pro Phe Pro Trp Gln Pro
            20

<210> SEQ ID NO 21
<211> LENGTH: 11
<212> TYPE: PRT
<213> ORGANISM: Artificial Sequence
<220> FEATURE:
<223> OTHER INFORMATION: deamidated  alpha-gliadin p60-70

<400> SEQUENCE: 21

Pro Phe Pro Gln Pro Glu Leu Pro Tyr Pro Gln
1               5                   10

<210> SEQ ID NO 22
<211> LENGTH: 5
<212> TYPE: PRT
<213> ORGANISM: Artificial Sequence
<220> FEATURE:
<223> OTHER INFORMATION: core of alpha-gliadin p57-73 QE65

<400> SEQUENCE: 22

Pro Glu Leu Pro Tyr
1               5

<210> SEQ ID NO 23
<211> LENGTH: 5
<212> TYPE: PRT
<213> ORGANISM: Artificial Sequence
<220> FEATURE:
<223> OTHER INFORMATION: gluten derived peptide

<400> SEQUENCE: 23

Pro Gln Leu Pro Tyr
1               5

<210> SEQ ID NO 24
```

```
<211> LENGTH: 5
<212> TYPE: PRT
<213> ORGANISM: Artificial Sequence
<220> FEATURE:
<223> OTHER INFORMATION: gluten derived peptide

<400> SEQUENCE: 24

Pro Gln Leu Ser Tyr
1               5

<210> SEQ ID NO 25
<211> LENGTH: 17
<212> TYPE: PRT
<213> ORGANISM: Artificial Sequence
<220> FEATURE:
<223> OTHER INFORMATION: gluten derived peptide

<400> SEQUENCE: 25

Pro Gln Pro Gln Pro Phe Leu Pro Gln Leu Pro Tyr Pro Gln Pro Gln
1               5                   10                  15

Ser

<210> SEQ ID NO 26
<211> LENGTH: 17
<212> TYPE: PRT
<213> ORGANISM: Artificial Sequence
<220> FEATURE:
<223> OTHER INFORMATION: gluten derived peptide

<400> SEQUENCE: 26

Pro Gln Pro Gln Pro Phe Leu Pro Glu Leu Pro Tyr Pro Gln Pro Gln
1               5                   10                  15

Ser

<210> SEQ ID NO 27
<211> LENGTH: 4
<212> TYPE: PRT
<213> ORGANISM: Artificial Sequence
<220> FEATURE:
<223> OTHER INFORMATION: core sequence
<220> FEATURE:
<221> NAME/KEY: MOD_RES
<222> LOCATION: (3)..(3)
<223> OTHER INFORMATION: I, L, M or P
<220> FEATURE:
<221> NAME/KEY: MOD_RES
<222> LOCATION: (4)..(4)
<223> OTHER INFORMATION: P, S or T

<400> SEQUENCE: 27

Pro Gln Xaa Xaa
1

<210> SEQ ID NO 28
<211> LENGTH: 17
<212> TYPE: PRT
<213> ORGANISM: Artificial Sequence
<220> FEATURE:
<223> OTHER INFORMATION: AAG17702 (141-157)

<400> SEQUENCE: 28

Pro Gln Gln Pro Phe Pro Gln Pro Gln Leu Pro Phe Pro Gln Gln Ser
1               5                   10                  15

Glu

<210> SEQ ID NO 29
```

```
<211> LENGTH: 17
<212> TYPE: PRT
<213> ORGANISM: Artificial Sequence
<220> FEATURE:
<223> OTHER INFORMATION: deamidated AAG17702 (141-157)

<400> SEQUENCE: 29

Pro Gln Gln Pro Phe Pro Gln Pro Glu Leu Pro Phe Pro Gln Gln Ser
1               5                   10                  15
Glu

<210> SEQ ID NO 30
<211> LENGTH: 10
<212> TYPE: PRT
<213> ORGANISM: Artificial Sequence
<220> FEATURE:
<223> OTHER INFORMATION: GLIA-20 wild-type

<400> SEQUENCE: 30

Pro Phe Arg Pro Gln Gln Pro Tyr Pro Gln
1               5                   10

<210> SEQ ID NO 31
<211> LENGTH: 10
<212> TYPE: PRT
<213> ORGANISM: Artificial Sequence
<220> FEATURE:
<223> OTHER INFORMATION: deamidated GLIA-20

<400> SEQUENCE: 31

Pro Phe Arg Pro Glu Gln Pro Tyr Pro Gln
1               5                   10

<210> SEQ ID NO 32
<211> LENGTH: 9
<212> TYPE: PRT
<213> ORGANISM: Artificial Sequence
<220> FEATURE:
<223> OTHER INFORMATION: DQ2-gamma-I wild-type

<400> SEQUENCE: 32

Pro Gln Gln Ser Phe Pro Gln Gln Gln
1               5

<210> SEQ ID NO 33
<211> LENGTH: 9
<212> TYPE: PRT
<213> ORGANISM: Artificial Sequence
<220> FEATURE:
<223> OTHER INFORMATION: deamdiated DQ2-gamma-I

<400> SEQUENCE: 33

Pro Gln Gln Ser Phe Pro Glu Gln Glu
1               5

<210> SEQ ID NO 34
<211> LENGTH: 9
<212> TYPE: PRT
<213> ORGANISM: Artificial Sequence
<220> FEATURE:
<223> OTHER INFORMATION: DQ2-gamma-II wild-type

<400> SEQUENCE: 34

Ile Gln Pro Gln Gln Pro Ala Gln Leu
1               5
```

```
<210> SEQ ID NO 35
<211> LENGTH: 9
<212> TYPE: PRT
<213> ORGANISM: Artificial Sequence
<220> FEATURE:
<223> OTHER INFORMATION: deamdiated DQ2-gamma-II

<400> SEQUENCE: 35

Ile Gln Pro Glu Gln Pro Ala Gln Leu
1               5

<210> SEQ ID NO 36
<211> LENGTH: 9
<212> TYPE: PRT
<213> ORGANISM: Artificial Sequence
<220> FEATURE:
<223> OTHER INFORMATION: DQ2-gamma-III wild-type

<400> SEQUENCE: 36

Gln Gln Pro Gln Gln Pro Tyr Pro Gln
1               5

<210> SEQ ID NO 37
<211> LENGTH: 9
<212> TYPE: PRT
<213> ORGANISM: Artificial Sequence
<220> FEATURE:
<223> OTHER INFORMATION: deamidated DQ2-gamma-III

<400> SEQUENCE: 37

Glu Gln Pro Glu Gln Pro Tyr Pro Glu
1               5

<210> SEQ ID NO 38
<211> LENGTH: 9
<212> TYPE: PRT
<213> ORGANISM: Artificial Sequence
<220> FEATURE:
<223> OTHER INFORMATION: DQ2-gamma-IV wild-type

<400> SEQUENCE: 38

Ser Gln Pro Gln Gln Gln Phe Pro Gln
1               5

<210> SEQ ID NO 39
<211> LENGTH: 9
<212> TYPE: PRT
<213> ORGANISM: Artificial Sequence
<220> FEATURE:
<223> OTHER INFORMATION: deamidated DQ2-gamma-IV

<400> SEQUENCE: 39

Ser Gln Pro Glu Gln Glu Phe Pro Gln
1               5

<210> SEQ ID NO 40
<211> LENGTH: 9
<212> TYPE: PRT
<213> ORGANISM: Artificial Sequence
<220> FEATURE:
<223> OTHER INFORMATION: Glu-5 wild-type

<400> SEQUENCE: 40

Gln Ile Pro Gln Gln Pro Gln Gln Phe
1               5

<210> SEQ ID NO 41
```

```
<211> LENGTH: 9
<212> TYPE: PRT
<213> ORGANISM: Artificial Sequence
<220> FEATURE:
<223> OTHER INFORMATION: deamidated Glu-5

<400> SEQUENCE: 41

Glu Ile Pro Glu Gln Pro Gln Gln Phe
1               5

<210> SEQ ID NO 42
<211> LENGTH: 10
<212> TYPE: PRT
<213> ORGANISM: Artificial Sequence
<220> FEATURE:
<223> OTHER INFORMATION: Glt-156 wild-type

<400> SEQUENCE: 42

Pro Phe Ser Gln Gln Gln Gln Ser Pro Phe
1               5                   10

<210> SEQ ID NO 43
<211> LENGTH: 10
<212> TYPE: PRT
<213> ORGANISM: Artificial Sequence
<220> FEATURE:
<223> OTHER INFORMATION: deamidated Glt-156

<400> SEQUENCE: 43

Pro Phe Ser Glu Gln Gln Glu Ser Pro Phe
1               5                   10

<210> SEQ ID NO 44
<211> LENGTH: 20
<212> TYPE: PRT
<213> ORGANISM: Artificial Sequence
<220> FEATURE:
<223> OTHER INFORMATION: DQ2-gamma-V

<400> SEQUENCE: 44

Leu Gln Pro Gln Gln Pro Phe Pro Gln Gln Pro Gln Gln Pro Tyr Pro
1               5                   10                  15

Gln Gln Pro Gln
            20

<210> SEQ ID NO 45
<211> LENGTH: 19
<212> TYPE: PRT
<213> ORGANISM: Artificial Sequence
<220> FEATURE:
<223> OTHER INFORMATION: alpha-gliadin p31-49

<400> SEQUENCE: 45

Leu Gly Gln Gln Gln Pro Phe Pro Pro Gln Gln Pro Tyr Pro Gln Pro
1               5                   10                  15

Gln Pro Phe

<210> SEQ ID NO 46
<211> LENGTH: 17
<212> TYPE: PRT
<213> ORGANISM: Artificial Sequence
<220> FEATURE:
<223> OTHER INFORMATION: variant of alpha-gliadin p57-73 QE65

<400> SEQUENCE: 46

Gln Leu Gln Pro Phe Pro Gln Pro Glu Leu Pro Tyr Pro Gln Pro Gln
```

```
                        1               5                  10                  15
Leu

<210> SEQ ID NO 47
<211> LENGTH: 12
<212> TYPE: PRT
<213> ORGANISM: Artificial Sequence
<220> FEATURE:
<223> OTHER INFORMATION: W03, B01

<400> SEQUENCE: 47

Gln Pro Phe Pro Gln Pro Gln Gln Pro Phe Pro Trp
1               5                   10

<210> SEQ ID NO 48
<211> LENGTH: 11
<212> TYPE: PRT
<213> ORGANISM: Artificial Sequence
<220> FEATURE:
<223> OTHER INFORMATION: W04

<400> SEQUENCE: 48

Pro Phe Pro Gln Pro Gln Gln Pro Ile Pro Val
1               5                   10

<210> SEQ ID NO 49
<211> LENGTH: 12
<212> TYPE: PRT
<213> ORGANISM: Artificial Sequence
<220> FEATURE:
<223> OTHER INFORMATION: W06

<400> SEQUENCE: 49

Gln Pro Phe Pro Gln Pro Gln Leu Pro Phe Pro Gln
1               5                   10

<210> SEQ ID NO 50
<211> LENGTH: 9
<212> TYPE: PRT
<213> ORGANISM: Artificial Sequence
<220> FEATURE:
<223> OTHER INFORMATION: DQ2-gamma-VII

<400> SEQUENCE: 50

Gln Gln Pro Gln Gln Pro Phe Pro Gln
1               5

<210> SEQ ID NO 51
<211> LENGTH: 9
<212> TYPE: PRT
<213> ORGANISM: Artificial Sequence
<220> FEATURE:
<223> OTHER INFORMATION: deamidated DQ2-gamma-VII

<400> SEQUENCE: 51

Glu Gln Pro Glu Gln Pro Phe Pro Gln
1               5

<210> SEQ ID NO 52
<211> LENGTH: 22
<212> TYPE: PRT
<213> ORGANISM: Artificial Sequence
<220> FEATURE:
<223> OTHER INFORMATION: gluten derived peptide

<400> SEQUENCE: 52
```

-continued

Pro Gln Gln Pro Gln Gln Pro Gln Gln Phe Pro Gln Pro Gln Gln
1               5                   10                  15

Pro Phe Pro Trp Gln Pro
            20

<210> SEQ ID NO 53
<211> LENGTH: 17
<212> TYPE: PRT
<213> ORGANISM: Artificial Sequence
<220> FEATURE:
<223> OTHER INFORMATION: gluten derived peptide

<400> SEQUENCE: 53

Gln Pro Gln Gln Pro Phe Pro Gln Pro Gln Gln Pro Phe Pro Trp Gln
1               5                   10                  15

Pro

<210> SEQ ID NO 54
<211> LENGTH: 17
<212> TYPE: PRT
<213> ORGANISM: Artificial Sequence
<220> FEATURE:
<223> OTHER INFORMATION: Q3 E10 variant

<400> SEQUENCE: 54

Gln Pro Gln Gln Pro Phe Pro Gln Pro Glu Gln Pro Phe Pro Trp Gln
1               5                   10                  15

Pro

<210> SEQ ID NO 55
<211> LENGTH: 17
<212> TYPE: PRT
<213> ORGANISM: Artificial Sequence
<220> FEATURE:
<223> OTHER INFORMATION: W03-E7

<400> SEQUENCE: 55

Gln Pro Glu Gln Pro Phe Pro Gln Pro Glu Gln Pro Phe Pro Trp Gln
1               5                   10                  15

Pro

<210> SEQ ID NO 56
<211> LENGTH: 12
<212> TYPE: PRT
<213> ORGANISM: Artificial Sequence
<220> FEATURE:
<223> OTHER INFORMATION: B01-E7

<400> SEQUENCE: 56

Gln Pro Phe Pro Gln Pro Glu Gln Pro Phe Pro Trp
1               5                   10

<210> SEQ ID NO 57
<211> LENGTH: 11
<212> TYPE: PRT
<213> ORGANISM: Artificial Sequence
<220> FEATURE:
<223> OTHER INFORMATION: W04-E7

<400> SEQUENCE: 57

Pro Phe Pro Gln Pro Glu Gln Pro Ile Pro Val
1               5                   10

<210> SEQ ID NO 58

-continued

```
<211> LENGTH: 12
<212> TYPE: PRT
<213> ORGANISM: Artificial Sequence
<220> FEATURE:
<223> OTHER INFORMATION: W06-E7

<400> SEQUENCE: 58

Gln Pro Phe Pro Gln Pro Glu Leu Pro Phe Pro Gln
1               5                   10

<210> SEQ ID NO 59
<211> LENGTH: 12
<212> TYPE: PRT
<213> ORGANISM: Artificial Sequence
<220> FEATURE:
<223> OTHER INFORMATION: W01

<400> SEQUENCE: 59

Leu Pro Tyr Pro Gln Pro Gln Leu Pro Tyr Pro Gln
1               5                   10

<210> SEQ ID NO 60
<211> LENGTH: 12
<212> TYPE: PRT
<213> ORGANISM: Artificial Sequence
<220> FEATURE:
<223> OTHER INFORMATION: W01-E7

<400> SEQUENCE: 60

Leu Pro Tyr Pro Gln Pro Glu Leu Pro Tyr Pro Gln
1               5                   10

<210> SEQ ID NO 61
<211> LENGTH: 12
<212> TYPE: PRT
<213> ORGANISM: Artificial Sequence
<220> FEATURE:
<223> OTHER INFORMATION: W02

<400> SEQUENCE: 61

Gln Pro Phe Pro Gln Pro Gln Leu Pro Tyr Pro Gln
1               5                   10

<210> SEQ ID NO 62
<211> LENGTH: 12
<212> TYPE: PRT
<213> ORGANISM: Artificial Sequence
<220> FEATURE:
<223> OTHER INFORMATION: W02-E7

<400> SEQUENCE: 62

Gln Pro Phe Pro Gln Pro Glu Leu Pro Tyr Pro Gln
1               5                   10

<210> SEQ ID NO 63
<211> LENGTH: 12
<212> TYPE: PRT
<213> ORGANISM: Artificial Sequence
<220> FEATURE:
<223> OTHER INFORMATION: W05

<400> SEQUENCE: 63

Gln Pro Phe Pro Gln Pro Gln Gln Pro Phe Ser Gln
1               5                   10

<210> SEQ ID NO 64
<211> LENGTH: 12
```

```
<212> TYPE: PRT
<213> ORGANISM: Artificial Sequence
<220> FEATURE:
<223> OTHER INFORMATION: W05-E7

<400> SEQUENCE: 64

Gln Pro Phe Pro Gln Pro Glu Gln Pro Phe Ser Gln
1               5                   10

<210> SEQ ID NO 65
<211> LENGTH: 12
<212> TYPE: PRT
<213> ORGANISM: Artificial Sequence
<220> FEATURE:
<223> OTHER INFORMATION: W07

<400> SEQUENCE: 65

Gln Pro Phe Pro Gln Pro Gln Gln Pro Phe Cys Gln
1               5                   10

<210> SEQ ID NO 66
<211> LENGTH: 12
<212> TYPE: PRT
<213> ORGANISM: Artificial Sequence
<220> FEATURE:
<223> OTHER INFORMATION: W07-E7

<400> SEQUENCE: 66

Gln Pro Phe Pro Gln Pro Glu Gln Pro Phe Cys Gln
1               5                   10

<210> SEQ ID NO 67
<211> LENGTH: 12
<212> TYPE: PRT
<213> ORGANISM: Artificial Sequence
<220> FEATURE:
<223> OTHER INFORMATION: synthetic peptide

<400> SEQUENCE: 67

Gln Pro Phe Pro Gln Pro Gln Leu Pro Tyr Ser Gln
1               5                   10

<210> SEQ ID NO 68
<211> LENGTH: 12
<212> TYPE: PRT
<213> ORGANISM: Artificial Sequence
<220> FEATURE:
<223> OTHER INFORMATION: W08-E7

<400> SEQUENCE: 68

Gln Pro Phe Pro Gln Pro Glu Leu Pro Tyr Ser Gln
1               5                   10

<210> SEQ ID NO 69
<211> LENGTH: 12
<212> TYPE: PRT
<213> ORGANISM: Artificial Sequence
<220> FEATURE:
<223> OTHER INFORMATION: W09

<400> SEQUENCE: 69

Pro Gln Pro Phe Leu Pro Gln Leu Pro Tyr Pro Gln
1               5                   10

<210> SEQ ID NO 70
<211> LENGTH: 12
<212> TYPE: PRT
```

```
<213> ORGANISM: Artificial Sequence
<220> FEATURE:
<223> OTHER INFORMATION: W09-E7

<400> SEQUENCE: 70

Pro Gln Pro Phe Leu Pro Glu Leu Pro Tyr Pro Gln
1               5                   10

<210> SEQ ID NO 71
<211> LENGTH: 12
<212> TYPE: PRT
<213> ORGANISM: Artificial Sequence
<220> FEATURE:
<223> OTHER INFORMATION: W10

<400> SEQUENCE: 71

Gln Gln Phe Ser Gln Pro Gln Gln Gln Phe Pro Gln
1               5                   10

<210> SEQ ID NO 72
<211> LENGTH: 12
<212> TYPE: PRT
<213> ORGANISM: Artificial Sequence
<220> FEATURE:
<223> OTHER INFORMATION: W10-E7

<400> SEQUENCE: 72

Gln Gln Phe Ser Gln Pro Glu Gln Gln Phe Pro Gln
1               5                   10

<210> SEQ ID NO 73
<211> LENGTH: 12
<212> TYPE: PRT
<213> ORGANISM: Artificial Sequence
<220> FEATURE:
<223> OTHER INFORMATION: W11

<400> SEQUENCE: 73

Gln Ala Phe Pro Gln Pro Gln Gln Thr Phe Pro His
1               5                   10

<210> SEQ ID NO 74
<211> LENGTH: 12
<212> TYPE: PRT
<213> ORGANISM: Artificial Sequence
<220> FEATURE:
<223> OTHER INFORMATION: W11-E7

<400> SEQUENCE: 74

Gln Ala Phe Pro Gln Pro Glu Gln Thr Phe Pro His
1               5                   10

<210> SEQ ID NO 75
<211> LENGTH: 16
<212> TYPE: PRT
<213> ORGANISM: Artificial Sequence
<220> FEATURE:
<223> OTHER INFORMATION: W12

<400> SEQUENCE: 75

Leu Gln Gln Gln Cys Ser Pro Val Ala Met Pro Gln Arg Leu Ala Arg
1               5                   10                  15

<210> SEQ ID NO 76
<211> LENGTH: 12
<212> TYPE: PRT
<213> ORGANISM: Artificial Sequence
```

```
<220> FEATURE:
<223> OTHER INFORMATION: W13

<400> SEQUENCE: 76

Gln Pro Phe Pro Gln Pro Gln Leu Pro Tyr Leu Gln
1               5                   10

<210> SEQ ID NO 77
<211> LENGTH: 12
<212> TYPE: PRT
<213> ORGANISM: Artificial Sequence
<220> FEATURE:
<223> OTHER INFORMATION: W13-E7

<400> SEQUENCE: 77

Gln Pro Phe Pro Gln Pro Glu Leu Pro Tyr Leu Gln
1               5                   10

<210> SEQ ID NO 78
<211> LENGTH: 12
<212> TYPE: PRT
<213> ORGANISM: Artificial Sequence
<220> FEATURE:
<223> OTHER INFORMATION: W14

<400> SEQUENCE: 78

Gln Gln Phe Ile Gln Pro Gln Gln Pro Phe Pro Gln
1               5                   10

<210> SEQ ID NO 79
<211> LENGTH: 12
<212> TYPE: PRT
<213> ORGANISM: Artificial Sequence
<220> FEATURE:
<223> OTHER INFORMATION: W14-E7

<400> SEQUENCE: 79

Gln Gln Phe Ile Gln Pro Glu Gln Pro Phe Pro Gln
1               5                   10

<210> SEQ ID NO 80
<211> LENGTH: 12
<212> TYPE: PRT
<213> ORGANISM: Artificial Sequence
<220> FEATURE:
<223> OTHER INFORMATION: W15

<400> SEQUENCE: 80

Leu Glu Arg Pro Trp Gln Gln Gln Pro Leu Pro Pro
1               5                   10

<210> SEQ ID NO 81
<211> LENGTH: 12
<212> TYPE: PRT
<213> ORGANISM: Artificial Sequence
<220> FEATURE:
<223> OTHER INFORMATION: W15-E7

<400> SEQUENCE: 81

Leu Glu Arg Pro Trp Gln Glu Gln Pro Leu Pro Pro
1               5                   10

<210> SEQ ID NO 82
<211> LENGTH: 12
<212> TYPE: PRT
<213> ORGANISM: Artificial Sequence
<220> FEATURE:
```

<223> OTHER INFORMATION: W16

<400> SEQUENCE: 82

Phe Pro Gln Pro Gln Gln Gln Phe Pro Gln Pro Gln
1               5                   10

<210> SEQ ID NO 83
<211> LENGTH: 12
<212> TYPE: PRT
<213> ORGANISM: Artificial Sequence
<220> FEATURE:
<223> OTHER INFORMATION: W16-E7

<400> SEQUENCE: 83

Phe Pro Gln Pro Glu Gln Glu Phe Pro Gln Pro Gln
1               5                   10

<210> SEQ ID NO 84
<211> LENGTH: 12
<212> TYPE: PRT
<213> ORGANISM: Artificial Sequence
<220> FEATURE:
<223> OTHER INFORMATION: W17

<400> SEQUENCE: 84

Gln Pro Phe Pro Gln Pro Gln Gln Pro Gln Leu Pro
1               5                   10

<210> SEQ ID NO 85
<211> LENGTH: 12
<212> TYPE: PRT
<213> ORGANISM: Artificial Sequence
<220> FEATURE:
<223> OTHER INFORMATION: W17-E7

<400> SEQUENCE: 85

Gln Pro Phe Pro Gln Pro Glu Gln Pro Gln Leu Pro
1               5                   10

<210> SEQ ID NO 86
<211> LENGTH: 16
<212> TYPE: PRT
<213> ORGANISM: Artificial Sequence
<220> FEATURE:
<223> OTHER INFORMATION: W18

<400> SEQUENCE: 86

Tyr Pro Gln Pro Gln Leu Pro Tyr Pro Gln Pro Gln Pro Phe Arg Pro
1               5                   10                  15

<210> SEQ ID NO 87
<211> LENGTH: 12
<212> TYPE: PRT
<213> ORGANISM: Artificial Sequence
<220> FEATURE:
<223> OTHER INFORMATION: W19

<400> SEQUENCE: 87

Pro Phe Pro Trp Gln Pro Gln Gln Pro Phe Pro Gln
1               5                   10

<210> SEQ ID NO 88
<211> LENGTH: 12
<212> TYPE: PRT
<213> ORGANISM: Artificial Sequence
<220> FEATURE:
<223> OTHER INFORMATION: W19-E7

```
<400> SEQUENCE: 88

Pro Phe Pro Trp Gln Pro Glu Gln Pro Phe Pro Gln
1               5                   10

<210> SEQ ID NO 89
<211> LENGTH: 12
<212> TYPE: PRT
<213> ORGANISM: Artificial Sequence
<220> FEATURE:
<223> OTHER INFORMATION: W20

<400> SEQUENCE: 89

Pro Ile Pro Gln Gln Pro Gln Gln Pro Phe Pro Leu
1               5                   10

<210> SEQ ID NO 90
<211> LENGTH: 12
<212> TYPE: PRT
<213> ORGANISM: Artificial Sequence
<220> FEATURE:
<223> OTHER INFORMATION: W20-E7

<400> SEQUENCE: 90

Pro Ile Pro Gln Gln Pro Glu Gln Pro Phe Pro Leu
1               5                   10

<210> SEQ ID NO 91
<211> LENGTH: 16
<212> TYPE: PRT
<213> ORGANISM: Artificial Sequence
<220> FEATURE:
<223> OTHER INFORMATION: W21

<400> SEQUENCE: 91

Gln Gly Gln Gln Gly Tyr Tyr Pro Ile Ser Pro Gln Gln Ser Gly Gln
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: W22

<400> SEQUENCE: 92

Gln Gly Gln Pro Gly Tyr Tyr Pro Thr Ser Pro Gln Gln Ile Gly Gln
1               5                   10                  15

<210> SEQ ID NO 93
<211> LENGTH: 12
<212> TYPE: PRT
<213> ORGANISM: Artificial Sequence
<220> FEATURE:
<223> OTHER INFORMATION: W23

<400> SEQUENCE: 93

Pro Phe Pro Gln Gln Pro Gln Gln Pro Tyr Pro Gln
1               5                   10

<210> SEQ ID NO 94
<211> LENGTH: 12
<212> TYPE: PRT
<213> ORGANISM: Artificial Sequence
<220> FEATURE:
<223> OTHER INFORMATION: W23-E7
```

```
<400> SEQUENCE: 94

Pro Phe Pro Glu Gln Pro Glu Gln Pro Tyr Pro Gln
1               5                   10

<210> SEQ ID NO 95
<211> LENGTH: 16
<212> TYPE: PRT
<213> ORGANISM: Artificial Sequence
<220> FEATURE:
<223> OTHER INFORMATION: W24

<400> SEQUENCE: 95

Pro Gly Gln Gly Gln Ser Gly Tyr Tyr Pro Thr Ser Pro Gln Gln Ser
1               5                   10                  15

<210> SEQ ID NO 96
<211> LENGTH: 11
<212> TYPE: PRT
<213> ORGANISM: Artificial Sequence
<220> FEATURE:
<223> OTHER INFORMATION: W25

<400> SEQUENCE: 96

Thr Pro Ile Gln Pro Gln Gln Pro Phe Pro Gln
1               5                   10

<210> SEQ ID NO 97
<211> LENGTH: 11
<212> TYPE: PRT
<213> ORGANISM: Artificial Sequence
<220> FEATURE:
<223> OTHER INFORMATION: W25-E7

<400> SEQUENCE: 97

Thr Pro Ile Gln Pro Glu Gln Pro Phe Pro Gln
1               5                   10

<210> SEQ ID NO 98
<211> LENGTH: 12
<212> TYPE: PRT
<213> ORGANISM: Artificial Sequence
<220> FEATURE:
<223> OTHER INFORMATION: W26

<400> SEQUENCE: 98

Pro Phe Pro Leu Gln Pro Gln Gln Pro Phe Pro Gln
1               5                   10

<210> SEQ ID NO 99
<211> LENGTH: 12
<212> TYPE: PRT
<213> ORGANISM: Artificial Sequence
<220> FEATURE:
<223> OTHER INFORMATION: W26-E7

<400> SEQUENCE: 99

Pro Phe Pro Leu Gln Pro Glu Gln Pro Phe Pro Gln
1               5                   10

<210> SEQ ID NO 100
<211> LENGTH: 11
<212> TYPE: PRT
<213> ORGANISM: Artificial Sequence
<220> FEATURE:
<223> OTHER INFORMATION: W27

<400> SEQUENCE: 100
```

Pro Phe Thr Gln Pro Gln Gln Pro Thr Pro Ile
1               5                   10

<210> SEQ ID NO 101
<211> LENGTH: 11
<212> TYPE: PRT
<213> ORGANISM: Artificial Sequence
<220> FEATURE:
<223> OTHER INFORMATION: W27-E7

<400> SEQUENCE: 101

Pro Phe Thr Gln Pro Glu Gln Pro Thr Pro Ile
1               5                   10

<210> SEQ ID NO 102
<211> LENGTH: 12
<212> TYPE: PRT
<213> ORGANISM: Artificial Sequence
<220> FEATURE:
<223> OTHER INFORMATION: W28

<400> SEQUENCE: 102

Pro Gln Gln Thr Phe Pro Gln Gln Pro Gln Leu Pro
1               5                   10

<210> SEQ ID NO 103
<211> LENGTH: 12
<212> TYPE: PRT
<213> ORGANISM: Artificial Sequence
<220> FEATURE:
<223> OTHER INFORMATION: W28-E7

<400> SEQUENCE: 103

Pro Gln Gln Thr Phe Pro Glu Gln Pro Gln Leu Pro
1               5                   10

<210> SEQ ID NO 104
<211> LENGTH: 16
<212> TYPE: PRT
<213> ORGANISM: Artificial Sequence
<220> FEATURE:
<223> OTHER INFORMATION: W29

<400> SEQUENCE: 104

Gly Gln Gly Gln Ser Gly Tyr Tyr Pro Thr Ser Pro Gln Gln Ser Gly
1               5                   10                  15

<210> SEQ ID NO 105
<211> LENGTH: 12
<212> TYPE: PRT
<213> ORGANISM: Artificial Sequence
<220> FEATURE:
<223> OTHER INFORMATION: W30

<400> SEQUENCE: 105

Pro Gln Gln Pro Phe Pro Gln Gln Pro Gln Gln Pro
1               5                   10

<210> SEQ ID NO 106
<211> LENGTH: 12
<212> TYPE: PRT
<213> ORGANISM: Artificial Sequence
<220> FEATURE:
<223> OTHER INFORMATION: W30-E7

<400> SEQUENCE: 106

```
Pro Gln Gln Pro Phe Pro Glu Gln Pro Gln Gln Pro
1               5                   10
```

<210> SEQ ID NO 107
<211> LENGTH: 12
<212> TYPE: PRT
<213> ORGANISM: Artificial Sequence
<220> FEATURE:
<223> OTHER INFORMATION: W31

<400> SEQUENCE: 107

```
Gln Pro Phe Pro Gln Leu Gln Gln Pro Gln Gln Pro
1               5                   10
```

<210> SEQ ID NO 108
<211> LENGTH: 12
<212> TYPE: PRT
<213> ORGANISM: Artificial Sequence
<220> FEATURE:
<223> OTHER INFORMATION: W31-E7

<400> SEQUENCE: 108

```
Gln Pro Phe Pro Gln Leu Glu Gln Pro Gln Gln Pro
1               5                   10
```

<210> SEQ ID NO 109
<211> LENGTH: 12
<212> TYPE: PRT
<213> ORGANISM: Artificial Sequence
<220> FEATURE:
<223> OTHER INFORMATION: W32

<400> SEQUENCE: 109

```
Pro Phe Pro Gln Gln Pro Gln Gln Pro Phe Pro Gln
1               5                   10
```

<210> SEQ ID NO 110
<211> LENGTH: 12
<212> TYPE: PRT
<213> ORGANISM: Artificial Sequence
<220> FEATURE:
<223> OTHER INFORMATION: W32-E7

<400> SEQUENCE: 110

```
Pro Phe Pro Gln Gln Pro Glu Gln Pro Phe Pro Gln
1               5                   10
```

<210> SEQ ID NO 111
<211> LENGTH: 11
<212> TYPE: PRT
<213> ORGANISM: Artificial Sequence
<220> FEATURE:
<223> OTHER INFORMATION: W33

<400> SEQUENCE: 111

```
Pro Phe Pro Gln Pro Gln Gln Thr Phe Pro Gln
1               5                   10
```

<210> SEQ ID NO 112
<211> LENGTH: 11
<212> TYPE: PRT
<213> ORGANISM: Artificial Sequence
<220> FEATURE:
<223> OTHER INFORMATION: W33-E7

<400> SEQUENCE: 112

```
Pro Phe Pro Gln Pro Glu Gln Thr Phe Pro Gln
```

<210> SEQ ID NO 113
<211> LENGTH: 16
<212> TYPE: PRT
<213> ORGANISM: Artificial Sequence
<220> FEATURE:
<223> OTHER INFORMATION: W34

<400> SEQUENCE: 113

Val Ala His Ala Ile Ile Met His Gln Gln Gln Gln Gln Gln Gln Glu
1               5                   10                  15

<210> SEQ ID NO 114
<211> LENGTH: 12
<212> TYPE: PRT
<213> ORGANISM: Artificial Sequence
<220> FEATURE:
<223> OTHER INFORMATION: W35

<400> SEQUENCE: 114

Pro Phe Pro Gln Gln Pro Gln Gln Gln Phe Pro Gln
1               5                   10

<210> SEQ ID NO 115
<211> LENGTH: 12
<212> TYPE: PRT
<213> ORGANISM: Artificial Sequence
<220> FEATURE:
<223> OTHER INFORMATION: W35-E7

<400> SEQUENCE: 115

Pro Phe Pro Gln Gln Pro Glu Gln Gln Phe Pro Gln
1               5                   10

<210> SEQ ID NO 116
<211> LENGTH: 16
<212> TYPE: PRT
<213> ORGANISM: Artificial Sequence
<220> FEATURE:
<223> OTHER INFORMATION: W36

<400> SEQUENCE: 116

Gln Tyr Glu Val Ile Arg Ser Leu Val Leu Arg Thr Leu Pro Asn Met
1               5                   10                  15

<210> SEQ ID NO 117
<211> LENGTH: 12
<212> TYPE: PRT
<213> ORGANISM: Artificial Sequence
<220> FEATURE:
<223> OTHER INFORMATION: W37

<400> SEQUENCE: 117

Gln Val Asp Pro Ser Gly Gln Val Gln Trp Pro Gln
1               5                   10

<210> SEQ ID NO 118
<211> LENGTH: 12
<212> TYPE: PRT
<213> ORGANISM: Artificial Sequence
<220> FEATURE:
<223> OTHER INFORMATION: W37-E7

<400> SEQUENCE: 118

Gln Val Asp Pro Ser Gly Glu Val Gln Trp Pro Gln
1               5                   10

```
<210> SEQ ID NO 119
<211> LENGTH: 12
<212> TYPE: PRT
<213> ORGANISM: Artificial Sequence
<220> FEATURE:
<223> OTHER INFORMATION: B02

<400> SEQUENCE: 119

Gln Pro Phe Pro Gln Pro Gln Gln Pro Phe Pro Leu
1               5                   10

<210> SEQ ID NO 120
<211> LENGTH: 12
<212> TYPE: PRT
<213> ORGANISM: Artificial Sequence
<220> FEATURE:
<223> OTHER INFORMATION: B02-E7

<400> SEQUENCE: 120

Gln Pro Phe Pro Gln Pro Glu Gln Pro Phe Pro Leu
1               5                   10

<210> SEQ ID NO 121
<211> LENGTH: 12
<212> TYPE: PRT
<213> ORGANISM: Artificial Sequence
<220> FEATURE:
<223> OTHER INFORMATION: B03

<400> SEQUENCE: 121

Gln Pro Phe Pro Gln Pro Gln Gln Pro Ile Pro Tyr
1               5                   10

<210> SEQ ID NO 122
<211> LENGTH: 12
<212> TYPE: PRT
<213> ORGANISM: Artificial Sequence
<220> FEATURE:
<223> OTHER INFORMATION: B03-E7

<400> SEQUENCE: 122

Gln Pro Phe Pro Gln Pro Glu Gln Pro Ile Pro Tyr
1               5                   10

<210> SEQ ID NO 123
<211> LENGTH: 12
<212> TYPE: PRT
<213> ORGANISM: Artificial Sequence
<220> FEATURE:
<223> OTHER INFORMATION: B04

<400> SEQUENCE: 123

Pro Gln Gln Pro Val Pro Gln Gln Pro Gln Pro Tyr
1               5                   10

<210> SEQ ID NO 124
<211> LENGTH: 12
<212> TYPE: PRT
<213> ORGANISM: Artificial Sequence
<220> FEATURE:
<223> OTHER INFORMATION: B04-E7

<400> SEQUENCE: 124

Pro Gln Gln Pro Val Pro Glu Gln Pro Gln Pro Tyr
1               5                   10
```

```
<210> SEQ ID NO 125
<211> LENGTH: 16
<212> TYPE: PRT
<213> ORGANISM: Artificial Sequence
<220> FEATURE:
<223> OTHER INFORMATION: B05

<400> SEQUENCE: 125

Pro Gln Pro Phe Pro Gln Gln Pro Ile Pro Gln Gln Pro Gln Pro Tyr
1               5                   10                  15

<210> SEQ ID NO 126
<211> LENGTH: 11
<212> TYPE: PRT
<213> ORGANISM: Artificial Sequence
<220> FEATURE:
<223> OTHER INFORMATION: B06

<400> SEQUENCE: 126

Gln Gln Pro Ile Pro Gln Gln Pro Gln Pro Tyr
1               5                   10

<210> SEQ ID NO 127
<211> LENGTH: 11
<212> TYPE: PRT
<213> ORGANISM: Artificial Sequence
<220> FEATURE:
<223> OTHER INFORMATION: B06-E7

<400> SEQUENCE: 127

Gln Gln Pro Ile Pro Glu Gln Pro Gln Pro Tyr
1               5                   10

<210> SEQ ID NO 128
<211> LENGTH: 12
<212> TYPE: PRT
<213> ORGANISM: Artificial Sequence
<220> FEATURE:
<223> OTHER INFORMATION: B07

<400> SEQUENCE: 128

Gln Gln Phe Pro Gln Pro Gln Gln Pro Phe Pro Gln
1               5                   10

<210> SEQ ID NO 129
<211> LENGTH: 12
<212> TYPE: PRT
<213> ORGANISM: Artificial Sequence
<220> FEATURE:
<223> OTHER INFORMATION: B07-E7

<400> SEQUENCE: 129

Gln Gln Phe Pro Gln Pro Glu Gln Pro Phe Pro Gln
1               5                   10

<210> SEQ ID NO 130
<211> LENGTH: 16
<212> TYPE: PRT
<213> ORGANISM: Artificial Sequence
<220> FEATURE:
<223> OTHER INFORMATION: B08

<400> SEQUENCE: 130

Pro Gln Gln Pro Ile Pro Gln Gln Pro Gln Pro Tyr Pro Gln Gln Pro
1               5                   10                  15
```

```
<210> SEQ ID NO 131
<211> LENGTH: 16
<212> TYPE: PRT
<213> ORGANISM: Artificial Sequence
<220> FEATURE:
<223> OTHER INFORMATION: B09

<400> SEQUENCE: 131

Gln Gln Pro Phe Pro Gln Gln Pro Phe Pro Gln Gln Pro Gln Pro Tyr
1               5                   10                  15

<210> SEQ ID NO 132
<211> LENGTH: 12
<212> TYPE: PRT
<213> ORGANISM: Artificial Sequence
<220> FEATURE:
<223> OTHER INFORMATION: B10

<400> SEQUENCE: 132

Gln Pro Phe Pro Gln Pro Gln Gln Pro Phe Ser Trp
1               5                   10

<210> SEQ ID NO 133
<211> LENGTH: 12
<212> TYPE: PRT
<213> ORGANISM: Artificial Sequence
<220> FEATURE:
<223> OTHER INFORMATION: B10-E7

<400> SEQUENCE: 133

Gln Pro Phe Pro Gln Pro Glu Gln Pro Phe Ser Trp
1               5                   10

<210> SEQ ID NO 134
<211> LENGTH: 12
<212> TYPE: PRT
<213> ORGANISM: Artificial Sequence
<220> FEATURE:
<223> OTHER INFORMATION: B11

<400> SEQUENCE: 134

Gln Pro Gln Pro Tyr Pro Gln Gln Pro Gln Pro Tyr
1               5                   10

<210> SEQ ID NO 135
<211> LENGTH: 12
<212> TYPE: PRT
<213> ORGANISM: Artificial Sequence
<220> FEATURE:
<223> OTHER INFORMATION: B11-E7

<400> SEQUENCE: 135

Gln Pro Gln Pro Tyr Pro Glu Gln Pro Gln Pro Tyr
1               5                   10

<210> SEQ ID NO 136
<211> LENGTH: 16
<212> TYPE: PRT
<213> ORGANISM: Artificial Sequence
<220> FEATURE:
<223> OTHER INFORMATION: B12

<400> SEQUENCE: 136

Pro Gln Gln Pro Phe Pro Gln Gln Pro Gln Pro Tyr Pro Gln Gln Pro
1               5                   10                  15

<210> SEQ ID NO 137
```

```
<211> LENGTH: 16
<212> TYPE: PRT
<213> ORGANISM: Artificial Sequence
<220> FEATURE:
<223> OTHER INFORMATION: B13

<400> SEQUENCE: 137

Pro Gln Pro Tyr Pro Gln Gln Pro Gln Pro Phe Pro Gln Gln Pro Pro
1               5                   10                  15

<210> SEQ ID NO 138
<211> LENGTH: 12
<212> TYPE: PRT
<213> ORGANISM: Artificial Sequence
<220> FEATURE:
<223> OTHER INFORMATION: B14

<400> SEQUENCE: 138

Ser Tyr Pro Val Gln Pro Gln Gln Pro Phe Pro Gln
1               5                   10

<210> SEQ ID NO 139
<211> LENGTH: 12
<212> TYPE: PRT
<213> ORGANISM: Artificial Sequence
<220> FEATURE:
<223> OTHER INFORMATION: B14-E7

<400> SEQUENCE: 139

Ser Tyr Pro Val Gln Pro Glu Gln Pro Phe Pro Gln
1               5                   10

<210> SEQ ID NO 140
<211> LENGTH: 12
<212> TYPE: PRT
<213> ORGANISM: Artificial Sequence
<220> FEATURE:
<223> OTHER INFORMATION: B15

<400> SEQUENCE: 140

Gln Pro Gln Pro Phe Pro Gln Gln Pro Ile Pro Gln
1               5                   10

<210> SEQ ID NO 141
<211> LENGTH: 12
<212> TYPE: PRT
<213> ORGANISM: Artificial Sequence
<220> FEATURE:
<223> OTHER INFORMATION: B15-E7

<400> SEQUENCE: 141

Gln Pro Gln Pro Phe Pro Glu Gln Pro Ile Pro Gln
1               5                   10

<210> SEQ ID NO 142
<211> LENGTH: 11
<212> TYPE: PRT
<213> ORGANISM: Artificial Sequence
<220> FEATURE:
<223> OTHER INFORMATION: B16

<400> SEQUENCE: 142

Gln Gln Pro Phe Pro Gln Gln Pro Ile Pro Gln
1               5                   10

<210> SEQ ID NO 143
<211> LENGTH: 11
```

```
<212> TYPE: PRT
<213> ORGANISM: Artificial Sequence
<220> FEATURE:
<223> OTHER INFORMATION: B16-E7

<400> SEQUENCE: 143

Gln Gln Pro Phe Pro Glu Gln Pro Ile Pro Gln
1               5                   10

<210> SEQ ID NO 144
<211> LENGTH: 16
<212> TYPE: PRT
<213> ORGANISM: Artificial Sequence
<220> FEATURE:
<223> OTHER INFORMATION: B17

<400> SEQUENCE: 144

Pro Gln Gln Pro Gln Pro Phe Pro Gln Gln Pro Val Pro Gln Gln Pro
1               5                   10                  15

<210> SEQ ID NO 145
<211> LENGTH: 12
<212> TYPE: PRT
<213> ORGANISM: Artificial Sequence
<220> FEATURE:
<223> OTHER INFORMATION: B18

<400> SEQUENCE: 145

Gln Pro Gln Pro Phe Pro Gln Gln Pro Ile Pro Leu
1               5                   10

<210> SEQ ID NO 146
<211> LENGTH: 12
<212> TYPE: PRT
<213> ORGANISM: Artificial Sequence
<220> FEATURE:
<223> OTHER INFORMATION: B18-E7

<400> SEQUENCE: 146

Gln Pro Gln Pro Phe Pro Glu Gln Pro Ile Pro Leu
1               5                   10

<210> SEQ ID NO 147
<211> LENGTH: 12
<212> TYPE: PRT
<213> ORGANISM: Artificial Sequence
<220> FEATURE:
<223> OTHER INFORMATION: B19

<400> SEQUENCE: 147

Pro Phe Pro Trp Gln Pro Gln Gln Pro Phe Pro Gln
1               5                   10

<210> SEQ ID NO 148
<211> LENGTH: 12
<212> TYPE: PRT
<213> ORGANISM: Artificial Sequence
<220> FEATURE:
<223> OTHER INFORMATION: B19-E7

<400> SEQUENCE: 148

Pro Phe Pro Trp Gln Pro Glu Gln Pro Phe Pro Gln
1               5                   10

<210> SEQ ID NO 149
<211> LENGTH: 12
<212> TYPE: PRT
```

<213> ORGANISM: Artificial Sequence
<220> FEATURE:
<223> OTHER INFORMATION: B20

<400> SEQUENCE: 149

Pro Phe Pro Leu Gln Pro Gln Gln Pro Phe Pro Gln
1               5                   10

<210> SEQ ID NO 150
<211> LENGTH: 12
<212> TYPE: PRT
<213> ORGANISM: Artificial Sequence
<220> FEATURE:
<223> OTHER INFORMATION: B20-E7

<400> SEQUENCE: 150

Pro Phe Pro Leu Gln Pro Glu Gln Pro Phe Pro Gln
1               5                   10

<210> SEQ ID NO 151
<211> LENGTH: 13
<212> TYPE: PRT
<213> ORGANISM: Artificial Sequence
<220> FEATURE:
<223> OTHER INFORMATION: B21

<400> SEQUENCE: 151

Gln Gln Pro Phe Pro Gln Pro Gln Gln Pro Phe Arg Gln
1               5                   10

<210> SEQ ID NO 152
<211> LENGTH: 13
<212> TYPE: PRT
<213> ORGANISM: Artificial Sequence
<220> FEATURE:
<223> OTHER INFORMATION: B21-E7

<400> SEQUENCE: 152

Gln Gln Pro Phe Pro Gln Pro Glu Gln Pro Phe Arg Gln
1               5                   10

<210> SEQ ID NO 153
<211> LENGTH: 12
<212> TYPE: PRT
<213> ORGANISM: Artificial Sequence
<220> FEATURE:
<223> OTHER INFORMATION: B22

<400> SEQUENCE: 153

Gln Gln Pro Phe Gln Pro Gln Gln Pro Phe Pro Gln
1               5                   10

<210> SEQ ID NO 154
<211> LENGTH: 12
<212> TYPE: PRT
<213> ORGANISM: Artificial Sequence
<220> FEATURE:
<223> OTHER INFORMATION: B22-E7

<400> SEQUENCE: 154

Gln Gln Pro Phe Gln Pro Glu Gln Pro Phe Pro Gln
1               5                   10

<210> SEQ ID NO 155
<211> LENGTH: 16
<212> TYPE: PRT
<213> ORGANISM: Artificial Sequence

```
<220> FEATURE:
<223> OTHER INFORMATION: B23

<400> SEQUENCE: 155

Asn Pro Leu Gln Pro Gln Gln Pro Phe Pro Leu Gln Pro Gln Pro Pro
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: B24

<400> SEQUENCE: 156

Pro Leu Gln Pro Gln Gln Pro Phe Pro Leu Gln Pro Gln Pro Pro Gln
1               5                   10                  15

<210> SEQ ID NO 157
<211> LENGTH: 12
<212> TYPE: PRT
<213> ORGANISM: Artificial Sequence
<220> FEATURE:
<223> OTHER INFORMATION: B25

<400> SEQUENCE: 157

Pro Phe Pro Gln Gln Pro Gln Gln Pro Phe Pro Gln
1               5                   10

<210> SEQ ID NO 158
<211> LENGTH: 12
<212> TYPE: PRT
<213> ORGANISM: Artificial Sequence
<220> FEATURE:
<223> OTHER INFORMATION: B25-E7

<400> SEQUENCE: 158

Pro Phe Pro Gln Gln Pro Glu Gln Pro Phe Pro Gln
1               5                   10

<210> SEQ ID NO 159
<211> LENGTH: 12
<212> TYPE: PRT
<213> ORGANISM: Artificial Sequence
<220> FEATURE:
<223> OTHER INFORMATION: B26

<400> SEQUENCE: 159

Pro Phe Pro Leu Gln Pro Gln Gln Pro Phe Pro Trp
1               5                   10

<210> SEQ ID NO 160
<211> LENGTH: 12
<212> TYPE: PRT
<213> ORGANISM: Artificial Sequence
<220> FEATURE:
<223> OTHER INFORMATION: B26-E7

<400> SEQUENCE: 160

Pro Phe Pro Leu Gln Pro Glu Gln Pro Phe Pro Trp
1               5                   10

<210> SEQ ID NO 161
<211> LENGTH: 13
<212> TYPE: PRT
<213> ORGANISM: Artificial Sequence
<220> FEATURE:
```

<223> OTHER INFORMATION: B27

<400> SEQUENCE: 161

Pro Asn Pro Leu Gln Pro Gln Gln Pro Phe Pro Leu Gln
1               5                   10

<210> SEQ ID NO 162
<211> LENGTH: 13
<212> TYPE: PRT
<213> ORGANISM: Artificial Sequence
<220> FEATURE:
<223> OTHER INFORMATION: B27-E7

<400> SEQUENCE: 162

Pro Asn Pro Leu Gln Pro Glu Gln Pro Phe Pro Leu Gln
1               5                   10

<210> SEQ ID NO 163
<211> LENGTH: 12
<212> TYPE: PRT
<213> ORGANISM: Artificial Sequence
<220> FEATURE:
<223> OTHER INFORMATION: B28

<400> SEQUENCE: 163

Thr Ile Pro Gln Gln Pro Gln Gln Pro Phe Pro Leu
1               5                   10

<210> SEQ ID NO 164
<211> LENGTH: 12
<212> TYPE: PRT
<213> ORGANISM: Artificial Sequence
<220> FEATURE:
<223> OTHER INFORMATION: B28-E7

<400> SEQUENCE: 164

Thr Ile Pro Gln Gln Pro Glu Gln Pro Phe Pro Leu
1               5                   10

<210> SEQ ID NO 165
<211> LENGTH: 12
<212> TYPE: PRT
<213> ORGANISM: Artificial Sequence
<220> FEATURE:
<223> OTHER INFORMATION: B29

<400> SEQUENCE: 165

Ser Phe Ser Gln Gln Pro Gln Gln Pro Phe Pro Leu
1               5                   10

<210> SEQ ID NO 166
<211> LENGTH: 12
<212> TYPE: PRT
<213> ORGANISM: Artificial Sequence
<220> FEATURE:
<223> OTHER INFORMATION: B29-E7

<400> SEQUENCE: 166

Ser Phe Ser Gln Gln Pro Glu Gln Pro Phe Pro Leu
1               5                   10

<210> SEQ ID NO 167
<211> LENGTH: 11
<212> TYPE: PRT
<213> ORGANISM: Artificial Sequence
<220> FEATURE:
<223> OTHER INFORMATION: B30

```
<400> SEQUENCE: 167

Gln Gln Pro Phe Pro Gln Gln Pro Phe Pro Gln
1               5                   10

<210> SEQ ID NO 168
<211> LENGTH: 11
<212> TYPE: PRT
<213> ORGANISM: Artificial Sequence
<220> FEATURE:
<223> OTHER INFORMATION: B30-E7

<400> SEQUENCE: 168

Gln Gln Pro Phe Pro Glu Gln Pro Phe Pro Gln
1               5                   10

<210> SEQ ID NO 169
<211> LENGTH: 12
<212> TYPE: PRT
<213> ORGANISM: Artificial Sequence
<220> FEATURE:
<223> OTHER INFORMATION: R01

<400> SEQUENCE: 169

Gln Pro Phe Pro Gln Pro Gln Gln Pro Ile Pro Gln
1               5                   10

<210> SEQ ID NO 170
<211> LENGTH: 12
<212> TYPE: PRT
<213> ORGANISM: Artificial Sequence
<220> FEATURE:
<223> OTHER INFORMATION: R01-E7

<400> SEQUENCE: 170

Gln Pro Phe Pro Gln Pro Glu Gln Pro Ile Pro Gln
1               5                   10

<210> SEQ ID NO 171
<211> LENGTH: 12
<212> TYPE: PRT
<213> ORGANISM: Artificial Sequence
<220> FEATURE:
<223> OTHER INFORMATION: R02

<400> SEQUENCE: 171

Gln Pro Phe Pro Gln Pro Gln Gln Pro Phe Pro Gln
1               5                   10

<210> SEQ ID NO 172
<211> LENGTH: 12
<212> TYPE: PRT
<213> ORGANISM: Artificial Sequence
<220> FEATURE:
<223> OTHER INFORMATION: R02-E7

<400> SEQUENCE: 172

Gln Pro Phe Pro Gln Pro Glu Gln Pro Phe Pro Gln
1               5                   10

<210> SEQ ID NO 173
<211> LENGTH: 12
<212> TYPE: PRT
<213> ORGANISM: Artificial Sequence
<220> FEATURE:
<223> OTHER INFORMATION: R03
```

<400> SEQUENCE: 173

Gln Pro Phe Pro Gln Pro Gln Gln Pro Thr Pro Ile
1               5                   10

<210> SEQ ID NO 174
<211> LENGTH: 12
<212> TYPE: PRT
<213> ORGANISM: Artificial Sequence
<220> FEATURE:
<223> OTHER INFORMATION: R03-E7

<400> SEQUENCE: 174

Gln Pro Phe Pro Gln Pro Glu Gln Pro Thr Pro Ile
1               5                   10

<210> SEQ ID NO 175
<211> LENGTH: 12
<212> TYPE: PRT
<213> ORGANISM: Artificial Sequence
<220> FEATURE:
<223> OTHER INFORMATION: R04

<400> SEQUENCE: 175

Pro Thr Pro Ile Gln Pro Gln Gln Pro Phe Pro Gln
1               5                   10

<210> SEQ ID NO 176
<211> LENGTH: 12
<212> TYPE: PRT
<213> ORGANISM: Artificial Sequence
<220> FEATURE:
<223> OTHER INFORMATION: R04-E7

<400> SEQUENCE: 176

Pro Thr Pro Ile Gln Pro Glu Gln Pro Phe Pro Gln
1               5                   10

<210> SEQ ID NO 177
<211> LENGTH: 12
<212> TYPE: PRT
<213> ORGANISM: Artificial Sequence
<220> FEATURE:
<223> OTHER INFORMATION: R05

<400> SEQUENCE: 177

Pro Ala Pro Ile Gln Pro Gln Gln Pro Phe Pro Gln
1               5                   10

<210> SEQ ID NO 178
<211> LENGTH: 12
<212> TYPE: PRT
<213> ORGANISM: Artificial Sequence
<220> FEATURE:
<223> OTHER INFORMATION: R05-E7

<400> SEQUENCE: 178

Pro Ala Pro Ile Gln Pro Glu Gln Pro Phe Pro Gln
1               5                   10

<210> SEQ ID NO 179
<211> LENGTH: 12
<212> TYPE: PRT
<213> ORGANISM: Artificial Sequence
<220> FEATURE:
<223> OTHER INFORMATION: R06

<400> SEQUENCE: 179

Pro Gln Gln Pro Phe Pro Gln Gln Pro Glu Gln Ile
1               5                   10

<210> SEQ ID NO 180
<211> LENGTH: 12
<212> TYPE: PRT
<213> ORGANISM: Artificial Sequence
<220> FEATURE:
<223> OTHER INFORMATION: R06-E7

<400> SEQUENCE: 180

Pro Gln Gln Pro Phe Pro Glu Gln Pro Glu Gln Ile
1               5                   10

<210> SEQ ID NO 181
<211> LENGTH: 12
<212> TYPE: PRT
<213> ORGANISM: Artificial Sequence
<220> FEATURE:
<223> OTHER INFORMATION: R07

<400> SEQUENCE: 181

Tyr Ser Pro Tyr Gln Pro Gln Gln Pro Phe Pro Gln
1               5                   10

<210> SEQ ID NO 182
<211> LENGTH: 12
<212> TYPE: PRT
<213> ORGANISM: Artificial Sequence
<220> FEATURE:
<223> OTHER INFORMATION: R07-E7

<400> SEQUENCE: 182

Tyr Ser Pro Tyr Gln Pro Glu Gln Pro Phe Pro Gln
1               5                   10

<210> SEQ ID NO 183
<211> LENGTH: 12
<212> TYPE: PRT
<213> ORGANISM: Artificial Sequence
<220> FEATURE:
<223> OTHER INFORMATION: R08

<400> SEQUENCE: 183

Pro Gln Gln Pro Phe Pro Gln Gln Pro Gln Gln Ile
1               5                   10

<210> SEQ ID NO 184
<211> LENGTH: 12
<212> TYPE: PRT
<213> ORGANISM: Artificial Sequence
<220> FEATURE:
<223> OTHER INFORMATION: R08-E7

<400> SEQUENCE: 184

Pro Gln Gln Pro Phe Pro Glu Gln Pro Gln Gln Ile
1               5                   10

<210> SEQ ID NO 185
<211> LENGTH: 12
<212> TYPE: PRT
<213> ORGANISM: Artificial Sequence
<220> FEATURE:
<223> OTHER INFORMATION: R09

<400> SEQUENCE: 185

Gln Leu Pro Leu Gln Pro Gln Gln Pro Phe Pro Gln
1               5                   10

<210> SEQ ID NO 186
<211> LENGTH: 12
<212> TYPE: PRT
<213> ORGANISM: Artificial Sequence
<220> FEATURE:
<223> OTHER INFORMATION: R09-E7

<400> SEQUENCE: 186

Gln Leu Pro Leu Gln Pro Glu Gln Pro Phe Pro Gln
1               5                   10

<210> SEQ ID NO 187
<211> LENGTH: 12
<212> TYPE: PRT
<213> ORGANISM: Artificial Sequence
<220> FEATURE:
<223> OTHER INFORMATION: R10

<400> SEQUENCE: 187

Pro Phe Pro Gln Gln Pro Glu Gln Ile Ile Ser Gln
1               5                   10

<210> SEQ ID NO 188
<211> LENGTH: 12
<212> TYPE: PRT
<213> ORGANISM: Artificial Sequence
<220> FEATURE:
<223> OTHER INFORMATION: R10-E7

<400> SEQUENCE: 188

Pro Phe Pro Gln Gln Pro Glu Gln Ile Ile Ser Gln
1               5                   10

<210> SEQ ID NO 189
<211> LENGTH: 12
<212> TYPE: PRT
<213> ORGANISM: Artificial Sequence
<220> FEATURE:
<223> OTHER INFORMATION: R11

<400> SEQUENCE: 189

Pro Phe Pro Gln Gln Pro Glu Gln Ile Ile Pro Gln
1               5                   10

<210> SEQ ID NO 190
<211> LENGTH: 12
<212> TYPE: PRT
<213> ORGANISM: Artificial Sequence
<220> FEATURE:
<223> OTHER INFORMATION: R11-E7

<400> SEQUENCE: 190

Pro Phe Pro Gln Gln Pro Glu Gln Ile Ile Pro Gln
1               5                   10

<210> SEQ ID NO 191
<211> LENGTH: 12
<212> TYPE: PRT
<213> ORGANISM: Artificial Sequence
<220> FEATURE:
<223> OTHER INFORMATION: R12

<400> SEQUENCE: 191

Gln Pro Phe Pro Gln Pro Gln Gln Gln Leu Pro Leu

```
1               5                   10
```

<210> SEQ ID NO 192
<211> LENGTH: 12
<212> TYPE: PRT
<213> ORGANISM: Artificial Sequence
<220> FEATURE:
<223> OTHER INFORMATION: R12-E7

<400> SEQUENCE: 192

```
Gln Pro Phe Pro Gln Pro Glu Gln Gln Leu Pro Leu
1               5                   10
```

<210> SEQ ID NO 193
<211> LENGTH: 12
<212> TYPE: PRT
<213> ORGANISM: Artificial Sequence
<220> FEATURE:
<223> OTHER INFORMATION: R13

<400> SEQUENCE: 193

```
Pro Gln Gln Pro Tyr Pro Gln Gln Pro Phe Pro Gln
1               5                   10
```

<210> SEQ ID NO 194
<211> LENGTH: 12
<212> TYPE: PRT
<213> ORGANISM: Artificial Sequence
<220> FEATURE:
<223> OTHER INFORMATION: R13-E7

<400> SEQUENCE: 194

```
Pro Gln Gln Pro Tyr Pro Glu Gln Pro Phe Pro Gln
1               5                   10
```

<210> SEQ ID NO 195
<211> LENGTH: 16
<212> TYPE: PRT
<213> ORGANISM: Artificial Sequence
<220> FEATURE:
<223> OTHER INFORMATION: R14

<400> SEQUENCE: 195

```
Gln Gln Pro Gln Gln Pro Phe Pro Leu Gln Pro Gln Gln Pro Val Pro
1               5                   10                  15
```

<210> SEQ ID NO 196
<211> LENGTH: 12
<212> TYPE: PRT
<213> ORGANISM: Artificial Sequence
<220> FEATURE:
<223> OTHER INFORMATION: R15

<400> SEQUENCE: 196

```
Ile Ile Pro Gln Gln Pro Gln Gln Pro Phe Pro Leu
1               5                   10
```

<210> SEQ ID NO 197
<211> LENGTH: 12
<212> TYPE: PRT
<213> ORGANISM: Artificial Sequence
<220> FEATURE:
<223> OTHER INFORMATION: R15-E7

<400> SEQUENCE: 197

```
Ile Ile Pro Gln Gln Pro Glu Gln Pro Phe Pro Leu
1               5                   10
```

```
<210> SEQ ID NO 198
<211> LENGTH: 12
<212> TYPE: PRT
<213> ORGANISM: Artificial Sequence
<220> FEATURE:
<223> OTHER INFORMATION: R16

<400> SEQUENCE: 198

Pro Glu Gln Ile Ile Pro Gln Gln Pro Gln Gln Pro
1               5                   10

<210> SEQ ID NO 199
<211> LENGTH: 12
<212> TYPE: PRT
<213> ORGANISM: Artificial Sequence
<220> FEATURE:
<223> OTHER INFORMATION: R16-E7

<400> SEQUENCE: 199

Pro Glu Gln Ile Ile Pro Glu Gln Pro Gln Gln Pro
1               5                   10

<210> SEQ ID NO 200
<211> LENGTH: 12
<212> TYPE: PRT
<213> ORGANISM: Artificial Sequence
<220> FEATURE:
<223> OTHER INFORMATION: R17

<400> SEQUENCE: 200

Gln Ser Ile Pro Gln Pro Gln Gln Pro Phe Pro Gln
1               5                   10

<210> SEQ ID NO 201
<211> LENGTH: 12
<212> TYPE: PRT
<213> ORGANISM: Artificial Sequence
<220> FEATURE:
<223> OTHER INFORMATION: R17-E7

<400> SEQUENCE: 201

Gln Ser Ile Pro Gln Pro Glu Gln Pro Phe Pro Gln
1               5                   10

<210> SEQ ID NO 202
<211> LENGTH: 11
<212> TYPE: PRT
<213> ORGANISM: Artificial Sequence
<220> FEATURE:
<223> OTHER INFORMATION: R18

<400> SEQUENCE: 202

Phe Leu Leu Gln Pro Gln Gln Pro Phe Ser Gln
1               5                   10

<210> SEQ ID NO 203
<211> LENGTH: 11
<212> TYPE: PRT
<213> ORGANISM: Artificial Sequence
<220> FEATURE:
<223> OTHER INFORMATION: R18-E7

<400> SEQUENCE: 203

Phe Leu Leu Gln Pro Glu Gln Pro Phe Ser Gln
1               5                   10
```

```
<210> SEQ ID NO 204
<211> LENGTH: 16
<212> TYPE: PRT
<213> ORGANISM: Artificial Sequence
<220> FEATURE:
<223> OTHER INFORMATION: R19

<400> SEQUENCE: 204

Gln Pro Phe Pro Leu Gln Pro Gln Gln Pro Val Pro Gln Gln Pro Gln
1               5                   10                  15

<210> SEQ ID NO 205
<211> LENGTH: 12
<212> TYPE: PRT
<213> ORGANISM: Artificial Sequence
<220> FEATURE:
<223> OTHER INFORMATION: R20

<400> SEQUENCE: 205

Pro Phe Pro Leu Gln Pro Gln Gln Pro Phe Ser Gln
1               5                   10

<210> SEQ ID NO 206
<211> LENGTH: 12
<212> TYPE: PRT
<213> ORGANISM: Artificial Sequence
<220> FEATURE:
<223> OTHER INFORMATION: R20-E7

<400> SEQUENCE: 206

Pro Phe Pro Leu Gln Pro Glu Gln Pro Phe Ser Gln
1               5                   10

<210> SEQ ID NO 207
<211> LENGTH: 12
<212> TYPE: PRT
<213> ORGANISM: Artificial Sequence
<220> FEATURE:
<223> OTHER INFORMATION: R21

<400> SEQUENCE: 207

Gln Val Gly Pro Ser Gly Gln Val Glu Trp Pro Gln
1               5                   10

<210> SEQ ID NO 208
<211> LENGTH: 12
<212> TYPE: PRT
<213> ORGANISM: Artificial Sequence
<220> FEATURE:
<223> OTHER INFORMATION: R21-E7

<400> SEQUENCE: 208

Gln Val Gly Pro Ser Gly Glu Val Glu Trp Pro Gln
1               5                   10

<210> SEQ ID NO 209
<211> LENGTH: 11
<212> TYPE: PRT
<213> ORGANISM: Artificial Sequence
<220> FEATURE:
<223> OTHER INFORMATION: R22

<400> SEQUENCE: 209

Leu Phe Pro Leu Pro Gln Gln Pro Phe Pro Gln
1               5                   10
```

```
<210> SEQ ID NO 210
<211> LENGTH: 11
<212> TYPE: PRT
<213> ORGANISM: Artificial Sequence
<220> FEATURE:
<223> OTHER INFORMATION: R22-E7

<400> SEQUENCE: 210

Leu Phe Pro Leu Pro Glu Gln Pro Phe Pro Gln
1               5                   10

<210> SEQ ID NO 211
<211> LENGTH: 12
<212> TYPE: PRT
<213> ORGANISM: Artificial Sequence
<220> FEATURE:
<223> OTHER INFORMATION: R23

<400> SEQUENCE: 211

Pro Gln Thr Gln Gln Pro Gln Gln Pro Phe Pro Gln
1               5                   10

<210> SEQ ID NO 212
<211> LENGTH: 12
<212> TYPE: PRT
<213> ORGANISM: Artificial Sequence
<220> FEATURE:
<223> OTHER INFORMATION: R23-E7

<400> SEQUENCE: 212

Pro Gln Thr Gln Gln Pro Glu Gln Pro Phe Pro Gln
1               5                   10

<210> SEQ ID NO 213
<211> LENGTH: 12
<212> TYPE: PRT
<213> ORGANISM: Artificial Sequence
<220> FEATURE:
<223> OTHER INFORMATION: R24

<400> SEQUENCE: 213

Leu Pro Phe Pro Gln Pro Gln Gln Pro Phe Val Val
1               5                   10

<210> SEQ ID NO 214
<211> LENGTH: 12
<212> TYPE: PRT
<213> ORGANISM: Artificial Sequence
<220> FEATURE:
<223> OTHER INFORMATION: R24-E7

<400> SEQUENCE: 214

Leu Pro Phe Pro Gln Pro Glu Gln Pro Phe Val Val
1               5                   10

<210> SEQ ID NO 215
<211> LENGTH: 12
<212> TYPE: PRT
<213> ORGANISM: Artificial Sequence
<220> FEATURE:
<223> OTHER INFORMATION: R25

<400> SEQUENCE: 215

Ile Ile Ser Gln Gln Pro Gln Gln Pro Phe Pro Leu
1               5                   10

<210> SEQ ID NO 216
```

```
<211> LENGTH: 12
<212> TYPE: PRT
<213> ORGANISM: Artificial Sequence
<220> FEATURE:
<223> OTHER INFORMATION: R25-E7

<400> SEQUENCE: 216

Ile Ile Ser Gln Gln Pro Glu Gln Pro Phe Pro Leu
1               5                   10

<210> SEQ ID NO 217
<211> LENGTH: 12
<212> TYPE: PRT
<213> ORGANISM: Artificial Sequence
<220> FEATURE:
<223> OTHER INFORMATION: R26

<400> SEQUENCE: 217

Pro Phe Pro Gln Gln Pro Gln Gln Pro Phe Pro Gln
1               5                   10

<210> SEQ ID NO 218
<211> LENGTH: 12
<212> TYPE: PRT
<213> ORGANISM: Artificial Sequence
<220> FEATURE:
<223> OTHER INFORMATION: R26-E7

<400> SEQUENCE: 218

Pro Phe Pro Gln Gln Pro Glu Gln Pro Phe Pro Gln
1               5                   10

<210> SEQ ID NO 219
<211> LENGTH: 12
<212> TYPE: PRT
<213> ORGANISM: Artificial Sequence
<220> FEATURE:
<223> OTHER INFORMATION: R27

<400> SEQUENCE: 219

Pro Gln Ser Gln Gln Pro Gln Gln Pro Phe Pro Gln
1               5                   10

<210> SEQ ID NO 220
<211> LENGTH: 12
<212> TYPE: PRT
<213> ORGANISM: Artificial Sequence
<220> FEATURE:
<223> OTHER INFORMATION: R27-E7

<400> SEQUENCE: 220

Pro Gln Ser Gln Gln Pro Glu Gln Pro Phe Pro Gln
1               5                   10

<210> SEQ ID NO 221
<211> LENGTH: 12
<212> TYPE: PRT
<213> ORGANISM: Artificial Sequence
<220> FEATURE:
<223> OTHER INFORMATION: R28

<400> SEQUENCE: 221

Pro Gln Gln Pro Phe Pro Gln Gln Pro Gln Gln Pro
1               5                   10

<210> SEQ ID NO 222
<211> LENGTH: 12
```

```
<212> TYPE: PRT
<213> ORGANISM: Artificial Sequence
<220> FEATURE:
<223> OTHER INFORMATION: R28-E7

<400> SEQUENCE: 222

Pro Gln Gln Pro Phe Pro Glu Gln Pro Gln Gln Pro
1               5                   10

<210> SEQ ID NO 223
<211> LENGTH: 12
<212> TYPE: PRT
<213> ORGANISM: Artificial Sequence
<220> FEATURE:
<223> OTHER INFORMATION: R29

<400> SEQUENCE: 223

Pro Phe Pro Gln Arg Pro Gln Gln Pro Phe Pro Gln
1               5                   10

<210> SEQ ID NO 224
<211> LENGTH: 12
<212> TYPE: PRT
<213> ORGANISM: Artificial Sequence
<220> FEATURE:
<223> OTHER INFORMATION: R29-E7

<400> SEQUENCE: 224

Pro Phe Pro Gln Arg Pro Glu Gln Pro Phe Pro Gln
1               5                   10

<210> SEQ ID NO 225
<211> LENGTH: 17
<212> TYPE: PRT
<213> ORGANISM: Artificial Sequence
<220> FEATURE:
<223> OTHER INFORMATION: gluten derived peptide

<400> SEQUENCE: 225

Gln Leu Gln Pro Phe Pro Gln Pro Glu Leu Pro Tyr Pro Gln Pro Gln
1               5                   10                  15

Pro

<210> SEQ ID NO 226
<211> LENGTH: 16
<212> TYPE: PRT
<213> ORGANISM: Artificial Sequence
<220> FEATURE:
<223> OTHER INFORMATION: NPL004
<220> FEATURE:
<221> NAME/KEY: MOD_RES
<222> LOCATION: (1)..(1)
<223> OTHER INFORMATION: pyroE
<220> FEATURE:
<221> NAME/KEY: MOD_RES
<222> LOCATION: (16)..(16)
<223> OTHER INFORMATION: amidated

<400> SEQUENCE: 226

Xaa Gln Pro Phe Pro Glu Gln Pro Glu Gln Ile Ile Pro Gln Gln Pro
1               5                   10                  15

<210> SEQ ID NO 227
<211> LENGTH: 15
<212> TYPE: PRT
<213> ORGANISM: Artificial Sequence
<220> FEATURE:
<223> OTHER INFORMATION: NPL005
```

```
<220> FEATURE:
<221> NAME/KEY: MOD_RES
<222> LOCATION: (1)..(1)
<223> OTHER INFORMATION: pyroE
<220> FEATURE:
<221> NAME/KEY: MOD_RES
<222> LOCATION: (15)..(15)
<223> OTHER INFORMATION: amididated

<400> SEQUENCE: 227

Xaa Tyr Gln Pro Tyr Pro Glu Gln Glu Gln Pro Ile Leu Gln Gln
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: NPL001
<220> FEATURE:
<221> NAME/KEY: MOD_RES
<222> LOCATION: (1)..(1)
<223> OTHER INFORMATION: pyroE
<220> FEATURE:
<221> NAME/KEY: MOD_RES
<222> LOCATION: (16)..(16)
<223> OTHER INFORMATION: amidated

<400> SEQUENCE: 228

Xaa Leu Gln Pro Phe Pro Gln Pro Glu Leu Pro Tyr Pro Gln Pro Gln
1               5                   10                  15

<210> SEQ ID NO 229
<211> LENGTH: 15
<212> TYPE: PRT
<213> ORGANISM: Artificial Sequence
<220> FEATURE:
<223> OTHER INFORMATION: NPL002
<220> FEATURE:
<221> NAME/KEY: MOD_RES
<222> LOCATION: (1)..(1)
<223> OTHER INFORMATION: pyroE
<220> FEATURE:
<221> NAME/KEY: MOD_RES
<222> LOCATION: (15)..(15)
<223> OTHER INFORMATION: amidated

<400> SEQUENCE: 229

Xaa Gln Pro Phe Pro Gln Pro Glu Gln Pro Phe Pro Trp Gln Pro
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: NPL003
<220> FEATURE:
<221> NAME/KEY: MOD_RES
<222> LOCATION: (1)..(1)
<223> OTHER INFORMATION: PyroE
<220> FEATURE:
<221> NAME/KEY: MOD_RES
<222> LOCATION: (16)..(16)
<223> OTHER INFORMATION: amidated

<400> SEQUENCE: 230

Xaa Pro Glu Gln Pro Ile Pro Glu Gln Pro Gln Pro Tyr Pro Gln Gln
1               5                   10                  15

<210> SEQ ID NO 231
```

```
<211> LENGTH: 16
<212> TYPE: PRT
<213> ORGANISM: Artificial Sequence
<220> FEATURE:
<223> OTHER INFORMATION: NPL030
<220> FEATURE:
<221> NAME/KEY: MOD_RES
<222> LOCATION: (1)..(1)
<223> OTHER INFORMATION: acetylated
<220> FEATURE:
<221> NAME/KEY: MOD_RES
<222> LOCATION: (16)..(16)
<223> OTHER INFORMATION: amidated

<400> SEQUENCE: 231

Gln Leu Gln Pro Phe Pro Gln Pro Glu Leu Pro Tyr Pro Gln Pro
1               5                   10                  15

Gln

<210> SEQ ID NO 232
<211> LENGTH: 15
<212> TYPE: PRT
<213> ORGANISM: Artificial Sequence
<220> FEATURE:
<223> OTHER INFORMATION: NPL031
<220> FEATURE:
<221> NAME/KEY: MOD_RES
<222> LOCATION: (1)..(1)
<223> OTHER INFORMATION: acetylated
<220> FEATURE:
<221> NAME/KEY: X
<222> LOCATION: (15)..(15)
<223> OTHER INFORMATION: amidated

<400> SEQUENCE: 232

Gln Gln Pro Phe Pro Gln Pro Glu Gln Pro Phe Pro Trp Gln Pro
1               5                   10                  15

<210> SEQ ID NO 233
<211> LENGTH: 16
<212> TYPE: PRT
<213> ORGANISM: Artificial Sequence
<220> FEATURE:
<223> OTHER INFORMATION: NPL032
<220> FEATURE:
<221> NAME/KEY: MOD_RES
<222> LOCATION: (1)..(1)
<223> OTHER INFORMATION: acetylated
<220> FEATURE:
<221> NAME/KEY: MOD_RES
<222> LOCATION: (16)..(16)
<223> OTHER INFORMATION: amidated

<400> SEQUENCE: 233

Phe Pro Glu Gln Pro Ile Pro Glu Gln Pro Gln Pro Tyr Pro Gln
1               5                   10                  15

Gln

<210> SEQ ID NO 234
<211> LENGTH: 4
<212> TYPE: PRT
<213> ORGANISM: Artificial Sequence
<220> FEATURE:
<223> OTHER INFORMATION: Fragment of SEQ ID NO:13 essential for T cell
      recognition

<400> SEQUENCE: 234

Pro Glu Leu Pro
1
```

```
<210> SEQ ID NO 235
<211> LENGTH: 7
<212> TYPE: PRT
<213> ORGANISM: Artificial Sequence
<220> FEATURE:
<223> OTHER INFORMATION: 7mer from SEQ ID NO:13

<400> SEQUENCE: 235

Gln Pro Glu Leu Pro Tyr Pro
1               5

<210> SEQ ID NO 236
<211> LENGTH: 7
<212> TYPE: PRT
<213> ORGANISM: Artificial Sequence
<220> FEATURE:
<223> OTHER INFORMATION: 7mer from SEQ ID NO:13

<400> SEQUENCE: 236

Pro Glu Leu Pro Tyr Pro Gln
1               5

<210> SEQ ID NO 237
<211> LENGTH: 7
<212> TYPE: PRT
<213> ORGANISM: Artificial Sequence
<220> FEATURE:
<223> OTHER INFORMATION: 7mer from SEQ ID NO:13

<400> SEQUENCE: 237

Pro Gln Pro Glu Leu Pro Tyr
1               5

<210> SEQ ID NO 238
<211> LENGTH: 7
<212> TYPE: PRT
<213> ORGANISM: Artificial Sequence
<220> FEATURE:
<223> OTHER INFORMATION: 7mer from SEQ ID NO:13

<400> SEQUENCE: 238

Phe Pro Gln Pro Glu Leu Pro
1               5

<210> SEQ ID NO 239
<211> LENGTH: 8
<212> TYPE: PRT
<213> ORGANISM: Artificial Sequence
<220> FEATURE:
<223> OTHER INFORMATION: 8mer from SEQ ID NO:13

<400> SEQUENCE: 239

Pro Glu Leu Pro Tyr Pro Gln Pro
1               5

<210> SEQ ID NO 240
<211> LENGTH: 8
<212> TYPE: PRT
<213> ORGANISM: Artificial Sequence
<220> FEATURE:
<223> OTHER INFORMATION: 8mer from SEQ ID NO:13

<400> SEQUENCE: 240

Gln Pro Glu Leu Pro Tyr Pro Gln
1               5
```

-continued

<210> SEQ ID NO 241
<211> LENGTH: 8
<212> TYPE: PRT
<213> ORGANISM: Artificial Sequence
<220> FEATURE:
<223> OTHER INFORMATION: 8mer from SEQ ID NO:13

<400> SEQUENCE: 241

Pro Gln Pro Glu Leu Pro Tyr Pro
1               5

<210> SEQ ID NO 242
<211> LENGTH: 8
<212> TYPE: PRT
<213> ORGANISM: Artificial Sequence
<220> FEATURE:
<223> OTHER INFORMATION: 8mer from SEQ ID NO:13

<400> SEQUENCE: 242

Phe Pro Gln Pro Glu Leu Pro Tyr
1               5

<210> SEQ ID NO 243
<211> LENGTH: 8
<212> TYPE: PRT
<213> ORGANISM: Artificial Sequence
<220> FEATURE:
<223> OTHER INFORMATION: 8mer from SEQ ID NO:13

<400> SEQUENCE: 243

Pro Phe Pro Gln Pro Glu Leu Pro
1               5

<210> SEQ ID NO 244
<211> LENGTH: 9
<212> TYPE: PRT
<213> ORGANISM: Artificial Sequence
<220> FEATURE:
<223> OTHER INFORMATION: 9mer from SEQ ID NO:13

<400> SEQUENCE: 244

Pro Glu Leu Pro Tyr Pro Gln Pro Gln
1               5

<210> SEQ ID NO 245
<211> LENGTH: 9
<212> TYPE: PRT
<213> ORGANISM: Artificial Sequence
<220> FEATURE:
<223> OTHER INFORMATION: 9mer from SEQ ID NO:13

<400> SEQUENCE: 245

Gln Pro Glu Leu Pro Tyr Pro Gln Pro
1               5

<210> SEQ ID NO 246
<211> LENGTH: 9
<212> TYPE: PRT
<213> ORGANISM: Artificial Sequence
<220> FEATURE:
<223> OTHER INFORMATION: 9mer from SEQ ID NO:13

<400> SEQUENCE: 246

Pro Gln Pro Glu Leu Pro Tyr Pro Gln
1               5

<210> SEQ ID NO 247

-continued

```
<211> LENGTH: 9
<212> TYPE: PRT
<213> ORGANISM: Artificial Sequence
<220> FEATURE:
<223> OTHER INFORMATION: 9mer from SEQ ID NO:13

<400> SEQUENCE: 247

Phe Pro Gln Pro Glu Leu Pro Tyr Pro
1               5

<210> SEQ ID NO 248
<211> LENGTH: 9
<212> TYPE: PRT
<213> ORGANISM: Artificial Sequence
<220> FEATURE:
<223> OTHER INFORMATION: 9mer from SEQ ID NO:13

<400> SEQUENCE: 248

Pro Phe Pro Gln Pro Glu Leu Pro Tyr
1               5

<210> SEQ ID NO 249
<211> LENGTH: 9
<212> TYPE: PRT
<213> ORGANISM: Artificial Sequence
<220> FEATURE:
<223> OTHER INFORMATION: 9mer from SEQ ID NO:13

<400> SEQUENCE: 249

Gln Pro Phe Pro Gln Pro Glu Leu Pro
1               5

<210> SEQ ID NO 250
<211> LENGTH: 10
<212> TYPE: PRT
<213> ORGANISM: Artificial Sequence
<220> FEATURE:
<223> OTHER INFORMATION: 10mer from SEQ ID NO:13

<400> SEQUENCE: 250

Gln Pro Glu Leu Pro Tyr Pro Gln Pro Gln
1               5                   10

<210> SEQ ID NO 251
<211> LENGTH: 10
<212> TYPE: PRT
<213> ORGANISM: Artificial Sequence
<220> FEATURE:
<223> OTHER INFORMATION: 10mer from SEQ ID NO:13

<400> SEQUENCE: 251

Pro Gln Pro Glu Leu Pro Tyr Pro Gln Pro
1               5                   10

<210> SEQ ID NO 252
<211> LENGTH: 10
<212> TYPE: PRT
<213> ORGANISM: Artificial Sequence
<220> FEATURE:
<223> OTHER INFORMATION: 10mer from SEQ ID NO:13

<400> SEQUENCE: 252

Pro Gln Pro Glu Leu Pro Tyr Pro Gln Pro
1               5                   10

<210> SEQ ID NO 253
<211> LENGTH: 10
```

```
<212> TYPE: PRT
<213> ORGANISM: Artificial Sequence
<220> FEATURE:
<223> OTHER INFORMATION: 10mer from SEQ ID NO:13

<400> SEQUENCE: 253

Phe Pro Gln Pro Glu Leu Pro Tyr Pro Gln
1               5                   10

<210> SEQ ID NO 254
<211> LENGTH: 10
<212> TYPE: PRT
<213> ORGANISM: Artificial Sequence
<220> FEATURE:
<223> OTHER INFORMATION: 10mer from SEQ ID NO:13

<400> SEQUENCE: 254

Pro Phe Pro Gln Pro Glu Leu Pro Tyr Pro
1               5                   10

<210> SEQ ID NO 255
<211> LENGTH: 10
<212> TYPE: PRT
<213> ORGANISM: Artificial Sequence
<220> FEATURE:
<223> OTHER INFORMATION: 10mer from SEQ ID NO:13

<400> SEQUENCE: 255

Gln Pro Phe Pro Gln Pro Glu Leu Pro Tyr
1               5                   10

<210> SEQ ID NO 256
<211> LENGTH: 10
<212> TYPE: PRT
<213> ORGANISM: Artificial Sequence
<220> FEATURE:
<223> OTHER INFORMATION: 10mer from SEQ ID NO:13

<400> SEQUENCE: 256

Leu Gln Pro Phe Pro Gln Pro Glu Leu Pro
1               5                   10

<210> SEQ ID NO 257
<211> LENGTH: 11
<212> TYPE: PRT
<213> ORGANISM: Artificial Sequence
<220> FEATURE:
<223> OTHER INFORMATION: 11mer from SEQ ID NO:13

<400> SEQUENCE: 257

Pro Gln Pro Glu Leu Pro Tyr Pro Gln Pro Gln
1               5                   10

<210> SEQ ID NO 258
<211> LENGTH: 11
<212> TYPE: PRT
<213> ORGANISM: Artificial Sequence
<220> FEATURE:
<223> OTHER INFORMATION: 11mer from SEQ ID NO:13

<400> SEQUENCE: 258

Phe Pro Gln Pro Glu Leu Pro Tyr Pro Gln Pro
1               5                   10

<210> SEQ ID NO 259
<211> LENGTH: 11
<212> TYPE: PRT
```

<213> ORGANISM: Artificial Sequence
<220> FEATURE:
<223> OTHER INFORMATION: 11mer from SEQ ID NO:13

<400> SEQUENCE: 259

Pro Phe Pro Gln Pro Glu Leu Pro Tyr Pro Gln
1               5                   10

<210> SEQ ID NO 260
<211> LENGTH: 11
<212> TYPE: PRT
<213> ORGANISM: Artificial Sequence
<220> FEATURE:
<223> OTHER INFORMATION: 11mer from SEQ ID NO:13

<400> SEQUENCE: 260

Gln Pro Phe Pro Gln Pro Glu Leu Pro Tyr Pro
1               5                   10

<210> SEQ ID NO 261
<211> LENGTH: 11
<212> TYPE: PRT
<213> ORGANISM: Artificial Sequence
<220> FEATURE:
<223> OTHER INFORMATION: 11mer from SEQ ID NO:13

<400> SEQUENCE: 261

Leu Gln Pro Phe Pro Gln Pro Glu Leu Pro Tyr
1               5                   10

<210> SEQ ID NO 262
<211> LENGTH: 12
<212> TYPE: PRT
<213> ORGANISM: Artificial Sequence
<220> FEATURE:
<223> OTHER INFORMATION: 12mer from SEQ ID NO:13

<400> SEQUENCE: 262

Phe Pro Gln Pro Glu Leu Pro Tyr Pro Gln Pro Gln
1               5                   10

<210> SEQ ID NO 263
<211> LENGTH: 12
<212> TYPE: PRT
<213> ORGANISM: Artificial Sequence
<220> FEATURE:
<223> OTHER INFORMATION: 12mer from SEQ ID NO:13

<400> SEQUENCE: 263

Pro Phe Pro Gln Pro Glu Leu Pro Tyr Pro Gln Pro
1               5                   10

<210> SEQ ID NO 264
<211> LENGTH: 12
<212> TYPE: PRT
<213> ORGANISM: Artificial Sequence
<220> FEATURE:
<223> OTHER INFORMATION: 12mer from SEQ ID NO:13

<400> SEQUENCE: 264

Gln Pro Phe Pro Gln Pro Glu Leu Pro Tyr Pro Gln
1               5                   10

<210> SEQ ID NO 265
<211> LENGTH: 12
<212> TYPE: PRT
<213> ORGANISM: Artificial Sequence

```
<220> FEATURE:
<223> OTHER INFORMATION: 12mer from SEQ ID NO:13

<400> SEQUENCE: 265

Leu Gln Pro Phe Pro Gln Pro Glu Leu Pro Tyr Pro
1               5                   10

<210> SEQ ID NO 266
<211> LENGTH: 13
<212> TYPE: PRT
<213> ORGANISM: Artificial Sequence
<220> FEATURE:
<223> OTHER INFORMATION: 13mer from SEQ ID NO:13

<400> SEQUENCE: 266

Pro Phe Pro Gln Pro Glu Leu Pro Tyr Pro Gln Pro Gln
1               5                   10

<210> SEQ ID NO 267
<211> LENGTH: 13
<212> TYPE: PRT
<213> ORGANISM: Artificial Sequence
<220> FEATURE:
<223> OTHER INFORMATION: 13mer from SEQ ID NO:13

<400> SEQUENCE: 267

Gln Pro Phe Pro Gln Pro Glu Leu Pro Tyr Pro Gln Pro
1               5                   10

<210> SEQ ID NO 268
<211> LENGTH: 13
<212> TYPE: PRT
<213> ORGANISM: Artificial Sequence
<220> FEATURE:
<223> OTHER INFORMATION: 13mer from SEQ ID NO:13

<400> SEQUENCE: 268

Leu Gln Pro Phe Pro Gln Pro Glu Leu Pro Tyr Pro Gln
1               5                   10

<210> SEQ ID NO 269
<211> LENGTH: 14
<212> TYPE: PRT
<213> ORGANISM: Artificial Sequence
<220> FEATURE:
<223> OTHER INFORMATION: 14mer from SEQ ID NO:13

<400> SEQUENCE: 269

Gln Pro Phe Pro Gln Pro Glu Leu Pro Tyr Pro Gln Pro Gln
1               5                   10

<210> SEQ ID NO 270
<211> LENGTH: 14
<212> TYPE: PRT
<213> ORGANISM: Artificial Sequence
<220> FEATURE:
<223> OTHER INFORMATION: 14mer from SEQ ID NO:13

<400> SEQUENCE: 270

Leu Gln Pro Phe Pro Gln Pro Glu Leu Pro Tyr Pro Gln Pro
1               5                   10

<210> SEQ ID NO 271
<211> LENGTH: 7
<212> TYPE: PRT
<213> ORGANISM: Artificial Sequence
<220> FEATURE:
```

```
<223> OTHER INFORMATION: 7mer from SEQ ID NO:14

<400> SEQUENCE: 271

Gln Pro Glu Gln Pro Phe Pro
1               5

<210> SEQ ID NO 272
<211> LENGTH: 7
<212> TYPE: PRT
<213> ORGANISM: Artificial Sequence
<220> FEATURE:
<223> OTHER INFORMATION: 7mer from SEQ ID NO:14

<400> SEQUENCE: 272

Pro Gln Pro Glu Gln Pro Phe
1               5

<210> SEQ ID NO 273
<211> LENGTH: 8
<212> TYPE: PRT
<213> ORGANISM: Artificial Sequence
<220> FEATURE:
<223> OTHER INFORMATION: 8mer from SEQ ID NO:14

<400> SEQUENCE: 273

Gln Pro Glu Gln Pro Phe Pro Trp
1               5

<210> SEQ ID NO 274
<211> LENGTH: 8
<212> TYPE: PRT
<213> ORGANISM: Artificial Sequence
<220> FEATURE:
<223> OTHER INFORMATION: 8mer from SEQ ID NO:14

<400> SEQUENCE: 274

Pro Gln Pro Glu Gln Pro Phe Pro
1               5

<210> SEQ ID NO 275
<211> LENGTH: 8
<212> TYPE: PRT
<213> ORGANISM: Artificial Sequence
<220> FEATURE:
<223> OTHER INFORMATION: 8mer from SEQ ID NO:14

<400> SEQUENCE: 275

Phe Pro Gln Pro Glu Gln Pro Phe
1               5

<210> SEQ ID NO 276
<211> LENGTH: 9
<212> TYPE: PRT
<213> ORGANISM: Artificial Sequence
<220> FEATURE:
<223> OTHER INFORMATION: 9mer from SEQ ID NO:14

<400> SEQUENCE: 276

Gln Pro Glu Gln Pro Phe Pro Trp Gln
1               5

<210> SEQ ID NO 277
<211> LENGTH: 9
<212> TYPE: PRT
<213> ORGANISM: Artificial Sequence
<220> FEATURE:
<223> OTHER INFORMATION: 9mer from SEQ ID NO:14
```

<400> SEQUENCE: 277

Pro Gln Pro Glu Gln Pro Phe Pro Trp
1               5

<210> SEQ ID NO 278
<211> LENGTH: 9
<212> TYPE: PRT
<213> ORGANISM: Artificial Sequence
<220> FEATURE:
<223> OTHER INFORMATION: 9mer from SEQ ID NO:14

<400> SEQUENCE: 278

Phe Pro Gln Pro Glu Gln Pro Phe Pro
1               5

<210> SEQ ID NO 279
<211> LENGTH: 9
<212> TYPE: PRT
<213> ORGANISM: Artificial Sequence
<220> FEATURE:
<223> OTHER INFORMATION: 9mer from SEQ ID NO:14

<400> SEQUENCE: 279

Pro Phe Pro Gln Pro Glu Gln Pro Phe
1               5

<210> SEQ ID NO 280
<211> LENGTH: 10
<212> TYPE: PRT
<213> ORGANISM: Artificial Sequence
<220> FEATURE:
<223> OTHER INFORMATION: 10mer from SEQ ID NO:14

<400> SEQUENCE: 280

Gln Pro Glu Gln Pro Phe Pro Trp Gln Pro
1               5                   10

<210> SEQ ID NO 281
<211> LENGTH: 10
<212> TYPE: PRT
<213> ORGANISM: Artificial Sequence
<220> FEATURE:
<223> OTHER INFORMATION: 10mer from SEQ ID NO:14

<400> SEQUENCE: 281

Pro Gln Pro Glu Gln Pro Phe Pro Trp Gln
1               5                   10

<210> SEQ ID NO 282
<211> LENGTH: 10
<212> TYPE: PRT
<213> ORGANISM: Artificial Sequence
<220> FEATURE:
<223> OTHER INFORMATION: 10mer from SEQ ID NO:14

<400> SEQUENCE: 282

Phe Pro Gln Pro Glu Gln Pro Phe Pro Trp
1               5                   10

<210> SEQ ID NO 283
<211> LENGTH: 10
<212> TYPE: PRT
<213> ORGANISM: Artificial Sequence
<220> FEATURE:
<223> OTHER INFORMATION: 10mer from SEQ ID NO:14

<400> SEQUENCE: 283

Pro Phe Pro Gln Pro Glu Gln Pro Phe Pro
1               5                   10

<210> SEQ ID NO 284
<211> LENGTH: 10
<212> TYPE: PRT
<213> ORGANISM: Artificial Sequence
<220> FEATURE:
<223> OTHER INFORMATION: 10mer from SEQ ID NO:14

<400> SEQUENCE: 284

Gln Pro Phe Pro Gln Pro Glu Gln Pro Phe
1               5                   10

<210> SEQ ID NO 285
<211> LENGTH: 11
<212> TYPE: PRT
<213> ORGANISM: Artificial Sequence
<220> FEATURE:
<223> OTHER INFORMATION: 11mer from SEQ ID NO:14

<400> SEQUENCE: 285

Pro Gln Pro Glu Gln Pro Phe Pro Trp Gln Pro
1               5                   10

<210> SEQ ID NO 286
<211> LENGTH: 11
<212> TYPE: PRT
<213> ORGANISM: Artificial Sequence
<220> FEATURE:
<223> OTHER INFORMATION: 11mer from SEQ ID NO:14

<400> SEQUENCE: 286

Phe Pro Gln Pro Glu Gln Pro Phe Pro Trp Gln
1               5                   10

<210> SEQ ID NO 287
<211> LENGTH: 11
<212> TYPE: PRT
<213> ORGANISM: Artificial Sequence
<220> FEATURE:
<223> OTHER INFORMATION: 11mer from SEQ ID NO:14

<400> SEQUENCE: 287

Pro Phe Pro Gln Pro Glu Gln Pro Phe Pro Trp
1               5                   10

<210> SEQ ID NO 288
<211> LENGTH: 11
<212> TYPE: PRT
<213> ORGANISM: Artificial Sequence
<220> FEATURE:
<223> OTHER INFORMATION: 11mer from SEQ ID NO:14

<400> SEQUENCE: 288

Gln Pro Phe Pro Gln Pro Glu Gln Pro Phe Pro
1               5                   10

<210> SEQ ID NO 289
<211> LENGTH: 12
<212> TYPE: PRT
<213> ORGANISM: Artificial Sequence
<220> FEATURE:
<223> OTHER INFORMATION: 12mer from SEQ ID NO:14

<400> SEQUENCE: 289

Phe Pro Gln Pro Glu Gln Pro Phe Pro Trp Gln Pro
1               5                   10

<210> SEQ ID NO 290
<211> LENGTH: 12
<212> TYPE: PRT
<213> ORGANISM: Artificial Sequence
<220> FEATURE:
<223> OTHER INFORMATION: 12mer from SEQ ID NO:14

<400> SEQUENCE: 290

Pro Phe Pro Gln Pro Glu Gln Pro Phe Pro Trp Gln
1               5                   10

<210> SEQ ID NO 291
<211> LENGTH: 12
<212> TYPE: PRT
<213> ORGANISM: Artificial Sequence
<220> FEATURE:
<223> OTHER INFORMATION: 12mer from SEQ ID NO:14

<400> SEQUENCE: 291

Gln Pro Phe Pro Gln Pro Glu Gln Pro Phe Pro Trp
1               5                   10

<210> SEQ ID NO 292
<211> LENGTH: 13
<212> TYPE: PRT
<213> ORGANISM: Artificial Sequence
<220> FEATURE:
<223> OTHER INFORMATION: 13mer from SEQ ID NO:14

<400> SEQUENCE: 292

Pro Phe Pro Gln Pro Glu Gln Pro Phe Pro Trp Gln Pro
1               5                   10

<210> SEQ ID NO 293
<211> LENGTH: 13
<212> TYPE: PRT
<213> ORGANISM: Artificial Sequence
<220> FEATURE:
<223> OTHER INFORMATION: 13mer from SEQ ID NO:14

<400> SEQUENCE: 293

Gln Pro Phe Pro Gln Pro Glu Gln Pro Phe Pro Trp Gln
1               5                   10

<210> SEQ ID NO 294
<211> LENGTH: 7
<212> TYPE: PRT
<213> ORGANISM: Artificial Sequence
<220> FEATURE:
<223> OTHER INFORMATION: Fragment of SEQ ID NO:16 essential for T cell
      recognition

<400> SEQUENCE: 294

Pro Ile Pro Glu Gln Pro Gln
1               5

<210> SEQ ID NO 295
<211> LENGTH: 8
<212> TYPE: PRT
<213> ORGANISM: Artificial Sequence
<220> FEATURE:
<223> OTHER INFORMATION: 8mer from SEQ ID NO:16

<400> SEQUENCE: 295

```
Pro Ile Pro Glu Gln Pro Gln Pro
1               5

<210> SEQ ID NO 296
<211> LENGTH: 8
<212> TYPE: PRT
<213> ORGANISM: Artificial Sequence
<220> FEATURE:
<223> OTHER INFORMATION: 8mer from SEQ ID NO:16

<400> SEQUENCE: 296

Gln Pro Ile Pro Glu Gln Pro Gln
1               5

<210> SEQ ID NO 297
<211> LENGTH: 9
<212> TYPE: PRT
<213> ORGANISM: Artificial Sequence
<220> FEATURE:
<223> OTHER INFORMATION: 9mer from SEQ ID NO:16

<400> SEQUENCE: 297

Pro Ile Pro Glu Gln Pro Gln Pro Tyr
1               5

<210> SEQ ID NO 298
<211> LENGTH: 9
<212> TYPE: PRT
<213> ORGANISM: Artificial Sequence
<220> FEATURE:
<223> OTHER INFORMATION: 9mer from SEQ ID NO:16

<400> SEQUENCE: 298

Gln Pro Ile Pro Glu Gln Pro Gln Pro
1               5

<210> SEQ ID NO 299
<211> LENGTH: 9
<212> TYPE: PRT
<213> ORGANISM: Artificial Sequence
<220> FEATURE:
<223> OTHER INFORMATION: 9mer from SEQ ID NO:16

<400> SEQUENCE: 299

Glu Gln Pro Ile Pro Glu Gln Pro Gln
1               5

<210> SEQ ID NO 300
<211> LENGTH: 10
<212> TYPE: PRT
<213> ORGANISM: Artificial Sequence
<220> FEATURE:
<223> OTHER INFORMATION: 10mer from SEQ ID NO:16

<400> SEQUENCE: 300

Pro Ile Pro Glu Gln Pro Gln Pro Tyr Pro
1               5                   10

<210> SEQ ID NO 301
<211> LENGTH: 10
<212> TYPE: PRT
<213> ORGANISM: Artificial Sequence
<220> FEATURE:
<223> OTHER INFORMATION: 10mer from SEQ ID NO:16

<400> SEQUENCE: 301
```

```
Gln Pro Ile Pro Glu Gln Pro Gln Pro Tyr
1               5                   10

<210> SEQ ID NO 302
<211> LENGTH: 10
<212> TYPE: PRT
<213> ORGANISM: Artificial Sequence
<220> FEATURE:
<223> OTHER INFORMATION: 10mer from SEQ ID NO:16

<400> SEQUENCE: 302

Glu Gln Pro Ile Pro Glu Gln Pro Gln Pro
1               5                   10

<210> SEQ ID NO 303
<211> LENGTH: 10
<212> TYPE: PRT
<213> ORGANISM: Artificial Sequence
<220> FEATURE:
<223> OTHER INFORMATION: 10mer from SEQ ID NO:16

<400> SEQUENCE: 303

Pro Glu Gln Pro Ile Pro Glu Gln Pro Gln
1               5                   10

<210> SEQ ID NO 304
<211> LENGTH: 11
<212> TYPE: PRT
<213> ORGANISM: Artificial Sequence
<220> FEATURE:
<223> OTHER INFORMATION: 11mer from SEQ ID NO:16

<400> SEQUENCE: 304

Pro Ile Pro Glu Gln Pro Gln Pro Tyr Pro Gln
1               5                   10

<210> SEQ ID NO 305
<211> LENGTH: 11
<212> TYPE: PRT
<213> ORGANISM: Artificial Sequence
<220> FEATURE:
<223> OTHER INFORMATION: 11mer from SEQ ID NO:16

<400> SEQUENCE: 305

Gln Pro Ile Pro Glu Gln Pro Gln Pro Tyr Pro
1               5                   10

<210> SEQ ID NO 306
<211> LENGTH: 11
<212> TYPE: PRT
<213> ORGANISM: Artificial Sequence
<220> FEATURE:
<223> OTHER INFORMATION: 11mer from SEQ ID NO:16

<400> SEQUENCE: 306

Glu Gln Pro Ile Pro Glu Gln Pro Gln Pro Tyr
1               5                   10

<210> SEQ ID NO 307
<211> LENGTH: 11
<212> TYPE: PRT
<213> ORGANISM: Artificial Sequence
<220> FEATURE:
<223> OTHER INFORMATION: 11mer from SEQ ID NO:16

<400> SEQUENCE: 307

Pro Glu Gln Pro Ile Pro Glu Gln Pro Gln Pro
```

```
1               5                   10
```

<210> SEQ ID NO 308
<211> LENGTH: 12
<212> TYPE: PRT
<213> ORGANISM: Artificial Sequence
<220> FEATURE:
<223> OTHER INFORMATION: 12mer from SEQ ID NO:16

<400> SEQUENCE: 308

```
Pro Ile Pro Glu Gln Pro Gln Pro Tyr Pro Gln Gln
1               5                   10
```

<210> SEQ ID NO 309
<211> LENGTH: 12
<212> TYPE: PRT
<213> ORGANISM: Artificial Sequence
<220> FEATURE:
<223> OTHER INFORMATION: 12mer from SEQ ID NO:16

<400> SEQUENCE: 309

```
Gln Pro Ile Pro Glu Gln Pro Gln Pro Tyr Pro Gln
1               5                   10
```

<210> SEQ ID NO 310
<211> LENGTH: 12
<212> TYPE: PRT
<213> ORGANISM: Artificial Sequence
<220> FEATURE:
<223> OTHER INFORMATION: 12mer from SEQ ID NO:16

<400> SEQUENCE: 310

```
Glu Gln Pro Ile Pro Glu Gln Pro Gln Pro Tyr Pro
1               5                   10
```

<210> SEQ ID NO 311
<211> LENGTH: 12
<212> TYPE: PRT
<213> ORGANISM: Artificial Sequence
<220> FEATURE:
<223> OTHER INFORMATION: 12mer from SEQ ID NO:16

<400> SEQUENCE: 311

```
Pro Glu Gln Pro Ile Pro Glu Gln Pro Gln Pro Tyr
1               5                   10
```

<210> SEQ ID NO 312
<211> LENGTH: 13
<212> TYPE: PRT
<213> ORGANISM: Artificial Sequence
<220> FEATURE:
<223> OTHER INFORMATION: 13mer from SEQ ID NO:16

<400> SEQUENCE: 312

```
Gln Pro Ile Pro Glu Gln Pro Gln Pro Tyr Pro Gln Gln
1               5                   10
```

<210> SEQ ID NO 313
<211> LENGTH: 13
<212> TYPE: PRT
<213> ORGANISM: Artificial Sequence
<220> FEATURE:
<223> OTHER INFORMATION: 13mer from SEQ ID NO:16

<400> SEQUENCE: 313

```
Glu Gln Pro Ile Pro Glu Gln Pro Gln Pro Tyr Pro Gln
1               5                   10
```

```
<210> SEQ ID NO 314
<211> LENGTH: 13
<212> TYPE: PRT
<213> ORGANISM: Artificial Sequence
<220> FEATURE:
<223> OTHER INFORMATION: 13mer from SEQ ID NO:16

<400> SEQUENCE: 314

Pro Glu Gln Pro Ile Pro Glu Gln Pro Gln Pro Tyr Pro
1               5                   10

<210> SEQ ID NO 315
<211> LENGTH: 14
<212> TYPE: PRT
<213> ORGANISM: Artificial Sequence
<220> FEATURE:
<223> OTHER INFORMATION: 14mer from SEQ ID NO:16

<400> SEQUENCE: 315

Glu Gln Pro Ile Pro Glu Gln Pro Gln Pro Tyr Pro Gln Gln
1               5                   10

<210> SEQ ID NO 316
<211> LENGTH: 14
<212> TYPE: PRT
<213> ORGANISM: Artificial Sequence
<220> FEATURE:
<223> OTHER INFORMATION: 14mer from SEQ ID NO:16

<400> SEQUENCE: 316

Pro Glu Gln Pro Ile Pro Glu Gln Pro Gln Pro Tyr Pro Gln
1               5                   10

<210> SEQ ID NO 317
<211> LENGTH: 6
<212> TYPE: PRT
<213> ORGANISM: Artificial Sequence
<220> FEATURE:
<223> OTHER INFORMATION: 6mer from SEQ ID NO:16

<400> SEQUENCE: 317

Gln Pro Glu Gln Pro Phe
1               5

<210> SEQ ID NO 318
<211> LENGTH: 16
<212> TYPE: PRT
<213> ORGANISM: Artificial Sequence
<220> FEATURE:
<223> OTHER INFORMATION: B08-E7

<400> SEQUENCE: 318

Pro Gln Gln Pro Ile Pro Glu Gln Pro Gln Pro Tyr Pro Gln Gln Pro
1               5                   10                  15

<210> SEQ ID NO 319
<211> LENGTH: 16
<212> TYPE: PRT
<213> ORGANISM: Artificial Sequence
<220> FEATURE:
<223> OTHER INFORMATION: B08-E2E7

<400> SEQUENCE: 319

Pro Glu Gln Pro Ile Pro Glu Gln Pro Gln Pro Tyr Pro Gln Gln Pro
1               5                   10                  15
```

```
<210> SEQ ID NO 320
<211> LENGTH: 16
<212> TYPE: PRT
<213> ORGANISM: Artificial Sequence
<220> FEATURE:
<223> OTHER INFORMATION: gluten derived peptide

<400> SEQUENCE: 320

Pro Gln Gln Pro Phe Pro Gln Pro Glu Gln Pro Phe Pro Trp Gln Pro
1               5                   10                  15

<210> SEQ ID NO 321
<211> LENGTH: 16
<212> TYPE: PRT
<213> ORGANISM: Artificial Sequence
<220> FEATURE:
<223> OTHER INFORMATION: gluten derived peptide

<400> SEQUENCE: 321

Phe Pro Glu Gln Pro Ile Pro Glu Gln Pro Gln Pro Tyr Pro Gln Gln
1               5                   10                  15

<210> SEQ ID NO 322
<211> LENGTH: 12
<212> TYPE: PRT
<213> ORGANISM: Artificial Sequence
<220> FEATURE:
<223> OTHER INFORMATION: R11E4E7

<400> SEQUENCE: 322

Pro Phe Pro Glu Gln Pro Glu Gln Ile Ile Pro Gln
1               5                   10

<210> SEQ ID NO 323
<211> LENGTH: 14
<212> TYPE: PRT
<213> ORGANISM: Artificial Sequence
<220> FEATURE:
<223> OTHER INFORMATION: gluten derived peptide

<400> SEQUENCE: 323

Gln Pro Phe Pro Gln Gln Pro Glu Gln Ile Ile Pro Gln Gln
1               5                   10

<210> SEQ ID NO 324
<211> LENGTH: 15
<212> TYPE: PRT
<213> ORGANISM: Artificial Sequence
<220> FEATURE:
<223> OTHER INFORMATION: oat avenin homologue of Av-alpha9A

<400> SEQUENCE: 324

Gln Tyr Gln Pro Tyr Pro Glu Gln Glu Gln Pro Ile Leu Gln Gln
1               5                   10                  15

<210> SEQ ID NO 325
<211> LENGTH: 17
<212> TYPE: PRT
<213> ORGANISM: Artificial Sequence
<220> FEATURE:
<223> OTHER INFORMATION: gluten derived peptide

<400> SEQUENCE: 325

Gln Leu Gln Pro Phe Pro Gln Pro Gln Leu Pro Tyr Pro Gln Pro Gln
1               5                   10                  15

Leu
```

<210> SEQ ID NO 326
<211> LENGTH: 17
<212> TYPE: PRT
<213> ORGANISM: Artificial Sequence
<220> FEATURE:
<223> OTHER INFORMATION: gluten derived peptide

<400> SEQUENCE: 326

Gln Leu Gln Pro Phe Pro Gln Pro Gln Leu Pro Tyr Pro Gln Pro Gln
1               5                   10                  15

Pro

<210> SEQ ID NO 327
<211> LENGTH: 17
<212> TYPE: PRT
<213> ORGANISM: Artificial Sequence
<220> FEATURE:
<223> OTHER INFORMATION: gluten derived peptide

<400> SEQUENCE: 327

Gln Leu Gln Pro Phe Pro Gln Pro Gln Leu Pro Tyr Leu Gln Pro Gln
1               5                   10                  15

Pro

<210> SEQ ID NO 328
<211> LENGTH: 17
<212> TYPE: PRT
<213> ORGANISM: Artificial Sequence
<220> FEATURE:
<223> OTHER INFORMATION: gluten derived peptide

<400> SEQUENCE: 328

Gln Leu Gln Pro Phe Pro Arg Pro Gln Leu Pro Tyr Pro Gln Pro Gln
1               5                   10                  15

Pro

<210> SEQ ID NO 329
<211> LENGTH: 17
<212> TYPE: PRT
<213> ORGANISM: Artificial Sequence
<220> FEATURE:
<223> OTHER INFORMATION: gluten derived peptide

<400> SEQUENCE: 329

Gln Leu Gln Pro Phe Pro Gln Pro Gln Leu Pro Tyr Ser Gln Pro Gln
1               5                   10                  15

Pro

<210> SEQ ID NO 330
<211> LENGTH: 17
<212> TYPE: PRT
<213> ORGANISM: Artificial Sequence
<220> FEATURE:
<223> OTHER INFORMATION: gluten derived peptide

<400> SEQUENCE: 330

Gln Leu Gln Pro Phe Leu Gln Pro Gln Leu Pro Tyr Ser Gln Pro Gln
1               5                   10                  15

Pro

<210> SEQ ID NO 331
<211> LENGTH: 17

<212> TYPE: PRT
<213> ORGANISM: Artificial Sequence
<220> FEATURE:
<223> OTHER INFORMATION: gluten derived peptide

<400> SEQUENCE: 331

Gln Leu Gln Pro Phe Pro Gln Pro Gln Leu Ser Tyr Ser Gln Pro Gln
1               5                   10                  15

Pro

<210> SEQ ID NO 332
<211> LENGTH: 17
<212> TYPE: PRT
<213> ORGANISM: Artificial Sequence
<220> FEATURE:
<223> OTHER INFORMATION: gluten derived peptide

<400> SEQUENCE: 332

Pro Gln Leu Pro Tyr Pro Gln Pro Gln Leu Pro Tyr Pro Gln Pro Gln
1               5                   10                  15

Pro

<210> SEQ ID NO 333
<211> LENGTH: 17
<212> TYPE: PRT
<213> ORGANISM: Artificial Sequence
<220> FEATURE:
<223> OTHER INFORMATION: gluten derived peptide

<400> SEQUENCE: 333

Pro Gln Leu Pro Tyr Pro Gln Pro Gln Leu Pro Tyr Pro Gln Pro Gln
1               5                   10                  15

Leu

<210> SEQ ID NO 334
<211> LENGTH: 17
<212> TYPE: PRT
<213> ORGANISM: Artificial Sequence
<220> FEATURE:
<223> OTHER INFORMATION: gluten derived peptide

<400> SEQUENCE: 334

Pro Gln Pro Gln Pro Phe Pro Pro Gln Leu Pro Tyr Pro Gln Pro Gln
1               5                   10                  15

Ser

<210> SEQ ID NO 335
<211> LENGTH: 17
<212> TYPE: PRT
<213> ORGANISM: Artificial Sequence
<220> FEATURE:
<223> OTHER INFORMATION: gluten derived peptide

<400> SEQUENCE: 335

Pro Gln Pro Gln Pro Phe Pro Pro Gln Leu Pro Tyr Pro Gln Thr Gln
1               5                   10                  15

Pro

<210> SEQ ID NO 336
<211> LENGTH: 17
<212> TYPE: PRT
<213> ORGANISM: Artificial Sequence
<220> FEATURE:
<223> OTHER INFORMATION: gluten derived peptide -continued

<400> SEQUENCE: 336

Pro Gln Pro Gln Pro Phe Pro Pro Gln Leu Pro Tyr Pro Gln Pro Pro
1               5                   10                  15

Pro

<210> SEQ ID NO 337
<211> LENGTH: 17
<212> TYPE: PRT
<213> ORGANISM: Artificial Sequence
<220> FEATURE:
<223> OTHER INFORMATION: gluten derived peptide

<400> SEQUENCE: 337

Gln Leu Gln Pro Phe Pro Gln Pro Glu Leu Pro Tyr Pro Gln Pro Gln
1               5                   10                  15

Leu

<210> SEQ ID NO 338
<211> LENGTH: 17
<212> TYPE: PRT
<213> ORGANISM: Artificial Sequence
<220> FEATURE:
<223> OTHER INFORMATION: gluten derived peptide

<400> SEQUENCE: 338

Gln Leu Gln Pro Phe Pro Gln Pro Glu Leu Pro Tyr Pro Gln Pro Gln
1               5                   10                  15

Pro

<210> SEQ ID NO 339
<211> LENGTH: 17
<212> TYPE: PRT
<213> ORGANISM: Artificial Sequence
<220> FEATURE:
<223> OTHER INFORMATION: gluten derived peptide

<400> SEQUENCE: 339

Gln Leu Gln Pro Phe Pro Gln Pro Glu Leu Pro Tyr Leu Gln Pro Gln
1               5                   10                  15

Pro

<210> SEQ ID NO 340
<211> LENGTH: 17
<212> TYPE: PRT
<213> ORGANISM: Artificial Sequence
<220> FEATURE:
<223> OTHER INFORMATION: gluten derived peptide

<400> SEQUENCE: 340

Gln Leu Gln Pro Phe Pro Arg Pro Glu Leu Pro Tyr Pro Gln Pro Gln
1               5                   10                  15

Pro

<210> SEQ ID NO 341
<211> LENGTH: 17
<212> TYPE: PRT
<213> ORGANISM: Artificial Sequence
<220> FEATURE:
<223> OTHER INFORMATION: gluten derived peptide

<400> SEQUENCE: 341

Gln Leu Gln Pro Phe Pro Gln Pro Glu Leu Pro Tyr Ser Gln Pro Gln

```
1               5                   10                  15
Pro

<210> SEQ ID NO 342
<211> LENGTH: 17
<212> TYPE: PRT
<213> ORGANISM: Artificial Sequence
<220> FEATURE:
<223> OTHER INFORMATION: gluten derived peptide

<400> SEQUENCE: 342

Gln Leu Gln Pro Phe Leu Gln Pro Glu Leu Pro Tyr Ser Gln Pro Gln
1               5                   10                  15

Pro

<210> SEQ ID NO 343
<211> LENGTH: 17
<212> TYPE: PRT
<213> ORGANISM: Artificial Sequence
<220> FEATURE:
<223> OTHER INFORMATION: gluten derived peptide

<400> SEQUENCE: 343

Gln Leu Gln Pro Phe Ser Gln Pro Glu Leu Pro Tyr Ser Gln Pro Gln
1               5                   10                  15

Pro

<210> SEQ ID NO 344
<211> LENGTH: 17
<212> TYPE: PRT
<213> ORGANISM: Artificial Sequence
<220> FEATURE:
<223> OTHER INFORMATION: gluten derived peptide

<400> SEQUENCE: 344

Gln Leu Gln Pro Phe Pro Gln Pro Glu Leu Ser Tyr Ser Gln Pro Gln
1               5                   10                  15

Pro

<210> SEQ ID NO 345
<211> LENGTH: 17
<212> TYPE: PRT
<213> ORGANISM: Artificial Sequence
<220> FEATURE:
<223> OTHER INFORMATION: gluten derived peptide

<400> SEQUENCE: 345

Pro Gln Leu Pro Tyr Pro Gln Pro Glu Leu Pro Tyr Pro Gln Pro Gln
1               5                   10                  15

Pro

<210> SEQ ID NO 346
<211> LENGTH: 17
<212> TYPE: PRT
<213> ORGANISM: Artificial Sequence
<220> FEATURE:
<223> OTHER INFORMATION: gluten derived peptide

<400> SEQUENCE: 346

Pro Gln Leu Pro Tyr Pro Gln Pro Glu Leu Pro Tyr Pro Gln Pro Gln
1               5                   10                  15

Leu
```

<210> SEQ ID NO 347
<211> LENGTH: 17
<212> TYPE: PRT
<213> ORGANISM: Artificial Sequence
<220> FEATURE:
<223> OTHER INFORMATION: gluten derived peptide

<400> SEQUENCE: 347

Pro Gln Pro Gln Pro Phe Pro Pro Glu Leu Pro Tyr Pro Gln Pro Gln
1               5                   10                  15

Ser

<210> SEQ ID NO 348
<211> LENGTH: 17
<212> TYPE: PRT
<213> ORGANISM: Artificial Sequence
<220> FEATURE:
<223> OTHER INFORMATION: gluten derived peptide

<400> SEQUENCE: 348

Pro Gln Pro Gln Pro Phe Pro Pro Glu Leu Pro Tyr Pro Gln Thr Gln
1               5                   10                  15

Pro

<210> SEQ ID NO 349
<211> LENGTH: 17
<212> TYPE: PRT
<213> ORGANISM: Artificial Sequence
<220> FEATURE:
<223> OTHER INFORMATION: gluten derived peptide

<400> SEQUENCE: 349

Pro Gln Pro Gln Pro Phe Pro Pro Glu Leu Pro Tyr Pro Gln Pro Pro
1               5                   10                  15

Pro

<210> SEQ ID NO 350
<211> LENGTH: 15
<212> TYPE: PRT
<213> ORGANISM: Artificial Sequence
<220> FEATURE:
<223> OTHER INFORMATION: gluten derived peptide

<400> SEQUENCE: 350

Pro Phe Arg Pro Glu Gln Pro Tyr Pro Gln Pro Gln Pro Gln Tyr
1               5                   10                  15

<210> SEQ ID NO 351
<211> LENGTH: 15
<212> TYPE: PRT
<213> ORGANISM: Artificial Sequence
<220> FEATURE:
<223> OTHER INFORMATION: gluten derived peptide

<400> SEQUENCE: 351

Pro Gln Gln Pro Gln Gln Ser Phe Pro Glu Gln Glu Gln Pro Ala
1               5                   10                  15

<210> SEQ ID NO 352
<211> LENGTH: 15
<212> TYPE: PRT
<213> ORGANISM: Artificial Sequence
<220> FEATURE:
<223> OTHER INFORMATION: gluten derived peptide

<400> SEQUENCE: 352

Gly Gln Gly Ile Ile Gln Pro Glu Gln Pro Ala Gln Leu Ile Arg
1               5                   10                  15

<210> SEQ ID NO 353
<211> LENGTH: 15
<212> TYPE: PRT
<213> ORGANISM: Artificial Sequence
<220> FEATURE:
<223> OTHER INFORMATION: gluten derived peptide

<400> SEQUENCE: 353

Pro Phe Pro Glu Gln Pro Glu Gln Pro Tyr Pro Gln Gln Pro Gln
1               5                   10                  15

<210> SEQ ID NO 354
<211> LENGTH: 15
<212> TYPE: PRT
<213> ORGANISM: Artificial Sequence
<220> FEATURE:
<223> OTHER INFORMATION: gluten derived peptide

<400> SEQUENCE: 354

Gln Gln Phe Ser Gln Pro Glu Gln Glu Phe Pro Gln Pro Gln Gln
1               5                   10                  15

<210> SEQ ID NO 355
<211> LENGTH: 15
<212> TYPE: PRT
<213> ORGANISM: Artificial Sequence
<220> FEATURE:
<223> OTHER INFORMATION: gluten derived peptide

<400> SEQUENCE: 355

Glu Ile Pro Gln Glu Gln Glu Ile Pro Glu Gln Pro Gln Gln Phe
1               5                   10                  15

<210> SEQ ID NO 356
<211> LENGTH: 15
<212> TYPE: PRT
<213> ORGANISM: Artificial Sequence
<220> FEATURE:
<223> OTHER INFORMATION: gluten derived peptide

<400> SEQUENCE: 356

Glu Gln Ser Glu Glu Ser Gln Gln Pro Phe Gln Pro Gln Pro Phe
1               5                   10                  15

<210> SEQ ID NO 357
<211> LENGTH: 15
<212> TYPE: PRT
<213> ORGANISM: Artificial Sequence
<220> FEATURE:
<223> OTHER INFORMATION: gluten derived peptide

<400> SEQUENCE: 357

Gln Gln Pro Pro Phe Ser Glu Gln Glu Glu Ser Pro Phe Ser Gln
1               5                   10                  15

<210> SEQ ID NO 358
<211> LENGTH: 15
<212> TYPE: PRT
<213> ORGANISM: Artificial Sequence
<220> FEATURE:
<223> OTHER INFORMATION: gluten derived peptide

<400> SEQUENCE: 358

```
Gln Gln Pro Pro Phe Ser Glu Glu Gln Glu Gln Pro Leu Pro Gln
1               5                   10                  15

<210> SEQ ID NO 359
<211> LENGTH: 17
<212> TYPE: PRT
<213> ORGANISM: Artificial Sequence
<220> FEATURE:
<223> OTHER INFORMATION: gluten derived peptide

<400> SEQUENCE: 359

Gln Leu Gln Pro Phe Pro Gln Pro Gln Leu Pro Tyr Pro Gln Pro Gln
1               5                   10                  15

Pro

<210> SEQ ID NO 360
<211> LENGTH: 20
<212> TYPE: PRT
<213> ORGANISM: Artificial Sequence
<220> FEATURE:
<223> OTHER INFORMATION: gluten derived peptide

<400> SEQUENCE: 360

Pro Gln Leu Pro Tyr Pro Gln Pro Gln Leu Pro Tyr Pro Gln Pro Gln
1               5                   10                  15

Leu Pro Tyr Pro
            20

<210> SEQ ID NO 361
<211> LENGTH: 20
<212> TYPE: PRT
<213> ORGANISM: Artificial Sequence
<220> FEATURE:
<223> OTHER INFORMATION: gluten derived peptide

<400> SEQUENCE: 361

Pro Gln Pro Phe Pro Pro Gln Leu Pro Tyr Pro Gln Pro Gln Leu Pro
1               5                   10                  15

Tyr Pro Gln Pro
            20

<210> SEQ ID NO 362
<211> LENGTH: 20
<212> TYPE: PRT
<213> ORGANISM: Artificial Sequence
<220> FEATURE:
<223> OTHER INFORMATION: gluten derived peptide

<400> SEQUENCE: 362

Met Gln Leu Gln Pro Phe Pro Gln Pro Gln Leu Pro Tyr Pro Gln Pro
1               5                   10                  15

Gln Leu Pro Tyr
            20

<210> SEQ ID NO 363
<211> LENGTH: 20
<212> TYPE: PRT
<213> ORGANISM: Artificial Sequence
<220> FEATURE:
<223> OTHER INFORMATION: gluten derived peptide

<400> SEQUENCE: 363

Pro Gln Leu Pro Tyr Pro Gln Pro Gln Leu Pro Tyr Pro Gln Pro Gln
1               5                   10                  15
```

```
Pro Phe Arg Pro
            20

<210> SEQ ID NO 364
<211> LENGTH: 20
<212> TYPE: PRT
<213> ORGANISM: Artificial Sequence
<220> FEATURE:
<223> OTHER INFORMATION: gluten derived peptide

<400> SEQUENCE: 364

Leu Gln Leu Gln Pro Phe Pro Gln Pro Gln Leu Pro Tyr Pro Gln Pro
1               5                   10                  15

Gln Pro Phe Arg
            20

<210> SEQ ID NO 365
<211> LENGTH: 20
<212> TYPE: PRT
<213> ORGANISM: Artificial Sequence
<220> FEATURE:
<223> OTHER INFORMATION: gluten derived peptide

<400> SEQUENCE: 365

Pro Gln Gln Pro Gln Gln Pro Gln Gln Pro Phe Pro Gln Pro Gln Gln
1               5                   10                  15

Pro Phe Pro Trp
            20

<210> SEQ ID NO 366
<211> LENGTH: 20
<212> TYPE: PRT
<213> ORGANISM: Artificial Sequence
<220> FEATURE:
<223> OTHER INFORMATION: gluten derived peptide

<400> SEQUENCE: 366

Gln Pro Phe Pro Gln Pro Gln Gln Pro Phe Pro Trp Gln Pro Gln Gln
1               5                   10                  15

Pro Phe Pro Gln
            20

<210> SEQ ID NO 367
<211> LENGTH: 20
<212> TYPE: PRT
<213> ORGANISM: Artificial Sequence
<220> FEATURE:
<223> OTHER INFORMATION: gluten derived peptide

<400> SEQUENCE: 367

Phe Pro Gln Gln Pro Gln Gln Pro Phe Pro Gln Pro Gln Leu Pro Phe
1               5                   10                  15

Pro Gln Gln Ser
            20

<210> SEQ ID NO 368
<211> LENGTH: 20
<212> TYPE: PRT
<213> ORGANISM: Artificial Sequence
<220> FEATURE:
<223> OTHER INFORMATION: gluten derived peptide

<400> SEQUENCE: 368

Pro Gln Gln Pro Gln Gln Pro Phe Pro Gln Pro Gln Gln Pro Ile Pro
```

```
1               5                   10                  15

Val Gln Pro Gln
            20

<210> SEQ ID NO 369
<211> LENGTH: 20
<212> TYPE: PRT
<213> ORGANISM: Artificial Sequence
<220> FEATURE:
<223> OTHER INFORMATION: gluten derived peptide

<400> SEQUENCE: 369

Leu Gln Leu Gln Pro Phe Pro Gln Pro Gln Leu Pro Tyr Pro Gln Pro
1               5                   10                  15

Gln Leu Pro Tyr
            20

<210> SEQ ID NO 370
<211> LENGTH: 20
<212> TYPE: PRT
<213> ORGANISM: Artificial Sequence
<220> FEATURE:
<223> OTHER INFORMATION: gluten derived peptide

<400> SEQUENCE: 370

Pro Gln Pro Phe Pro Pro Gln Leu Pro Tyr Pro Gln Pro Gln Leu Pro
1               5                   10                  15

Tyr Pro Gln Pro
            20

<210> SEQ ID NO 371
<211> LENGTH: 20
<212> TYPE: PRT
<213> ORGANISM: Artificial Sequence
<220> FEATURE:
<223> OTHER INFORMATION: gluten derived peptide

<400> SEQUENCE: 371

Met Gln Leu Gln Pro Phe Pro Gln Pro Gln Leu Pro Tyr Pro Gln Pro
1               5                   10                  15

Gln Leu Pro Tyr
            20

<210> SEQ ID NO 372
<211> LENGTH: 20
<212> TYPE: PRT
<213> ORGANISM: Artificial Sequence
<220> FEATURE:
<223> OTHER INFORMATION: gluten derived peptide

<400> SEQUENCE: 372

Gln Pro Phe Pro Gln Pro Gln Gln Pro Phe Pro Trp Gln Pro Gln Gln
1               5                   10                  15

Pro Phe Pro Gln
            20

<210> SEQ ID NO 373
<211> LENGTH: 20
<212> TYPE: PRT
<213> ORGANISM: Artificial Sequence
<220> FEATURE:
<223> OTHER INFORMATION: gluten derived peptide

<400> SEQUENCE: 373
```

Pro Gln Gln Pro Gln Gln Pro Phe Pro Gln Pro Gln Pro Ile Pro
1               5                   10                  15

Val Gln Pro Gln
            20

<210> SEQ ID NO 374
<211> LENGTH: 20
<212> TYPE: PRT
<213> ORGANISM: Artificial Sequence
<220> FEATURE:
<223> OTHER INFORMATION: gluten derived peptide

<400> SEQUENCE: 374

Pro Gln Gln Gln Gln Pro Phe Pro Gln Pro Gln Gln Pro Phe Ser Gln
1               5                   10                  15

Gln Pro Gln Gln
            20

<210> SEQ ID NO 375
<211> LENGTH: 20
<212> TYPE: PRT
<213> ORGANISM: Artificial Sequence
<220> FEATURE:
<223> OTHER INFORMATION: gluten derived peptide

<400> SEQUENCE: 375

Gln Gln Pro Gln Gln Pro Phe Pro Gln Pro Gln Leu Pro Phe Pro Gln
1               5                   10                  15

Gln Ser Glu Gln
            20

<210> SEQ ID NO 376
<211> LENGTH: 20
<212> TYPE: PRT
<213> ORGANISM: Artificial Sequence
<220> FEATURE:
<223> OTHER INFORMATION: gluten derived peptide

<400> SEQUENCE: 376

Trp Pro Gln Gln Gln Pro Phe Pro Gln Pro Gln Gln Pro Phe Cys Gln
1               5                   10                  15

Gln Pro Gln Gln
            20

<210> SEQ ID NO 377
<211> LENGTH: 20
<212> TYPE: PRT
<213> ORGANISM: Artificial Sequence
<220> FEATURE:
<223> OTHER INFORMATION: gluten derived peptide

<400> SEQUENCE: 377

Leu Gln Leu Gln Pro Phe Pro Gln Pro Gln Leu Pro Tyr Ser Gln Pro
1               5                   10                  15

Gln Pro Phe Arg
            20

<210> SEQ ID NO 378
<211> LENGTH: 20
<212> TYPE: PRT
<213> ORGANISM: Artificial Sequence
<220> FEATURE:
<223> OTHER INFORMATION: gluten derived peptide

<400> SEQUENCE: 378

```
Leu Gln Pro Phe Pro Gln Pro Gln Phe Leu Pro Gln Leu Pro Tyr
1               5                   10                  15

Pro Gln Pro Gln
            20
```

<210> SEQ ID NO 379
<211> LENGTH: 20
<212> TYPE: PRT
<213> ORGANISM: Artificial Sequence
<220> FEATURE:
<223> OTHER INFORMATION: gluten derived peptide

<400> SEQUENCE: 379

```
Ser Gln Gln Pro Gln Gln Phe Ser Gln Pro Gln Gln Phe Pro
1               5                   10                  15

Gln Pro Gln Gln
            20
```

<210> SEQ ID NO 380
<211> LENGTH: 20
<212> TYPE: PRT
<213> ORGANISM: Artificial Sequence
<220> FEATURE:
<223> OTHER INFORMATION: gluten derived peptide

<400> SEQUENCE: 380

```
Gln Ala Phe Pro Gln Pro Gln Gln Thr Phe Pro His Gln Pro Gln Gln
1               5                   10                  15

Gln Phe Pro Gln
            20
```

<210> SEQ ID NO 381
<211> LENGTH: 20
<212> TYPE: PRT
<213> ORGANISM: Artificial Sequence
<220> FEATURE:
<223> OTHER INFORMATION: gluten derived peptide

<400> SEQUENCE: 381

```
Cys Lys Val Phe Leu Gln Gln Gln Cys Ser Pro Val Ala Met Pro Gln
1               5                   10                  15

Arg Leu Ala Arg
            20
```

<210> SEQ ID NO 382
<211> LENGTH: 20
<212> TYPE: PRT
<213> ORGANISM: Artificial Sequence
<220> FEATURE:
<223> OTHER INFORMATION: gluten derived peptide

<400> SEQUENCE: 382

```
Leu Gln Leu Gln Pro Phe Pro Gln Pro Gln Leu Pro Tyr Leu Gln Pro
1               5                   10                  15

Gln Pro Phe Arg
            20
```

<210> SEQ ID NO 383
<211> LENGTH: 20
<212> TYPE: PRT
<213> ORGANISM: Artificial Sequence
<220> FEATURE:
<223> OTHER INFORMATION: gluten derived peptide

```
<400> SEQUENCE: 383

Gln Gln Gln Phe Ile Gln Pro Gln Pro Phe Pro Gln Gln Pro Gln
1               5                   10                  15

Gln Thr Tyr Pro
            20

<210> SEQ ID NO 384
<211> LENGTH: 20
<212> TYPE: PRT
<213> ORGANISM: Artificial Sequence
<220> FEATURE:
<223> OTHER INFORMATION: gluten derived peptide

<400> SEQUENCE: 384

Ser His Ile Pro Gly Leu Glu Arg Pro Trp Gln Gln Gln Pro Leu Pro
1               5                   10                  15

Pro Gln Gln Thr
            20

<210> SEQ ID NO 385
<211> LENGTH: 20
<212> TYPE: PRT
<213> ORGANISM: Artificial Sequence
<220> FEATURE:
<223> OTHER INFORMATION: gluten derived peptide

<400> SEQUENCE: 385

Ser Gln Gln Pro Gln Gln Pro Phe Pro Gln Pro Gln Gln Gln Phe Pro
1               5                   10                  15

Gln Pro Gln Gln
            20

<210> SEQ ID NO 386
<211> LENGTH: 20
<212> TYPE: PRT
<213> ORGANISM: Artificial Sequence
<220> FEATURE:
<223> OTHER INFORMATION: gluten derived peptide

<400> SEQUENCE: 386

Gln Gln Pro Phe Pro Gln Pro Gln Gln Pro Leu Pro Phe Pro Gln
1               5                   10                  15

Gln Pro Gln Gln
            20

<210> SEQ ID NO 387
<211> LENGTH: 20
<212> TYPE: PRT
<213> ORGANISM: Artificial Sequence
<220> FEATURE:
<223> OTHER INFORMATION: gluten derived peptide

<400> SEQUENCE: 387

Pro Gln Leu Pro Tyr Pro Gln Pro Gln Leu Pro Tyr Pro Gln Pro Gln
1               5                   10                  15

Pro Phe Arg Pro
            20

<210> SEQ ID NO 388
<211> LENGTH: 20
<212> TYPE: PRT
<213> ORGANISM: Artificial Sequence
<220> FEATURE:
<223> OTHER INFORMATION: gluten derived peptide
```

-continued

<400> SEQUENCE: 388

Gln Pro Phe Pro Gln Pro Gln Gln Pro Phe Pro Trp Gln Pro Gln Gln
1               5                   10                  15

Pro Phe Pro Gln
            20

<210> SEQ ID NO 389
<211> LENGTH: 20
<212> TYPE: PRT
<213> ORGANISM: Artificial Sequence
<220> FEATURE:
<223> OTHER INFORMATION: gluten derived peptide

<400> SEQUENCE: 389

Phe Pro Glu Leu Gln Gln Pro Ile Pro Gln Gln Pro Gln Gln Pro Phe
1               5                   10                  15

Pro Leu Gln Pro
            20

<210> SEQ ID NO 390
<211> LENGTH: 20
<212> TYPE: PRT
<213> ORGANISM: Artificial Sequence
<220> FEATURE:
<223> OTHER INFORMATION: gluten derived peptide

<400> SEQUENCE: 390

Gln Gly Gln Gln Gly Tyr Tyr Pro Ile Ser Pro Gln Gln Ser Gly Gln
1               5                   10                  15

Gly Gln Gln Pro
            20

<210> SEQ ID NO 391
<211> LENGTH: 20
<212> TYPE: PRT
<213> ORGANISM: Artificial Sequence
<220> FEATURE:
<223> OTHER INFORMATION: gluten derived peptide

<400> SEQUENCE: 391

Leu Gln Pro Gly Gln Gly Gln Pro Gly Tyr Tyr Pro Thr Ser Pro Gln
1               5                   10                  15

Gln Ile Gly Gln
            20

<210> SEQ ID NO 392
<211> LENGTH: 20
<212> TYPE: PRT
<213> ORGANISM: Artificial Sequence
<220> FEATURE:
<223> OTHER INFORMATION: gluten derived peptide

<400> SEQUENCE: 392

Gln Gln Phe Leu Gln Pro Gln Gln Pro Phe Pro Gln Gln Pro Gln Gln
1               5                   10                  15

Pro Tyr Pro Gln
            20

<210> SEQ ID NO 393
<211> LENGTH: 20
<212> TYPE: PRT
<213> ORGANISM: Artificial Sequence
<220> FEATURE:

<223> OTHER INFORMATION: gluten derived peptide

<400> SEQUENCE: 393

Pro Gly Gln Gly Gln Ser Gly Tyr Tyr Pro Thr Ser Pro Gln Gln Ser
1               5                   10                  15

Gly Gln Lys Gln
            20

<210> SEQ ID NO 394
<211> LENGTH: 20
<212> TYPE: PRT
<213> ORGANISM: Artificial Sequence
<220> FEATURE:
<223> OTHER INFORMATION: gluten derived peptide

<400> SEQUENCE: 394

Thr Pro Ile Gln Pro Gln Gln Pro Phe Pro Gln Gln Pro Gln Gln Pro
1               5                   10                  15

Gln Gln Pro Phe
            20

<210> SEQ ID NO 395
<211> LENGTH: 20
<212> TYPE: PRT
<213> ORGANISM: Artificial Sequence
<220> FEATURE:
<223> OTHER INFORMATION: gluten derived peptide

<400> SEQUENCE: 395

Pro Gln Gln Pro Gln Gln Pro Phe Pro Leu Gln Pro Gln Gln Pro Phe
1               5                   10                  15

Pro Gln Gln Pro
            20

<210> SEQ ID NO 396
<211> LENGTH: 20
<212> TYPE: PRT
<213> ORGANISM: Artificial Sequence
<220> FEATURE:
<223> OTHER INFORMATION: gluten derived peptide

<400> SEQUENCE: 396

Pro Phe Thr Gln Pro Gln Gln Pro Thr Pro Ile Gln Pro Gln Gln Pro
1               5                   10                  15

Phe Pro Gln Gln
            20

<210> SEQ ID NO 397
<211> LENGTH: 20
<212> TYPE: PRT
<213> ORGANISM: Artificial Sequence
<220> FEATURE:
<223> OTHER INFORMATION: gluten derived peptide

<400> SEQUENCE: 397

Pro Gln Gln Pro Phe Pro Gln Pro Gln Gln Thr Phe Pro Gln Gln Pro
1               5                   10                  15

Gln Leu Pro Phe
            20

<210> SEQ ID NO 398
<211> LENGTH: 20
<212> TYPE: PRT
<213> ORGANISM: Artificial Sequence
<220> FEATURE:
<223> OTHER INFORMATION: gluten derived peptide

<400> SEQUENCE: 398

Gly Gln Gly Gln Ser Gly Tyr Tyr Pro Thr Ser Pro Gln Gln Ser Gly
1               5                   10                  15

Gln Glu Ala Thr
            20

<210> SEQ ID NO 399
<211> LENGTH: 20
<212> TYPE: PRT
<213> ORGANISM: Artificial Sequence
<220> FEATURE:
<223> OTHER INFORMATION: gluten derived peptide

<400> SEQUENCE: 399

Pro Leu Gln Pro Gln Gln Pro Phe Pro Gln Gln Pro Gln Gln Pro Phe
1               5                   10                  15

Pro Gln Pro Gln
            20

<210> SEQ ID NO 400
<211> LENGTH: 20
<212> TYPE: PRT
<213> ORGANISM: Artificial Sequence
<220> FEATURE:
<223> OTHER INFORMATION: gluten derived peptide

<400> SEQUENCE: 400

Gln Pro Phe Pro Gln Leu Gln Gln Pro Gln Gln Pro Leu Pro Gln Pro
1               5                   10                  15

Gln Gln Pro Gln
            20

<210> SEQ ID NO 401
<211> LENGTH: 20
<212> TYPE: PRT
<213> ORGANISM: Artificial Sequence
<220> FEATURE:
<223> OTHER INFORMATION: gluten derived peptide

<400> SEQUENCE: 401

Gln Gln Pro Phe Pro Gln Gln Pro Gln Gln Pro Phe Pro Gln Pro Gln
1               5                   10                  15

Gln Pro Ile Pro
            20

<210> SEQ ID NO 402
<211> LENGTH: 20
<212> TYPE: PRT
<213> ORGANISM: Artificial Sequence
<220> FEATURE:
<223> OTHER INFORMATION: gluten derived peptide

<400> SEQUENCE: 402

Pro Gln Gln Pro Phe Pro Gln Pro Gln Gln Thr Phe Pro Gln Gln Pro
1               5                   10                  15

Gln Leu Pro Phe
            20

<210> SEQ ID NO 403
<211> LENGTH: 20
<212> TYPE: PRT

-continued

```
<213> ORGANISM: Artificial Sequence
<220> FEATURE:
<223> OTHER INFORMATION: gluten derived peptide

<400> SEQUENCE: 403

Val Ala His Ala Ile Ile Met His Gln Gln Gln Gln Gln Gln Gln Glu
1               5                   10                  15

Gln Lys Gln Gln
            20

<210> SEQ ID NO 404
<211> LENGTH: 20
<212> TYPE: PRT
<213> ORGANISM: Artificial Sequence
<220> FEATURE:
<223> OTHER INFORMATION: gluten derived peptide

<400> SEQUENCE: 404

Pro Gln Gln Pro Phe Pro Gln Gln Pro Gln Gln Gln Phe Pro Gln Pro
1               5                   10                  15

Gln Gln Pro Gln
            20

<210> SEQ ID NO 405
<211> LENGTH: 20
<212> TYPE: PRT
<213> ORGANISM: Artificial Sequence
<220> FEATURE:
<223> OTHER INFORMATION: gluten derived peptide

<400> SEQUENCE: 405

Gln Gln Pro Ala Gln Tyr Glu Val Ile Arg Ser Leu Val Leu Arg Thr
1               5                   10                  15

Leu Pro Asn Met
            20

<210> SEQ ID NO 406
<211> LENGTH: 20
<212> TYPE: PRT
<213> ORGANISM: Artificial Sequence
<220> FEATURE:
<223> OTHER INFORMATION: gluten derived peptide

<400> SEQUENCE: 406

Ala Thr Ala Asn Met Gln Val Asp Pro Ser Gly Gln Val Gln Trp Pro
1               5                   10                  15

Gln Gln Gln Pro
            20

<210> SEQ ID NO 407
<211> LENGTH: 20
<212> TYPE: PRT
<213> ORGANISM: Artificial Sequence
<220> FEATURE:
<223> OTHER INFORMATION: gluten derived peptide

<400> SEQUENCE: 407

Gln Pro Phe Pro Gln Pro Gln Gln Pro Phe Pro Trp Gln Pro Gln Gln
1               5                   10                  15

Pro Phe Pro Gln
            20

<210> SEQ ID NO 408
<211> LENGTH: 20
```

<212> TYPE: PRT
<213> ORGANISM: Artificial Sequence
<220> FEATURE:
<223> OTHER INFORMATION: gluten derived peptide

<400> SEQUENCE: 408

Trp Gln Pro Gln Gln Pro Phe Pro Gln Pro Gln Gln Pro Phe Pro Leu
1               5                   10                  15

Gln Pro Gln Gln
            20

<210> SEQ ID NO 409
<211> LENGTH: 20
<212> TYPE: PRT
<213> ORGANISM: Artificial Sequence
<220> FEATURE:
<223> OTHER INFORMATION: gluten derived peptide

<400> SEQUENCE: 409

Gln Pro Gln Gln Pro Phe Pro Gln Pro Gln Gln Pro Ile Pro Tyr Gln
1               5                   10                  15

Pro Gln Gln Pro
            20

<210> SEQ ID NO 410
<211> LENGTH: 20
<212> TYPE: PRT
<213> ORGANISM: Artificial Sequence
<220> FEATURE:
<223> OTHER INFORMATION: gluten derived peptide

<400> SEQUENCE: 410

Gln Pro Gln Gln Pro Gln Pro Phe Pro Gln Gln Pro Val Pro Gln Gln
1               5                   10                  15

Pro Gln Pro Tyr
            20

<210> SEQ ID NO 411
<211> LENGTH: 20
<212> TYPE: PRT
<213> ORGANISM: Artificial Sequence
<220> FEATURE:
<223> OTHER INFORMATION: gluten derived peptide

<400> SEQUENCE: 411

Pro Gln Pro Phe Pro Gln Gln Pro Ile Pro Gln Gln Pro Gln Pro Tyr
1               5                   10                  15

Pro Gln Gln Pro
            20

<210> SEQ ID NO 412
<211> LENGTH: 20
<212> TYPE: PRT
<213> ORGANISM: Artificial Sequence
<220> FEATURE:
<223> OTHER INFORMATION: gluten derived peptide

<400> SEQUENCE: 412

Gln Gln Pro Gln Pro Phe Ser Gln Gln Pro Ile Pro Gln Gln Pro Gln
1               5                   10                  15

Pro Tyr Pro Gln
            20

<210> SEQ ID NO 413

```
<211> LENGTH: 20
<212> TYPE: PRT
<213> ORGANISM: Artificial Sequence
<220> FEATURE:
<223> OTHER INFORMATION: gluten derived peptide

<400> SEQUENCE: 413

Gln Ser Gln Gln Gln Phe Pro Gln Pro Gln Pro Phe Pro Gln Gln
1               5                   10                  15

Pro Gln Gln Pro
        20

<210> SEQ ID NO 414
<211> LENGTH: 20
<212> TYPE: PRT
<213> ORGANISM: Artificial Sequence
<220> FEATURE:
<223> OTHER INFORMATION: gluten derived peptide

<400> SEQUENCE: 414

Pro Gln Pro Phe Pro Gln Gln Pro Ile Pro Gln Gln Pro Gln Pro Tyr
1               5                   10                  15

Pro Gln Gln Pro
        20

<210> SEQ ID NO 415
<211> LENGTH: 20
<212> TYPE: PRT
<213> ORGANISM: Artificial Sequence
<220> FEATURE:
<223> OTHER INFORMATION: gluten derived peptide

<400> SEQUENCE: 415

Gln Gln Pro Phe Pro Gln Gln Pro Phe Pro Gln Gln Pro Gln Pro Tyr
1               5                   10                  15

Pro Gln Gln Pro
        20

<210> SEQ ID NO 416
<211> LENGTH: 20
<212> TYPE: PRT
<213> ORGANISM: Artificial Sequence
<220> FEATURE:
<223> OTHER INFORMATION: gluten derived peptide

<400> SEQUENCE: 416

Pro Gln Gln Pro Gln Gln Pro Phe Pro Gln Pro Gln Gln Pro Phe Ser
1               5                   10                  15

Trp Gln Pro Gln
        20

<210> SEQ ID NO 417
<211> LENGTH: 20
<212> TYPE: PRT
<213> ORGANISM: Artificial Sequence
<220> FEATURE:
<223> OTHER INFORMATION: gluten derived peptide

<400> SEQUENCE: 417

Gln Pro Gln Pro Tyr Pro Gln Gln Pro Gln Pro Tyr Pro Gln Gln Pro
1               5                   10                  15

Phe Gln Pro Gln
        20
```

-continued

```
<210> SEQ ID NO 418
<211> LENGTH: 20
<212> TYPE: PRT
<213> ORGANISM: Artificial Sequence
<220> FEATURE:
<223> OTHER INFORMATION: gluten derived peptide

<400> SEQUENCE: 418

Gln Gln Pro Phe Pro Gln Gln Pro Phe Pro Gln Gln Pro Gln Pro Tyr
1               5                   10                  15

Pro Gln Gln Pro
            20

<210> SEQ ID NO 419
<211> LENGTH: 20
<212> TYPE: PRT
<213> ORGANISM: Artificial Sequence
<220> FEATURE:
<223> OTHER INFORMATION: gluten derived peptide

<400> SEQUENCE: 419

Pro Gln Pro Tyr Pro Gln Gln Pro Gln Gln Phe Pro Gln Gln Pro Pro
1               5                   10                  15

Phe Cys Gln Gln
            20

<210> SEQ ID NO 420
<211> LENGTH: 20
<212> TYPE: PRT
<213> ORGANISM: Artificial Sequence
<220> FEATURE:
<223> OTHER INFORMATION: gluten derived peptide

<400> SEQUENCE: 420

Phe Gln Gln Pro Gln Gln Ser Tyr Pro Val Gln Pro Gln Gln Pro Phe
1               5                   10                  15

Pro Gln Pro Gln
            20

<210> SEQ ID NO 421
<211> LENGTH: 20
<212> TYPE: PRT
<213> ORGANISM: Artificial Sequence
<220> FEATURE:
<223> OTHER INFORMATION: gluten derived peptide

<400> SEQUENCE: 421

Tyr Pro Gln Gln Pro Gln Pro Phe Pro Gln Gln Pro Ile Pro Gln Gln
1               5                   10                  15

Pro Gln Pro Tyr
            20

<210> SEQ ID NO 422
<211> LENGTH: 20
<212> TYPE: PRT
<213> ORGANISM: Artificial Sequence
<220> FEATURE:
<223> OTHER INFORMATION: gluten derived peptide

<400> SEQUENCE: 422

Gln Gln Gln Pro Phe Pro Gln Gln Pro Ile Pro Gln Gln Pro Gln Pro
1               5                   10                  15

Tyr Pro Gln Gln
            20
```

-continued

<210> SEQ ID NO 423
<211> LENGTH: 20
<212> TYPE: PRT
<213> ORGANISM: Artificial Sequence
<220> FEATURE:
<223> OTHER INFORMATION: gluten derived peptide

<400> SEQUENCE: 423

Gln Pro Gln Gln Pro Gln Pro Phe Pro Gln Gln Pro Val Pro Gln Gln
1               5                   10                  15

Pro Gln Pro Tyr
            20

<210> SEQ ID NO 424
<211> LENGTH: 20
<212> TYPE: PRT
<213> ORGANISM: Artificial Sequence
<220> FEATURE:
<223> OTHER INFORMATION: gluten derived peptide

<400> SEQUENCE: 424

Gln Pro Gln Pro Phe Pro Gln Gln Pro Ile Pro Leu Gln Pro His Gln
1               5                   10                  15

Pro Tyr Thr Gln
            20

<210> SEQ ID NO 425
<211> LENGTH: 20
<212> TYPE: PRT
<213> ORGANISM: Artificial Sequence
<220> FEATURE:
<223> OTHER INFORMATION: gluten derived peptide

<400> SEQUENCE: 425

Leu Pro Arg Pro Gln Gln Pro Phe Pro Trp Gln Pro Gln Gln Pro Phe
1               5                   10                  15

Pro Gln Pro Gln
            20

<210> SEQ ID NO 426
<211> LENGTH: 20
<212> TYPE: PRT
<213> ORGANISM: Artificial Sequence
<220> FEATURE:
<223> OTHER INFORMATION: gluten derived peptide

<400> SEQUENCE: 426

Gln Gln Pro Phe Pro Leu Gln Pro Gln Gln Pro Phe Pro Gln Pro Gln
1               5                   10                  15

Pro Phe Pro Gln
            20

<210> SEQ ID NO 427
<211> LENGTH: 20
<212> TYPE: PRT
<213> ORGANISM: Artificial Sequence
<220> FEATURE:
<223> OTHER INFORMATION: gluten derived peptide

<400> SEQUENCE: 427

Pro Phe Pro Gln Gln Pro Gln Gln Pro Phe Pro Gln Pro Gln Gln Pro
1               5                   10                  15

Phe Arg Gln Gln
            20

```
<210> SEQ ID NO 428
<211> LENGTH: 20
<212> TYPE: PRT
<213> ORGANISM: Artificial Sequence
<220> FEATURE:
<223> OTHER INFORMATION: gluten derived peptide

<400> SEQUENCE: 428

Pro Gln Gln Pro Phe Gln Pro Gln Gln Pro Phe Pro Gln Gln Thr Ile
1               5                   10                  15

Pro Gln Gln Pro
            20

<210> SEQ ID NO 429
<211> LENGTH: 20
<212> TYPE: PRT
<213> ORGANISM: Artificial Sequence
<220> FEATURE:
<223> OTHER INFORMATION: gluten derived peptide

<400> SEQUENCE: 429

Asn Pro Leu Gln Pro Gln Gln Pro Phe Pro Leu Gln Pro Gln Pro Pro
1               5                   10                  15

Gln Gln Pro Phe
            20

<210> SEQ ID NO 430
<211> LENGTH: 20
<212> TYPE: PRT
<213> ORGANISM: Artificial Sequence
<220> FEATURE:
<223> OTHER INFORMATION: gluten derived peptide

<400> SEQUENCE: 430

Asn Pro Leu Gln Pro Gln Gln Pro Phe Pro Leu Gln Pro Gln Pro Pro
1               5                   10                  15

Gln Gln Pro Phe
            20

<210> SEQ ID NO 431
<211> LENGTH: 20
<212> TYPE: PRT
<213> ORGANISM: Artificial Sequence
<220> FEATURE:
<223> OTHER INFORMATION: gluten derived peptide

<400> SEQUENCE: 431

Pro Phe Pro Gln Gln Pro Gln Gln Pro Phe Pro Gln Pro Gln Gln Pro
1               5                   10                  15

Phe Arg Gln Gln
            20

<210> SEQ ID NO 432
<211> LENGTH: 20
<212> TYPE: PRT
<213> ORGANISM: Artificial Sequence
<220> FEATURE:
<223> OTHER INFORMATION: gluten derived peptide

<400> SEQUENCE: 432

Gln Pro Gln Gln Pro Phe Pro Leu Gln Pro Gln Gln Pro Phe Pro Trp
1               5                   10                  15

Gln Pro Gln Gln
```

```
<210> SEQ ID NO 433
<211> LENGTH: 20
<212> TYPE: PRT
<213> ORGANISM: Artificial Sequence
<220> FEATURE:
<223> OTHER INFORMATION: gluten derived peptide

<400> SEQUENCE: 433

Thr Phe Pro Pro Ser Gln Gln Pro Asn Pro Leu Gln Pro Gln Gln Pro
1               5                   10                  15

Phe Pro Leu Gln
            20

<210> SEQ ID NO 434
<211> LENGTH: 20
<212> TYPE: PRT
<213> ORGANISM: Artificial Sequence
<220> FEATURE:
<223> OTHER INFORMATION: gluten derived peptide

<400> SEQUENCE: 434

Pro Gln Gln Thr Ile Pro Gln Gln Pro Gln Gln Pro Phe Pro Leu Gln
1               5                   10                  15

Pro Gln Gln Pro
            20

<210> SEQ ID NO 435
<211> LENGTH: 20
<212> TYPE: PRT
<213> ORGANISM: Artificial Sequence
<220> FEATURE:
<223> OTHER INFORMATION: gluten derived peptide

<400> SEQUENCE: 435

Gln Pro Gln Gln Pro Phe Ser Phe Ser Gln Gln Pro Gln Gln Pro Phe
1               5                   10                  15

Pro Leu Gln Pro
            20

<210> SEQ ID NO 436
<211> LENGTH: 20
<212> TYPE: PRT
<213> ORGANISM: Artificial Sequence
<220> FEATURE:
<223> OTHER INFORMATION: gluten derived peptide

<400> SEQUENCE: 436

Gln Gln Pro Phe Pro Gln Gln Pro Phe Pro Gln Gln Pro Gln Pro Tyr
1               5                   10                  15

Pro Gln Gln Pro
            20

<210> SEQ ID NO 437
<211> LENGTH: 20
<212> TYPE: PRT
<213> ORGANISM: Artificial Sequence
<220> FEATURE:
<223> OTHER INFORMATION: gluten derived peptide

<400> SEQUENCE: 437

Gln Gln Leu Pro Leu Gln Pro Gln Gln Pro Phe Pro Gln Pro Gln Gln
1               5                   10                  15
```

```
Pro Ile Pro Gln
        20

<210> SEQ ID NO 438
<211> LENGTH: 20
<212> TYPE: PRT
<213> ORGANISM: Artificial Sequence
<220> FEATURE:
<223> OTHER INFORMATION: gluten derived peptide

<400> SEQUENCE: 438

Ser Ile Pro Gln Pro Gln Gln Pro Phe Pro Gln Pro Gln Gln Pro Phe
1               5                   10                  15

Pro Gln Ser Gln
        20

<210> SEQ ID NO 439
<211> LENGTH: 20
<212> TYPE: PRT
<213> ORGANISM: Artificial Sequence
<220> FEATURE:
<223> OTHER INFORMATION: gluten derived peptide

<400> SEQUENCE: 439

Gln Pro Phe Pro Gln Pro Gln Gln Pro Thr Pro Ile Gln Pro Gln Gln
1               5                   10                  15

Pro Phe Pro Gln
        20

<210> SEQ ID NO 440
<211> LENGTH: 20
<212> TYPE: PRT
<213> ORGANISM: Artificial Sequence
<220> FEATURE:
<223> OTHER INFORMATION: gluten derived peptide

<400> SEQUENCE: 440

Gln Pro Phe Pro Gln Pro Gln Gln Pro Thr Pro Ile Gln Pro Gln Gln
1               5                   10                  15

Pro Phe Pro Gln
        20

<210> SEQ ID NO 441
<211> LENGTH: 20
<212> TYPE: PRT
<213> ORGANISM: Artificial Sequence
<220> FEATURE:
<223> OTHER INFORMATION: gluten derived peptide

<400> SEQUENCE: 441

Pro Ala Pro Ile Gln Pro Gln Gln Pro Phe Pro Gln Gln Pro Gln Gln
1               5                   10                  15

Pro Phe Pro Gln
        20

<210> SEQ ID NO 442
<211> LENGTH: 20
<212> TYPE: PRT
<213> ORGANISM: Artificial Sequence
<220> FEATURE:
<223> OTHER INFORMATION: gluten derived peptide

<400> SEQUENCE: 442

Pro Gln Gln Pro Phe Pro Gln Gln Pro Glu Gln Ile Ile Pro Gln Gln
1               5                   10                  15
```

```
Pro Gln Gln Pro
        20

<210> SEQ ID NO 443
<211> LENGTH: 20
<212> TYPE: PRT
<213> ORGANISM: Artificial Sequence
<220> FEATURE:
<223> OTHER INFORMATION: gluten derived peptide

<400> SEQUENCE: 443

Gln Tyr Ser Pro Tyr Gln Pro Gln Gln Pro Phe Pro Gln Pro Gln Gln
1               5                   10                  15

Pro Thr Pro Ile
        20

<210> SEQ ID NO 444
<211> LENGTH: 20
<212> TYPE: PRT
<213> ORGANISM: Artificial Sequence
<220> FEATURE:
<223> OTHER INFORMATION: gluten derived peptide

<400> SEQUENCE: 444

Ser Gln Gln Pro Gln Arg Pro Gln Gln Pro Phe Pro Gln Gln Pro Gln
1               5                   10                  15

Gln Ile Ile Pro
        20

<210> SEQ ID NO 445
<211> LENGTH: 20
<212> TYPE: PRT
<213> ORGANISM: Artificial Sequence
<220> FEATURE:
<223> OTHER INFORMATION: gluten derived peptide

<400> SEQUENCE: 445

Gln Gln Leu Pro Leu Gln Pro Gln Gln Pro Phe Pro Gln Pro Gln Gln
1               5                   10                  15

Pro Ile Pro Gln
        20

<210> SEQ ID NO 446
<211> LENGTH: 20
<212> TYPE: PRT
<213> ORGANISM: Artificial Sequence
<220> FEATURE:
<223> OTHER INFORMATION: gluten derived peptide

<400> SEQUENCE: 446

Phe Pro Leu Gln Pro Gln Gln Pro Phe Pro Gln Gln Pro Glu Gln Ile
1               5                   10                  15

Ile Ser Gln Gln
        20

<210> SEQ ID NO 447
<211> LENGTH: 20
<212> TYPE: PRT
<213> ORGANISM: Artificial Sequence
<220> FEATURE:
<223> OTHER INFORMATION: gluten derived peptide

<400> SEQUENCE: 447

Pro Gln Gln Pro Phe Pro Gln Gln Pro Glu Gln Ile Ile Pro Gln Gln
```

```
                1               5                  10                  15
Pro Gln Gln Pro
            20

<210> SEQ ID NO 448
<211> LENGTH: 20
<212> TYPE: PRT
<213> ORGANISM: Artificial Sequence
<220> FEATURE:
<223> OTHER INFORMATION: gluten derived peptide

<400> SEQUENCE: 448

Phe Pro Gln Gln Pro Gln Gln Pro Phe Pro Gln Pro Gln Gln Gln Leu
1               5                  10                  15

Pro Leu Gln Pro
            20

<210> SEQ ID NO 449
<211> LENGTH: 20
<212> TYPE: PRT
<213> ORGANISM: Artificial Sequence
<220> FEATURE:
<223> OTHER INFORMATION: gluten derived peptide

<400> SEQUENCE: 449

Ser Pro Gln Pro Gln Gln Pro Tyr Pro Gln Gln Pro Phe Pro Gln Gln
1               5                  10                  15

Pro Gln Gln Pro
            20

<210> SEQ ID NO 450
<211> LENGTH: 20
<212> TYPE: PRT
<213> ORGANISM: Artificial Sequence
<220> FEATURE:
<223> OTHER INFORMATION: gluten derived peptide

<400> SEQUENCE: 450

Gln Gln Pro Gln Gln Pro Phe Pro Leu Gln Pro Gln Gln Pro Val Pro
1               5                  10                  15

Gln Gln Pro Gln
            20

<210> SEQ ID NO 451
<211> LENGTH: 20
<212> TYPE: PRT
<213> ORGANISM: Artificial Sequence
<220> FEATURE:
<223> OTHER INFORMATION: gluten derived peptide

<400> SEQUENCE: 451

Gln Pro Gln Gln Ile Ile Pro Gln Gln Pro Gln Gln Pro Phe Pro Leu
1               5                  10                  15

Gln Pro Gln Gln
            20

<210> SEQ ID NO 452
<211> LENGTH: 20
<212> TYPE: PRT
<213> ORGANISM: Artificial Sequence
<220> FEATURE:
<223> OTHER INFORMATION: gluten derived peptide

<400> SEQUENCE: 452
```

```
Pro Gln Gln Pro Phe Pro Gln Gln Pro Glu Gln Ile Ile Pro Gln Gln
1               5                   10                  15

Pro Gln Gln Pro
        20

<210> SEQ ID NO 453
<211> LENGTH: 20
<212> TYPE: PRT
<213> ORGANISM: Artificial Sequence
<220> FEATURE:
<223> OTHER INFORMATION: gluten derived peptide

<400> SEQUENCE: 453

Gln Thr Gln Gln Ser Ile Pro Gln Pro Gln Gln Pro Phe Pro Gln Pro
1               5                   10                  15

Gln Gln Pro Phe
        20

<210> SEQ ID NO 454
<211> LENGTH: 20
<212> TYPE: PRT
<213> ORGANISM: Artificial Sequence
<220> FEATURE:
<223> OTHER INFORMATION: gluten derived peptide

<400> SEQUENCE: 454

Gln Gln Pro Phe Leu Leu Gln Pro Gln Gln Pro Phe Ser Gln Pro Gln
1               5                   10                  15

Gln Pro Phe Leu
        20

<210> SEQ ID NO 455
<211> LENGTH: 20
<212> TYPE: PRT
<213> ORGANISM: Artificial Sequence
<220> FEATURE:
<223> OTHER INFORMATION: gluten derived peptide

<400> SEQUENCE: 455

Gln Gln Pro Gln Gln Pro Phe Pro Leu Gln Pro Gln Gln Pro Val Pro
1               5                   10                  15

Gln Gln Pro Gln
        20

<210> SEQ ID NO 456
<211> LENGTH: 20
<212> TYPE: PRT
<213> ORGANISM: Artificial Sequence
<220> FEATURE:
<223> OTHER INFORMATION: gluten derived peptide

<400> SEQUENCE: 456

Glu Gln Ile Ile Ser Gln Gln Pro Phe Pro Leu Gln Pro Gln Gln Pro
1               5                   10                  15

Phe Ser Gln Pro
        20

<210> SEQ ID NO 457
<211> LENGTH: 20
<212> TYPE: PRT
<213> ORGANISM: Artificial Sequence
<220> FEATURE:
<223> OTHER INFORMATION: gluten derived peptide

<400> SEQUENCE: 457
```

Asn Met Gln Val Gly Pro Ser Gly Gln Val Glu Trp Pro Gln Gln
1               5                   10                  15

Pro Leu Pro Gln
            20

<210> SEQ ID NO 458
<211> LENGTH: 20
<212> TYPE: PRT
<213> ORGANISM: Artificial Sequence
<220> FEATURE:
<223> OTHER INFORMATION: gluten derived peptide

<400> SEQUENCE: 458

Pro Gln Gln Leu Phe Pro Leu Pro Gln Gln Pro Phe Pro Gln Pro Gln
1               5                   10                  15

Gln Pro Phe Pro
            20

<210> SEQ ID NO 459
<211> LENGTH: 20
<212> TYPE: PRT
<213> ORGANISM: Artificial Sequence
<220> FEATURE:
<223> OTHER INFORMATION: gluten derived peptide

<400> SEQUENCE: 459

Pro Gln Thr Gln Gln Pro Gln Gln Pro Phe Pro Gln Pro Gln Gln Pro
1               5                   10                  15

Gln Gln Leu Phe
            20

<210> SEQ ID NO 460
<211> LENGTH: 20
<212> TYPE: PRT
<213> ORGANISM: Artificial Sequence
<220> FEATURE:
<223> OTHER INFORMATION: gluten derived peptide

<400> SEQUENCE: 460

Ser Pro Gln Gln Pro Gln Leu Pro Phe Pro Gln Pro Gln Gln Pro Phe
1               5                   10                  15

Val Val Val Val
            20

<210> SEQ ID NO 461
<211> LENGTH: 20
<212> TYPE: PRT
<213> ORGANISM: Artificial Sequence
<220> FEATURE:
<223> OTHER INFORMATION: gluten derived peptide

<400> SEQUENCE: 461

Phe Pro Gln Gln Pro Glu Gln Ile Ile Ser Gln Gln Pro Gln Gln Pro
1               5                   10                  15

Phe Pro Leu Gln
            20

<210> SEQ ID NO 462
<211> LENGTH: 20
<212> TYPE: PRT
<213> ORGANISM: Artificial Sequence
<220> FEATURE:
<223> OTHER INFORMATION: gluten derived peptide

```
<400> SEQUENCE: 462

Pro Ala Pro Ile Gln Pro Gln Gln Pro Phe Pro Gln Gln Pro Gln Gln
1               5                   10                  15

Pro Phe Pro Gln
            20

<210> SEQ ID NO 463
<211> LENGTH: 20
<212> TYPE: PRT
<213> ORGANISM: Artificial Sequence
<220> FEATURE:
<223> OTHER INFORMATION: gluten derived peptide

<400> SEQUENCE: 463

Pro Gln Glu Pro Gln Gln Leu Phe Pro Gln Ser Gln Gln Pro Gln Gln
1               5                   10                  15

Pro Phe Pro Gln
            20

<210> SEQ ID NO 464
<211> LENGTH: 20
<212> TYPE: PRT
<213> ORGANISM: Artificial Sequence
<220> FEATURE:
<223> OTHER INFORMATION: gluten derived peptide

<400> SEQUENCE: 464

Ser Pro Gln Pro Gln Gln Pro Tyr Pro Gln Gln Pro Phe Pro Gln Gln
1               5                   10                  15

Pro Gln Gln Pro
            20

<210> SEQ ID NO 465
<211> LENGTH: 20
<212> TYPE: PRT
<213> ORGANISM: Artificial Sequence
<220> FEATURE:
<223> OTHER INFORMATION: gluten derived peptide

<400> SEQUENCE: 465

Pro Thr Pro Ile Gln Pro Gln Gln Pro Phe Pro Gln Arg Pro Gln Gln
1               5                   10                  15

Pro Phe Pro Gln
            20

<210> SEQ ID NO 466
<211> LENGTH: 16
<212> TYPE: PRT
<213> ORGANISM: Artificial Sequence
<220> FEATURE:
<223> OTHER INFORMATION: gluten derived peptide

<400> SEQUENCE: 466

Gln Leu Gln Pro Phe Pro Gln Pro Glu Leu Pro Tyr Pro Gln Pro Gln
1               5                   10                  15

<210> SEQ ID NO 467
<211> LENGTH: 17
<212> TYPE: PRT
<213> ORGANISM: Artificial Sequence
<220> FEATURE:
<223> OTHER INFORMATION: gluten derived peptide

<400> SEQUENCE: 467
```

```
Gln Pro Glu Gln Pro Phe Pro Gln Pro Glu Gln Pro Phe Pro Trp Gln
1               5                   10                  15
Pro
```

<210> SEQ ID NO 468
<211> LENGTH: 16
<212> TYPE: PRT
<213> ORGANISM: Artificial Sequence
<220> FEATURE:
<223> OTHER INFORMATION: gluten derived peptide

<400> SEQUENCE: 468

```
Gly Gln Gln Pro Phe Pro Gln Pro Glu Gln Pro Phe Pro Leu Gln Gly
1               5                   10                  15
```

<210> SEQ ID NO 469
<211> LENGTH: 16
<212> TYPE: PRT
<213> ORGANISM: Artificial Sequence
<220> FEATURE:
<223> OTHER INFORMATION: gluten derived peptide

<400> SEQUENCE: 469

```
Gly Gln Gln Pro Phe Pro Gln Pro Glu Gln Pro Ile Pro Tyr Gln Gly
1               5                   10                  15
```

<210> SEQ ID NO 470
<211> LENGTH: 16
<212> TYPE: PRT
<213> ORGANISM: Artificial Sequence
<220> FEATURE:
<223> OTHER INFORMATION: gluten derived peptide

<400> SEQUENCE: 470

```
Gly Gln Gln Pro Phe Pro Gln Pro Glu Gln Pro Phe Pro Gln Ser Gly
1               5                   10                  15
```

<210> SEQ ID NO 471
<211> LENGTH: 16
<212> TYPE: PRT
<213> ORGANISM: Artificial Sequence
<220> FEATURE:
<223> OTHER INFORMATION: gluten derived peptide

<400> SEQUENCE: 471

```
Gly Gln Gln Pro Phe Pro Gln Pro Glu Gln Pro Thr Pro Ile Gln Gly
1               5                   10                  15
```

<210> SEQ ID NO 472
<211> LENGTH: 16
<212> TYPE: PRT
<213> ORGANISM: Artificial Sequence
<220> FEATURE:
<223> OTHER INFORMATION: gluten derived peptide

<400> SEQUENCE: 472

```
Gly Gln Gln Pro Phe Pro Gln Pro Glu Gln Glu Phe Pro Gln Pro Gly
1               5                   10                  15
```

<210> SEQ ID NO 473
<211> LENGTH: 16
<212> TYPE: PRT
<213> ORGANISM: Artificial Sequence
<220> FEATURE:
<223> OTHER INFORMATION: gluten derived peptide

<400> SEQUENCE: 473

Gly Gln Pro Phe Pro Trp Gln Pro Glu Gln Pro Phe Pro Gln Pro Gly
1               5                   10                  15

<210> SEQ ID NO 474
<211> LENGTH: 16
<212> TYPE: PRT
<213> ORGANISM: Artificial Sequence
<220> FEATURE:
<223> OTHER INFORMATION: gluten derived peptide

<400> SEQUENCE: 474

Gly Gln Pro Phe Pro Leu Gln Pro Glu Gln Pro Phe Pro Gln Pro Gly
1               5                   10                  15

<210> SEQ ID NO 475
<211> LENGTH: 16
<212> TYPE: PRT
<213> ORGANISM: Artificial Sequence
<220> FEATURE:
<223> OTHER INFORMATION: gluten derived peptide

<400> SEQUENCE: 475

Gly Gln Tyr Ser Pro Tyr Gln Pro Glu Gln Pro Phe Pro Gln Pro Gly
1               5                   10                  15

<210> SEQ ID NO 476
<211> LENGTH: 16
<212> TYPE: PRT
<213> ORGANISM: Artificial Sequence
<220> FEATURE:
<223> OTHER INFORMATION: gluten derived peptide

<400> SEQUENCE: 476

Gly Gln Ser Tyr Pro Val Gln Pro Glu Gln Pro Phe Pro Gln Pro Gly
1               5                   10                  15

<210> SEQ ID NO 477
<211> LENGTH: 16
<212> TYPE: PRT
<213> ORGANISM: Artificial Sequence
<220> FEATURE:
<223> OTHER INFORMATION: gluten derived peptide

<400> SEQUENCE: 477

Gly Gln Pro Ala Pro Ile Gln Pro Glu Gln Pro Phe Pro Gln Gln Gly
1               5                   10                  15

<210> SEQ ID NO 478
<211> LENGTH: 16
<212> TYPE: PRT
<213> ORGANISM: Artificial Sequence
<220> FEATURE:
<223> OTHER INFORMATION: gluten derived peptide

<400> SEQUENCE: 478

Gly Gln Pro Thr Pro Ile Gln Pro Glu Gln Pro Phe Pro Gln Gln Gly
1               5                   10                  15

<210> SEQ ID NO 479
<211> LENGTH: 16
<212> TYPE: PRT
<213> ORGANISM: Artificial Sequence
<220> FEATURE:
<223> OTHER INFORMATION: gluten derived peptide

<400> SEQUENCE: 479

```
Pro Gln Gln Pro Ile Pro Glu Gln Pro Gln Tyr Pro Gln Gln Pro
1               5                   10                  15
```

<210> SEQ ID NO 480
<211> LENGTH: 16
<212> TYPE: PRT
<213> ORGANISM: Artificial Sequence
<220> FEATURE:
<223> OTHER INFORMATION: gluten derived peptide

<400> SEQUENCE: 480

```
Gly Phe Ser Phe Ser Gln Gln Pro Glu Gln Pro Phe Pro Leu Gln Gly
1               5                   10                  15
```

<210> SEQ ID NO 481
<211> LENGTH: 16
<212> TYPE: PRT
<213> ORGANISM: Artificial Sequence
<220> FEATURE:
<223> OTHER INFORMATION: gluten derived peptide

<400> SEQUENCE: 481

```
Gly Gln Gln Ala Phe Pro Gln Pro Glu Gln Thr Phe Pro His Gln Gly
1               5                   10                  15
```

<210> SEQ ID NO 482
<211> LENGTH: 16
<212> TYPE: PRT
<213> ORGANISM: Artificial Sequence
<220> FEATURE:
<223> OTHER INFORMATION: gluten derived peptide

<400> SEQUENCE: 482

```
Gly Gln Pro Phe Pro Gln Gln Pro Glu Gln Ile Ile Pro Gln Gln Gly
1               5                   10                  15
```

<210> SEQ ID NO 483
<211> LENGTH: 16
<212> TYPE: PRT
<213> ORGANISM: Artificial Sequence
<220> FEATURE:
<223> OTHER INFORMATION: gluten derived peptide

<400> SEQUENCE: 483

```
Gly Gln Pro Gln Gln Pro Phe Pro Glu Gln Pro Glu Gln Ile Ile Gly
1               5                   10                  15
```

<210> SEQ ID NO 484
<211> LENGTH: 16
<212> TYPE: PRT
<213> ORGANISM: Artificial Sequence
<220> FEATURE:
<223> OTHER INFORMATION: gluten derived peptide

<400> SEQUENCE: 484

```
Gly Gln Gln Pro Phe Pro Gln Pro Glu Gln Glu Leu Pro Leu Gln Gly
1               5                   10                  15
```

<210> SEQ ID NO 485
<211> LENGTH: 16
<212> TYPE: PRT
<213> ORGANISM: Artificial Sequence
<220> FEATURE:
<223> OTHER INFORMATION: gluten derived peptide

<400> SEQUENCE: 485

```
Gly Gln Pro Glu Gln Pro Tyr Pro Glu Gln Pro Phe Pro Gln Gln Gly
```

```
<210> SEQ ID NO 486
<211> LENGTH: 16
<212> TYPE: PRT
<213> ORGANISM: Artificial Sequence
<220> FEATURE:
<223> OTHER INFORMATION: gluten derived peptide

<400> SEQUENCE: 486

Gly Met Gln Val Gly Pro Ser Gly Glu Val Glu Trp Pro Gln Gln Gly
1               5                   10                  15
```

AGENTS FOR THE TREATMENT OF CELIAC DISEASE

RELATED APPLICATIONS

This application is a national stage filing under 35 U.S.C. §371 of International Application No. PCT/AU2009/001556 filed Nov. 30, 2009, and which claims the benefit of U.S. Provisional Application Ser. No. 61/118,643, filed Nov. 30, 2008, the entire contents of each of which are incorporated by reference herein.

FIELD OF THE INVENTION

The present invention relates to compositions and methods for treatment of a subject who is sensitive to gluten, in particular a subject who has celiac disease, and diagnosis thereof and assays and kits for use therein.

BACKGROUND OF THE INVENTION

Celiac disease, also known as coeliac disease or celiac sprue (coeliac sprue), affects approximately 1% of people in Europe and North America. In many of those affected, celiac disease is unrecognised, but this clinical oversight is now being rectified with greater clinical awareness. A gluten free diet is the only current treatment for celiac disease, and because regular ingestion of as little as 50 mg of gluten (equivalent to $\frac{1}{100}^{th}$ of a standard slice of bread) damages the small intestine, chronic inflammation of the small bowel is commonplace in subjects on a gluten free diet. Persistent inflammation of the small intestine has been shown to increase the risk of cancer, osteoporosis and death. As gluten is so widely used, for example, in commercial soups, sauces, ice-creams, etc., maintaining a gluten free diet is difficult.

Celiac disease occurs in genetically susceptible individuals who possess either HLA-DQ2 encoded by HLA-DQA1*05 and HLA-DQB1*02 (accounting for about 90% of individuals), variants of HLA-DQ2, or HLA-DQ8. Such individuals mount an inappropriate HLA-DQ2-and/or DQ8-restricted CD4$^+$ T cell-mediated immune response to peptides derived from the aqueous-insoluble proteins of wheat flour, gluten, and related proteins in rye and barley.

All gluten proteins are considered toxic in celiac disease. In 2006, the NCBI public database Genbank included 345 entries for gluten proteins from bread-making wheat (*Triticum aestivum*), barley (*Hordein vulgare*) and rye (*Secale cerale*).

Predictive approaches have catalogued several hundred distinct putatively "toxic" gluten peptides based upon searches for homologues of known epitopes of intestinal T cell clones, or for gluten sequences predicted or proven to bind to HLA-DQ2 in vitro, having the motif favouring deamidation by tissue transglutaminase (tTG), and/or sequences resistant to proteolysis.

Authoritative reviews report there being fifty or so "immunodominant" T cell epitopes in gluten relevant to celiac disease. However, T cells raised against hordein or barley have not yet been studied, and HLA-DQ2-restricted T cell epitopes derived from high molecular weight (HMW) glutenin are yet to be defined.

Despite the large number of gluten peptides incriminated in celiac disease, the protease-resistant α-gliadin 33mer LQLQPFPQPQLPYPQPQLPYPQPQLPYPQPQPF (SEQ ID NO:1; α2-gliadin 56-88) deamidated by tTG: LQLQPF-PQPELPYPQPELPYPQPELPYPQPQPF (SEQ ID NO:2) is widely regarded as the optimal stimulatory peptide (for intestinal T cell lines raised against protease-digested gluten) in HLA-DQ2 associated celiac disease. The underlining of Q residues in SEQ ID NO:1, and throughout this disclosure, indicates a glutamine residue amenable to deamidation catalysed by tTG or consistent with the amino-acid motif that predicts susceptibility to deamidation by tTG, i.e., Q-->E.

This α-gliadin 33mer (SEQ ID NO:1; α2-gliadin 56-88) was recovered from a digestate of the recombinant α2-gliadin, it incorporates multiple overlapping epitopes previously identified using intestinal T cell clones and lines, and also fresh peripheral blood T cells from HLA-DQ2$^+$ donors affected by celiac disease after in vivo gluten challenge. These epitopes include DQ2-α-I: PFPQPELPY (SEQ ID NO:3); DQ2-α-II: PQPELPYPQ (SEQ ID NO:4); and DQ2-α-III: PYPQPELPY (SEQ ID NO:5). Indeed, in vivo gluten challenge in HLA-DQ2$^+$ celiac disease patients induces peripheral blood CD4$^+$ T cells that are specific for a single 11mer sequence in the α-gliadin protein sequence, p60-70 PFPQPQLPYPQ (SEQ ID NO:6), that is optimally bioactive when flanked by three further residues at both the N- and C-terminal, α-gliadin p57-73 QLQPFPQPQLPYPQPQS (SEQ ID NO:7) and deamidated by tTG or Q65 substituted for glutamate, α-gliadin p57-73 QE65 QLQPFPQP ELPYPQPQS (SEQ ID NO:8) that includes DQ2-α-I (SEQ ID NO:3) and DQ2-α-II (SEQ ID NO:4). However, there are hundreds of wheat, rye and barley gluten proteins, and the DQ2-α-I, DQ2-α-II, and DQ2-α-III epitopes together typically account for no more than half the toxic T cell stimulatory properties of gluten in HLA-DQ2$^+$ celiac disease. Additional epitopes of relevance to celiac disease are disclosed in WO 01/25793, WO 03/104273 and WO 05/105129.

Although T cells have not been raised against barley hordein or rye secalin, proteins closely related to wheat gluten, the toxicity of barley and rye is ascribed to T cells specific for epitopes in wheat gluten, especially DQ2-α-I (SEQ ID NO:3) or DQ2-α-II (SEQ ID NO:4), that are cross-reactive with related hordein and secalin sequences deamidated by tTG, in particular PFPQPQQPF (SEQ ID NO:9) deamidated to Hα9/Sα9 PFPQPEQPF (SEQ ID NO:10; DQ2-ω-I) or PQP QQPFPQ (SEQ ID NO:11) deamidated to Hα2/Sα2 PQP EQPFPQ (SEQ ID NO:12), respectively.

Amongst authorities in the field, there is disagreement regarding the dominance, hierarchy, and redundancy of particular peptides in inducing T-cell stimulation in celiac disease.

Understanding the consistency and relative contribution of particular peptides to the T cell stimulatory capacity of gluten has application. Provided they consistently account for a substantial proportion of the T cell response to gluten, dominant T cell stimulatory peptides might alone or collectively enable the development of antigen-specific therapeutics and diagnostics.

In principle, antigen-specific therapy is an attractive strategy to treat autoimmune and allergic diseases. Whole protein-based approaches to desensitisation are effective for human allergic conditions and also treatment and prevention of autoimmunity and allograft rejection in experimental animal models. However, wider application of protein-based antigen-specific therapy has been limited by the small but recognised risk of anaphylaxis and because relevant antigens may not be suitable as pharmaceuticals or are simply not understood in sufficient detail to permit pharmaceutical development.

The risk of anaphylaxis can be minimised and problems of formulation overcome using short linear, aqueous soluble peptides, encompassing sequences from the disease-relevant antigen recognised by pathogenic CD4$^+$ T cells. Peptide-based therapeutic vaccines are effective in inbred mouse models of autoimmunity and allograft rejection in which relevant immunodominant epitopes and their cognate CD4+ T cells are defined. However, even for strongly HLA-associated human immune diseases, identification of pathogenic CD4+ T cell epitopes with sufficient confidence to support rational drug design and pharmaceutical development has been very limited.

In many cases, this uncertainty is due to the fact that reported T cell responses in patients are at the limits of detection, usually depend upon in vitro expansion which may be primary or recall T cell responses, and can often also be found in healthy HLA matched individuals. These technical challenges have resulted in the compromise that peptide selection for therapeutic vaccines tends to be based upon in vitro binding affinity for disease-relevant HLA molecules, rather than their unequivocal definition as epitopes for immunodominant pathogenic T cells. A further consequence is that peptide-based compounds designed in this manner tend to encompass an expended cocktail of peptides. It might be expected that the larger the cocktail, the greater the likelihood of difficulties in formulation, stability and adverse effects, but also the more likely that T cells specific for peptides in the cocktail consistently make a substantial contribution to the pathogenic T cell response in patients.

Given the large number of toxic gluten peptides, the inventors have sought to identify an optimal non-redundant set of immunodominant peptides from which a minimal mixture could be selected for use in a peptide-based immunotherapy capable of modulating the immune response of an individual to gluten. The inventors have sought to identify immunodominant peptides useful in the treatment of celiac disease by specifically modifying the pathogenic T cell response to gluten and to therefore provide a vaccine effective against celiac disease. The same peptide mixture is also useful in diagnosis and monitoring immunomodulatory therapeutics in celiac disease.

SUMMARY OF THE INVENTION

The present inventors have identified three dominant T cell stimulatory peptides which together can be used as an agent in an immunotherapy or vaccine to modulate the T cell response to three or more gluten peptides and to provide tolerance to gluten, allowing treatment of celiac disease. Accordingly, in one aspect the present invention provides an agent comprising i) a first peptide comprising the amino acid sequence LQPFPQPELPYPQPQ (SEQ ID NO:13), or a biologically active fragment or variant thereof, ii) a second peptide comprising the amino acid sequence QPFPQPEQPFPWQP (SEQ ID NO:14), or a biologically active fragment or variant thereof, and iii) a third peptide comprising the amino acid sequence PEQPIPEQPQPYPQQ (SEQ ID NO:16), or a biologically active fragment or variant thereof.

SEQ ID NO:13 (LQPFPQPELPYPQPQ) encompasses two overlapping epitopes, PFPQPELPY (SEQ ID NO:3) and PQPELPYPQ (SEQ ID NO:4), SEQ ID NO:14 (QPFPQPEQPFPWQP) encompasses two overlapping epitopes, PFPQPEQPF (SEQ ID NO:10) and PQPEQPFPW (SEQ ID NO:15; DQ2-ω-II), and SEQ ID NO:16 PEQPIPEQPQPYPQQ encompasses the epitope PIPEQPQPY (SEQ ID NO:17; DQ2-Hor-I) and also the predicted epitope EQPIPEQPQ (SEQ ID NO:18) interchangeable with QQPIPEQPQ (SEQ ID NO:19).

In an embodiment, the first, second and/or third peptides comprise an N terminal acetyl group or pyroglutamate group and/or a C terminal amide group. More preferably, the first, second and/or third peptides comprise an N terminal pyroglutamate group and a C terminal amide group.

In a further embodiment, the first, second and/or third peptides are conjugated to a compound. Examples of suitable compounds include, but are not limited to, an adjuvant, and an MHC molecule or binding fragment thereof.

In a preferred embodiment, each peptide is provided as a separate molecule. However, in an alternate embodiment, two or three of the first, second and third peptides, or biologically active fragment or variant of one or more thereof, are on a single polypeptide chain.

In a further embodiment, the agent comprises one or more additional peptides comprising an amino acid sequence selected from the group consisting of SEQ ID NOs:47, 48, 56, 57, 58, 59, 60, 61, 62, 63, 64, 65, 66, 67, 68, 75, 76, 77, 78, 79, 80, 81, 89, 90, 91, 92, 95, 102, 103, 104, 116, 117, 118, 119, 120, 121, 122, 123, 124, 125, 126, 127, 128, 129, 130, 131, 132, 133, 136, 169, 170, 171, 172, 173, 174, 177, 178, 179, 180, 183, 184, 187, 188, 189, 190, 191, 192, 209, 210, or a biologically active fragment or variant of any one or more thereof.

The additional peptides allow for a wider effective treatment group and greater breadth of treatment or diagnosis. Particularly, the use of additional peptides can increase the likelihood that the agent can abolish inflammation or damage in response to gluten ingestion and allow a celiac disease subject to have a normal diet. Additionally, when the agent is used as a diagnostic, it is advantageous to have more targets and this is achieved by providing more peptides that might be in their deamidated or wild-type form from the list SEQ ID NOs:47, 48, 56, 57, 58, 59, 60, 61, 62, 63, 64, 65, 66, 67, 68, 75, 76, 77, 78, 79, 80, 81, 89, 90, 91, 92, 95, 102, 103, 104, 116, 117, 118, 119, 120, 121, 122, 123, 124, 125, 126, 127, 128, 129, 130, 131, 132, 133, 136, 169, 170, 171, 172, 173, 174, 177, 178, 179, 180, 183, 184, 187, 188, 189, 190, 191, 192, 209, 210.

In another aspect, the present invention provides an agent comprising one or more polynucleotides encoding i) a first peptide comprising the amino acid sequence LQPFPQPELPYPQPQ (SEQ ID NO:13), or a biologically active fragment or variant thereof, ii) a second peptide comprising the amino acid sequence QPFPQPEQPFPWQP (SEQ ID NO:14), or a biologically active fragment or variant thereof, iii) a third peptide comprising the amino acid sequence PEQPIPEQPQPYPQQ (SEQ ID NO:16), or a biologically active fragment or variant thereof, and iv) optionally one or more additional peptides comprising an amino acid sequence selected from the group consisting of SEQ ID NO:47, 48, 56, 57, 58, 59, 60, 61, 62, 63, 64, 65, 66, 67, 68, 75, 76, 77, 78, 79, 80, 81, 89, 90, 91, 92, 95, 102, 103, 104, 116, 117, 118, 119, 120, 121, 122, 123, 124, 125, 126, 127, 128, 129, 130, 131, 132, 133, 136, 169, 170, 171, 172, 173, 174, 177, 178, 179, 180, 183, 184, 187, 188, 189, 190, 191, 192, 209, 210, or a biologically active fragment or variant of any one or more thereof.

The one or more peptides, or biologically active fragments or variants thereof, may be encoded by one or more polynucleotides. Thus, at least some of the one or more peptides, or biologically active fragments or variants thereof, may be transcribed and translated from a single polynucleotide as a single polypeptide chain.

The agent may also be a mixture of peptides and polynucleotides. Thus, in a further aspect the present invention provides an agent comprising i) a first peptide as defined herein or a polynucleotide therefor, ii) a second peptide as defined herein or a polynucleotide therefor, and iii) a third peptide as defined herein or a polynucleotide therefor. As the skilled person would appreciate, one or more of the peptides may be a biologically active fragment or variant of the defined peptide sequence.

In another aspect, the present invention provides a substantially purified and/or recombinant peptide comprising, more preferably consisting of, an amino acid sequence as shown in any one or more of SEQ ID NO:16, 69, 73, 75, 78, 80, 87, 91, 92, 95, 96, 98, 100, 104, 107, 113, 116, 117, 123, 138, 144, 147, 149, 153, 155, 156, 159, 161, 163, 165, 179, 181, 185, 187, 189, 195, 196, 198, 202, 204, 205, 207, 209, 215, or 223, or a biologically active fragment or variant of any one further or more thereof. In a preferred embodiment of this aspect, the peptide is 19 amino acids or less in length.

In a further preferred embodiment of the above aspect, the peptide comprises the amino acid sequence PEQPIPEQPQPYPQQ (SEQ ID NO:16), or a biologically active fragment or variant thereof.

In a further aspect, provided is an isolated and/or exogenous polynucleotide encoding at least one peptide of the invention.

In a further aspect, provided is a vaccine comprising an agent of the invention, a peptide of the invention, and/or a polynucleotide of the invention, and a pharmaceutically acceptable carrier.

In an embodiment, the vaccine comprises an adjuvant.

In another aspect, provided is an isolated antigen presenting cell comprising an agent of the invention, a peptide of the invention, and/or a polynucleotide of the invention. Examples of antigen presenting cell useful for the invention include, but are not limited to, a dendritic cell, macrophage, B-lymphocyte or a liver sinusoidal endothelial cell. In a preferred embodiment, the antigen presenting cell is a dendritic cell.

In an aspect, provided is a method of modulating a T cell response to a gluten peptide in a subject who is sensitive to gluten, the method comprising administering to the subject an effective amount of the agent of the invention, the peptide of the invention, the polynucleotide of the invention, the vaccine of the invention, and/or the antigen presenting cell of the invention.

In another aspect, provided is a method of inducing immune tolerance to a gluten peptide in a subject who is sensitive to gluten, the method comprising administering to the subject an effective amount of the agent of the invention, the peptide of the invention, the polynucleotide of the invention, the vaccine of the invention, and/or the antigen presenting cell of the invention.

In a further aspect, provided is a method of treating celiac disease, the method comprising administering to a subject who is sensitive to gluten an effective amount of the agent of the invention, the peptide of the invention, the polynucleotide of the invention, the vaccine of the invention, and/or the antigen presenting cell of the invention.

In yet a further aspect, provided is a method of modifying cytokine secretion in a subject who is sensitive to gluten, the method comprising administering to the subject an effective amount of the agent of the invention, the peptide of the invention, the polynucleotide of the invention, the vaccine of the invention, and/or the antigen presenting cell of the invention.

In one embodiment, interleukin-2 (IL-2), interferon gamma (IFNγ) and/or tumour necrosis factor alpha (TNFα) secretion is reduced. In another embodiment, interleukin-10 (IL-10) secretion is increased.

Also provided is the use of the agent of the invention, the peptide of the invention, the polynucleotide of the invention, the vaccine of the invention, and/or the antigen presenting cell of the invention of the invention for the manufacture of a medicament for modulating a T cell response, inducing immune tolerance, treating celiac disease, and/or modifying cytokine secretion, in a subject who is sensitive to gluten.

In a further aspect, the present invention provides a method for diagnosing celiac disease in a subject, the method comprising contacting a sample from the subject with the agent of the invention, the peptide of the invention and/or the vaccine of the invention and determining in vitro whether one or more of the peptides defined herein bind T cells in the sample, wherein the binding of one or more of the peptides to T cells indicates that the subject has, or is susceptible to, celiac disease.

Also provided is the use of the above diagnostic method to monitor progression of celiac disease and/or to determine the efficacy of a method involving administering to the subject who is sensitive to gluten an effective amount of the agent of the invention, the peptide of the invention, the polynucleotide of the vaccine of the invention and/or the antigen presenting cell of the invention.

In another aspect, the present invention provides a kit for carrying out the above diagnostic method, the kit comprising the agent of the invention, the peptide of the invention and/or the vaccine of the invention, and means to detect binding of one or more of the peptides to T cells. The kit may also include instructions for use. The kit may also comprise means for detecting recognition of the agent by T cells.

In a further aspect, the present invention provides a method for producing the antigen presenting cell of the invention, the method comprising i) obtaining an antigen presenting cell, and ii) contacting the cell in vitro with the agent of the invention, the peptide of the invention, the polynucleotide of the invention, and/or the vaccine of the invention.

Also provided is the use of the agent of the invention, the peptide of the invention, the polynucleotide of the invention, the vaccine of the invention, and/or the antigen presenting cell of the invention in diagnosis or therapy.

In another aspect, the present invention provides a method of making a vaccine of the invention, the method comprising combining the first, second and third peptides, and optionally one or more additional peptides selected from the group consisting of SEQ ID NOs:47, 48, 56, 57, 58, 59, 60, 61, 62, 63, 64, 65, 66, 67, 68, 75, 76, 77, 78, 79, 80, 81, 89, 90, 91, 92, 95, 102, 103, 104, 116, 117, 118, 119, 120, 121, 122, 123, 124, 125, 126, 127, 128, 129, 130, 131, 132, 133, 136, 169, 170, 171, 172, 173, 174, 177, 178, 179, 180, 183, 184, 187, 188, 189, 190, 191, 192, 209, 210, or a biologically active fragment or variant of any one or more thereof, with a pharmaceutically acceptable carrier and optionally an adjuvant.

In another aspect, the present invention provides a method of determining whether a composition or food is capable of causing celiac disease, the method comprising detecting the presence of the agent of the invention, the peptide of the invention and/or the polynucleotide of the invention in the composition or a food sample.

In a further aspect, the present invention provides a method of identifying a protease that can cleave a peptide as defined herein, the method comprising contacting the peptide with a protease under conditions to effect specific cleavage of the peptide to produce a proteolytic product and detecting the proteolytic product produced.

In another aspect, provided is a method for improving the half life and/or bioavailability of a peptide when administered to a subject, the method comprising modifying the N terminus of the peptide to include an N terminal acetyl or pyroglutamate and modifying the C terminus of the peptide to include a C terminal amide.

In an embodiment, the peptide is for administering to a subject to induce immune tolerance.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE DRAWINGS

FIG. 4: shows T cells in blood after wheat challenge responded to a highly consistent hierarchy of gluten peptides.

FIGS. 7A-C: show the sequences of peptides verified as T-cell stimulatory peptides, their hierarchy, dominance and recognition by T-cell clones raised against the most active peptides after wheat, barley or rye gluten challenge.

FIGS. 14A and B: show the proliferative capacity of gliadin-specific T cells to cognate antigen is diminished following repeat administration of NexVax2 (SEQ ID NOs:228, 229 and 230) and restored in the presence of IL-2.

FIGS. 17A and 17B: schedule for dosing, meals and blood collection of vaccination protocol.

DETAILED DESCRIPTION OF THE INVENTION

General Techniques and Definitions

Figure 1:
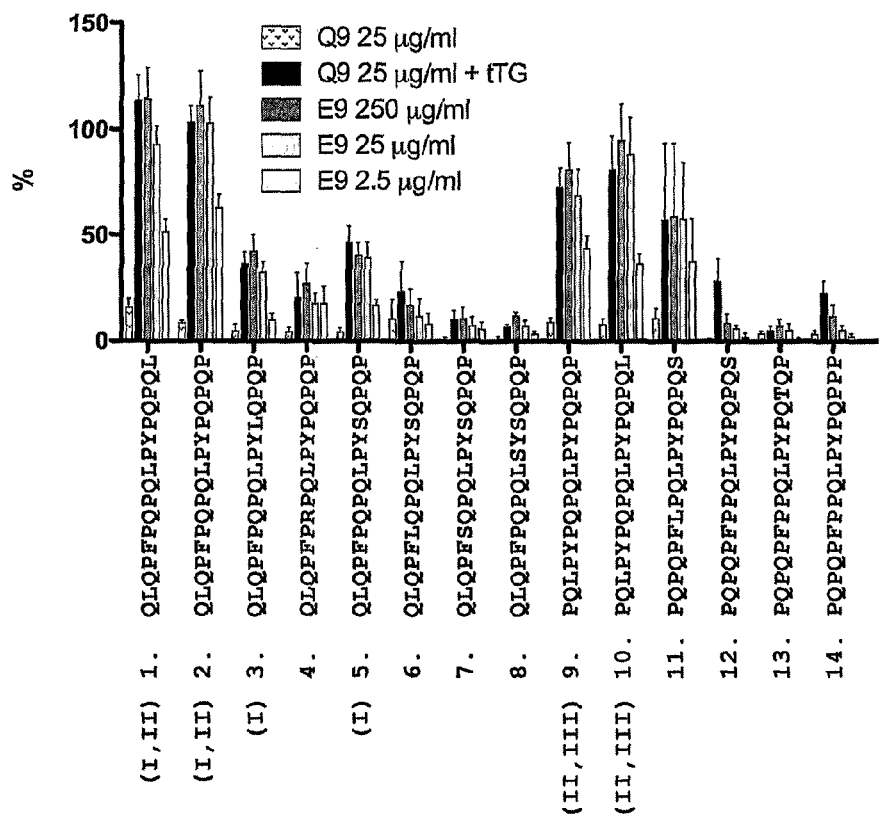
FIG. 1: shows the relative frequencies of gluten peptide-specific T cells detected by IFNγ ELISpot in PBMC collected on day-6 after HLA-DQ2$^+$ celiac disease donors commence wheat to polymorphisms of α-gliadin 57-73 and α-gliadin 57-73 QE65 (SEQ ID NOs:7 and 8, respectively).

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984); J. Sambrook et al., Molecular Cloning: A Laboratory Manual, Cold Spring Harbour Laboratory Press (1989); T. A. Brown (editor), Essential Molecular Biology: A Practical Approach, Volumes 1 and 2, IRL Press (1991); D. M. Glover and B. D. Hames (editors), DNA Cloning: A Practical Approach, Volumes 1-4, IRL Press (1995 and 1996); F. M. Ausubel et al. (editors), Current Protocols in Molecular Biology, Greene Pub. Associates and Wiley-Interscience (1988, including all updates until present); Ed Harlow and David Lane (editors) Antibodies: A Laboratory Manual, Cold Spring Harbour Laboratory, (1988); and J. E. Coligan et al. (editors), Current Protocols in Immunology, John Wiley & Sons (including all updates until present).

As used in the subject specification, the singular forms "a", "an" and "the" include plural aspects unless the context clearly dictates otherwise. Thus, for example, reference to "a peptide" includes a single peptide, as well as two or more peptides and so forth. Furthermore, an antigen presenting cell is usually provided as a population of such cells.

The term "celiac disease" refers to a chronic inflammatory disease of the small intestine. The disease encompasses a spectrum of conditions characterised by varying degrees of gluten sensitivity, including a severe form characterised by a flat small intestinal mucosa (hyperplastic villous atrophy) and other forms characterised by milder symptoms including fatigue, chronic diarrhea, malabsorption of nutrients, weight loss, abdominal distension, anemia as well as a substantially enhanced risk for the development of osteoporosis and intestinal malignancies (lymphoma and carcinoma).

The term "sensitive to gluten" refers to the state in which any one or more of the symptoms of celiac disease or an inappropriate T cell response are exhibited by a subject exposed to gluten, or peptide fragment thereof. In a subject who is not sensitive to gluten, there is little or no T cell response caused by ingestion of gluten. By contrast, in a subject sensitive to gluten there is an inappropriate CD4+ T cell mediated immune response to peptides derived from gluten after ingestion thereof.

The terms "immune tolerance", "immunological tolerance", "tolerance" or "desensitise" are here defined as to make a sensitised or hypersensitive subject, less sensitive, insensitive or nonreactive to gluten by reducing the immunological reactivity of a subject towards gluten. Immune tolerance may be generated, for example, by exposure of mucosal surfaces to tolerance-inducing antigenic fragments of gluten as defined herein. Mucosal administration of both high- and low-dose antigen may result in immune tolerance, in which the immune response to subsequent systemic administration of antigen is reduced. At least two mechanisms of immune tolerance may exist. Tolerance to high-doses of an antigen appears to occur by inactivation or clonal deletion of Th1 and Th2 cells. In contrast, tolerance to low doses of antigen leads to bystander immune suppression mediated by stimulation of Treg cells to produce suppressive cytokines such as interleukin-4 (IL-4), interleukin-10 (IL-10) and TGFβ.

The term "inducing immune tolerance" as used herein refers to bringing about, producing, or causing immune tolerance to gluten in a subject sensitive to gluten.

The term "hypersensitive" is here defined as abnormally susceptible physiologically to gluten.

The term "anergy" refers to a state of reversible unresponsiveness or hyporesponsiveness of a T cell (or B cell) to an antigen.

As used herein, "Treg" refers to a subclass of T cells whose major role is to bring T cell-mediated immunity during an immune reaction to an end, and to suppress auto-reactive T cells that escaped negative selection in the thymus. A "Treg response", as used herein, is characterised by the differentiation and proliferation of the population of CD4+ or CD8+ Treg cells which express the forkhead family transcription factor FOXP3 (forkhead box p3) and/or the MHC Class II associated protein LAG-3, and/or express high levels of the IL-2 receptor alpha chain (CD25). There is also a minor population of MHC Class I-restricted CD8+ FOXP3-expressing Treg cells.

The presence of Treg cells in the peripheral circulation or spleen may be determined by analysis of CD4+/CD25+ expression. This may conveniently be achieved using flow cytometry. In addition, Treg cells may be quantified by determining levels of FOXP3 mRNA in peripheral blood- or spleen-derived mononuclear cells by quantitative reverse transcriptase polymerase chain reaction (PCR). In addition, the induction of a Treg response in vivo may be assessed by the measurement of Treg-associated cytokines from peripheral blood- or lymph node-derived mononuclear lymphocytes. Treg cells typically show higher expression levels of the anti-inflammatory cytokines such as IL-10 and TGFβ and the presence of these mediators may be determined by methods known in the art, such as flow cytometry, immunohistochemical staining or ELISA.

The term "T cell stimulatory peptide" or "stimulatory peptide" refers to a peptide or epitope capable of activating a T cell.

The term "activate" or "activating" or "activation" in relation to a T cell refers to the presentation by an MHC molecule on one cell of an epitope to an appropriate T cell receptor on a second (T) cell, together with binding of a co-stimulatory molecule by the T cell, thereby eliciting a "T cell response".

As used herein, "toxic peptide" refers to a peptide that stimulates T cell activation in a subject.

The term "expansion" as used herein refers to the proliferation and amplification of a T cell population following T cell activation.

The term "immunodominant" refers to a subunit of a peptide (epitope) that is most easily recognised by the immune system and thus most influences the specificity of an induced immune response, such as a T cell response. "Immunodominant" may be used interchangeably with "dominant" herein.

As used herein, the term "modulating a T cell response" refers to regulating or adjusting a T cell response in a subject sensitive to gluten, such that the T cell response to gluten is reduced or lessened.

As used herein, "modifying cytokine secretion" refers to changing or altering somewhat the secretion of cytokines by a subject sensitive to gluten, such that the effects of gluten sensitivity in the subject are reduced or lessened. The term encompasses both increased secretion of a particular cytokine or combination of cytokines and decreased secretion of a particular cytokine or combination of cytokines.

As used herein, "epitope" refers to that portion of an antigen or a peptide that is recognised by the immune system, for example, a T cell receptor or the major histocompatibility complex (MHC) class I or class II, an antibody, a B cell receptor, which portion is sufficient for high affinity binding. Generally, a linear epitope for recognition will be at least about 7 amino acids in length, and may be 8 amino acids, 9 amino acids, 10 amino acids, or more.

The term "polyepitope" refers to the presence of two or more epitopes (peptides) linked in a single polypeptide chain.

As used herein, "antigen" and "immunogen" and variations thereof are generally used interchangeably and refer to the epitope-containing structure recognised by the immune system.

The term "gluten" or "gluten protein" encompasses alpha (α), beta (β), gamma (γ) and omega (ω) gliadins, and low and high molecular weight (LMW and HMW) glutenins in wheat, B, C and D hordeins in barley, β, γ and ω secalins in rye, and optionally avenins in oats. "Gluten peptides" are peptides derived from, or encompassed within, one or more of the gluten proteins.

The term "gliadin" refers to the aqueous alcohol-soluble fraction of gluten, particularly, but not exclusively, gluten derived from wheat, for example *Triticum aestivum*.

The term "glutenin" refers to the aqueous alcohol-insoluble fraction of gluten, particularly but not exclusively, gluten derived from wheat, for example *Triticum aestivum*.

As used herein, "hordein" or "barley hordein" refers to gluten derived from barley, *Hordein vulgare*.

As used herein, "secalin" or "rye secalin" refers to gluten derived from rye, *Secale cerale*.

As used herein, "avedin" or "oat avedin" refers to gluten derived from oats, *Avena sativa*.

Tissue "transglutaminase" is a crucial factor in celiac disease because it promotes gluten-specific T cell responses. Tissue transglutaminase causes selective deamidation of gluten, which in turn, causes the generation of a series of gluten peptides that bind to HLA-DQ2 or -DQ8 molecules with high affinity. The resulting HLA-DQ2 (DQ8)-gluten peptide interaction triggers the proinflammatory CD4 T cell response. Thus, the term "deamidation" refers to the conversion of glutamine to glutamic acid, or to the conversion of asparagine to aspartic acid. As used herein, deamidation refers particularly to the conversion of glutamine to glutamic acid in gluten, a process that increases the propensity of gluten peptides to activate T cells.

The terms "human leukocyte antigen" and "HLA" are here defined as a genetic fingerprint on human white blood cells and platelets, composed of proteins that play a critical role in activating the body's immune system to respond to foreign organisms. In humans and other animals, the HLA is also referred to as the "major histocompatibility complex" (MHC).

As used herein, the term "agent" refers to a collection of peptides and/or polynucleotides. The peptides and/or polynucleotides may be in the same composition (such as a vaccine), in different compositions or a combination thereof (for example, the first and second peptide defined herein in one composition, and the third in a separate composition). If in different compositions, they will preferably be in close proximity, such as in a kit. Accordingly, the methods of the invention contemplate providing (for example administering to a subject) the individual component peptides and/or polynucleotides of an agent of the invention in a single composition (vaccine), or sequentially in different compositions or a combination thereof.

The term "subject" includes inter alia an individual, patient, target, host or recipient regardless of whether the subject is a human or non-human animal including mammalian species and also avian species. The term "subject", therefore, includes a human, non-human primate (for example, gorilla, marmoset, African Green Monkey), livestock animal (for example, sheep, cow, pig, horse, donkey, goat), laboratory test animal (for example, rat, mouse, rabbit, guinea pig, hamster), companion animal (for example, dog, cat), captive wild animal (for example, fox, deer, game animals) and avian species including poultry birds (for example, chickens, ducks, geese, turkeys). The preferred subject, however, is a human, more preferably a human who is HLA-DQ2+.

Peptides

The terms "peptide", "polypeptide", and "protein" can generally be used interchangeably and encompass biologically active fragments, variants including homologues, and salts. However, the term "peptide" is typically used to refer to relatively short molecules comprising less than 50, more preferably less than 25, amino acids.

The overall length of each peptide defined herein may be, for example, 7 to 50 amino acids, such as 7, 8, 9, 10, 11, 12, 13, 14, 15, 16, 17, 18, 19, 20, 25, 30, 35, 40, 45, or 50 amino acids. It is contemplated that shorter peptides may prove useful, particularly those that are 20 or fewer amino acids in length, in therapeutics to reduce the likelihood of anaphylaxis but longer peptides with multiple epitopes are likely to be as effective as multiple short peptides in functional T cell-based diagnostics in vitro.

As used herein, a "biologically active fragment" consists of fewer amino acids than that of the reference peptide defined, for example, by the sequence of SEQ ID NOs:13, 14 or 16. Preferably, biologically active fragments are capable of generating a substantially equal or greater T cell response in a subject sensitive to gluten as the peptide from which it is derived. In another embodiment, biologically active fragments are capable of generating at least 50%, more preferably at least 75% of the T cell response in a subject sensitive to gluten as the peptide from which it is derived. In an embodiment, biologically active fragments are 14, 13, 12, 11, 10, 9, 8 and no less than 7 amino acids in length. Deletions and/or additions at either end of any of the peptides are particularly contemplated.

Examples of biologically active fragments of the peptide provided as SEQ ID NO:13 are those which include PELP (SEQ ID NO:234), which has been found to be essential for T cell recognition.

Accordingly suitable 7mer fragments of SEQ ID NO:13 include, but are not limited to:

| | |
|---|---|
| QPELPYP; | (SEQ ID NO: 235) |
| PELPYPQ; | (SEQ ID NO: 236) |
| PQPELPY and | (SEQ ID NO: 237) |
| FPQPELP. | (SEQ ID NO: 238) |

Suitable 8mer fragments of SEQ ID NO:13 include, but are not limited to:

| | |
|---|---|
| PELPYPQP; | (SEQ ID NO: 239) |
| QPELPYPQ; | (SEQ ID NO: 240) |
| PQPELPYP; | (SEQ ID NO: 241) |
| FPQPELPY and | (SEQ ID NO: 242) |
| PFPQPELP. | (SEQ ID NO: 243) |

Suitable 9mer fragments of SEQ ID NO:13 include, but are not limited to:

| | |
|---|---|
| PELPYPQPQ; | (SEQ ID NO: 244) |
| QPELPYPQP; | (SEQ ID NO: 245) |
| PQPELPYPQ; | (SEQ ID NO: 246) |
| FPQPELPYP; | (SEQ ID NO: 247) |
| PFPQPELPY and | (SEQ ID NO: 248) |
| QPFPQPELP. | (SEQ ID NO: 249) |

Suitable 10mer fragments of SEQ ID NO:13 include, but are not limited to:

| | |
|---|---|
| QPELPYPQPQ; | (SEQ ID NO: 250) |
| PQPELPYPQP; | (SEQ ID NO: 251) |
| PQPELPYPQP; | (SEQ ID NO: 252) |
| FPQPELPYPQ; | (SEQ ID NO: 253) |
| PFPQPELPYP; | (SEQ ID NO: 254) |
| QPFPQPELPY and | (SEQ ID NO: 255) |
| LQPFPQPELP. | (SEQ ID NO: 256) |

Suitable 11mer fragments of SEQ ID NO:13 include, but are not limited to:

| | |
|---|---|
| PQPELPYPQPQ; | (SEQ ID NO: 257) |
| FPQPELPYPQP; | (SEQ ID NO: 258) |
| PFPQPELPYPQ; | (SEQ ID NO: 259) |
| QPFPQPELPYP and | (SEQ ID NO: 260) |
| LQPFPQPELPY. | (SEQ ID NO: 261) |

Suitable 12mer fragments of SEQ ID NO:13 include, but are not limited to:

```
    FPQPELPYPQPQ;       (SEQ ID NO: 262)

PFPQPELPYPQP;       (SEQ ID NO: 263)

QPFPQPELPYPQ        (SEQ ID NO: 264)
    and

LQPFPQPELPYP.       (SEQ ID NO: 265)
```

Suitable 13mer fragments of SEQ ID NO:13 include, but are not limited to:

```
    PFPQPELPYPQPQ;      (SEQ ID NO: 266)

QPFPQPELPYPQP       (SEQ ID NO: 267)
    and

LQPFPQPELPYPQ.      (SEQ ID NO: 268)
```

Suitable 14mer fragments of SEQ ID NO:13 include, but are not limited to:

```
    QPFPQPELPYPQPQ      (SEQ ID NO: 269)
    and

LQPFPQPELPYPQP.     (SEQ ID NO: 270)
```

Examples of biologically active fragments of the peptide provided as SEQ ID NO:14 are those which include QPEQPF (SEQ ID NO:317), which has been found to be essential for T cell recognition.

Suitable 7mer fragments of SEQ ID NO:14 include, but are not limited to:

```
    QPEQPFP             (SEQ ID NO: 271)
    and

PQPEQPF             (SEQ ID NO: 272).
```

Suitable 8mer fragments of SEQ ID NO:14 include, but are not limited to:

```
    QPEQPFPW;           (SEQ ID NO: 273)

PQPEQPFP            (SEQ ID NO: 274)
    and

FPQPEQPF.           (SEQ ID NO: 275)
```

Suitable 9mer fragments of SEQ ID NO:14 include, but are not limited to:

```
    QPEQPFPWQ;          (SEQ ID NO: 276)

PQPEQPFPW;          (SEQ ID NO: 277)

FPQPEQPFP           (SEQ ID NO: 278)
    and

PFPQPEQPF.          (SEQ ID NO: 279)
```

Suitable 10mer fragments of SEQ ID NO:14 include, but are not limited to:

```
    QPEQPFPWQP;         (SEQ ID NO: 280)

PQPEQPFPWQ;         (SEQ ID NO: 281)

FPQPEQPFPW;         (SEQ ID NO: 282)

PFPQPEQPFP          (SEQ ID NO: 283)
    and

QPFPQPEQPF.         (SEQ ID NO: 284)
```

Suitable 11mer fragments of SEQ ID NO:14 include, but are not limited to:

```
    PQPEQPFPWQP;        (SEQ ID NO: 285)

FPQPEQPFPWQ;        (SEQ ID NO: 286)

PFPQPEQPFPW         (SEQ ID NO: 287)
    and

QPFPQPEQPFP.        (SEQ ID NO: 288)
```

Suitable 12mer fragments of SEQ ID NO:14 include, but are not limited to:

```
    FPQPEQPFPWQP;       (SEQ ID NO: 289)

PFPQPEQPFPWQ        (SEQ ID NO: 290)
    and

QPFPQPEQPFPW.       (SEQ ID NO: 291)
```

Suitable 13mer fragments of SEQ ID NO:14 include, but are not limited to:

```
    PFPQPEQPFPWQP       (SEQ ID NO: 292)
    and

QPFPQPEQPFPWQ.      (SEQ ID NO: 293)
```

Examples of biologically active fragments of the peptide provided as SEQ ID NO:16 are those which include PIPEQPQ (SEQ ID NO:294), which is expected to be essential for T cell recognition.

Suitable 8mer fragments of SEQ ID NO:16 include, but are not limited to:

```
    PIPEQPQP            (SEQ ID NO: 295)
    and

QPIPEQPQ.           (SEQ ID NO: 296)
```

Suitable 9mer fragments of SEQ ID NO:16 include, but are not limited to:

```
    PIPEQPQPY;          (SEQ ID NO: 297)

QPIPEQPQP           (SEQ ID NO: 298)
    and

EQPIPEQPQ.          (SEQ ID NO: 299)
```

Suitable 10mer fragments of SEQ ID NO:16 include, but are not limited to:

```
    PIPEQPQPYP;         (SEQ ID NO: 300)

QPIPEQPQPY;         (SEQ ID NO: 301)

EQPIPEQPQP          (SEQ ID NO: 302)
``` and

PEQPIPEQPQ.                (SEQ ID NO: 303)

Suitable 11mer fragments of SEQ ID NO:16 include, but are not limited to:

```
PIPEQPQPYPQ;       (SEQ ID NO: 304)

QPIPEQPQPYP;       (SEQ ID NO: 305)

EQPIPEQPQPY        (SEQ ID NO: 306)
and

PEQPIPEQPQP.       (SEQ ID NO: 307)
```

Suitable 12mer fragments of SEQ ID NO:16 include, but are not limited to:

```
PIPEQPQPYPQQ;      (SEQ ID NO: 308)

QPIPEQPQPYPQ;      (SEQ ID NO: 309)

EQPIPEQPQPYP       (SEQ ID NO: 310)
and

PEQPIPEQPQPY.      (SEQ ID NO: 311)
```

Suitable 13mer fragments of SEQ ID NO:16 include, but are not limited to:

```
QPIPEQPQPYPQQ;     (SEQ ID NO: 312)

EQPIPEQPQPYPQ      (SEQ ID NO: 313)
and

PEQPIPEQPQPYP.     (SEQ ID NO: 314)
```

Suitable 14mer fragments of SEQ ID NO:16 include, but are not limited to:

```
EQPIPEQPQPYPQQ     (SEQ ID NO: 315)
and

PEQPIPEQPQPYPQ.    (SEQ ID NO: 316)
```

In one embodiment, the agent or vaccine comprises more than one biologically active peptide fragment of the peptide of SEQ ID NO:13, 14 and/or 16. For example, the peptide of SEQ ID NO:13 could be substituted for two separate peptides, one recognised by T cells specific for DQ2-α-I (SEQ ID NO:3) and the other recognised by T cells specific for DQ2-α-II (SEQ ID NO:4).

It has been determined that within the PELP fragment of SEQ ID NO:13 essential for T cell recognition, the E must be present or may optionally be a D. No other substitution allows for T cell recognition. Accordingly, any variant or fragment of SEQ ID NO:13 must comprise the region PELP or PDLP.

Biologically active variants include peptides which vary by one or more amino acids from the defined peptide, which are also known in the art as homologues. For example, a variant can comprise one or more amino acid substitutions in any one or more of the peptides. As used herein, "substituted" or "substitution" includes substitution, replacement, addition, insertion, omission and/or deletion (as such variants may also be fragments) of an amino acid residue(s). In particular, this refers to peptides having conservative substitution without losing, or significantly diminishing, their use in the methods of the invention. Preferably, biologically active variants are capable of generating a substantially equal or greater T cell response in a subject sensitive to gluten as the peptide from which it is derived. In another embodiment, biologically active variants are capable of generating at least 50%, more preferably at least 75% of the T cell response in a subject sensitive to gluten as the peptide from which it is derived.

Biologically active variants of the peptides may be identified by modifying the sequence of each peptide and then assaying the resulting peptide for the ability to stimulate an immune response, for example, production of T cells.

In an embodiment, no more than 5, more preferably no more than 4, more preferably no more than 3, more preferably no more than 2, and even more preferably only 1 amino acid in a defined peptide is varied (by substitution, deletion or addition), when compared to a peptide sequence defined herein.

In an alternate embodiment, the percentage identity between a particular sequence (variant) and a reference sequence (peptide defined herein) is at least about 60% or at least about 70% or at least about 80% or at least about 90% or at least about 95% or above such as at least about 96%, 97%, 98%, 99% or greater. Percentage identity can be determined using readily available software packages, such as BLAST (www.ncbi.nlm.nih.gov/) and GAP.

In one embodiment, the second peptide comprises the amino acid sequence PQQPFPQPEQPFPWQP (SEQ ID NO:320), or a biologically active fragment or variant thereof.

In another embodiment, the third peptide comprises the amino acid sequence FPEQPIPEQPQPYPQQ (SEQ ID NO:321), or a biologically active fragment or variant thereof.

Natural amino acids include alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y), valine (V), hydroxyproline (O and/or Hyp), isodityrosine (IDT), and di-isodityrosine (di-IDT). Hydroxyproline, isodityrosine, and di-isodityrosine are formed post-translationally. Use of natural amino acids, in particular the 20 genetically encoded amino acids, is particularly contemplated.

Substitutions may be conservative amino acid substitutions, in which the substituted amino acid has similar structural or chemical properties with the corresponding amino acid in the reference sequence. Alternatively, the substitutions may be non-conservative amino acid substitutions as long as the desired activity is maintained.

By way of example, conservative amino acid substitutions involve substitution of one aliphatic or hydrophobic amino acids, for example, alanine, valine, leucine and isoleucine, with another; substitution of one hydroxyl-containing amino acid, for example, serine and threonine, with another; substitution of one acidic residue, for example, glutamic acid or aspartic acid, with another; replacement of one amide-containing residue, for example, asparagine and glutamine, with another; replacement of one aromatic residue, for example, phenylalanine and tyrosine, with another; replacement of one basic residue, for example, lysine, arginine and histidine, with another; and replacement of one small amino acid, for example, alanine, serine, threonine, methionine, and glycine, with another.

Such conservative substitutions are shown in Table 1 under the heading of preferred substitutions. If such substitutions do not result in a change in functional activity, then more substantial changes, denoted exemplary substitutions in Table 1, may be introduced, and the resulting variant analysed for functional activity.

TABLE 1

Amino acid substitutions.

| Original Residue | Exemplary Substitutions | Preferred Substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly(G) | Pro | Pro |
| His (H) | Asn; Gln; Lys; Arg | Arg |
| Ile (I) | Leu; Val; Met; Ala; Phe; norleucine | Leu |
| Leu (L) | norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala | Leu |
| Pro (P) | Gly | Gly |
| Ser(S) | Thr | Thr |
| Thr (T) | Ser | Ser |
| Trp (W) | Tyr | Tyr |
| Tyr (Y) | Trp; Phe; Thr; Ser | Phe |
| Val (V) | Leu, Ile, Met; Phe; Ala; norleucine | Leu |

Peptide variants may be produced by mutagenesis or other chemical methods. Alanine scanning is a useful technique for identifying important amino acids. In this technique, an amino acid residue is replaced by Ala and its effect on the peptide's activity is determined. For example, cysteine residues may be substituted to minimise dimerisation via disulfide linkages. Each of the amino acid residues of the peptide is analysed in this manner to determine the important regions of the peptide. Means for preparing such peptides are well understood in the art.

In addition to naturally occurring amino acids, non-naturally occurring amino acids, or modified amino acids, are also contemplated and within the scope of the invention. In fact, as used herein, "amino acid" refers to naturally occurring amino acids, non-naturally occurring amino acids, and amino acid analogues, and to the D or L stereoisomers of each.

A non-limiting list of non-conventional and/or non-natural amino acids which may be used as suitable substitutions for the naturally occurring amino acids and their standard abbreviations is set out in Table 2.

TABLE 2

Non-conventional amino acids.

| Non-conventional amino acid | Abbreviation |
|---|---|
| α-aminobutyric acid | Abu |
| α-amino-α-methylbutyrate | Mgabu |
| α-methylaminoisobutyrate | Maib |
| α-methyl-γ-aminobutyrate | Mgabu |
| α-methylcyclohexylalanine | Mchexa |
| α-methylcyclopentylalanine | Mcpen |
| α-methyl-α-naphthylalanine | Manap |
| α-methylpenicillamine | Mpen |
| α-naphthylalanine | Anap |
| γ-aminobutyric acid | Gabu |
| aminocyclopropane-carboxylate | Cpro |
| aminoisobutyric acid | Aib |
| aminonorbornyl-carboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| D-N-methylmethionine | Dnmmet |
| D-N-methylornithine | Dnmorn |
| D-N-methylphenylalanine | Dnmphe |
| D-N-methylproline | Dnmpro |
| D-N-methylserine | Dnmser |
| D-N-methylthreonine | Dnmthr |
| D-N-methyltryptophan | Dnmtrp |
| D-N-methyltyrosine | Dnmtyr |
| D-N-methylvaline | Dnmval |
| L-t-butylglycine | Tbug |
| L-ethylglycine | Etg |
| L-homophenylalanine | Hphe |
| L-methylethylglycine | Metg |
| L-norleucine | Nle |
| L-norvaline | Nva |
| L-α-methylalanine | Mala |
| L-α-methylarginine | Marg |
| L-α-methylasparagine | Masn |
| L-α-methylaspartate | Masp |
| L-α-methyl-t-butylglycine | Mtbug |
| L-α-methylcysteine | Mcys |
| L-α-methylglutamate | Mglu |
| L-α-methylglutamine | Mgln |
| L-α-methylhistidine | Mhis |
| L-α-methylhomophenylalanine | Mhphe |
| L-α-methylisoleucine | Mile |
| L-α-methylleucine | Mleu |
| L-α-methyllysine | Mlys |
| L-α-methylmethionine | Mmet |
| L-α-methylnorleucine | Mnle |
| L-α-methylnorvaline | Mnva |
| L-α-methylornithine | Morn |
| L-α-methylphenylalanine | Mphe |
| L-α-methylproline | Mpro |
| L-α-methylserine | Mser |
| L-α-methylthreonine | Mthr |

TABLE 2-continued

Non-conventional amino acids.

| | |
|---|---|
| L-α-methyltryptophan | Mtrp |
| L-α-methyltyrosine | Mtyr |
| L-α-methylvaline | Mval |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisoleucine | Nmile |
| L-N-methylleucine | mleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-N-methylhomophenylalanine | Nmhphe |
| L-O-methylserine | Omser |
| L-O-methylhomoserine | Omhser |
| N-(4-aminobutyl)glycine | Nglu |
| N-(2-aminoethyl)glycine | Naeg |
| N-(3-aminopropyl)glycine | Norn |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(3-indolylethyl)glycine | Nhtrp |
| N-(2-carbamylethyl)glycine | Ngln |
| N-(2-carboxyethyl)glycine | Nglu |
| N-(1-methylpropyl)glycine | Nile |
| N-(2-methylpropyl)glycine | Nleu |
| N-(1-methylethyl)glycine | Nval |
| N-(2-methylthioethyl)glycine | Nmet |
| N-amino-α-methylbutyrate | Nmaabu |
| N-benzylglycine | Nphe |
| N-(carbamylmethyl)glycine | Nasn |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(hydroxyethyl)glycine | Nser |
| N-(p-hydroxyphenyl)glycine | Nhtyr |
| N-(imidazolylethyl)glycine | Nhis |
| N-methyl-γ-aminobutyrate | Nmgabu |
| N-methylaminoisobutyrate | Nmaib |
| N-methylcyclohexylalanine | Nmchexa |
| N-methylcyclopentylalanine | Nmcpen |
| N-methylglycine | Nala |
| N-methyl-α-naphthylalanine | Nmanap |
| N-methylpenicillamine | Nmpen |
| N-(thiomethyl)glycine | Ncys |
| penicillamine | Pen |
| N-(N-(3,3-diphenylpropyl)carbamylmethyl)glycine | Nnbhe |
| N-(N-(2,2-diphenylethyl)carbamylmethyl)glycine | Nnbhm |
| 1-carboxy-1-(2,2-diphenylethylamino)cyclopropane | Nmbc |

Included within the scope of the present invention is an agent comprising a peptide that is modified during or after translation or synthesis (for example, by farnesylation, prenylation, myristoylation, glycosylation, palmitoylation, acetylation, phosphorylation (such as phosphotyrosine, phosphoserine or phosphothreonine), amidation, derivatisation by known protecting/blocking groups, proteolytic cleavage, linkage to an antibody molecule or other cellular ligand, and the like). Any of the numerous chemical modification methods known within the art may be utilised including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

The phrases "protecting group" and "blocking group" as used herein, refers to modifications to the peptide which protect it from undesirable chemical reactions, particularly in vivo. Examples of such protecting groups include esters of carboxylic acids and boronic acids, ethers of alcohols and acetals, and ketals of aldehydes and ketones. Examples of suitable groups include acyl protecting groups such as, for example, furoyl, formyl, adipyl, azelayl, suberyl, dansyl, acetyl, theyl, benzoyl, trifluoroacetyl, succinyl and methoxysuccinyl; aromatic urethane protecting groups such as, for example, benzyloxycarbonyl (Cbz); aliphatic urethane protecting groups such as, for example, t-butoxycarbonyl (Boc) or 9-fluorenylmethoxy-carbonyl (FMOC); pyroglutamate and amidation. Many other modifications providing increased potency, prolonged activity, ease of purification, and/or increased half-life will be known to the person skilled in the art.

In one embodiment, one of more glutamate residues of one or more of the peptides may be generated by tTG activity upon a peptide. In alternate embodiment, this reaction occurs in vivo following administration.

The peptides may comprise one or more modifications, which may be natural post-translation modifications or artificial modifications. The modification may provide a chemical moiety (typically by substitution of a hydrogen, for example, of a C—H bond), such as an amino, acetyl, acyl, carboxy, hydroxy or halogen (for example, fluorine) group, or a carbohydrate group. Typically, the modification is present on the N- or C-terminal. Furthermore, one or more of the peptides may be PEGylated, where the PEG (polyethyleneoxy group) provides for enhanced lifetime in the blood stream. One or more of the peptides may also be combined as a fusion or chimeric protein with other proteins, or with specific binding agents that allow targeting to specific moieties on a target cell.

Peptide variants may be obtained in which the peptide has been chemically modified at the level of amino acid side chains, of amino acid chirality, and/or of the peptide backbone.

Particular changes can be made to the peptides having SEQ ID NOs:13, 14 and/or 16 to improve resistance to degradation or optimise solubility properties or otherwise improve bioavailability compared to the parent peptide, thereby providing peptides having similar or improved therapeutic, diagnostic and/or pharmacokinetic properties. A preferred such modification includes the use of an N-terminal acetyl group or pyroglutamate and/or a C terminal amide. Such modifications have been shown in Table 5 which significantly increase the half life and bioavailability of the peptides compared to the parent peptides having a free N and C terminus. Whilst N terminal acetylation and C terminal amidation are suggested in the art in relation to therapeutic peptides, the use of an N-terminal pyroglutamate in the context of inducing immune tolerance has not previously been discussed. It is anticipated that other peptides useful for inducing immune tolerance could also benefit from an N terminal acetyl or pyroglutamate and/or a C terminal amide and accordingly, in a further aspect there is provided a method bioavailability of a peptide comprising modifying the N terminus of the peptide by the addition of an N terminal acetyl or pyroglutamate and modifying the C terminus of the peptide by the addition of a C terminal amide. In a particular embodiment, the peptide comprises the amino acid sequence provided as SEQ ID NOs:228, 229 and/or 230.

In one embodiment, the peptide variant of SEQ ID NO:13 has the sequence:

```
                              (SEQ ID NO: 228; NPL001)
    pyroELQPFPQPELPYPQPQ-amide;
or
                              (SEQ ID NO: 231; NPL030)
    Ac-QLQPFPQPELPYPQPQ-amide.
```

In another embodiment, the peptide variant of SEQ ID NO:14 has the sequence:

```
                              (SEQ ID NO: 229; NPL002)
    pyroEQPFPQPEQPFPWQP-amide;
or
                              (SEQ ID NO: 232; NPL031)
    Ac-QQPFPQPEQPFPWQP-amide.
```

In another embodiment, the peptide variant of SEQ ID NO:16 has the sequence:

```
                              (SEQ ID NO: 230; NPL003)
    pyroEPEQPIPEQPQPYPQQ-amide;
or
                              (SEQ ID NO: 233; NPL032)
    Ac-FPEQPIPEQPQPYPQQ-amide.
```

The term "pyroE" indicates N-terminal pyroglutamate, and the term "Ac" indicates N-terminal acetyl.

In a particular embodiment, the agent or vaccine comprises NPL001, NPL002 and NPL003. Such agent or vaccine is described herein as NexVax2.

In another embodiment, the peptide variant of SEQ ID NO:13 has the sequence:

```
    LPYPQPELPYPQ.        (SEQ ID NO: 60; W01-E7)
```

In another embodiment, at least one glutamine in any one of the peptides is substituted by a glutamate.

Certain peptides described herein may exist in particular geometric or stereoisomeric forms. The present invention contemplates all such forms, including cis- (Z) and trans- (E) isomers, R- and S-enantiomers, diastereomers, (D)-isomers, (L)-isomers, the racemic mixtures thereof, and other mixtures thereof, as, falling within the scope of the invention. Additional asymmetric carbon atoms may be present in a substituent, such as an alkyl group. All such isomers, as well as mixtures thereof, are intended to be included in this invention.

In another example, to prevent cleavage by peptidases, any one or more of the peptides may include a non cleavable peptide bond in place of a particularly sensitive peptide bond to provide a more stable peptide. Such non cleavable peptide bonds may include beta amino acids.

In certain embodiments, any one or more of the peptides may include a functional group, for example, in place of the scissile peptide bond, which facilitates inhibition of a serine-, cysteine- or aspartate-type protease, as appropriate. For example, the invention includes a peptidyl diketone or a peptidyl keto ester, a peptide haloalkylketone, a peptide sulfonyl fluoride, a peptidyl boronate, a peptide epoxide, a peptidyl diazomethane, a peptidyl phosphonate, isocoumarins, benzoxazin-4-ones, carbamates, isocyantes, isatoic anhydrides or the like. Such functional groups have been provided in other peptide molecules, and general routes for their synthesis are known.

A variant may be a mimetic. The term "mimetic" is intended to refer to a substance which has some chemical similarity to the molecule it mimics and retains a particular activity of interest (for example, inducing tolerance). The underlying rationale behind the use of peptide mimetics, is that the peptide backbone of proteins exists chiefly to orient amino acid side chains in such a way as to facilitate molecular interactions, such as those of T cell and MHC-peptide, antibody and antigen, enzyme and substrate or scaffolding proteins. A peptide mimetic is designed to permit molecular interactions similar to the natural molecule. Mimetics include olefins, phosphonates, aza-amino acid analogues and the like. Persons skilled in the art would readily appreciate methods for designing mimetics of peptides and would be able to utilise them to design mimetics of the peptides defined herein.

The peptides may be analysed by hydrophilicity analysis, which can be used to identify the hydrophobic and hydrophilic regions of the peptide, thus aiding in the design of peptides for experimental manipulation, such as in binding experiments, antibody synthesis, etc. Secondary structural analysis may also be performed to identify regions of a peptide that adopt specific structural motifs. Manipulation, translation, secondary structure prediction, hydrophilicity and hydrophobicity profiles, open reading frame prediction and plotting, and determination of sequence homologies, can be accomplished using computer software programs available in the art. Other methods of structural analysis including, but not limited to, X-ray crystallography, mass spectrometry and gas chromatography, computer modelling, optical rotary dispersion (ORD), or circular dichroism (CD) may also be used.

The peptides, fragments or variants may be in a salt form, preferably, a pharmaceutically acceptable salt form. "A pharmaceutically acceptable salt form" includes the conventional non-toxic salts or quaternary ammonium salts of a peptide, for example, from non-toxic organic or inorganic acids. Conventional non-toxic salts include, for example, those derived from inorganic acids such as hydrochloride, hydrobromic, sulphuric, sulfonic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The peptides can be provided in the agent or vaccine as separate peptides or linked, for example, in a polyepitope structure. In one embodiment, the peptides may be presented in a single polypeptide chain (polyepitope string), i.e., in a linear or circular arrangement. In another embodiment, the peptides can be presented in a multiple antigen presentation system, particularly based on a dendrimer backbone such as polylysine. A polylysine backbone provides a non-linear, branched arrangement of epitopes. This system provides the advantage over a polyepitope string that the peptides do not interfere with each other or be laible to cleavage into cryptic epitopes and thus are able to induce a full T cell response.

Conjugates

One or more of the peptides may be conjugated to a compound using standard methods. Examples of compounds to which the peptides can be conjugated include but are not limited to a radioisotope, a fluorescent label, a chemiluminescent compound, an enzyme label, a free radical, an avidinbiotin label, a bacteriophage label, a compound that increases the half life of the peptide in a subject, an adjuvant, an MHC molecule or fragment thereof.

The compound may facilitate detection and/or isolation or increase immunogenicity of the conjugated peptide.

"Conjugated" as used herein means coupled via covalent or non-covalent bonds. While covalent bonds are preferred, the compound may also be linked to the peptide via complexation without covalent linkage, for example, via hydrogen bonds or electrostatic, hydrophobic, etc., interaction.

Typical radioactive isotopes include $^{3}H$, $^{125}I$, $^{131}I$, $^{32}P$, $^{35}S$, $^{14}C$, $^{51}Cr$, $^{36}Cl$, $^{57}Co$, $^{58}Co$, $^{59}Fe$, $^{75}Se$, and $^{152}Eu$.

Typical fluorescent labels include fluorescein isothiocyanate, rhodamine, phycoerythrin, phycocyanin, allophycocyanin, o-phthaldehyde, and fluorescamine.

Typical chemiluminescent compounds include luminol, isoluminol, aromatic acridinium esters, imidazoles, acridinium salts, and the oxalate esters. Typical bioluminescent compounds include luciferin, luciferase, and aequorin.

Typical enzyme labels include alkaline phosphatase, beta-galactosidase, glucose-6-phosphate dehydrogenase, maleate dehydrogenase, glucose oxidase, and peroxidase.

In one embodiment, a non-specific linker is included between the compound and the peptide to which it is conjugated. Such a linker is not involved in peptide activity. Rather the linker may serve as a spacer between the peptide and a functional moiety. Uses for a linker include immobilization of the peptide, such as to aid purification or detection. Alternatively, a linker may allow attachment of a compound to the peptide that enables specific delivery of the peptide to a particular target, such as a cell or tissue, spatially or temporally. When used as a vaccine, one or more of the peptides may be coupled to a linker that serves as a spacer between the peptide and an immunogenic carrier, or permits improved coupling between the peptide and the immunogenic carrier and prevents the formation of cryptic epitopes.

In one embodiment, one or more of the peptides are covalently coupled to an adjuvant (immunogenic carrier protein), such as diphtheria toxoid (DT), keyhole limpet hemocyanin (KLH), tetanus toxoid (TT) or the nuclear protein of influenza virus (NP), to increase their immunogenicity, using any of several conjugation chemistries known in the art. A non-specific linker can be present between the peptide and the immunogenic carrier and is preferably joined to the peptide or co-synthesised to facilitate coupling to the immunogenic carrier and/or to serve as a spacer between the peptide and the immunogenic carrier.

When used as a diagnostic agent, one or more of the peptides are preferably conjugated to an immunogenic carrier that was not previously used for vaccination. When monitoring the success of vaccination, this prevents the diagnostic agent from reacting to antibodies that were formed against the carrier fraction of the vaccine.

In one embodiment, the compound is an MHC class II molecule or peptide binding fragment thereof. The MHC class II molecule may be purified from a biological sample. Alternatively, the MHC class II molecule may be recombinantly produced. A peptide binding fragment of the MHC class II molecule can be obtained, for example, by enzymatic cleavage of the purified or recombinant intact molecule. Alternatively, the peptide binding fragment may be recombinantly produced. In a preferred embodiment, the compound is a recombinant two domain MHC class II molecule.

In their most basic form, the two domain MHC class II molecule comprises the α1 and β1 domain of a mammalian MHC class II molecule wherein the amino terminus of the α1 domain is covalently linked to the carboxy terminus of the β1 domain and wherein the polypeptide does not include the α2 or β2 domains. The two domain MHC class II molecule is associated by covalent or non-covalent interaction with a peptide defined herein. In certain embodiments, the peptide is covalently linked to the amino terminus of the β1 domain of the class II molecule. The two domain MHC class II molecule may also comprise a detectable label, such as a fluorescent label, or a toxin. Where the detectable label or toxin is to be covalently linked to the MHC molecule in a directed manner (i.e., rather than being randomly attached) it will generally be linked to the carboxy terminus of the molecule so as to minimise interference with the peptide antigen linked at the amino terminus.

In vitro, the two domain MHC class II molecule may be used to detect and quantify T-cells, and regulate T-cell function. Thus, such molecules loaded with a selected peptide may be used to detect, monitor and quantify the population of T cells that are specific for that peptide. The two domain MHC class II molecule/peptide conjugate may also be used to induce anergy of gluten-specific T-cells, alleviating symptoms associated with celiac disease. Alternatively, such molecules may be conjugated with a toxin to more directly kill the disease-causing T cells. Suitable toxins include protein toxins (for example, ricin, diphtheria, and *Pseudomonas* toxin), chemotherapeutic agents (for example, doxorubicin, daunorubicin, methotrexate, cytotoxin, and antisense RNA), antibodies to a cytotoxic T-cell surface molecule, lipases, and radioisotopes emitting "hard", for example, beta radiation.

Design of Recombinant MHC Class II NaI Molecule

The amino acid sequences of mammalian MHC class II α and β chain proteins, as well as nucleic acids encoding these proteins, are well known in the art and available from numerous sources including GenBank.

Typically, the α1 domain is regarded as comprising about residues 1-90 of the mature α chain. The native peptide linker region between the α1 and α2 domains of the MHC class II protein spans from about amino acid 76 to about amino acid 93 of the α chain, depending on the particular α chain under consideration. Thus, an α1 domain may include about amino acid residues 1-90 of the α chain, but one of skill in the art will recognise that the C-terminal cut-off of this domain is not necessarily precisely defined, and, for example, might occur at any point between amino acid residues 70-100 of the α chain. The composition of the α1 domain may also vary outside of these parameters depending on the mammalian species and the particular a chain in question.

Similarly, the β1 domain is typically regarded as comprising about residues 1-90 of the mature β chain. The linker region between the β1 and β2 domains of the MHC class II protein spans from about amino acid 85 to about amino acid 100 of the β chain, depending on the particular β chain under consideration. Thus, the β1 protein may include about amino acid residues 1-100, but one of skill in the art will again recognise that the C-terminal cut-off of this domain is not necessarily precisely defined, and, for example, might occur at any point between amino acid residues 75-105 of the β chain.

When selecting the sequence of a particular domain for inclusion in a recombinant molecule, it is preferable that the entire domain be included; to ensure that this is done, the domain sequence may be extended to include part of the linker, or even part of the adjacent domain. The precise number of amino acids in the α1 and β1 domains varies depending on the species of mammal, as well as between classes of genes within a species. Rather than a precise structural definition based on the number of amino acids, it is the maintenance of domain function that is important when selecting the amino acid sequence of a particular domain. Moreover, one of skill in the art will appreciate that domain function may also be maintained if somewhat less than the entire amino acid sequence of the selected domain is utilised. For example, a number of amino acids at either the amino or carboxy terminii of the α1 domain may be omitted without affecting domain function. Typically however, the number of amino acids omitted from either terminus of the domain sequence will be no greater than 10, and more typically no greater than 5. Similarly, the α1 and β1 domains may include one or more amino acid sequence variations compared to the naturally occurring form providing domain function is maintained.

The functional activity of a particular selected domain may be assessed in the context of the peptide loaded MHC class II β1α1 molecule. For example, to test a particular β1 domain, it will be linked to a functional α1 domain, the resultant MHC class II β1α1 molecule peptide loaded and tested for its ability to bind to and/or inhibit antigen specific T cell function, for example, T cell proliferation.

Nucleic acid molecules encoding these domains may be produced by standard means, such as amplification by the PCR. Standard approaches for designing primers for amplifying open reading frames encoding these domain may be employed. Libraries suitable for the amplification of these domains include, for example, cDNA libraries prepared from the mammalian species in question; such libraries are available commercially, or may be prepared by standard methods. Thus, for example, constructs encoding the β1 and α1 polypeptides may be produced by PCR using four primers: primers B1 and B2 corresponding to the 5' and 3' ends of the β1 coding region, and primers A1 and A2 corresponding to the 5' and 3' ends of the α1 coding region. Following PCR amplification of the α1 and β1 domain coding regions, these amplified nucleic acid molecules may each be cloned into standard cloning vectors, or the molecules may be ligated together and then cloned into a suitable vector. To facilitate convenient cloning of the two coding regions, restriction endonuclease recognition sites may be designed into the PCR primers. For example, primers B2 and A1 may each include a suitable site such that the amplified fragments may be readily ligated together following amplification and digestion with the selected restriction enzyme. In addition, primers B1 and A2 may each include restriction sites to facilitate cloning into the polylinker site of the selected vector. Ligation of the two domain coding regions is performed such that the coding regions are operably linked, i.e., to maintain the open reading frame. Where the amplified coding regions are separately cloned, the fragments may be subsequently released from the cloning vector and gel purified, preparatory to ligation.

In certain embodiments, a peptide linker is provided between the β1 and α1 domains. Typically, this linker is between 2 and 25 amino acids in length, and serves to provide flexibility between the domains such that each domain is free to fold into its native conformation. The linker sequence may conveniently be provided by designing the PCR primers to encode the linker sequence. Thus, in the example described above, the linker sequence may be encoded by one of the B2 or A1 primers, or a combination of each of these primers.

Variant MHC domain polypeptides may be produced by manipulating the nucleotide sequence of the molecule encoding the domain, for example by site-directed mutagenesis or the PCR.

Genetic Linkage of Antigenic Peptide to MHC Class II NaI Molecule

The MHC Class II β1α1 molecule is used in conjunction with a peptide defined herein. The MHC Class II β1α1 molecule may be "loaded" with the peptide in a number of ways, including by covalent attachment of the peptide to the MHC molecule. This may be conveniently achieved by operably linking a nucleic acid sequence encoding the selected peptide to the 5' end of the construct encoding the MHC molecule such that, the expressed peptide is linked to the N-terminus of β1 of the MHC Class II β1α1 molecule. One convenient way of obtaining this result is to incorporate a sequence encoding the peptide into the PCR primers used to amplify the MHC coding regions. Typically, a sequence encoding a linker peptide sequence will be included between the molecules encoding the antigenic peptide and the MHC polypeptide. For linking antigens to the MHC polypeptide, the linker should be sufficiently long to permit the antigenic peptide to fit into the peptide groove of the MHC polypeptide.

This genetic system for linkage of the antigenic peptide to the MHC molecule is particularly useful where a number of MHC molecules with differing antigenic peptides are to be produced. The described system permits the construction of an expression vector in which a unique restriction site is included at the 5' end of the MHC coding region (i.e., at the 5' end of β1 of the MHC Class II β1α1 molecule). In conjunction with such a construct, a library of antigenic peptide-encoding sequences is made, with each antigen-coding region flanked by sites for the selected restriction enzyme. The inclusion of a particular antigen into the MHC molecule is then performed simply by (a) releasing the antigen-coding region with the selected restriction enzyme, (b) cleaving the MHC construct with the same restriction enzyme, and (c) ligating the antigen coding region into the MHC construct. In this manner, a large number of MHC-polypeptide constructs can be made and expressed in a short period of time.

Antigen Loading of Empty β1α1 and α1α2 Molecules

Where the MHC Class II β1α1 molecule is expressed and purified in an empty form (i.e., without attached antigenic peptide), the antigenic peptide may be loaded into the molecules using standard methods. Such methods include simple co-incubation of the purified MHC molecule with a purified preparation of the peptide.

By way of example, empty MHC Class II β1α1 molecules (1 mg/ml; 40 uM) may be loaded by incubation with a 10-fold molar excess of peptide (1 mg/ml; 400 uM) at room temperature, for 24 hours. Thereafter, excess unbound peptide may be removed by dialysis against PBS at 4° C. for 24 hours. As is known in the art, peptide binding to MHC Class II β1α1 molecules can be quantified by silica gel thin layer chromatography (TLC) using radiolabeled peptide. Based on such quantification, the loading may be altered (for example, by changing the molar excess of peptide or the time of incubation) to obtain the desired result.

Polynucleotides

The terms "nucleic acid", "nucleic acid molecule", "nucleic acid sequence" and "polynucleotide" can generally be used interchangeably and encompass biologically active fragments, and variants including homologues.

The overall length of each constituent polynucleotide of an agent may be, for example, 21 to 150 nucleotides, such as, 21, 22, 23, 24, 25, 26, 27, 28, 29, 30, 31, 32, 33, 34, 35, 36, 37, 38, 39, 40, 41, 42, 43, 44, 45, 50, 60, 70, 80, 90, 100, 110, 120, 130, 140, 150 nucleotides.

A "biologically active fragment" of a nucleic acid molecule consists of fewer nucleotides than that of the reference peptide encoding polynucleotide sequence and has a length of at least about 21 nucleotides, and may have a length of at least about 35 nucleotides.

The terms "biologically active variant" and "biologically active fragment" have analogous meanings to those ascribed above with regard to the peptides defined herein.

A "biologically active variant" may comprise a sequence of nucleotides having at least 60% identity to the reference peptide encoding polynucleotide sequence. Percentage identity can be determined using readily available software packages, such as BLAST (www.ncbi.nlm.nih.gov/) and GAP.

Alternatively, or in addition, the "biologically active variant" may hybridise to the reference peptide encoding nucleotide sequence (or a complementary form thereof) under low stringency conditions. Reference herein to "low stringency" refers to at least about 0 to at least about 15% v/v formamide and from at least about 1 M to at least about 2 M salt for hybridization, and at least about 1 M to at least about 2 M salt for washing conditions. Generally, low stringency is at from about 25-30° C. to about 42° C. The temperature may be altered and higher temperatures used to replace formamide and/or to give alternative stringency conditions. Alternative stringency conditions may be applied where necessary, such as medium or high stringency. Reference herein to "medium stringency" refers to from at least about 16% v/v to at least about 30% v/v formamide and from at least about 0.5 M to at least about 0.9 M salt for hybridization, and at least about 0.5 M to at least about 0.9 M salt for washing conditions. Reference herein to "high stringency" refers to from at least about 31% v/v to at least about 50% v/v formamide and from at least about 0.01 M to at least about 0.15 M salt for hybridization, and at least about 0.01 M to at least about 0.15 M salt for washing conditions.

In general, washing is carried out at $Tm=69.3+0.41$ (G+C) %. However, the Tm of a duplex nucleic acid molecule decreases by 1° C. with every increase of 1% in the number of mismatch base pairs. Formamide is optional in these hybridization conditions.

Particularly preferred levels of stringency are defined as follows: low stringency is 6×SSC buffer, 0.1% w/v SDS at 25-42° C.; moderate stringency is 2×SSC buffer, 0.1% w/v SDS at 20-65° C.; high stringency is 0.1×SSC buffer, 0.1% w/v SDS at, at least 65° C.

Biological variants include polynucleotides that vary by one or more nucleotides from the reference polynucleotide. For example, a variant can comprise a substitution of one or more naturally occurring nucleotides with an analogue (such as the morpholine ring), methylated nucleotide, internucleotide modifications such as uncharged linkages (for example, methyl phosphonates, phosphotriesters, phosphoamidates, carbamates, etc.), charged linkages (for example, phosphorothioates, phosphorodithioates, etc.), pendent moieties (for example, polypeptides), intercalators (for example, acridine, psoralen, etc.), chelators, alkylators and modified linkages (for example, α-anomeric nucleic acids, etc.). Polynucleotides encoding one or more of the peptides may be provided in a vector.

A polynucleotide encoding one or more of the peptides defined herein can be used for the recombinant production of the peptides using techniques well known in the art. Alternatively, the polynucleotide can be used to immunise/tolerise a subject to gluten.

A polynucleotide for use in the invention includes a DNA sequence that can be derived from one or more of the peptides, bearing in mind the degeneracy of codon usage. This is well known in the art, as is knowledge of codon usage in different expression hosts, which is helpful in optimizing the recombinant expression of the peptides.

When the polynucleotide is used for the recombinant production of one or more of the peptides, the polynucleotide may include the coding sequence for the peptides alone or the coding sequence for the peptides in reading frame with other coding sequences, such as those encoding a leader or secretory sequence, a pre-, or pro-or prepro-protein sequence, linker peptide sequence, or other fusion peptide portions. For example, a marker sequence which facilitates purification of the fused peptide can be encoded. In certain embodiments, the marker sequence is a hexa-histidine peptide, as provided in the pQE vector (Qiagen, Inc.), or is an HA tag, or is glutathione-S-transferase. The polynucleotide may also contain non-coding 5' and 3' sequences, such as transcribed, non-translated sequences, splicing and polyadenylation signals, ribosome binding sites and sequences that stabilise mRNA.

Antigen Presenting Cells

The agent and/or peptides defined herein may be delivered by loading APCs with, for example, the first, second and third peptides, a biologically active fragment or variant of one or more thereof, and/or a polynucleotide encoding one or more thereof.

Preferably, the APCs are selected from the group consisting of dendritic cells, macrophages, B-lymphocytes and liver sinusoidal endothelial cells that express MHC class II molecules shared with the MHC phenotype of the subject. For example, the APCs may express HLA-DQ2 (for example, HLA DQA1*05 and HLA DQB1*02) and/or HLA DQ8. The APCs employed for this purpose may be isolated from the subject to whom they are to be delivered after loading, or they may be obtained from an allo-matched subject.

By "loading" an APC it is meant that the APC is incubated or transfected with the peptides, a biologically active fragment or variant of one or more thereof, or a polynucleotide encoding one or more thereof. Loading an APC can be achieved by using conventional nucleic acid transfection methods, such as lipid-mediated transfection, electroporation, and calcium phosphate transfection.

Peptide Production

The peptides can be prepared in any suitable manner. For example, the peptides can be recombinantly and/or synthetically produced.

The peptides may be synthesised by standard chemistry techniques, including synthesis by automated procedure using a commercially available peptide synthesiser. In general, peptide analogues are prepared by solid-phase peptide synthesis methodology which may involve coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminal. After the last residue has been attached, the protected peptide-resin is treated with hydrogen fluoride to cleave the peptide from the resin, as well as deprotect the side chain functional groups. Crude product can be further purified by gel filtration, high pressure liquid chromatography (HPLC), partition chromatography, or ion-exchange chromatography.

If desired, and as outlined above, various groups may be introduced into the peptide of the agent during synthesis or during expression, which allow for linking to other molecules or to a surface. For example, cysteines can be used to make thioethers, histidines for linking to a metal ion complex, carboxyl groups for forming amides or esters, amino groups for forming amides, and the like.

The peptides may also be produced using cell-free translation systems. Standard translation systems, such as reticulocyte lysates and wheat germ extracts, use RNA as a template; whereas "coupled" and "linked" systems start with DNA templates, which are transcribed into RNA then translated.

Alternatively, the peptides may be produced by transfecting host cells with expression vectors that comprise a polynucleotide(s) that encodes one or more peptides.

For recombinant production, a recombinant construct comprising a sequence which encodes one or more of the peptides is introduced into host cells by conventional methods such as calcium phosphate transfection, DEAE-dextran mediated transfection, microinjection, cationic lipid-mediated transfection, electroporation, transduction, scrape lading, ballistic introduction or infection.

One or more of the peptides may be expressed in suitable host cells, such as, for example, mammalian cells (for example, COS, CHO, BHK, 293 HEK, VERO, HeLa, HepG2, MDCK, W138, or NIH 3T3 cells), yeast (for example, *Saccharomyces* or *Pichia*), bacteria (for example, *E. coli, P. pastoris*, or *B. subtilis*), insect cells (for example, baculovirus in Sf9 cells) or other cells under the control of appropriate promoters using conventional techniques. Following transformation of the suitable host strain and growth of the host strain to an appropriate cell density, the cells are harvested by centrifugation, disrupted by physical or chemical means, and the resulting crude extract retained for further purification of the peptide or variant thereof.

Suitable expression vectors include, for example, chromosomal, non-chromosomal and synthetic polynucleotides, for example, derivatives of SV40, bacterial plasmids, phage DNAs, yeast plasmids, vectors derived from combinations of plasmids and phage DNAs, viral DNA such as vaccinia viruses, adenovirus, adeno-associated virus, lentivirus, canary pox virus, fowl pox virus, pseudorabies, baculovirus, herpes virus and retrovirus. The polynucleotide may be introduced into the expression vector by conventional procedures known in the art.

The polynucleotide which encodes one or more peptides may be operatively linked to an expression control sequence, i.e., a promoter, which directs mRNA synthesis. Representative examples of such promoters include the LTR or SV40 promoter, the *E. coli* lac or trp, the phage lambda PL promoter and other promoters known to control expression of genes in prokaryotic or eukaryotic cells or in viruses. The expression vector may also contain a ribosome binding site for translation initiation and a transcription terminator.

The expression vectors may also include an origin of replication and a selectable marker, such as the ampicillin resistance gene of *E. coli* to permit selection of transformed cells, i.e., cells that are expressing the heterologous polynucleotide. The nucleic acid molecule encoding one or more of the peptides may be incorporated into the vector in frame with translation initiation and termination sequences.

One or more of the peptides can be recovered and purified from recombinant cell cultures (i.e., from the cells or culture medium) by well known methods including ammonium sulphate or ethanol precipitation, acid extraction, anion or cation exchange chromatography, phosphocellulose chromatography, hydrophobic interaction chromatography, affinity chromatography, hydroxyapatite chromatography, lectin chromatography, and HPLC. Well known techniques for refolding proteins may be employed to regenerate active conformation when the peptide is denatured during isolation and or purification.

To produce a glycosylated peptide, it is preferred that recombinant techniques be used. To produce a glycosylated peptide, it is preferred that mammalian cells such as, COS-7 and Hep-G2 cells be employed in the recombinant techniques.

The peptides can also be prepared by cleavage of longer peptides, especially from food extracts.

Pharmaceutically acceptable salts of the peptides can be synthesised from the peptides which contain a basic or acid moiety by conventional chemical methods. Generally, the salts are prepared by reacting the free base or acid with stoichiometric amounts or with an excess of the desired salt-forming inorganic or organic acid or base in a suitable solvent.

Vaccines and Administration

The invention also provides a vaccine comprising the first, second and third peptides, a biologically active fragment or variant of one or more thereof, and/or a polynucleotide encoding one or more thereof. Also provided is a vaccine comprising a peptide of the invention and/or a polynucleotide of the invention.

As used herein, the term "vaccine" refers to a composition comprising or encoding peptides that can be administered to a subject sensitive to gluten to modulate the subject's response to gluten. The vaccine may reduce the immunological reactivity of a subject towards gluten. Preferably, the vaccine induces tolerance to gluten.

Administration of the vaccine to a subject may induce tolerance by clonal deletion of gluten-specific effector T cell populations, for example, gluten-specific $CD4^+$ T cells, or by inactivation (anergy) of said T cells such that they become less responsive, preferably, unresponsive to subsequent exposure to gluten (or peptides thereof).

Alternatively, or in addition, administration of the vaccine may modify the cytokine secretion profile of the subject (for example, result in decreased IL-4, IL-2, $TNF\alpha$ and/or $IFN\gamma$, and/or increased IL-10). The vaccine may induce suppressor T cell subpopulations, for example Treg cells, to produce IL-10 and/or $TGF\beta$ and thereby suppress gluten-specific effector T cells.

The vaccine of the invention can be used for prophylactic treatment of a subject capable of developing sensitivity to gluten, for example, diagnosed as carrying the HLA-DQ2 and/or HLA-DQ8 gene and/or ongoing treatment of a subject who is sensitive to gluten, for example, a subject who has celiac disease. There is considerable animal data to support the prophylactic activity of immunodominant peptides for various autoimmune and model immune conditions, for example, experimental allergic encephalitis.

As used herein, the term "treatment" includes abrogating, inhibiting, slowing, or reversing the progression of a disease or condition, or ameliorating or preventing a clinical symptom of the disease (for example, celiac disease) or condition.

The amount of vaccine (or agent, peptide, polynucleotide and/or APC) to be administered is referred to as the "effective amount". The term "effective amount" means the amount sufficient to provide the desired therapeutic or physiological effect when administered under appropriate or sufficient conditions. Single or multiple doses may be administered. Undesirable effects, for example, side effects, are sometimes manifested along with the desired therapeutic effect; hence, a practitioner balances the potential benefits against the potential risks in determining an appropriate "effective amount". The exact amount required will vary from subject to subject, depending on the species, age, size and general condition of the subject, mode of administration and the like. Thus, it may not be possible to specify an exact "effective amount". However, an appropriate "effective amount" in any individual case may be determined by one of ordinary skill in the art using only routine experimentation.

The vaccine (or agent, peptide, polynucleotide and/or APC) modifies the T cell response to wheat, barley and rye in the subject, and preferably wheat, barley, rye and oats, as represented by gliadin, secalin, hordein, glutenin and optionally avedin proteins. Thus, a subject treated according to the invention preferably is able to eat at least wheat, rye, barley and optionally oats without a significant T cell response which would normally lead to symptoms of celiac disease.

The individual components of an agent of the invention may be administered in the same composition or in different compositions or a combination thereof (for example, the first and second peptide defined herein in one composition, and the third peptide in a separate composition). If in different compositions, they may be administered simultaneously or sequentially.

The agent or vaccine may include a pharmaceutically acceptable carrier. The term "pharmaceutically acceptable carrier" refers to molecular entities and compositions that do not produce an allergic, toxic or otherwise adverse reaction when administered to a subject, particularly a mammal, and more particularly a human. The pharmaceutically acceptable carrier may be solid or liquid. Useful examples of pharmaceutically acceptable carriers include, but are not limited to, diluents, excipients, solvents, surfactants, suspending agents, buffering agents, lubricating agents, adjuvants, vehicles, emulsifiers, absorbants, dispersion media, coatings, stabilizers, protective colloids, adhesives, thickeners, thixotropic agents, penetration agents, sequestering agents, isotonic and absorption delaying agents that do not affect the activity of the active agents of the invention.

The carrier can be any of those conventionally used and is limited only by chemico-physical considerations, such as solubility and lack of reactivity with the active agent, and by the route of administration. Suitable carriers for this invention include those conventionally used, for example, water, saline, aqueous dextrose, lactose, Ringer's solution, a buffered solution, hyaluronan, glycols, starch, cellulose, glucose, lactose, sucrose, gelatin, malt, rice, flour, chalk, silica gel, magnesium stearate, sodium stearate, glycerol monostearate, sodium chloride, glycerol, propylene glycol, water, ethanol, and the like. Liposomes may also be used as carriers.

Techniques for preparing pharmaceutical compositions are generally known in the art as exemplified by Remington's Pharmaceutical Sciences, 16th Ed. Mack Publishing Company, 1980.

The term "adjuvant" generally refers to an immunostimulatory substance designed to enhance the immunogenicity of one or more peptides defined herein. Preferably, the adjuvant does not produce a Th1 response and further, promotes immune tolerance and/or reduces inflammation. Suitable adjuvants include 1) an aluminium-based mineral salt adjuvant, for instance an Al(OH)$_3$ gel or aluminium phosphate, but may also be a salt of calcium, iron or zinc; and 2) dexamethasone (Kang et al., 2008).

Administered may be orally, topically (percutaneous), parenterally, by inhalation spray or rectally in dosage unit formulations containing conventional non-toxic pharmaceutically acceptable carriers. The term "parenteral", as used herein includes intravenous, intraarterial, intraperitoneal, intramuscular, subcutaneous, subconjunctival, intracavity, transdermal and subcutaneous injection, aerosol for administration to lungs or nasal cavity, or administration by infusion by, for example, osmotic pump.

The active compounds of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to methods known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets

Tablets containing the active ingredient in admixture with pharmaceutically acceptable excipients may also be manufactured by known methods. The excipients used may be for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous Suspensions

Aqueous suspensions normally contain the active materials in admixture with excipients suitable for the manufacture of aqueous suspensions. Such excipients may include: (1) suspending agents such as sodium carboxymethylcellulose, methylcellulose, hydroxypropylmethylcellulose, sodium alginate, polyvinylpyrrolidone, gum tragacanth and gum acacia; or (2) dispersing or wetting agents such as PEG esters of $C_2$-$C_{18}$ fatty acids, Tween® 80 or polyethylene oxide sorbitan monooleate, Brij® or polyoxyethylene alcohol, Triton™-X or Polyethylene glycol p-isooctylphenyl ether, Triton™-N or Polyoxyethylene branched nonylcyclohexyl ether, and Triton™ A-20 or 4-(1,1,3,3-Tetramethylbutyl) phenol, polymer with formaldehyde and oxirane, DECON, Tris or 2-amino-2-hydroxymethyl-1,3-propanediol and Cremophor® EL or polyoxyl 35 hydrogenated castor oil.

The aqueous suspensions may also contain one or more preservatives, for example, ethyl or n-propyl p-hydroxybenzoate; one or more colouring agents; one or more flavouring agents; and one or more sweetening agents such as sucrose, aspartame or saccharin.

Oily Suspensions

Oily suspension may be formulated by suspending the active ingredient in a vegetable oil, for example arachis oil, olive oil, sesame oil or coconut oil, a fish oil which contains omega 3 fatty acid, or in a mineral oil such as liquid paraffin. The oily suspensions may contain a thickening agent, for example beeswax, hard paraffin or cetyl alcohol. Sweetening agents and flavouring agents may be added to provide a palatable oral preparation. These compositions may be preserved by the addition of an antioxidant such as ascorbic acid.

Dispersible Powders and Granules

Dispersible powders and granules are suitable for the preparation of an aqueous suspension. They provide the active ingredient in a mixture with a dispersing or wetting agent, a suspending agent and one or more preservatives. Suitable dispersing or wetting agents and suspending agents are exemplified by those already mentioned above. Additional excipients, for example, those sweetening, flavouring and colouring agents described above may also be present.

Emulsion

The pharmaceutical composition(s) may also be in the form of oil-in-water emulsions. The oily phase may be a vegetable oil such as olive oil or arachis oils, or a mineral oil such as liquid paraffin or a mixture thereof. Suitable emulsifying agents include gum acacia, gum tragacanth, soy bean, lecithin, polyoxyethylene oxide sorbitan monooleate (Tween® 80). The emulsions may also contain sweetening and flavouring agents.

Syrups and Elixirs

Syrups and elixirs may be formulated with sweetening agents, for example, glycerol, propylene glycol, sorbitol, aspartame or sucrose. Such formulations may also contain a demulcent, preservative, flavouring and colouring agents.

Injectables

The pharmaceutical composition(s) may be in the form of a sterile injectable aqueous or oleagenous suspension. This suspension may be formulated according to known methods using those suitable dispersing or wetting agents and suspending agents which have been mentioned above. The sterile injectable preparation may be a suspension in a non-toxic parenterally-acceptable diluent or solvent, for example as a solution in 1,3-butanediol. Among the acceptable carriers that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid find use in the preparation of injectables.

Compositions suitable for parenteral administration include, but are not limited to, aqueous and non-aqueous sterile injection solutions. Examples of appropriate delivery mechanisms for subcutaneous administration include, but are not limited to, implants, depots, needles, capsules, and osmotic pumps.

Sustained-Release Compositions

Sustained-release compositions may be prepared. Suitable examples of sustained-release preparations include semipermeable matrices of solid hydrophobic polymers which matrices are in the form of shaped articles, for example, films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

The active agent may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macro-emulsions.

Microencapsulation for sustained release has been successfully performed with human growth hormone (rhGH), interferon (rhIFN), interleukin-2, and MN rgp120. The sustained-release formulations of these proteins were developed using PLGA polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition.

Gene Therapy

In a further embodiment, a polynucleotide encoding one or more peptides defined herein is inserted into a recombinant expression vector for the purposes of administration to the subject.

The term "recombinant expression vector" refers to a plasmid, virus or other vehicle known in the art that has been manipulated by insertion or incorporation nucleic acid encoding one or peptides. Such expression vectors contain a promoter sequence which facilitates the efficient transcription in the host of the inserted genetic sequence. The expression vector typically contains an origin of replication, a promoter, as well as specific genes which allow phenotypic selection of the transformed cells.

In one embodiment, the viral vector is derived from adeno-associated virus (AAV) and comprises a constitutive or regulatable promoter capable of driving sufficient levels of expression of the peptides defined herein. Preferably, the viral vector comprises inverted terminal repeat sequences of AAV, such as those described in WO 93/24641. In a preferred embodiment, the viral vector comprises polynucleotide sequences of the pTR-UF5 plasmid. The pTR-UF5 plasmid is a modified version of the pTR.sub.BS-UF/UF1/UF2/UFB series of plasmids (Zolotukiin et al., 1996; Klein et al., 1998).

Promoters useful with the subject invention include, for example, the cytomegalovirus immediate early promoter (CMV), the human elongation factor 1-α promoter (EF1), the small nuclear RNA promoters (U1a and U1b), α-myosin heavy chain promoter, Simian virus 40 promoter (SV40), Rous sarcoma virus promoter (RSV), adenovirus major late promoter, β-actin promoter and hybrid regulatory element comprising a CMV enhancer/β-actin promoter. These promoters have been shown to be active in a wide range of mammalian cells.

The promoters are operably linked with heterologous polynucleotide encoding one or more peptides defined herein. By "operably linked," it is intended that the-promoter element is positioned relative to the coding sequence to be capable of effecting expression of the coding sequence.

Also contemplated for use with the vectors of the present invention are inducible and cell type specific promoters, for example, Tet-inducible promoters (Clontech, Palo Alto, Calif.) and VP16-LexA promoters (Nettelbeck et al., 1998).

Transcriptional enhancer elements which can function to increase levels of transcription from a given promoter can also be included in the vector. Enhancers can generally be placed in either orientation, 3' or 5', with respect to promoter sequences. In addition to the natural enhancers, synthetic enhancers can be used in the present invention, for example, a synthetic enhancer randomly assembled from Spc5-12-derived elements including muscle-specific elements, serum response factor binding element (SRE), myocyte-specific enhancer factor-1 (MEF-1), myocyte-specific enhancer factor-2 (MEF-2), transcription enhancer factor-1 (TEF-1) and SP-1 (Li et al., 1999; Deshpande et al., 1997; Stewart et al., 1996; Mitchell and Tjian, 1989; Briggs et al., 1986; Pitluk et al., 1991) can be used in the vector.

The gene therapy methods can be performed by ex vivo or in vivo treatment of the patient's cells or tissues. Vectors can be introduced into suitable cells, cell lines or tissue using methods known in the art. The viral particles and vectors can be introduced into cells or tissue in vitro or in vivo. Methods contemplated include transfection, transduction, injection and inhalation, for example, vectors can be introduced into cells using liposomes containing the subject vectors, by direct transfection with vectors alone, electroporation or by particle bombardment.

Dosage

It is especially advantageous to formulate the active in dosage unit form for ease of administration and uniformity of dosage. "Dosage unit form" as used herein refers to physically discrete units suited as unitary dosages for the subject to be treated; each unit containing a predetermined quantity of active agent calculated to produce the desired therapeutic effect in association with the required pharmaceutical carrier. The specification for the dosage unit forms are dictated by and directly dependent on the unique characteristics of the active agent and the particular therapeutic effect to be achieved, and the limitations inherent in the art of compounding such an active agent for the treatment of subjects. Alternatively, the compositions may be presented in multi-dose form.

Examples of dosage units include sealed ampoules and vials and may be stored in a freeze-dried condition requiring only the addition of the sterile liquid carrier immediately prior to use.

The agent or vaccine may also be included in a container, pack, or dispenser together with instructions for administration.

The actual amount administered (or dose or dosage) and the rate and time-course of administration will depend on the nature and severity of the condition being treated. Prescription of treatment, for example, decisions on dosage, timing, frequency, etc., is within the responsibility of general practitioners or specialists (including human medical practicitioner, veterinarian or medical scientist) and typically takes account of the disorder to be treated, the condition of the subject, the site of delivery, the method of administration and other factors known to practitioners. Examples of techniques and protocols can be found in Remington's Pharmaceutical Sciences, 18th Ed. (1990), Mack Publishing, Company, Easton, Pa., U.S.A.). The dose, dose frequency, duration, route of administration and need for maintenance therapy could be based upon the criteria for other peptide immunotherapeutics.

Effective amounts may be measured from ng/kg body weight to g/kg body weight per minute, hour, day, week or month.

When in vivo administration of an agent or vaccine of the invention is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature.

Toxicity and therapeutic efficacy of the agent or vaccine can be determined by standard pharmaceutical procedures in cell cultures or experimental animals by determining the $IC_{50}$ and the maximal tolerated dose. The data obtained from these cell culture assays and animal studies can be used to formulate a range suitable for humans.

Diagnosis and Efficacy of Treatment

The peptides defined herein are also useful as a diagnostic agent.

In one example, gluten tolerance is assessed by measuring IL-10 and/or TGFβ secreted from stimulated cells, for example, Treg cells, exposed to the peptides defined herein. Treg cells are characterised by their capacity to produce large amounts of IL-10 and TGFβ. IL-10 is considered to be one of the main cytokines involved in immunosuppression; a target for suppression seems to be the transcriptional control of IL-2 in effector cells.

In another example, gluten tolerance is assessed by measuring IFNγ secreted from stimulated cells, for example, gluten-specific $CD4^+$ T cells.

The diagnostic test may be performed in vitro using whole blood or cells isolated and/or fractionated therefrom.

In one example, the cells have been previously exposed to one or more of the peptides (either alone, conjugated to an MHC molecule or fragment thereof, or peptide loaded APC). In another example, the cells are stimulated in vitro by coincubation with the peptides (either alone, conjugated to an MHC molecule or fragment thereof, or peptide loaded APC).

The direct T cell mediated effects of the agent can be monitored by functional assays utilising cells isolated from peripheral blood or tissue (for example, the small intestine). Effects of peptide administration down stream to cognate T cells could be assessed using immune cell types, tissues, biological fluids (for example, plasma, intestinal secretions, urine or stool).

In general the biological effects of peptides recognised by cognate T cells are either pro-inflammatory or tolerogenic, depending on the dose regimen, mode of administration and whether the peptides are modified or co-administered with another compound that has immunological properties, for example, an adjuvant. These and other peptides selected for use in peptide based therapeutic vaccines are generally short (<29 amino acids), aqueous-soluble, without innate immune effects and recognised by a substantial proportion of pathogenic T ells. Based upon observations in animal models of T cell mediated disease and in other human diseases, initial administration would be followed by activation of cognate T cells. However, repeated administration of the agent is expected to induce T cell anergy and/or tolerance. Ongoing regular peptide administration would be expected to maintain tolerance to gluten, suppress inflammation in the small intestine and inhibit pro-inflammatory gluten-specific T cells throughout the body.

Hence, the key marker of therapeutic success would be the absence of inflammation in the small intestine following deliberate gluten ingestion. Surrogate markers of immunity likely to predict normal or inflamed intestinal tissue after gluten ingestion includes a wide range of assays utilizing pure or crude mixtures of immune cells, biological fluids, or tissue samples, to measure soluble or cell-associated proteins or small molecules associated with immune activation, inflammation, or tolerance. These assays are well-known to immunologists, immuno-histologists, and clinicians familiar with immune diseases in rodents, humans, and in particular, celiac disease. Markers, more specifically, that assess the activity of celiac disease and gluten-induced immunity include small bowel histology, serum IgA and IgG specific gliadin (protein or peptide) and for various host proteins including tTG.

Generic and specific markers of immunity in celiac disease that might be adapted for use in monitoring the peptide immunotherapy for celiac disease or for diagnosis of celiac disease include the following:

(a) Direct effects of peptides on the $CD4^+$ T cell isolated from blood or tissue can be monitored ex vivo/in vitro by peptide-stimulated cytokine release, T-cell proliferation, or determination of $CD4^+$ T cell markers that may be altered in vivo.

(b) The frequency and phenotype of individual $CD4^+$ T cells specific for the peptides or gluten generally can be assessed by direct enumeration of cells, for example, by FACS analysis. Oral ingestion of gluten in patients with celiac disease normally following a gluten free diet is known to stimulate T cells specific for the peptides and gluten generally. A clinical test such as gluten challenge may be used to assess the T cells induced in blood or other tissues. The phenotype of isolated T cells could then be assessed fresh or following short-term expansion in vitro. Assays of T cells may rely upon MHC-peptide complexes, antigen-stimulated intracellular cytokine, or other cell surface markers induced on antigen-activated T cells. Functional status of CD4⁺ T cells is correlated with the presence of various cell-surface and intra-cellular markers, for example, activation markers including CD25 and CD69, or of "tolerance" and regulatory T cell function, for example, GITR and FOXP3. Production of cytokines such as IFNγ, IL-4, IL-5 and IL-13, and of IL-17 would be considered pro-inflammatory for classic Th1, Th2 or Th17 pro-inflammatory immune responses. In contrast, secretion of IL-10 and TGFβ are associated with tolerogenic immune responses. It would be expected markers of pro-inflammatory immune responses would decline and/or markers of tolerogenic immune responses would strengthen.

(c) Effects of peptides on CD4⁺ T cells can also be measured using mixtures of cells, for example, whole blood, PBMC, mononuclear cells isolated from tissue, or using tissue incubated with the peptides. Assays capable of measuring individual or multiple proteins or RNA encoding relevant immunological or disease-associated proteins such as cytokines and chemokines could be assessed after short-term incubation with the peptides. Assays such as IFNγ ELISpot using PBMC before and or after administration of gluten or peptides themselves to the patient, or multiplex assays of chemokines and cytokines using PBMC are capable of detecting the biological effects of peptide-specific T cells from patients. The therapeutic effect of the peptides would be indicated by a shift from markers associated with pro-inflammatory immune responses to markers associated with immune tolerance (for example, IL-10) and general reduction in pro-inflammatory markers such as IFNγ.

(d) Effects of peptides on tissue may be practical; functional assays could take the form of direct application of peptide to the skin to assess delayed-type hypersensitivity, as in the Mantoux test for tuberculosis, which involves intradermal application of PPD (purified protein derivative) and assessment of the diameter of redness at the injection site 24-72 h later. The peptides may also be applied to other mucosal and skin sites to assess in the same manner. In clinical practice, it is both the peptide and grain derived protein-stimulated immune response that is important in celiac disease. For example, it is predicted that immunotherapy using the selected peptides would not only lead to suppression of the immune response stimulated by T cells specific for the peptides but also "tolerance" would be "infectious" and also lead to suppression of pro-inflammatory immunity to other gluten-derived peptides and gluten itself. Hence, the effects of the peptide therapy could also be monitored using gluten from various grains (wheat, rye, barley) in celiac disease, in place of peptide in the assays described above. Indeed, peptide therapy for cat-sensitive asthma has been monitored by such a skin test utilizing the whole protein antigen from which the therapeutic peptides are derived (Oldfield et al., 2002).

(e) Ultimately, the clinical effects of the peptide immunotherapy would be assessed by histologic examination of tissues exposed to dietary gluten, typically the small bowel, but in experimental settings oral and rectal mucosa have also bee assessed, and in principle other sites such as oesophagus and colon might also be assessed. Tissue from these sites could be collected by direct visualization, typically by endoscopic biopsy. Direct visualization by endoscopy has also been used to diagnose celiac disease according to the appearance of the mucosa-villous atrophy can be assessed by standard as well as magnifying and capsule endoscopy. Hence, the tolerogenic effects of the peptides may be assessed simply by detection of macroscopic tissue damage in the gastrointestinal tract.

(f) Immunoglobulin specific for the peptides or other gluten peptides, or autoantigens relevant to celiac disease would provide markers of gluten immunity relevant to disease activity, and to opsonising activity that may compromise the therapeutic effects of the peptides themselves.

(g) Presence of markers associated with anaphylaxis, such as peptide- or gluten-specific IgE or histamine release by peripheral blood basophils may also be used to predict complications of peptide immunotherapy and need to adjust or cease therapy.

Food Test

The invention also provides a method of determining whether a composition or food is capable of causing celiac disease, the method comprising detecting the presence of the agent of the invention, the peptide of the invention and/or the polynucleotide of the invention in the composition or a food sample. Typically this is performed by using a binding assay in which one or more compounds which bind one or more peptides defined herein in a specific manner is contacted with the composition and the formation of peptide/compound complex(es) is detected and used to ascertain the presence of the peptide(s). In one example, the compound is an antibody. Any suitable format of binding assay can be used. Typically, the assay utilises monoclonal antibodies to gluten peptides in a non-competitive, sandwich type ELISA. Food samples may first be extracted, optionally diluted and then tested in the assay.

The composition or food typically comprises material from a plant that expresses gluten. Such material may be a plant part, such as a harvested product (for example, seed). The material may be processed products of the plant material, such as a flour or food that comprises gluten. The processing of food material and testing in suitable binding assays is routine (see for example, Kricka, 1998). The composition or food material may be treated with tTG prior to being contacted with the compound.

In one embodiment, the composition or food material is contacted with at least 2, 3, 5, 10 or more antibodies which are specific for peptides defined herein in deamidated and/or non-deamidated form. Preferably, the antibodies are directed against sequences that are protease resistant and allow for the detection of α, β, γ and ω gliadins, and LMW and HMW glutenins in wheat, B,C and D hordeins in barley, β, γ and ω secalins in rye, and optionally avenins in oats.

Antibodies directed against the peptides/epitopes defined herein may be provided in kit form for use in an assay for the detection and/or quantification of gluten in foods.

Protease Identification

The present invention also provides a method of identifying a protease that can cleave a peptide as defined herein, the method comprising contacting the peptide with a protease under conditions to effect specific cleavage of the peptide to produce a proteolytic product and detecting the proteolytic product produced. In one example, the proteolytic product is detected, for example, using SDS-PAGE, HPLC, ELIZA, or Western Blot. In a further example, the peptide is fused to a fluorescent donor and a quenching acceptor so as to enable intramolecular resonance energy transfer between the fluorescent donor and the quenching acceptor. Upon cleavage, the donor and acceptor are separated, allowing detection of the donor's fluorescent emission. Typically the peptide separates the fluorescent donor and the quenching acceptor at a distance of less than about 100 angstroms. The fluorescent donor can be attached to the peptide's C-terminus, and the quenching acceptor can be attached to the peptide's N-terminus, or vice versa.

EXAMPLES

Example 1

Determination of Immunodominant Peptides

Subjects

Volunteers were adults aged 18-70 years and following strict gluten free diet. All volunteers possessed genes encoding both HLA DQAB1*05 and HLA DQB1*02 as determined by PCR with sequence-specific primer mixes of peripheral blood DNA (Bunce et al., 1995; Olerup et al., 1993; Mullighan et al., 1997). Volunteers with celiac disease were diagnosed on the basis of ESPGAN criteria (Report of Working Group of European Society of Paediatric Gastroenterology and Nutrition, 1990). Subjects with celiac disease undergoing gluten challenge were on gluten free diet for at least 1 month and claimed to be compliant (positive tTG-IgA or EMA was an exclusion). Healthy HLA DQ2 subjects (endosmysial IgA negative) had followed a strict gluten free diet for 4 weeks before commencing gluten challenge.

Three-Day Gluten Challenge

Wheat Challenge:

Two 50 g slices for breakfast and for lunch of either Sainsbury's "standard white sandwich bread" (UK—to assess the Pilot library), or otherwise Baker's Delight "white bread block loaf").

Barley Challenge:

Pearl barley (Ward McKenzie, Altona, Australia) cooked as risotto (150 g dry weight daily). Risotto servings were divided into equal servings for breakfast, lunch and dinner.

Rye Challenge:

Daily consumption of 100 g dry weight rye flour in the form of muffins eaten throughout the course of the day beginning at breakfast. Rye flour-sourced was either from rye grown in "isolation" at Long Ashton Research Station, UK and subsequently hand milled (for assessment of the Pilot library), or from Biodynamic rye flour (Eden Valley Biodynamic Farm, Dumbleyung, Australia).

Combined Wheat, Barley and Rye Challenge:

Two muffins consisting of 25 g wheat flour (White Wings, Goodman Fielder, Australia), 22 g barley flour (Four Leaf Milling, Tarlee, South Australia), and 22 g rye flour (Four Leaf Milling, Tarlee, South Australia) were eaten each day.

Antigens

Synthetic peptides (purity >70%) were purchased from Research Genetics (USA), Mimotopes (Australia), or Pepscan (Netherlands). Deamidation with guinea pig liver tTG (Sigma T5398) was as described previously (Anderson et al., 2000). Peptides (2 mg/ml) or gliadin (Sigma G3375) were incubated for 4 hours, 37° C. in 10-fold excess with chymotrypsin (Sigma C3142) or trypsin (Sigma T1426) in ammonium bicarbonate (pH 8), or with pepsin (Sigma P6887) in 5% acetic acid (pH 2.5), then neutralised to pH 7 with NaOH, and finally boiled for 15 minutes. Prolamin protein concentrations were determined by BCA method (Pierce, USA). Hordein and secalin fractions were prepared from rye and barley grown in isolation from other grains, hand-milled flour, and fractionated according to published methods (Tatham, A. S., Gilbert, S. M., Fido R. J., and Shewry, R. Extraction, separation, and purification of wheat gluten proteins and related proteins of barley, rye, and oats. In: Marsh M, ed., Celiac disease methods and protocols. Totowa: Humana (2000) pp 55-73).

Peptide Libraries

Wheat, barley and rye gluten peptide libraries were designed by alignment and phylogeny ("Pilot" library, see Sequence Listing, Tables 3 and 4, or using a customised algorithm applied to entries for gliadins, glutenins, hordeins and secalins in NCBI Genbank at 2006 in their genome-encoded (wildtype) sequence ("Comprehensive" library), or both wildtype and in silico tTG deamidated sequence ("Verification" library) according to defined deamidation motifs (Beissbarth, et al., 2005).

TABLE 3

Gluten peptide libraries.

| Library | Pilot | Comprehensive | Verification |
|---|---|---|---|
| Aim | Feasability of comprehensive T cell eptiope mapping in celiac disease | 1. Define hierarchy and identity of T cell stimulatory wheat, barley, rye and oat gluten peptides; and 2. Define lead compound for peptide-based therapeutic vaccine for HLA DQ2+ celiac disease | Define the range of peptides in gluten recognised by celiac donor-derived intestinal and peripheral blood T cell clones specific for immunodominant epitopes |
| Use | PBMCs in (polyclonal) T cell IFNγ ELISpot assay drawn day0 vs. day-6 of gluten challenge of HLA DQ2+ celiac vs. healthy UK donors | Same as Pilot, but scaled up to confirm Pilot data and test all gluten proteins from wheat, rye, and barley. | T cell clones from peripheral blood and intestinal biopsies |
| Genbank Database Search | September 2001 Species: T. aestivum (wheat), T. aestivum subsp. Terms: alpha-gliadin, beta-gliadin, gamma-gliadin, omega-gliadin | June 2003 Species: T. aestivum (wheat), H. vulgare (barley), S. cerale (rye) Terms: gluten, gliadin, glutenin, hordein, secalin | October 2006 Species: T. aestivum (wheat), T. aestivum subsp., H. vulgare (barley), S. cerale (rye) Terms: gliadin, hordein, secalin |
| Search results | 61 α/β-, 47 γ-, 3 ω-gliadins | 53 α/β-, 53 γ-, 2 ω-gliadins, 77 LMW, 55 HMW glutenins, 59 hordeins, 14 secalins | 58 α/β-, 48 γ-, 5 ω-gliadins 86 hordeins, 16 secalins |
| Design | All wild-type 12mers Alignment by phylogeny MegaAlign ClustalW | All wild-type 12mers Library algorithm | All wild-type and tTG-deamidated 10mers: gliadin, hordein, and secalin |

TABLE 3-continued

Gluten peptide libraries.

| Library | Pilot | Comprehensive | Verification |
|---|---|---|---|
| Size | 652 20mers encompassing 3997 12mers and 3372 9mers | 20mers (12mers, 9mers)<br>Gliadin: 721 (4465, 3739)<br>LMW glutenin: 645 (3945, 3164)<br>HMW glutenin: 786 (4799, 3630)<br>Hordein: 416 (2672, 2413)<br>Secalin: 155 (957, 811) | 18mers (10mers, 9mers)<br>Gliadin: 1363 (8114, 7561)<br>Hordein: 1338 (8557, 8117)<br>Secalin: 327 (2105, 1955) |
| Termini | H—, —OH (free) | H—, —OH (free) | H—, —OH (free) |
| Amount | 0.6 µmol | 1 µmol | 4x 0.5 µmol: gliadin, hordein, secalin |
| QA | 2 standards per 96 20mers<br>Amino acid analysis and HPLC:<br>IKDFHVYFRESRDALWKGPG<br>Purity 50, 41-56% (median, range, n = 7)<br>VLQQHNIAHGSSQVLQESTY<br>Purity 17, 16-23% (n = 7) | 2 standards per 96 20mers<br>Amino acid analysis and HPLC:<br>IKDFHVYFRESRDALWKGPG<br>Purity 64, 55-71% (median, range, n = 31)<br>One 20mer from each 96 block<br>Purity 36, range: 5-68% (n = 31) | All assessed by LC-MS.<br>1320/1363 gliadin 18mers,<br>1311/1338 hordein 18mers,<br>and 321/327 secalin 18mers.<br>10mer sequences in 27 hordein and 6 secalin 18mers with incorrect mass were synthesised as 108 12mers (all with correct mass) |
| Dissolution | ACN 10% 0.1M HEPES | 50% Aqueous acetonitrile | 50% Aqueous acetonitrile |
| Stock | 10 mg/ml | 50 mg/mL | 25 mg/mL |

ELISpot Assay

IFNγ ELISpot assays (Mabtech, Sweden) using 96 well plates (MSIP-S45-10; Millipore, Bedford, Mass.) were performed using Peripheral blood mononuclear cells (PBMC) from blood drawn between 0800 hours and midday on the sixth day after commencing gluten challenge as previously described. Briefly, ELISpot plates were coated with sterile capture anti-cytokine antibody at 1:100 concentration (50 µl/well) diluted in PBS and wrapped in foil overnight at 4° C. Prior to use, each plate was washed three times with sterile PBS and non-specific binding blocked by addition of RPMI with 10% FCS (50 µl/well) for 2 hours at 37° C. Antigen at 5× concentration was added to each well (25 µl) followed by addition of freshly isolated PBMC suspended in complete medium (100 µl) and incubated overnight (16-20 hours) at 37° C. in a 5% $CO_2$ incubator. Cells and culture medium were then discarded and the plate washed once with cold distilled water then three times with PBS with 0.05% Tween-20 (Sigma P2287, St Louis, USA) and three times in PBS (200 µl/well each wash). Biotinylated anti-cytokine mAb (1:1000) diluted in PBS with 0.5% FCS (50 µl/well) was incubated for 2 hours at room temperature. Wells were washed six times with PBS (200 µl/well), and Streptavidin-ALP (1:1000) added (50 µl/well) and incubated for 1 hour at room temperature. After washing, BCIP-NBT developer substrate was added (50 µl/well) and spots allowed to develop. Developing was terminated by washing under cold water when spots were first visible. The number of spot-forming units (SFU) in individual wells was enumerated with computer-assisted video image analysis (AID ELISpot Reader System, AID Autoimmun Diagnostika GmbH, Strassberg, Germany). *Mycobacterium tuberculosis* purified protein derivative (PPD RT49) (5 µg/ml) and/or tetanus toxoid (CSL) (10 light forming units/ml) were positive control antigens.

Isolation of T Cell Clones

PBMC were isolated from heparinised whole blood using Ficoll-Paque Plus in Leucosep tubes. Lamina propria mononuclear cells (LPMC) were isolated from small intestinal biopsies by first treating samples with 1 mM DTT in PBS, followed by two incubations at 37° C. for 30 minutes in 2.4 U/mL Dispase II. Biopsies were then minced and incubated at 37° C. for 1 hour in 2 U/mL Liberase Blendzyme 3 and RPMI. PBMC and LPMC were washed three times in PBS. Typically, between 0.5 and $1×10^6$ LPMC were recovered and were mixed with 1.5-3 million autologous PBMC irradiated at 2000 rads.

PBMC and LPMC were stained with 0.1 µM CFSE and were plated out in 96 well plates at $2×10^5$ cells/well, as previously described (Mannering et al., 2003; Mannering et al., 2005). Peptide and protein antigens were used at 32 µg/mL and 100 µg/mL respectively. Between 7 and 10 days later, CD4$^+$ proliferation was measured by flow cytometry (FACSAria, BD). CD4$^+$CFSE$^{dim}$ PI-cells were sorted into a single well of a 96 well plate containing $2×10^5$ PBMC (irradiated at 2000 rads), $2×10^4$ JY-EBV (irradiated at 5000 rads), 20 U/mL recombinant human IL-2, 5 ng/mL recombinant human IL-4 and 30 ng/mL anti-CD3 (OKT3) in media. Cells were fed every 7 days for 2 weeks with media containing cytokines to give a final concentration of 20 U/mL IL-2 and 5 ng/mL IL-4. On day 25, growing clones were identified and expanded into 48 well plates in media including 20 U/mL IL-2 and 5 ng/mL IL-4. Antigen specificity was determined by $^3$H-thymidine proliferation assay or IFNγ ELISpot. Large scale expansion of specific clones was carried out in culture flasks containing 30 ng/mL OKT3 in 15 ml media with $5×10^7$ PBMC (irradiated 2000 rads) and $5×10^6$ JY-EBV (irradiated 5000 rads). After 24 hours, IL-2 was added to a final concentration of 50 U/mL. On day-3, the expansion was washed and resuspended in 25 ml of media containing 50 U/mL IL-2. On day-7, the cells were split in half and topped up with 12.5 ml of media containing IL-2 at a final concentration of 50 U/mL. Expanded cells were examined for antigen specificity on day-10 by $^3$H-thymidine proliferation assay or IFNγ ELISpot.

Characterisation of T Cell Clones

Expanded antigen-specific clones were tested for clonality using the IOTest Beta Mark (Beckman Coulter). Negative clones were confirmed as clonal by PCR of the TCR Vβ chains. HLA-restriction was determined by anti-HLA-DR (10 µg/ml Clone L243) and HLA-DQ (10 µg/ml Clone SPVL3) antibodies. Secretion of IFNγ, IL-4, IL-5, IL-10, IL-13, and IL-17 by clones to cognate antigen was determined in ELISpot assays utilising irradiated APCs (2000 rads) from HLA DQ2$^+$ HLA DQ8$^-$ donors. Lysine scans of SEQ ID NOs:228, 229, and 230 (NPL001, NPL002, and NPL003, respectively) were carried out in ELISpot or proliferation assays using clones specific for these peptides.

Data Analysis

ELISpot responses were considered significant when SFU were both greater than four times medium alone and greater than 10 SFU/well. Proliferation assays were considered significant when stimulation indices (SI) were greater than 3. Data sets were normalised for inter-donor or inter-clone variability by expressing SFU or SI as a percentage of the most reactive peptide, peptide pool, or cocktail tested. Reactive peptides and peptide pools were assigned a "score" between 0 and 100, equal to the mean normalised response of donors who responded to at least one peptide or pool.

Example 2

Determination of the Primary Dominant Peptides Using Fresh Polyclonal T Cells Induced by In Vivo Gluten Challenge In previous studies, it has been found that gluten-specific T cells are at their peak in blood 6 days after HLA DQ2+ celiac disease donors commence oral gluten challenge. On day-6, IFNγ ELISpot responses of PBMC from celiac disease donors to optimal concentrations of tTG-treated gliadin (500 μg/ml) and α-gliadin p57-73 QE65 (SEQ ID NO:8) encompassing DQ2-α-I (SEQ ID NO:3) and DQ2-α-II (SEQ ID NO:4) epitopes were significantly correlated (r=0.80, p<0.0001). Median IFNγ ELISpot responses to 17mer were 51% (n=17, range: 0-155%) of those to tTG-treated gliadin (500 μg/ml). However, the α-gliadin p57-73 QE65 (SEQ ID NO:8) was not always immuno-dominant. IFNγ ELISpot responses were equivalent to less than 5% of those to tTG-treated gliadin in 3/17 donors (Anderson et al., 2005).

Based upon these observations, it is clear that gluten peptides additional to the α-gliadin p57-73 QE65 (SEQ ID NO:8) and peptides including the epitopes SEQ ID NOs:4 and/or 5 must also stimulate a substantial population of T cells induced by in vivo gluten challenge. The inventors were not confident that a peptide-based immunotherapy utilising α-gliadin p57-73 QE65 (SEQ ID NO:8) and peptides including the epitopes SEQ ID NOs:4 and/or 5 would alone consistently target a sufficiently large proportion of the disease-relevant gluten-specific T cell population. The inventors hypothesised that either α-gliadin p57-73 QE65 (SEQ ID NO:8) and peptides including the epitopes SEQ ID NOs:4 and/or 5 were partial agonists and that sequences related to SEQ ID NOs:8, 4 and/or 5 would stimulate substantially more T cells, or that additional peptides encompassing immuno-dominant epitopes are present amongst gluten proteins expressed by wheat, barley or rye.

Homology Searches

Almost all substitutions to the core five amino acids, PELPY (SEQ ID NO:22) of α-gliadin p57-73 QE65 (SEQ ID NO:8) abolish its recognition by peripheral blood T cells induced by gluten challenge.

SwissProt and Trembl databases were searched for cereal genes encoding 17mers with the sequence PELPY (SEQ ID NO:22) the equivalent wild-type sequence, PQLPY (SEQ ID NO:23). Thirteen wheat α-gliadin 17mers were found with PQLPY and one with PQLSY (SEQ ID NO:24) at positions 8-12, but none had the sequence PELPY. With reference to FIG. 1, ELISpot responses are shown from a variety of 17mers with T cell epitopes DQ2-α-I (SEQ ID NO:3), DQ2-α-II (SEQ ID NO:4), and DQ2-α-III (SEQ ID NO:5), which derive from a highly polymorphic region of the α-gliadin family of proteins. Normalised IFNγ ELISpot responses of PBMC from 8 celiac disease donors (6 days after commencing wheat gluten challenge) to fourteen naturally occurring α-gliadin 17mers, each of which include the core sequence PQLPY (SEQ ID NO:23) or PQLSY (SEQ ID NO:24) are shown in FIG. 1. 17mers are assessed with or without pre-treatment with tTG or when glutamine at position 9 (Q9) is replaced by glutamate (E9). Data represent mean±SEM of donor ELISpot responses normalised against that to α-gliadin p57-73 QE65 (25 μg/ml).

Two 17mers that differed from α-gliadin p57-73 QE65 (SEQ ID NO:8) only by having serine substituted for proline or leucine at the C-terminal were as active as SEQ ID NO:8 when pretreated with tTG or when glutamine was substituted for glutamate at position 9. 17mers including both DQ2-α-II (SEQ ID NO:4), and either DQ2-α-I (SEQ ID NO:3) or DQ2-α-III (SEQ ID NO:5) stimulate greatest numbers of T cells. These findings were in agreement with those reported by Arentz-Hansen et al., 2000 in which a panel of intestinal T cell clones recognised five of eleven structurally distinct recombinant α-gliadins, but only those that included DQ2-α-I (SEQ ID NO:3), DQ2-α-II (SEQ ID NO:4) or DQ2-α-III (SEQ ID NO:5). Several other deamidated polymorphisms of α-gliadin p57-73 were weakly active and one that was not among those studied by Arentz-Hansen et al., 2000, PQPQPFLPQLPYPQPQS (SEQ ID NO:25; W09), was almost as active as 17mers encompassing DQ2-α-II (SEQ ID NO:4) and DQ2-α-III (SEQ ID NO:5) when pre-treated with tTG or with glutamate at position 9, PQPQPFLPELPYPQPQS (SEQ ID NO:26). Based upon a previous substitution scan of α-gliadin p57-73 QE65, the inventors undertook a more permissive search for homologues with a core sequence PQ[ILMP][PST] (SEQ ID NO:27) (Anderson et al., 2006)

Twelve gliadin, glutenin, hordein and secalin sequences were synthesised but only one, the ω-gliadin peptide, AAG17702 (141-157) was more active than medium alone. This ω-gliadin peptide, PQQPFPQPQLPFPQQSE (SEQ ID NO:28; AAD17702 (141-157)) was 32±6% as active as α-gliadin p57-73 QE65 when pre-treated with tTG or with glutamate at position 9, PQQPFPQPELPFPQQSE (SEQ ID NO:29) (25 μg/ml; mean±SEM, n=5 donors).

Figure 2:
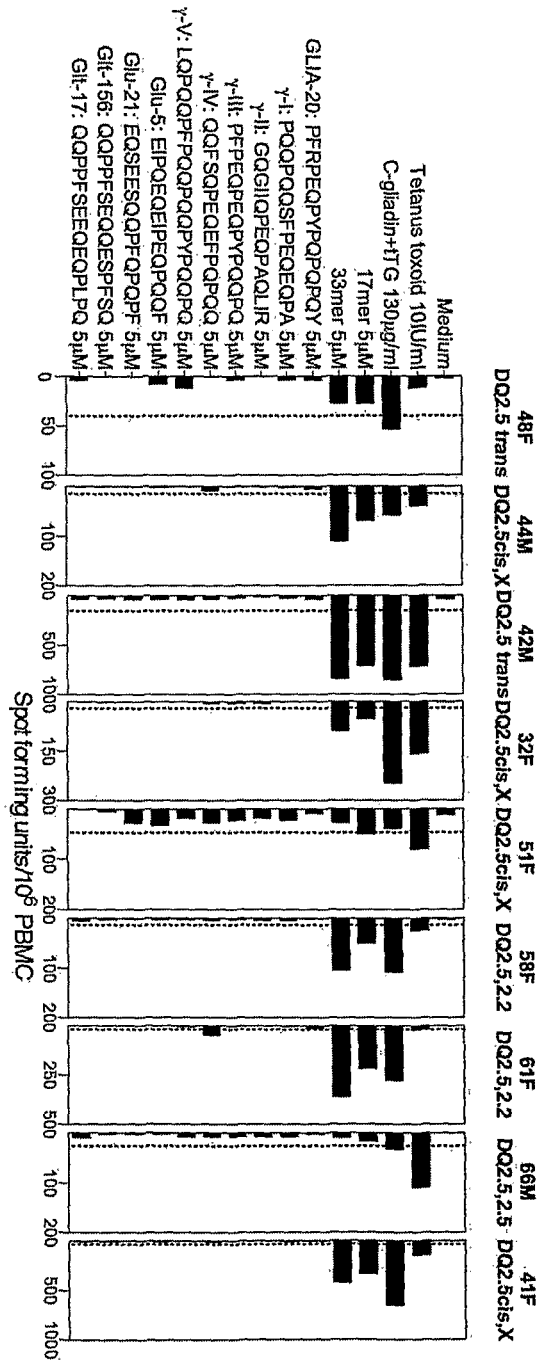
FIG. 2: shows IFNγ ELISpot responses of peripheral blood T cells to a variety of T cell epitopes (SEQ ID NOs:2, 46, 31, 33, 35, 37, 39, 41, 43, and 44).

Epitopes for Intestinal Clones and In Vivo Gluten-Induced Peripheral Blood Polyclonal T Cells The inventors then assessed deamidated 15mers encompassing epitopes reported for intestinal T cell clones: GLIA-20 PFRPQQPYPQ (SEQ ID NO:30) in its deamidated form PFRPEQPYPQ (SEQ ID NO:31), DQ2-γ-I PQQSFPQQQ (SEQ ID NO:32) in its deamidated form PQQSFPEQE (SEQ ID NO:33), DQ2-γ-II IQPQQPAQL (SEQ ID NO:34) in its deamidated form IQPEQPAQL (SEQ ID NO:35), DQ2-γ-III QQPQQPYPQ (SEQ ID NO:36) in its deamidated form EQPEQPYPE (SEQ ID NO:37), DQ2-γ-IV SQPQQQFPQ (SEQ ID NO:38) in its deamidated form SQPEQEFPQ (SEQ ID NO:39), Glu 5 QIPQQPQQF (SEQ ID NO:40) in its deamidated form QIPEQPQQF (SEQ ID NO:41), and Glt-156 PFSQQQQSPF (SEQ ID NO:42) in its deamidated form PFSEQQESPF (SEQ ID NO:43), and also DQ2-γ-V LQPQQPF-PQQPQQPYPQQPQ (SEQ ID NO:44), and α-gliadin p31-49 LGQQQPFPPQQPYPQPQPF (SEQ ID NO:45) (over the range 0.1-100 μg/ml). In 8/9 HLA DQ2 celiac disease donors, IFNγ ELISpot responses to deamidated gliadin were detected (median 23, range: 13-153 SFU/million PBMC). FIG. 2 shows 7 donors responded to the variant of deamidated α-gliadin p57-73 QE65 with leucine at position 17 QLQPF-PQPELPYPQPQL (SEQ ID NO:46) encompassing DQ2-α-I (SEQ ID NO:3) and DQ2-α-II (SEQ ID NO:4) (5 μM) and a 33mer LQLQPFPQPELPYPQPELPYPQPELPYPQPQPF (SEQ ID NO:2; deamidated α2-gliadin 56-88) (5 μM) encompassing overlapping tandem repeats of DQ2-α-I (SEQ ID NO:3) and DQ2-α-II (SEQ ID NO:4), and DQ2-α-III (SEQ ID NO:5). At an optimal concentration (50 µM), the difference between IFNγ ELISpot responses stimulated by the 17mer and 33mer were not significant. One donor responded to the 15mer encompassing deamidated DQ2-γ-IV (SEQ ID NO:39), but none of the other nine epitopes were recognised by PBMC collected on day 6 after wheat gluten challenge.

The inventors concluded that, in most individuals with HLA DQ2+ celiac disease, peptides encompassing DQ2-α-I (SEQ ID NO:3), DQ2-α-II (SEQ ID NO:4) or the related DQ2α-III (SEQ ID NO:5) epitope make a substantial contribution to the T-cell stimulatory activity of gluten in vivo, but many other published gluten epitopes make little if any consistent contribution to the peptides recognised by CD4+ T cells induced in blood after gluten exposure in vivo. Conversely, other sequences that might have potent T stimulatory activity may have been overlooked because only a minority of gluten proteins have been systematically assessed in functional assays. A new approach was needed to comprehensively assess candidate T cell epitopes in gluten from wheat, rye and barley for their contribution to the gluten-specific T cell response associated with celiac disease.

Comprehensive *Triticum aestivum* Gliadin Peptide Library

In 2001, there were 111 entries in Genbank for *T. aestivum* α-, γ-, and ω-gliadin proteins. Traditional approaches to CD4+ T-cell epitope mapping with 15-20mer peptides overlapping by 10-12 amino acids spanning each polypeptide would have produced impractically large libraries to synthesise and screen. But phylogeny analysis and alignment of gliadin sequences by ClustalW indicate substantial sequence similarities within and between each phylogenetic sub-family of gliadins (Anderson, 1991). Alignment of polypeptides and systematic but not computer-assisted design indicated that a 652-member library of 20mers overlapping by 12 amino acids would be sufficient to encompass the unique 12mers in 111 gliadins entries then present in Genbank (see Table 3). Divided into 83 pools of up to 8 peptides with and without pre-treatment by tTG, this library was practical to screen before and on day-6 after gluten challenge (one well for each pool) using PBMC from 100 ml blood in overnight IFNγ ELISpot assays. A further collection of 100 ml blood on day-7 could then be used to verify findings and assess individual peptides in positive pools.

Disease Specificity of T Cell Responses to Gliadin Peptide Pools

Figure 3:
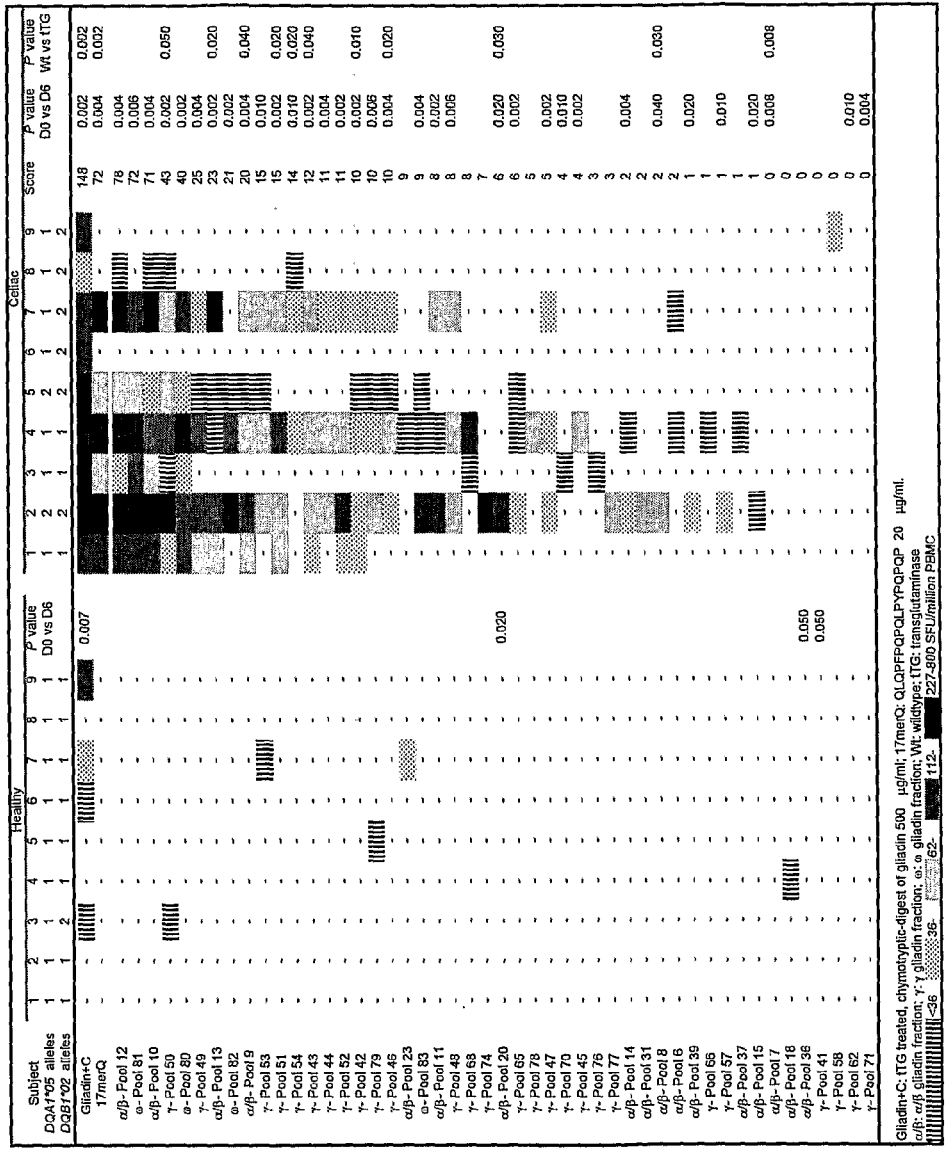
FIG. 3: shows the frequencies of gluten peptide-specific T cells detected by IFNγ ELISpot in PBMC collected on Day-6 after HLA-DQ2$^+$ celiac disease donors commence wheat, rye or barley challenge reveals a clear hierarchy of responses.

In the initial study, the pilot gliadin library was assessed using overnight ELISpot assays to measure the frequencies of IFNγ-secreting T cells in blood from HLA-DQ2+DQ8− celiac disease donors on long-term gluten free diet (GFD) (n=9) and also healthy HLA-DQ2+DQ8− volunteers (n=9) on GFD for 4 weeks, long enough for gluten challenge to be able to induce peripheral blood T cells in celiac volunteers (Anderson et al., 2005). Amongst the healthy donors, increases in responses to three of 83 pools reached statistical significance following gluten challenge (p<0.05, Wilcoxon paired rank sum), but were inconsistent, weak and unaffected by deamidation (see FIG. 3).

Amongst the nine celiac subjects there were 7 "responders" who, on day-6 after commencing gluten challenge, had at least one peptide pool that stimulated a response more than 10 SFU/well and more than four times that elicited by medium alone ("background"). Comparing SFU on day-6 with day-0 in the 9 celiac disease donors, there was significant induction (p<0.05, one tail Wilcoxon paired rank sum) of T cells specific for 34 pools including one (pool 20) that was also weakly recognised by healthy donors after gluten challenge. Amongst celiac disease donors, tTG pre-treatment increased (p<0.05, one tail Wilcoxon paired rank sum) the frequency of peripheral blood T cells that recognised chymotrypsin pre-treated gliadin and also 11 of the peptide pools tested.

In order to define a hierarchy based upon the consistency and relative contribution of pools (or in later experiments, peptides) to the overall gliadin-specific T cell population, a "score" between 0 and 100 was calculated according to the average of "responder's"—IFNγ ELISpot (SFU/well) responses above "background" on day-6 or day-7 expressed as a percentage of their maximal response to any pool (or library peptide).

From the total of 83 tTG-treated pools, 18 (22%) had a "score" over 10 on day-6 and all were associated with significant induction of responses between day-0 and day-6, while 5/9 and 7/12 pools scoring between 5 and 10 or between 1 and 5, respectively, on day-6 were associated with significant induction of responses between day-0 and day 6. Six other pools were associated with significant induction of responses but had scores less than 1. During subsequent analysis of peptide libraries, a "score" of 5 or greater for pools or peptides was set as an arbitrary cut-off value for T cell responses to be considered "positive" and warranting further mapping.

It was also apparent from this initial experience that utilizing pools of gliadin peptides was relatively inefficient as almost one quarter of pools were positive and required deconvolution. In subsequent experiments, individual peptides rather than pools were assessed. To enable as many peptides to be screened as possible using PBMC from a single 300 ml blood collection, all peptides were tTG-treated (as tTG treatment was never associated with reduction in ELISpot responses) and libraries were screened only on day-6 or day-0.

In 4/7 "responders", α-gliadin pools 10 or 12 with 20mers encompassing DQ2-α-I (SEQ ID NO:3), DQ2-α-II (SEQ ID NO:4), and/or DQ2-α-III (SEQ ID NO:5) epitopes were the most active, and in the other 3 responders, ω-gliadin pool 81 was the most active. Overall, α-gliadin pool 12 had the highest score (78) and next was ω-gliadin pool 81 (72). Individual tTG-treated peptides from pools 7-13, 42-53, 68, and 78-82 were assessed with PBMC collected from 5/7 responders on day-7 (see FIG. 4).

In all cases, several peptides from each pool were reactive. Peptides encompassing DQ2-α-II (SEQ ID NO:4) and DQ2-α-I (SEQ ID NO:3) and/or DQ2-α-III (SEQ ID NO:5) epitopes were confirmed as the five most active in the gliadin 20mer library, but four ω-gliadin 20mers from pools 80 and 81 were 53-65% as active as the most active α-gliadin 20mer. All four of the ω-gliadin 20mers included sequences homologous to DQ2-α-I (SEQ ID NO:3) and/or DQ2-α-II (SEQ ID NO:4): namely, QPFPQPQQPFPW (SEQ ID NO:47; W03; B01), PFPQPQQPIPV (SEQ ID NO:48; W04), QPFPQPQLPFPQ (SEQ ID NO:49; W06) encompassed in SEQ ID NO:28, and three included sequences reported to be recognised by DQ2-γ-VII epitope QQPQQPFPQ (SEQ ID NO:50) when deamidated to EQPEQPFPQ (SEQ ID NO:51) specific intestinal T cell clones.

Figure 5:
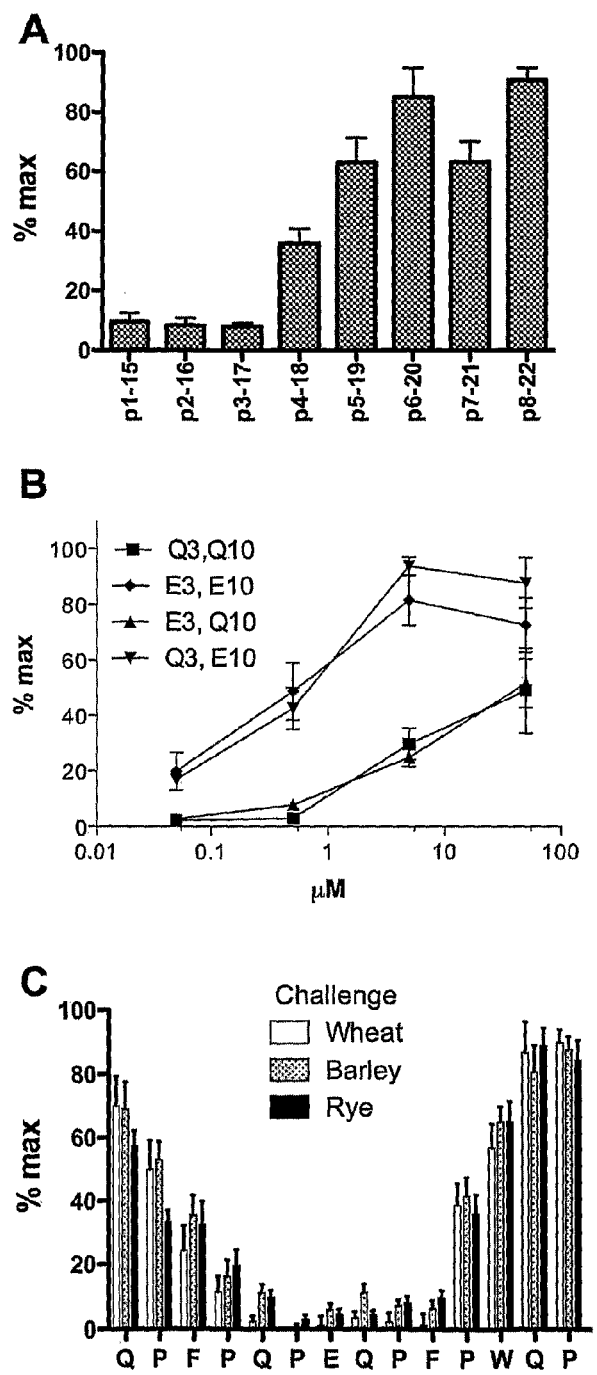
FIG. 5: shows fine-mapping of the immunodominant ω-gliadin peptide, PQQPQQPQQPFPQPQQPFPWQP (SEQ ID NO:52).

FIG. 5 shows IFNγ ELISpot responses of PBMC from celiac disease donors after wheat challenge to fine map the immunogenic region of deamidated PQQPQQPQQPF-PQPQQPFPWQP (SEQ ID NO:52) (as previously described in WO 2005/105129). Tissue transglutaminase-treated 15mers spanning SEQ ID NO:52 are expressed as a percentage of the most active 15mer for each donor (mean±SEM, n=8) (A). The T-cell stimulatory activity of SEQ ID NO:52 could be almost completely attributed to the deamidated sequence encompassing homologues of DQ2-α-I (SEQ ID NO:3) and DQ2-α-II (SEQ ID NO:4), QPFPQPQQPFPW (SEQ ID NO:47). FIG. 5B shows IFNγ ELISpot responses of PBMC from celiac disease donors after wheat challenge normalised against maximal individual donor responses to the Q3 E10 variant (mean±SEM, n=6). Deamidation of Q10 in QPQQPFPQPQQPFPWQP (SEQ ID NO:53) to QPQQPFPQPEQPFPWQP (SEQ ID NO:54) is sufficient to convey optimal immunogenicity and the double deamidated sequence, QPEQPFPQPEQPFPWQP (SEQ ID NO:55; W03-E7), is equivalent in bioactivity. FIG. 5C shows IFNγ ELISpot responses of PBMC from celiac disease donors after wheat (n=7), barley (n=9), or rye challenge (n=10) normalised against the most active lysine-substituted 15mer for individual donors (mean±SEM). Lysine-substitution of the central PQPEQPF sequence (SEQ ID NO:272) of NPL002: pyroEQPFPQPEQPFPWQP-amide (SEQ ID NO:229) (32 μg/ml) abolished the bioactivity of this peptide. Preincubation of PBMC from HLA DQA1*05 DQB1*02 homozygotes and heterozygotes with anti-HLA-DQ but not -DR abolished overnight IFNγ ELISpot responses to this peptide (data not shown).

The peptide hierarchy observed in the initial experiment was verified by separately assessing all 652 individual 20mers in the Pilot Gliadin library using PBMC collected 6 days after wheat challenge from 13 further HLA-DQ2$^+$8$^-$ donors (see FIG. 4). Again there was no clear difference in activity between 20mers including DQ2-α-II (SEQ ID NO:4) and DQ2-α-I (SEQ ID NO:3) and/or DQ2-α-III (SEQ ID NO:5), suggesting that fresh polyclonal T cells are rarely specific for DQ2-α-I (SEQ ID NO:3) but not DQ2-α-III (SEQ ID NO:5) or vice versa.

PBMC from 6 HLA-DQ2$^+$8$^+$ celiac disease donors on day-6 after commencing wheat challenge were screened against each of the 652 individual 20mers in the Pilot gliadin library (see FIG. 4). The α-gliadin peptides that were most active in HLA-DQ2$^+$8$^-$ celiac disease donors were also the most active in 4 HLA-DQ2$^+$8$^+$ celiac disease donors after gluten challenge.

PBMC from 6 HLA-DQ2$^+$8$^+$ celiac disease donors on day-6 after commencing 3-day challenge with pure rye were screened against each of the 652 individual 20mers in the Pilot gliadin library (see FIG. 4). The hierarchy of T-cell stimulatory gliadin 20mers was strikingly different from that observed after challenge with wheat (see FIG. 4). T cells measured by the overnight IFNγ ELISpot assay in blood after rye challenge rarely recognised 20mers including DQ2-α-I (SEQ ID NO:3), DQ2-α-II (SEQ ID NO:4), or DQ2-α-III (SEQ ID NO:5) epitopes. Instead the ω-gliadin 20mers including QPFPQPQQPFPW (SEQ ID NO:47) and QPFPQPQQPIPV (SEQ ID NO:48) were immunodominant.

This observation suggested that although T cell clones raised against deamidated wheat gluten or gliadin in vitro may often be promiscuous in their recognition of immunodominant gliadin peptides as reported by Vader et al., 2003, fresh polyclonal T cells induced by in vivo gluten challenge do discriminate between closely related sequences. Hence, the conclusion by Vader et al., 2003 that the T cell stimulatory activity of hordeins and secalins from barley and rye was substantially attributable to the deamidated variants of sequences PFPQPQQPF (SEQ ID NO:9) and PQPQQPFPQ (SEQ ID NO:11) being homologues of DQ2-α-I (SEQ ID NO:3) and DQ2-α-II (SEQ ID NO:4) was not confirmed using fresh PBMC from celiac disease donors after in vivo challenge with rye. Furthermore, it was apparent that a substantial proportion of T cells specific for the dominant sequences QPFPQPQQPFPW (SEQ ID NO:47) and PFPQPQQPIPV (SEQ ID NO:48) induced by rye challenge in vivo did not recognise DQ2-α-I (SEQ ID NO:3), DQ2-α-II (SEQ ID NO:4), or DQ2-α-III (SEQ ID NO:5) epitopes.

Furthermore, when compared to T cells specific for the immunodominant α- and ω-gliadin peptides, T cells specific for many epitopes reported for gliadin-specific T cell clones make little or no contribution to the overall gliadin-specific T cell population present in blood on day-6 of wheat challenge (see FIG. 2). Therefore, the inventors concluded that the immunodominance and relevance of gluten epitopes previously reported for intestinal T cell lines and clones in vitro frequently diverges from that measured by an overnight assay of polyclonal T cells in blood freshly isolated from celiac disease donors after in vivo gluten challenge.

Next the inventors sought to confirm and extend the hierarchy of T-cell stimulatory peptides to all gluten proteins from bread-making wheat (*T. aestivum*), barley and rye in HLA-DQ2$^+$8$^-$ celiac disease donors. To deal with the increasing number of gluten proteins in the NCBI Genbank and to design peptide libraries for LMW glutenins, HMW glutenins, hordeins and secalins, the inventors developed a novel algorithm to design customised libraries of minimal size to accommodate all unique sequences of, for example, 12mers within longer peptides, for example, 20mers. Beissbarth, T., et al., 2005. 20mer libraries encompassing all unique 12mers allowed wheat gluten to be assessed with PBMC from two 300 ml blood samples, and hordeins and secalins each with a single 300 ml blood collection. Comprehensive 20mer libraries were designed and synthesised as screening grade Pepsets (see Table 3), encompassing all unique 12mers in Genbank polypeptide entries present in June 2003 for gliadins (108 entries, 721 20mers encompassing 4465 unique 12mer candidate epitopes), LMW glutenins (77 entries, 645 20mers, 3945 12mer candidates) and HMW glutenins (55 entries, 786 20mers, 4799 12mer candidates) of *T. aestivum*, hordeins of *H. vulgare* (59 entries, 416 20mers, 2672 12mer candidates), and secalins of *S. cereale* (14 entries, 155 20mers, 957 12mer candidates).

PBMC from HLA-DQ2$^+$8$^-$ celiac disease donors collected on day-6 after commencing 3-day wheat challenge were used to screen the tTG-treated gliadin library and half the LMW glutenin library (n=20), and the second half of the LMW glutenin library and HMW glutenin library (n=26). PBMC from 21 celiac disease donors 6 days after commencing barley challenge were used to screen the hordein library, and PBMC from 19 further donors 6-days after commencing rye challenge were used to screen the secalin library. IFNγ ELISpot responses to tTG-treated Pepset library peptides were above background levels in 27/46 donors after wheat challenge, in 12/21 after barley challenge and 8/19 after rye challenge.

To facilitate selection of 20mers for fine mapping in "second round" libraries, the inventors adapted an expectation maximization (EM) approach used for analysis of microarray data (Beissbarth et al. (2005). All individual donor datasets were analysed by the EM algorithm to derive the variables λ and p to describe the IFNγ ELISpot response to each 20mer. The variable λ describes the relative strength of the ELISpot response, and the variable p describes the proportion of donors responding. Each first round library 20mer was fine mapped in second round libraries if the product of λ.p was at least 5% of the most active first round library peptide for each grain.

Second round libraries were designed by reducing selected 20mers to 9 overlapping 12mers. If any 12mer incorporated glutamine at position 7 and it conformed to the deamidation motif defined for tTG (QX$_1$PX$_3$, or QX$_1$X$_2$[F,Y,W,I,L,V], where X$_1$ and X$_3$ are not proline) then a 16mer was designed, whereby the 12mer with glutamine at position 7 was flanked by the native residues at positions −1 and 13 and by glycine at positions −2 and 14. This strategy allowed the central, potentially deamidated glutamine residue to be accommodated at anchor positions 4, 6 or 7 in any potential 9mer HLA-DQ2-peptide-binding sequence. If selected 20mers did not include any 12mer sequences with glutamine at position 7, then two 16mers overlapping by 12 residues were synthesised. Some second round 16mers with a central glutamine residue susceptible to tTG-mediated deamidation were also synthesised with glutamine replaced by glutamate (in silico deamidation).

The wheat second round library consisted of 551 16mers (including 113 glutamate-substituted 16mers) that were tested using PBMC from 34 celiac disease donors after wheat challenge (including 26 responders), the barley library had eighty-nine 16mers and included 9 substituted with glutamate that were tested using PBMC from 10 celiac disease donors after barley challenge (including 8 responders), and the rye library had sixty-four 16mers and included 11 substituted with glutamate that was tested using PBMC from 11 celiac disease donors after rye challenge (including 11 responders).

Figure 6:
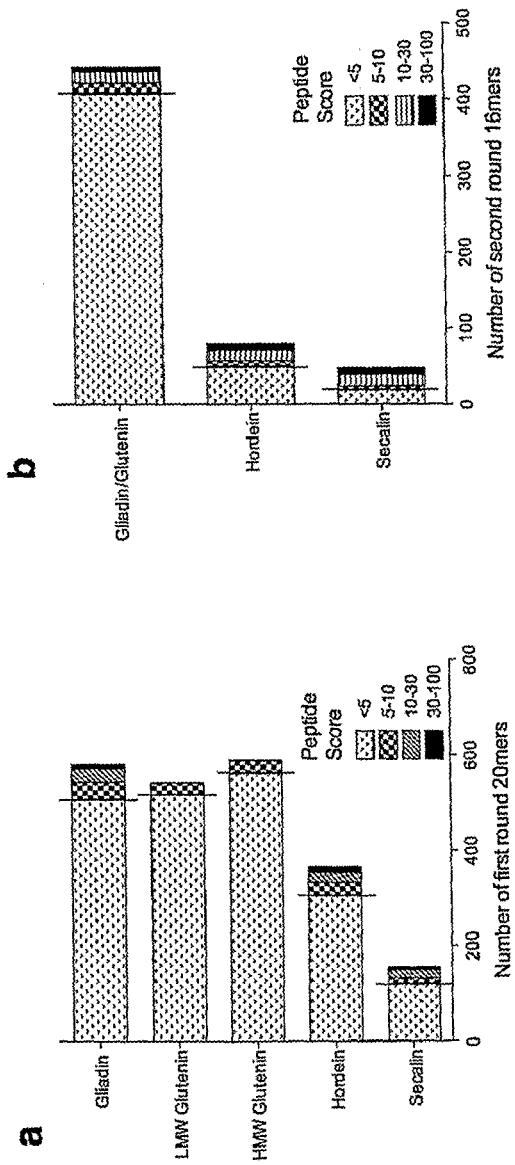
FIG. 6: shows clear hierarchy of peptides in the Comprehensive peptide libraries.

Hierarchy of stimulatory peptides was clearly demonstrated for each grain (see FIG. 6). Amongst the combined 652 20mers in the gliadin Pilot and 2723 20mers in the Comprehensive libraries, 34 (1%) had a score ≥30, 300 (9%) had a score ≥5, while 2111 had a score of 0. One hundred and seventy-one of the 300 (57%) tTG-treated first round 20mers with scores of ≥5 generated second-round tTG-treated 16mers with scores ≥5, and amongst these second round 16mers there were 89 unique sequences (see FIG. 7). These 89 confirmed T-cell stimulatory sequences in the second round included 32 derived from gliadins, 1 from LMW glutenins, 4 from HMW glutenins, 30 from hordeins, and 29 from secalins, 5 were common to prolamin families in two different grains and 1 was in three prolamin families in all three grains.

All 89 confirmed T cell stimulatory 16mers contained proline and/or glutamine.

Bioactivity following deamidation of second round peptides by tTG was the same as synthesising peptides with glutamate replacing glutamine residues predicted to be susceptible to tTG (data not shown).

Exceptions to the requirement for deamidation were the closely related but infrequently recognised HMW glutenin 16mers W21 QGQQGYYPISPQQSGQ (SEQ ID NO:91), W22 QGQPGYYPTSPQQIGQ (SEQ ID NO:92), W24 PGQGQSGYYPTSPQQS (SEQ ID NO:95), and W29 GQGQSGYYPTSPQQSG (SEQ ID NO:104), and the gliadin W36 QYEVIRSLVLRTLPNM (SEQ ID NO:116). Peptides were considered "dominant" for a particular celiac donor if they elicited at least 70% of the response of the most active peptide in each library for that donor. In the wheat, rye and barley second round, ten 16mers and thirty-one 12mers with corresponding glutamate substituted sequences (SEQ ID NOs:47, 48, 56, 57, 58, 59, 60, 61, 62, 63, 64, 65, 66, 67, 68, 75, 76, 77, 78, 79, 80, 81, 89, 90, 91, 92, 95, 102, 103, 104, 116, 117, 118, 119, 120, 121, 122, 123, 124, 125, 126, 127, 128, 129, 130, 131, 132, 133, 136, 169, 170, 171, 172, 173, 174, 177, 178, 179, 180, 183, 184, 187, 188, 189, 190, 191, 192, 209, 210) were dominant in at least 1 donor, while only four 16mers and twenty-one 12mers (with corresponding glutamate-substituted variants) were dominant in more than 10% of donors (SEQ ID NOs:47, 48, 56, 57, 58, 59, 60, 61, 62, 63, 64, 80, 81, 119, 120, 121, 122, 123, 124, 125, 126, 127, 128, 129, 130, 131, 132, 133, 136, 169, 170, 171, 172, 173, 174, 179, 180, 183, 184, 187, 188, 191, 192). The highest scoring second round wheat gluten-, hordein- and secalin-derived 16mers were dominant in more than 50% and overall were recognised by more than 80% of donors.

Figure 8:
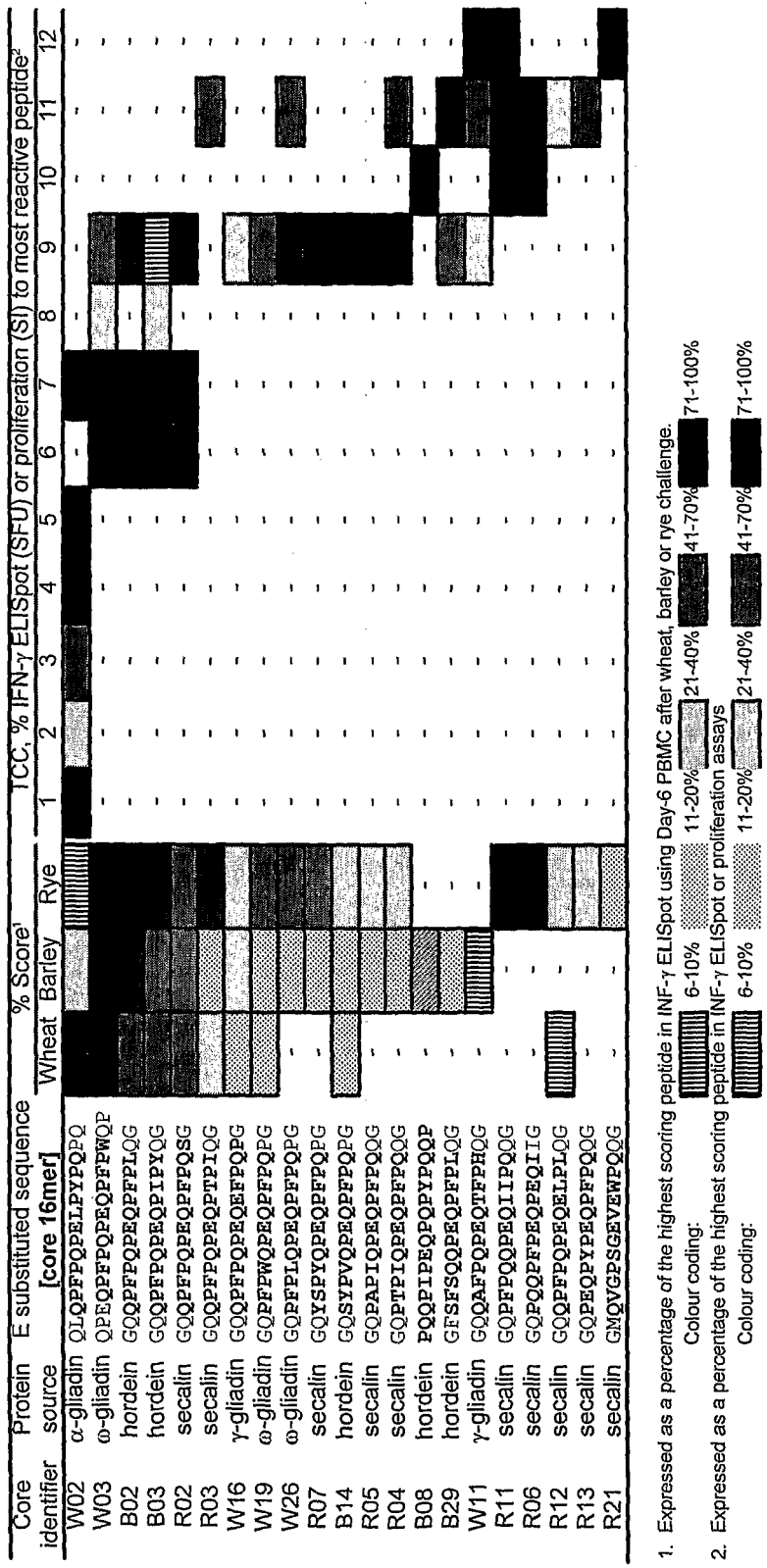
FIG. 8: shows the hierarchy of T-cell stimulatory peptides differs according to the whether celiac disease donors undergo wheat, barley or rye challenge.

The hierarchy and dominance of stimulatory peptides was strikingly different according to the grain consumed (see FIG. 8). The stimulatory capacity of peptides sharing the sequence motif QQPFPQPEQP(F,I)P(W,L,Y,Q)(Q,S) was not specific to any grain, ω-gliadin 17mer W03-E7 QPEQPFPQP EQPFPWQP (SEQ ID NO:55) was consistently the most active of this family and is the universal dominant T cell stimulatory peptide in gluten. Other peptides were dominant almost exclusively after only one grain. For example, the α-gliadin 17mer QLQPFPQPELPYPQPQP (SEQ ID NO:225; encompassing SEQ ID NO:62 (W02-E7) including DQ2-α-I (SEQ ID NO:3), and DQ2-α-II (SEQ ID NO:4)) was dominant only after wheat gluten challenge, the hordein 16mer B08-E7 PQQPIPEQPQPYPQQP (SEQ ID NO:318; encompassing SEQ ID NO:127 (B06-E7)) only after barley gluten challenge, and the secalin sequence QPFPQQPEQI-IPQQ (SEQ ID NO:323; encompassing SEQ ID NO:190 (R11-E7)) only after rye gluten challenge. Other peptides including the motif QPFP(W,L,Y,V,I)QPEQPFPQ elicited relatively stronger responses after barley or rye than wheat gluten challenge. The "grain specificity" of dominant T-cell stimulatory peptides provided a functional definition for redundancy of T cell recognition that compliments the traditional approach to determination of cross-reactivity based on T cell clones.

T cell clones were raised from intestinal biopsies or PBMC from celiac disease donors to dominant deamidated peptides. The cytokine profiles of T-cell clones were Th1 or Th0, and all were HLA-DQ2 restricted. Minimal core sequences were determined using lysine scans of the parent peptide. T cell clones raised against NPL001 (SEQ ID NO:228) were specific for DQ2-α-I (SEQ ID NO:3) or DQ2-α-II (SEQ ID NO:4), and against NPL002 (SEQ ID NO:229) were specific for DQ2-ω-I PFPQPEQPF (SEQ ID NO:10) or DQ2-ω-II PQPEQPFPW (SEQ ID NO:15). Single T cell clones raised against NPL003 (SEQ ID NO:230) were specific for DQ2-Hor-I PIPEQPQPY (SEQ ID NO:17), and the fully deamidated variant of SEQ ID NO:189, pyroEQPFPEQPEQI-IPQQP-amide (SEQ ID NO:226; NPL004) (core 9mer not determined, DQ2-SEC-I). One further clone raised against deamidated gliadin was specific for W11-E7 QAFPQPEQT-FPH (SEQ ID NO:74) (9mer core not determined). Each of the clones were screened against the second round tTG-treated gliadin/glutenin, hordein, and secalin libraries and also a further Verification 18mer library (see Table 3) encompassing all unique 10mers encoded by T. aestivum gliadins, H. vulgare hordeins and S. cereale secalins in their wild-type sequence and with in silico deamidation (glutamate replacing glutamine according to the tTG deamidation motif). There was little cross-reactivity of clones for dominant stimulatory peptides, but substantial redundancy of peptide recognition for many of sub-dominant gluten peptides. Altogether, 11 clones specific for 6 epitopes, DQ2-α-I (SEQ ID NO:3), DQ2-α-II (SEQ ID NO:4), DQ2-ω-I (SEQ ID NO:10), DQ2-ω-II (SEQ ID NO:15), DQ2-Hor-I (SEQ ID NO:17), and DQ2-Sec-I (SEQ ID NO:226) present in 4 dominant T cell stimulatory peptides, W02-E7, W03-E7, B08-E2E7, and R11-E4E7 (SEQ ID NOs:62, 55, 319, 322 respectively) recognised 22/37 gliadin/glutenin, 26/30 hordein, and 22/29 secalin sequences confirmed as stimulatory peptides in FIG. 7.

Figure 9:
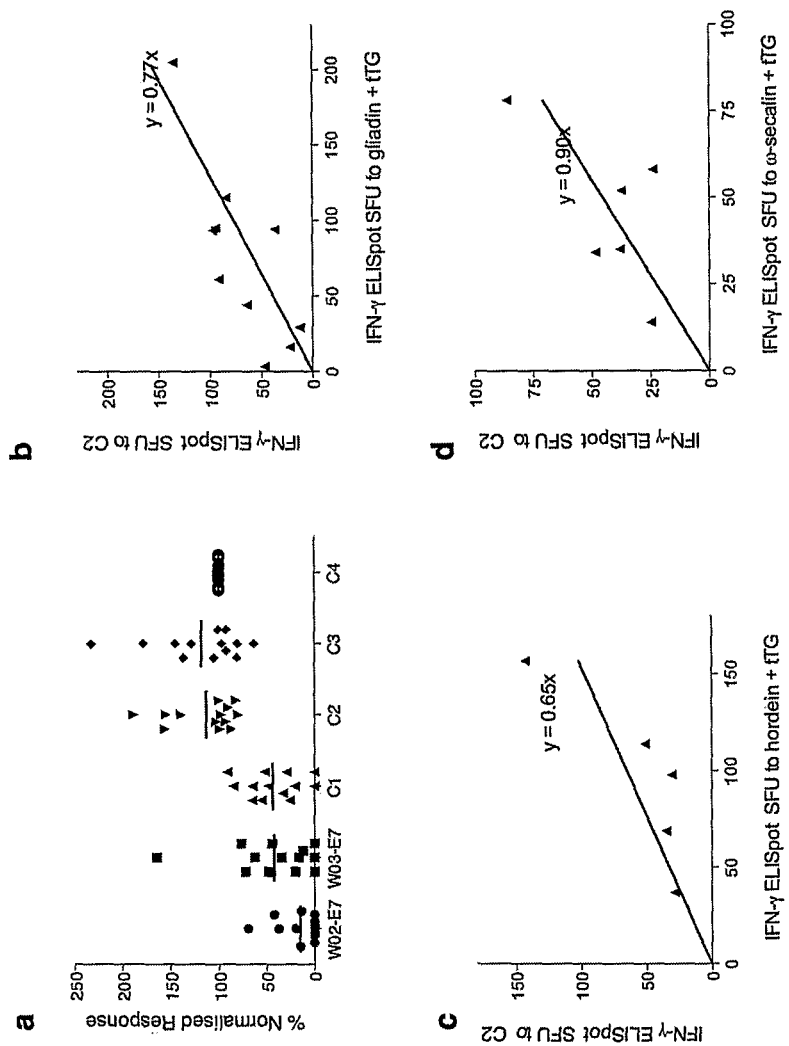
FIG. 9: shows that certain mixes of dominant T-cell stimulatory gluten peptides activate substantially larger numbers of T cells in blood collected after in vivo challenge with gluten-containing grains.

IFNγ ELISpot assay using PBMC collected from HLA-DQ2$^+$ celiac disease donors after gluten challenge with muffins made from an equal mixture of wheat, barley and rye flour was used to compare the relative frequency of T cells specific for W02-E7, W03-E7, B08-E2E7, and R11-E4E7 (SEQ ID NOs:62, 55, 319, 322 respectively), together with an atypical rare dominant gliadin peptide W36 (SEQ ID NO:116) and an oat avenin homologue of Av-α9A QYQPYPEQEQPILQQ (SEQ ID NO:323; see FIG. 9A). The response to the equimolar mixture of W02-E7, W03-E7, B08-E2E7 (SEQ ID NOs: 62, 55, 319; Cocktail 2) at an optimal concentration was no different from the mixture of 6 peptides, but clearly greater than W02-E7 (SEQ ID NOs:62) and/or W03-E7 (SEQ ID NOs:55). When Cocktail 2 (50 μM) was assessed after either wheat, barley or rye gluten challenge it stimulated IFNγ ELISpot responses equivalent to at least two-thirds of that stimulated by optimal concentrations of tTG-treated gliadin, hordein, or ω-secalin (320 μg/ml), respectively (see FIGS. 9B, C, and D).

To improve their chemical stability and increase resistance to exopeptidases, peptides were synthesised as acetate salts of "capped" N-pyroglutamate, C-amide: NPL001 (SEQ ID NO:228), NPL002 (SEQ ID NO:229) and NPL003 (SEQ ID NO:230) 15mers or 16mers with glutamate at sites predicted to be deamidated by tTG. Indeed, capping extended the half-lives of peptides from 10-12 minutes for free peptides: NPL033, NPL038, and NPL034 (SEQ ID NOs:13, 320 and 321) after bolus intradermal injection of 0.9 mg in 0.1 ml in an adult rat to 26-28 minutes with N-pyroglutamate and C-amidation (SEQ ID NOs:228, 229 and 230) or 19-24 minutes with N-acetylation and C-amidation (SEQ ID NOs:231, 232, and 233), (see Table 4). Bioavailability, as measured by area under the curve analysis, was also substantially increased by as much as thirty-four times with addition of N-pyroglutamate or N-acetyl, and C-amidation capping.

them are therefore likely to be critical to the design of a peptide-based therapeutic vaccine or in functional diagnostics that are consistently applicable to HLA-DQ2-associated celiac disease.

These findings emphasise that in vitro approaches reliant on expansion of rare antigen-specific T cells frequently do not necessarily translate to epitopes relevant in vivo after acute disease reactivation. Indeed the majority of non-redundant dominant T cell stimulatory peptides identified in the present study have not been previously described in functional studies utilising T cell clones and lines. Since comprehensive epitope mapping using T cells elicited in vivo by the pathogenic antigen has not been carried out previously, this study provides the first true test of an in vitro approach to mapping epitopes relevant to an immune human disease. The prior art does not describe the manner in which non-redundant dominant T cell stimulatory peptides would be selected for peptide-based immunotherapy to maximise the number of T cells targeted in the greatest number of patients while also minimising the number of peptides to simplify formulation.

However, additional peptides are likely to add to the T cell stimulatory capacity and consistency of donor T cell responses of this mixture after wheat, barley or rye challenge. Gluten peptides with the highest "scores" but not recognised by T cell clones specific for DQ2-α-I (SEQ ID NO:3), DQ2-α-II (SEQ ID NO:4), DQ2-ω-I (SEQ ID NO:10), DQ2-ω-II (SEQ ID NO:15), or DQ2-Hor-I (SEQ ID NO:17) are the most likely to add further to the T cell stimulatory capacity of the mixture. Increasing the proportion of gluten-specific T cells consistently targeted by a peptide mixture is likely to improve its therapeutic or diagnostic utility for HLA-DQ2$^+$8$^-$

TABLE 4

Pharmacokinetics of derivatised T-cell stimulatory peptides.

| Free N- and C-terminals | N-Acetyl and C-amide | N-pyroGlu and C-amide |
|---|---|---|
| LQPFPQPELPYPQPQ (SEQ ID NO: 13) NPL033 T1/2 10.2 minutes AUC 2618 | N-Acetyl-QLQPFPQPELPYPQPQ-amide (SEQ ID NO: 231) NPL030 T1/2 19.4 minutes AUC 43474 | pyroE-LQPFPQPELPYPQPQ-amide (SEQ ID NO: 228) NPL001 T1/2 28.20 minutes AUC 89350 |
| PQQPFPQPEQPFPWQP (SEQ ID NO: 320) T1/2 13.2 minutes AUC 22393 | N-Acetyl-QQPFPQPEQPFPWQP-amide (SEQ ID NO: 232) NPL031 T1/2 22.9 minutes AUC 80263 | pyroE-QPFPQPEQPFPWQP-amide (SEQ ID NO: 229) NPL002 T1/2 27.18 minutes AUC 81514 |
| FPEQPIPEQPQPYPQQ (SEQ ID NO: 321) T1/2 12.5 minutes AUC 8206 | N-Acetyl-FPEQPIPEQPQPYPQQ-amide (SEQ ID NO: 233) NPL032 T1/2 24.2 minutes AUC 79439 | pyroE-PEQPIPEQPQPYPQQ-amide (SEQ ID NO: 230) NPL003 T1/2 25.98 minutes AUC 51390 |

T1/2 half life, and AUC area under the curve (bioavailability) after intradermal bolus injection 0.9 mg in 0.1 ml saline of equimolar mixture of NPL001+2+3, NPL033+38+34, or NPL030+31+32

The inventors findings support the notion that peptides encompassing epitopes present in NPL001 (SEQ ID NO:228), NPL002 (SEQ ID NO:229) and NPL003 (SEQ ID NO:230), are dominant, non-redundant, and consistently contribute a substantial proportion of the T-cell stimulatory activity of gluten. These 3 peptides or the epitopes within celiac disease, but may also complicate formulation, compromise chemical stability, and increase the likelihood of adverse effects.

On the other hand, NPL001 (SEQ ID NO:228) could be substituted with a single peptide, for example, including the sequence LPYPQPELPYPQ (SEQ ID NO:60; W01-E7) recognised by T cell clones specific for DQ2-α-I (SEQ ID NO:3), and also T cell clones DQ2-α-II (SEQ ID NO:4). Alternatively, NPL001 (SEQ ID NO:228) could be substituted for two separate peptides, one recognised by T cell clones specific for DQ2-α-I (SEQ ID NO:3), and the other recognised by T cell clones specific for DQ2-α-II (SEQ ID NO:4). The same principle could be applied to NPL002 (SEQ ID NO:229) and NPL003 (SEQ ID NO:230). This may be advantageous to improve formulation and stability.

Example 3

NexVax2 in Mouse Model

The optimal administration and dose regimen of a peptide-based therapeutic vaccine to induce clinical tolerance to gluten and remission of celiac disease while consuming gluten is not known. However, an essential property of any peptide-based therapeutic would be its ability to activate cognate T cells in the target organ in vivo.

The interaction between NPL001 (SEQ ID NO:228) and cognate T cells in vivo has been modelled by developing transgenic Black-6 mice expressing functional HLA-DR3 and -DQ2 (but not murine MHC Class II molecules) on antigen presenting cells (APC) who are transferred $3\times10^6$ CFSE labelled CD4 T cells specific for NPL001 (Chen Z., et al., 2006). The donor mouse (HH8-1) is transgenic for the NPL001-specific T cell receptor and human CD4 expressed on T cells, and also expresses HLA-DR3 DQ2 on APC. Overall 96% of the CD4$^+$ T cells in the HH8-1 mouse are clonal and specific for NPL001 (results not shown).

Figure 10:
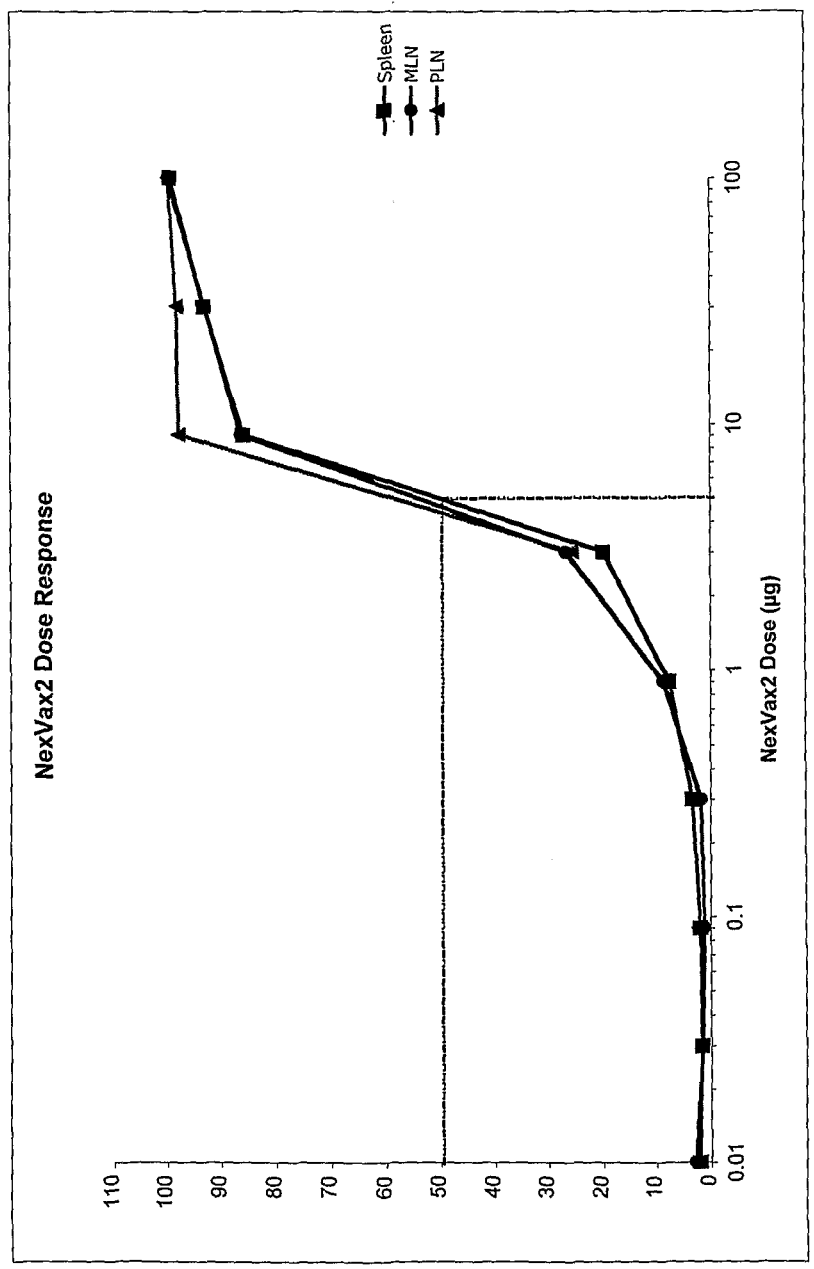
FIG. 10: shows the combination of NPL001 (SEQ ID NO:228), NPL002 (SEQ ID NO:229), and NPL003 (SEQ ID NO:230)(NexVax2) activates T cells specific for NPL001 (SEQ ID NO:228), in the gut (mesenteric lymph nodes, MLN) as well as spleen and local draining popliteal lymph nodes (PLN) following subcutaneous administration to the hind-leg. The proliferation of NPL001-specific T cells is very similar at the three anatomic sites despite the peptides being delivered to the hind-leg. Proliferation of T cells is dose dependent.

Four days after subcutaneous administration (in the hind foot hock) of an equimolar mixture of NPL001, NPL002 and NPL003 in 50 μl saline, spleen, gut-draining mesenteric lymph nodes (MLN) and the local draining popliteal lymph nodes (PLN) are harvested. Isolated mononuclear cells are stained for hCD4, and the T-cell receptor α- and β-chains expressed on the HH8-1 NPL001-specific T cells (Vα8 and Vβ8). Proliferation of transferred CFSE labelled cells is measured as the % of CFSE$^{pos}$ cells having undergone one or more division, as indicated by dilution of CFSE staining FIG. 10 shows dose dependent proliferation of T cells specific for NPL001 is observed following subcutaneous administration of between 0.9 and 30 μg, half-maximal response is achieved with 5 μg. No clinical toxicity is observed with these or doses as high as 900 μg, despite the T cells having a Th1 phenotype and secreting IFNγ upon stimulation with NPL001.

This mouse model has the potential to allow the demonstration of (i) proof-of-principle, (ii) mechanism of action and (iii) optimisation of dose regime for the induction of tolerance following administration of NexVax2 therapeutic vaccine (an equimolar mixture of NPL001, NPL002 and NPL003 in saline). In the previous mouse studies the inventors have demonstrated that a single dose of NexVax2, or the relevant peptide component NPL001, is bioactive in vivo. Administration of NPL001 induces proliferation of HH8-1 gliadin-specific T cells in an adoptive transfer model at the highest dose to be administered in Phase 1b human clinical trials. The dose response for the activation of transgenic NPL001-specific T cells was subsequently determined. Based on this preliminary data, the ability of NexVax2 therapeutic vaccine to modulate gliadin-specific T cell responses and mechanism of action can be addressed in a biologically relevant mouse model.

The objective of the study was to determine whether repeat administration of the therapeutic vaccine, NexVax2, using a regime designed to induce immunological tolerance is capable of modulating the gliadin-specific T cell response in a gliadin-specific TCR-Tg mouse model.

Animals were identified, allocated to experimental groups and treated as in Table 5 below.

TABLE 5

Allocation of animals to experimental groups.

| Group | Dose of NexVax2 | Number of Doses | Mouse Number | Number per group |
|---|---|---|---|---|
| A | 10 μg | 14 daily dose | 5A1, 5A2 | 2 |
| B | 3 μg | 14 daily dose | 5B1, 5B2 | 2 |
| C | 1 μg | 14 daily dose | 5C1, 5C2 | 2 |
| D | 0.3 μg | 14 daily dose | 5D1, 5D2 | 2 |
| E | 0 (Saline control) | 14 daily dose | 5E | 1 |
| F | 10 μg | 1 dose on final day of treatment regime | 5F | 1 |

The intradermal/subcutaneous route of administration was selected as this is the intended route of administration in man. The dosage was selected to cover the dose-response range that resulted in stimulation of all gliadin-specific T cells in the adoptive transfer model (10 μg) to low dose (0.3 μg) that did not result in proliferation of CFSE-labelled gliadin-specific TCR-Tg T cells in the previous study (Nexpep3).

All peptides were GMP grade. The formulations were prepared by Nexpep Pty Ltd, and the concentration of peptide was adjusted for purity. NexVax2 consists of 3 peptides (NPL001, NPL002 and NPL003) each at 6 mg/ml in saline.

The stated dose is the quantity of each peptide in NexVax2, not the total peptide concentration (i.e., 10 μg NexVax2 contains 10 μg NPL001, 10 μg NPL002 and 10 μg NPL003). NPL001 was provided at 6 mg/ml in saline. Peptides were stored at −80° C. prior to injection.

Animals and Management

All experiments were carried out with the approval of the University of Melbourne Animal Ethics Committee, AEC Register No 0707287.

Fourteen female HH8-1 and 4 hCD4.IAE$^{-/-}$.DR3.DQ2 transgenic mice on the C57BL/6 background were used. All mice were bred at the University of Melbourne, Department of Microbiology and Immunology Animal Facility. Mice were raised on a gluten-free diet (SF07-036) supplied by Specialty Feeds Pty Ltd, Perth Western Australia. Each animal was numbered by ear-punching according to the Animal Facility protocol which identified it individually within the study and which corresponded to that animal's number. The animals were housed individually or in groups of up to 4 mice in cages with stainless steel grid tops and solid bottoms. Wood shavings were used as bedding, and tissues supplied for nesting material. Each cage was supplied with a water bottle containing acidified water and food hopper containing gluten-free mouse food. The room was maintained between 21° C. and 24° C. The range for relative humidity was 37-58%. A 12 hour light/dark cycle was in operation (light hours 0700-1900) with a minimum of 15 air changes per hour.

NexVax2 was diluted to 200 μg/ml in sterile saline, aliquoted and stored at −80° C. for use. For each treatment, an aliquot was thawed and diluted in sterile saline. Groups of female HH8-1 mice (n=2) were injected subcutaneously on the flank with 50 μl containing a titrating dose of NexVax2 (10 μg, 3 μg, 1 μg and 0.3 μg) diluted in saline or saline alone. Mice were injected daily for 14 days. One mouse received a single dose of 10 μg NexVax2 on the final day of the treatment regime.

Mice were monitored daily for swelling or irritation at the injection site, symptoms of adverse systemic response (hunched or ruffled appearance, lethargy, shivering, moribund). The onset, intensity and duration of any signs were recorded.

A blood sample was collected from the retro-orbital sinus prior to administration of peptide and by cardiac puncture following $CO_2$ euthanasia at the completion of the experiment. Blood was stored at 4° C. overnight, the clot removed and serum collected following centrifugation. Sera were stored at −80° C. for future analysis if required.

Mice were killed by $CO_2$ euthanasia 3 days after the final administration of peptide and the spleens were collected. Single cell suspensions were prepared by sieving through 70 μm nylon mesh cell strainers. Red blood cells were removed from spleens by Tris ammonium chloride lysis. $CD4^+$ T cells were isolated by negative depletion using the $CD4^+$ T cell isolation kit (Miltenyi Biotech) according to the manufacturer's instructions. Gliadin-specific T cells were enriched from the spleens of 4 naïve HH8-1 mice using the same protocol. APC were prepared from the spleens of three $hCD4.IAE^{-/-}$. DR3-DQ2 transgenic mice. Single cell suspensions were prepared as above. Splenocytes were gamma irradiated (2,200 rads) before use as APC.

Cells were phenotyped by antibody staining and FACS analysis. Gliadin-specific $CD4^+$ T cells were identified by staining with TCR Vα8.3 and human CD4, and surface stained with anti-CD25 and anti-GITR monoclonal antibodies. Intracellular FoxP3 expression was determined using a FoxP3 staining kit (eBiosciences) according to the manufacturer's instructions. Samples were fixed in FACS fixative (1% paraformaldehyde, 2% glucose in PBS) and analysed by flow cytometry on the LSR II (BD Bioscience). IFNγ and IL-10 producing T cells were identified by intracellular cytokine staining following stimulation with PMA/Ionomycin.

Briefly, $1 \times 10^6$ splenoctyes from treated mice were cultured for 6 hours in complete DMEM (DMEM supplemented with 10% heat inactivated foetal calf serum, 2 mM glutamine, non-essential amino acids, 50 μM 2-mercaptoethanol, penicillin and streptomycin) and 5 μg/ml Brefeldin A with or without 50 ng/ml PMA and 500 ng/ml Ionomycin. Cells were then stained for the surface molecules (TCR Vβ8.3 and human CD4), washed then fixed with 1% paraformaldehyde/ 30 minutes, washed twice and then incubated with anti-IFNγ or anti-IL-10 antibody diluted in PBS containing 0.2% Saponin. Samples were analysed by flow cytometry on the LSR II (BD Bioscience) gating on TCR $VIβ8.3^+$, human $CD4^+$ lymphocytes.

$2 \times 10^4$ purified T cells from each mouse were cultured in triplicate in round-bottomed 96 well plates in complete DMEM with $3 \times 10^5$ gamma-irradiated APC in the presence or absence of 2 μg/ml NPL001 at 37° C./5% $CO_2$. Following 72 hours of culture, supernatants were collected and stored at −80° C. for analysis of the cytokine secretion.

Samples were tested for the presence of mouse IL-2, IL-4, IL-5, IL-6, IL-10, IL-12p70, TNFα and IFNγ by cytometric bead array flexset (CBA, BD Bioscience) according to the manufacturers' instructions. Samples were analysed by flow cytometry on the FACS Canto (BD Biosciences), and data analysed using FCAP Array software (BD Bioscience).

Supernatants from cultured splenocytes were tested neat and at 1:10 dilution. The concentration of cytokine was determined against the provided standards diluted from 2500-10 pg/ml.

$2 \times 10^4$ purified CD4 T cells from NexVax2-treated HH8-1 mice were cultured with irradiated syngeneic spleen cells (2,200 rads, $3 \times 10^5$/well) in triplicate assays in the presence of 0, 0.02, 0.2, 2 or 10 μg/ml NPL001 peptide. For suppression assays, $2 \times 10^4$ naïve HH8-1 CD4 T cells (responders) were cultured with an equal number (1:1) of $CD4^+$ T cells from NexVax2-treated mice, titrated NPL001 peptide and irradiated syngeneic spleen cells (2,200 rads, $3 \times 10^5$/well) in triplicate assays. In a separate assay naïve responders were cultured with $CD4^+$ T cells from NexVax2-treated mice at responder:suppressor ratios of 1:1, 3:1 and 9:1 in the presence of sub-optimal concentration of NPL001 peptide (0.2 μg/ml) and APC.

T cell proliferation was measured by the addition of 1 μCi $^3$H-thymidine for the last 24 hours of the 96 hour cultures. Results are recorded as counts per minute (cpm), with the mean of each triplicate plotted and error bars representing the standard deviation.

RNA was extracted from $5 \times 10^5$-$2 \times 10^6$ purified T cells from NexVax2 treated mice using RNAeasy Plus™ RNA extraction kit (QIAGEN) according to the manufacturers instructions. RNA was stored at −80° C. for future analysis if required.

Mice were monitored daily for any apparent adverse response following treatment. There were no unscheduled deaths during the observation period. There were no systemic adverse signs noted in any animal during the observation period. All mice remained apparently healthy, with no observable decline in activity or appearance. No local inflammation at the site of injection was observed in the mice immunised with peptide in saline or saline alone.

Phenotype Analysis

Figure 11A:
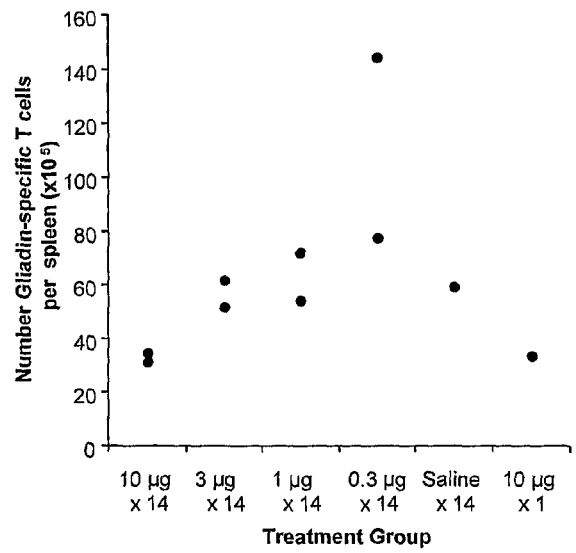
FIGS. 11A and B: show repeat administration of NexVax2 (SEQ ID NOs:228, 229 and 230) leads to the reduction in the proportion (A) and number (B) of gliadin-specific CD4$^+$ T cells in the spleen.
Figure 11B:
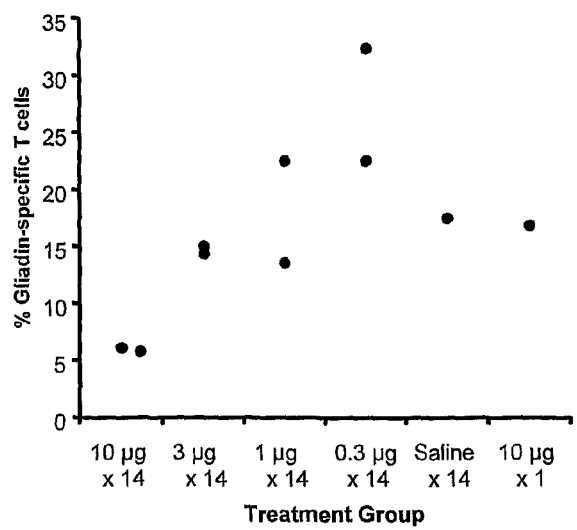

Peptide immunotherapy has been associated with the induction of peripheral tolerance mediated by the induction of thymically derived or de novo generated $CD4^+$ $CD25^+$ $FoxP3^+$ regulatory T (Treg) cells. Additionally, such induction is associated with generation of IL-10 secreting peptide induced Treg cells. The effect of repeat administration of NexVax2 on the number and phenotype of splenic gliadin-specific T cells was determined. Gliadin-specific T cells in the spleen were identified by TCR Vβ8.3 and CD4 expression. The proportion of gliadin-specific T cells in the lymphocyte gate and the total number per spleen was determined. See FIG. 11, which shows repeat administration of NexVax2 leads to the reduction in the proportion (A) and number (B) of gliadin-specific $CD4^+$ T cells in the spleen. HH8-1 gliadin-specific TCR transgenic mice were injected subcutaneously daily for 14 days with the indicated amount of NexVax2. Spleens were harvested 3 days after the final injection, processed and stained with antibodies to identify transgenic T cells (Vβ8.3 and hCD4). The total number of transgenic T cells was calculated from the total cell spleen cell counts. Dots indicate individual mice.

Treatment with multiple doses NexVax2 at the highest dose tested (10 μg) resulted in an apparent decrease in both the proportion and number of gliadin-specific T cells by approximately 50-65%, suggesting either antigen-induced cell death or recruitment of these cells away from the spleen.

Figure 12A:
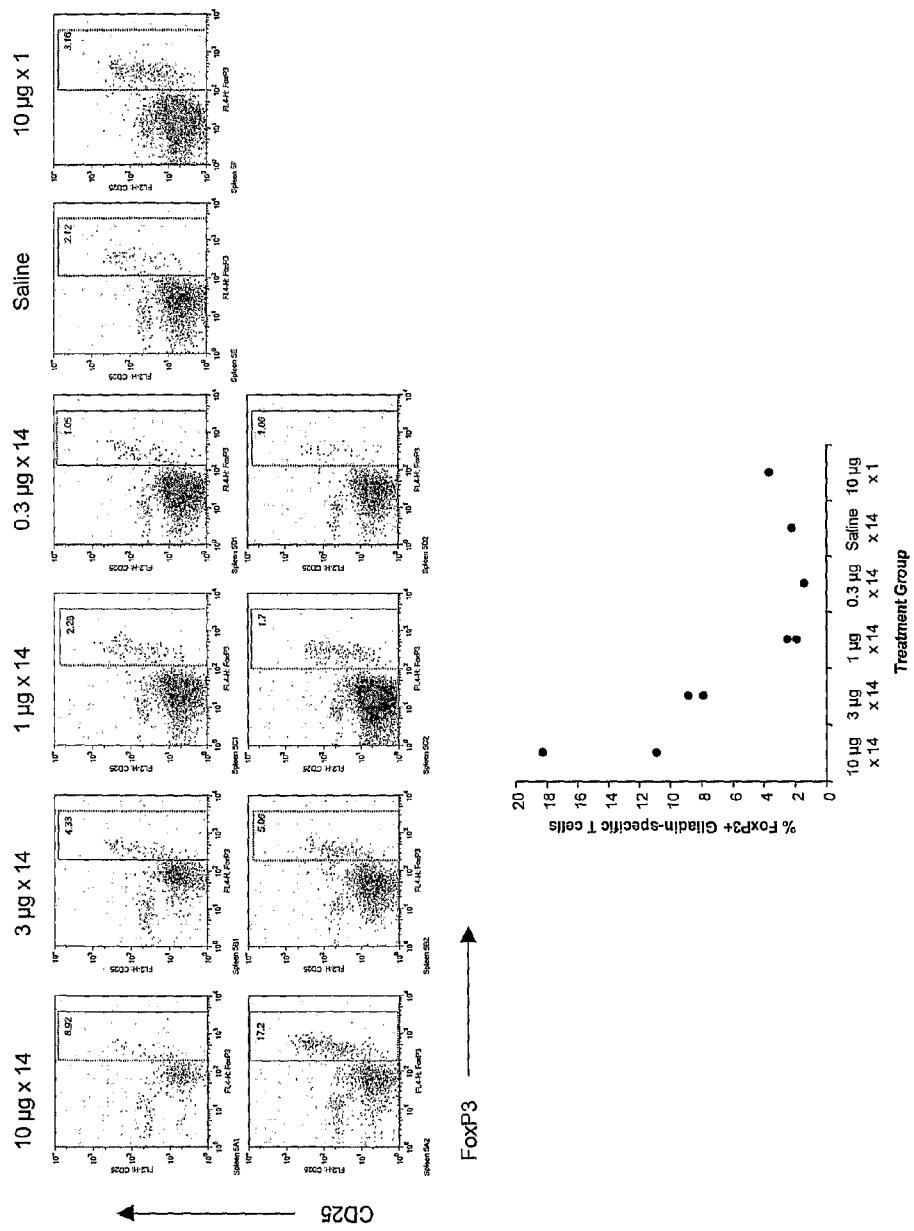
FIGS. 12A and B: show repeat administration of NexVax2 leads to the induction of Treg cells.
Figure 12B:
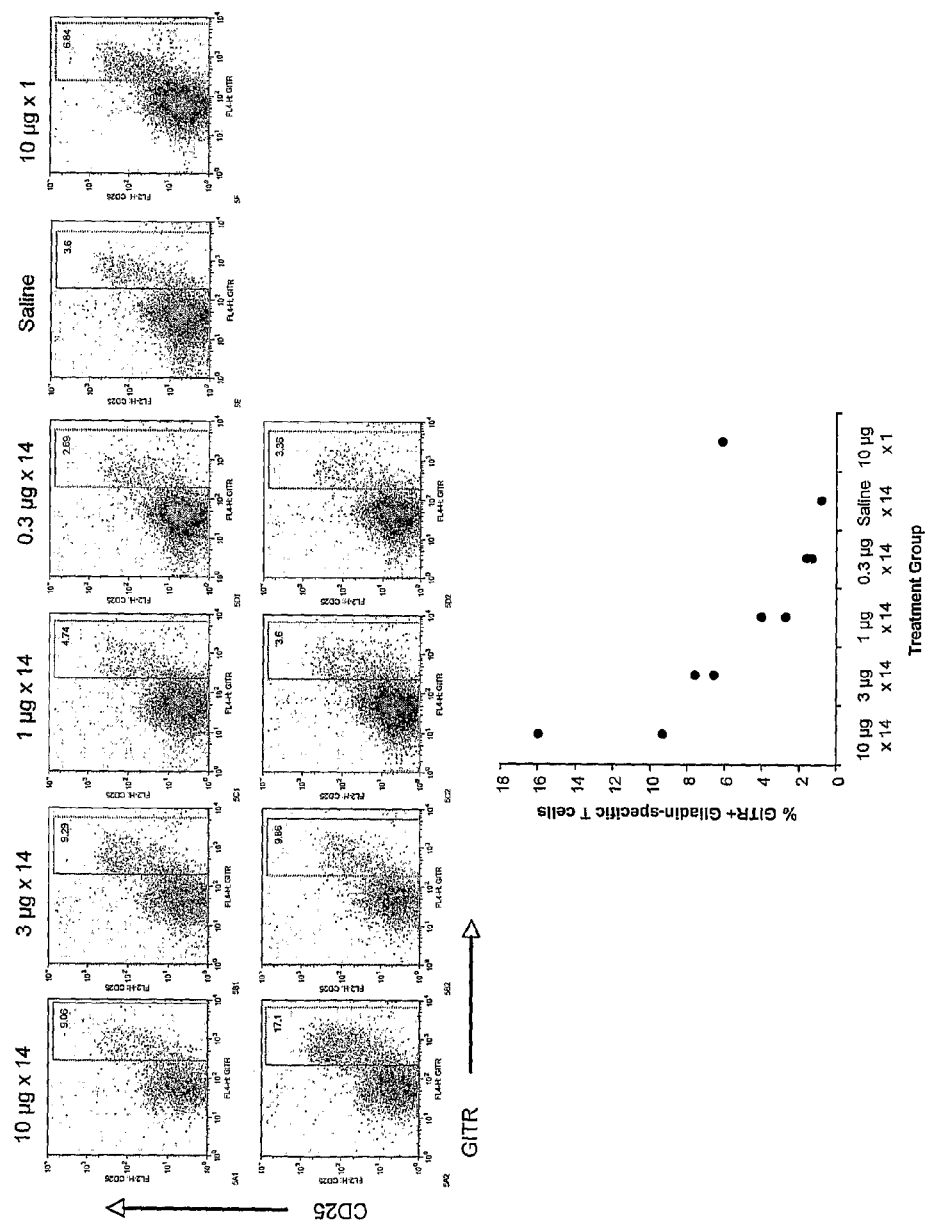

In order to determine whether the repeat administration of NexVax2 induced a Treg population, gliadin-specific T cells were identified by TCR Vβ8.3 and CD4 expression and the proportion of these expressing CD25 and FoxP3 (see FIG. 12A) or CD25 and GITR (see FIG. 12B) determined. FIG. 12 shows repeat administration of NexVax2 leads to the induction of Treg cells. HH8-1 gliadin-specific TCR transgenic mice were injected subcutaneously daily for 14 days with the indicated amount of NexVax2. Spleens were harvested 3 days after the final injection, processed and stained with antibodies to TCR Vα8.3, CD4, CD25, FoxP3 and GITR. FACS plots of gliadin-specific, CD4 lymphocytes expression CD25 and FoxP3 (A) or CD25 and GITR (B) are shown. Treatment with multiple doses of 10 μg or 3 μg NexVax2 resulted in an increased proportion of gliadin-specific Treg cells in the spleen in a dose-dependent manner. Glucocorticoid-Induced TNF Receptor (GITR) is expressed predominantly on CD25$^+$ Treg cells. Staining revealed that the CD25$^+$ population of gliadin-specific T cells co-expressed GITR. The percentage of GITR$^+$ cells increased in proportion with the expression of CD25 following NexVax2 administration.

Figure 13:
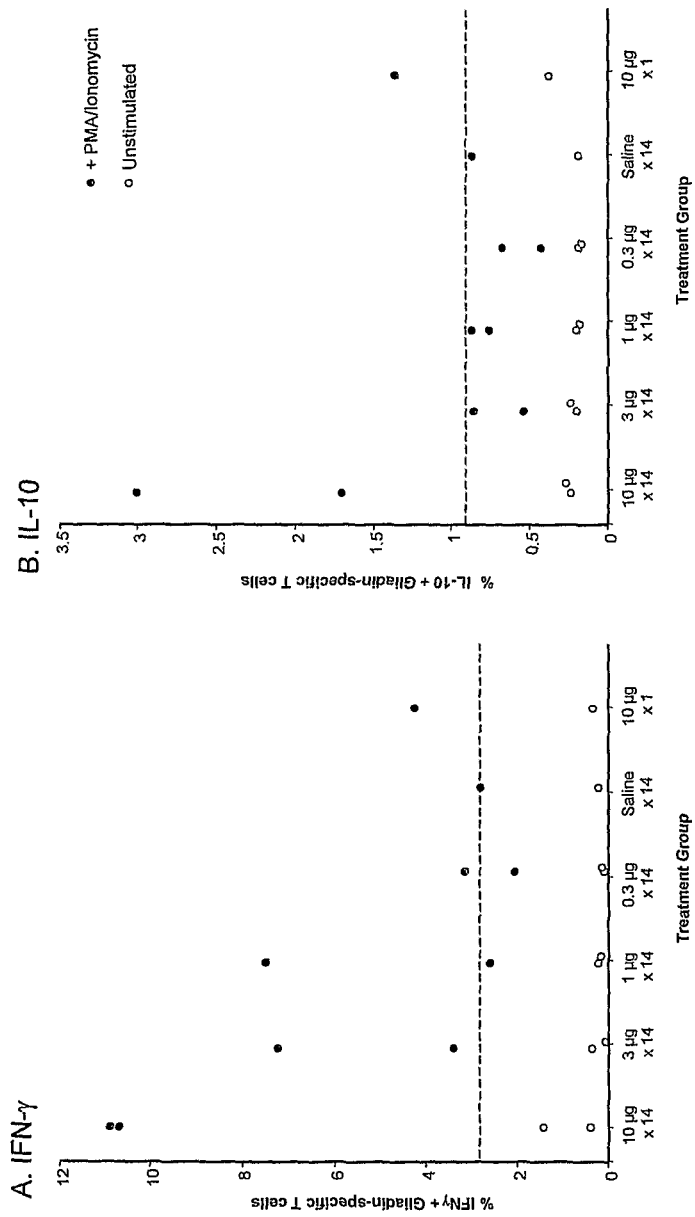
FIG. 13: shows repeat administration of NexVax2 (SEQ ID NOs:228, 229 and 230) results in an increase in the proportion of IFNγ and IL-10 producing cells directly ex-vivo.

The proportion of gliadin-specific T cells with the capacity to produce IFNγ or IL-10 directly ex-vivo in response to non-specific activation was examined. Splenocytes were cultured with and without PMA/Ionomycin in the presence of Brefeldin A. IFNγ and IL-10 production by gliadin-specific T cells was determined by flow cytometry. FIG. 13 shows repeat administration of NexVax2 results in an increase in the proportion of IFNγ and IL-10 producing cells directly ex vivo. HH8-1 mice received daily subcutaneous. administration of 10, 3, 1, or 0.3 μg NexVax2 in saline or saline alone for 14 days, or a single administration of 10 μg NexVax2 on day-14. Three days after the final injection, mice were killed and the proportion of splenic TCR Vβ8.3/hCD4$^+$ cells expressing IFNγ (A) or IL-10 (B) was determined by intracellular cytokine staining and flow cytometry following a 6 hour incubation in the presence or absence of PMA/Ionomycin. Dots represent individual mice and the dotted line indicates the proportion of cytokine positive cells in naïve HH8-1 mice.

Repeat administration of 10 μg NexVax2 resulted in an increased proportion of IFNγ producing gliadin-specific T cells, and a small but consistent increase in the proportion of IL-10 producing gliadin-specific T cells. Repeat administration of 1 or 3 μg NexVax2 resulted in an increase in the frequency of IFNγ producing T cells in one of the two mice tested in each group.

Proliferative Response to Peptide

The proliferative capacity of gliadin-specific T cells following repeat administration of NexVax2 was examined in order to determine whether these cells have an anergic phenotype. Failure to proliferate in vitro is a feature of both CD25$^+$/FoxP3$^+$ Treg cells and IL-10 producing peptide-induced Treg cells. This reduction in the ability to proliferate is reversible by the addition of IL-2 to cultures.

Purified CD4$^+$ splenic T cells were cultured in the presence of gamma-irradiated APC from hCD4.IAE$^{-/-}$.DR3.DQ2 transgenic mice and graded concentrations of cognate peptide, NPL001. Proliferation was measured by the incorporation of $^3$H-Thymidine for the final 24 hours of the 4 day culture (see FIG. 14A). FIG. 14 shows the proliferative capacity of gliadin-specific T cells to cognate antigen is diminished following repeat administration of NexVax2 and restored in the presence of IL-2. HH8-1 mice received daily subcutaneous administration of 10, 3, 1, or 0.3 μg NexVax2 in saline or saline alone for 14 days, or a single administration of 10 μg NexVax2 on day-14. Three days after the final injection, mice were killed and CD4$^+$ T cells purified and cultured with NPL001 peptide and irradiated APCs in the presence or absence of 10 U/ml IL-2. After 72 hours, wells were pulsed with 1 μCi 3H-Thymidine for 24 hours and plates were harvested and counted.

A. Proliferative Response of Mice Treated with Indicated Dose of NexVax2 to 0.2 μg/ml NPL001 Peptide.

B. Proliferative Dose-Response of naïve and Repeat Administration of 10 μg NexVax2 to NPL001.

Error bars represent standard deviation of triplicate cultures.

T cells from antigen naïve, saline-treated mice proliferated well in response to NPL001, whereas T cells from NexVax2-treated mice showed a substantial reduction in their capacity to respond to NPL001, particularly evident at sub-optimal peptide concentration (0.2 μg/ml). Repeat administration with 10 μg NexVax2 led to a 90-97% reduction in the proliferative response to 0.2 μg/ml NPL001. The reduction in proliferation was dose dependent, and even the lowest dose administered (0.3 μg) resulted in a 20-37% reduction in proliferation at sub-optimal peptide concentrations. The addition of 10 U/ml IL-2 to the cultures induced a low level of proliferation in the absence of peptide (approximately twice the background), however in the presence of peptide the unresponsive state of T cells from NexVax2-treated mice was reversed, such that the response of peptide-treated mice was the equivalent to the saline-treated control.

Failure to proliferate in response to NexVax2 administration was observed over a range of doses (see FIG. 14B). This was particularly evident following administration of the highest dose of NexVax2 (10 μg) and was less effective following treatment with lower NexVax2 doses, particularly in response to maximal peptide stimulation (data not shown).

Suppression of naïve HH8-1 T Cell Activation

The observed failure to proliferate could be a result of an anergic phenotype, where the T cells themselves have become less sensitive to antigen stimulation, or due to the presence of a Treg population. Thus, the ability of treatment with NexVax2 to generate a Treg population capable of suppressing the proliferative response of naïve gliadin-specific T cells to NPL001 peptide in in vitro culture was assessed.

Figure 15A:
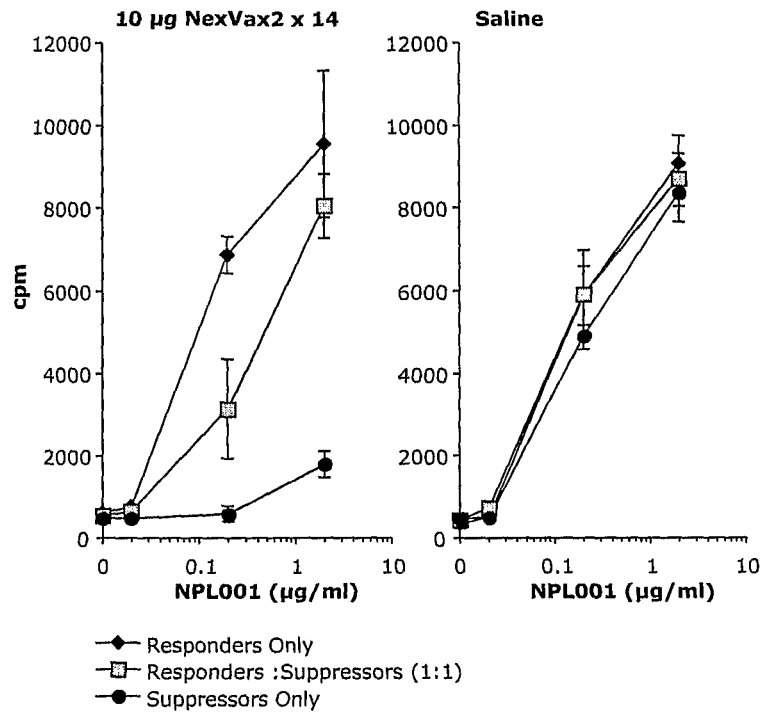
FIGS. 15A and B: show T cells from mice treated with NexVax2 (SEQ ID NOs:228, 229 and 230) are able to suppress the proliferation of naïve gliadin-specific T cells.
Figure 15B:
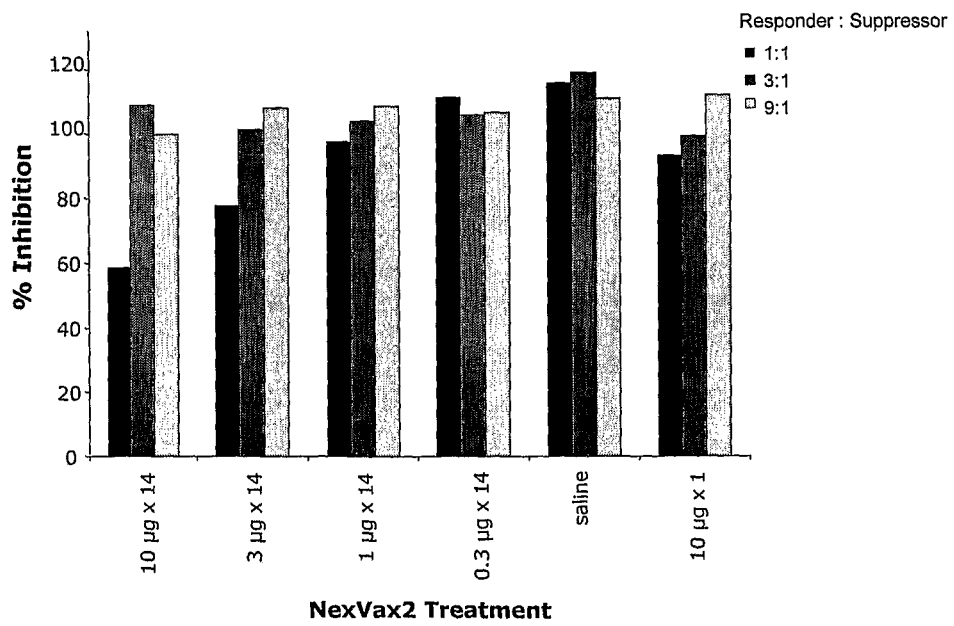

FIG. 15 shows T cells from mice treated with NexVax2 are able to suppress the proliferation of naïve gliadin-specific T cells. HH8-1 mice received daily subcutaneous. administration of 10, 3, 1, or 0.3 μg NexVax2 in saline or saline alone for 14 days, or a single administration of 10 μg NexVax2 on day-14. Three days after the final injection, purified CD4$^+$ T cells from treated mice (suppressors) were co-cultured with T cells untreated HH8-1 mice (responders), NPL001 peptide and irradiated APC. After 72 hours, wells were pulsed with 1 μCi 3H-Thymidine for 24 hours and plates were harvested and counted. In FIG. 15A, T cells from 10 μg NexVax2×14-treated mice (left panel) or saline-treated mice (right panel) were co-cultured with an equal number of naive HH8-1 CD4$^+$ T cells and titrated NPL001 peptide. In FIG. 15B, a constant number of naïve HH8-1 T cells (2×104) were co-cultured with titrated numbers of NexVax2-treated T cells (2×10000, 6.6×1000, 2.2×1000) and 0.2 μg/ml NPL001. The average inhibition of naïve responder proliferation was calculated from the 2 mice in each treatment group. Error bars represent standard deviation of triplicate cultures.

Purified T cells from NexVax2 treated mice were co-cultured with naïve HH8-1 gliadin-specific T cells at a 1:1 ratio in the presence of a titrated dose of NPL001 (see FIG. 15A) or at responder:suppressor ratio of 1:1, 3:1 or 9:1 in the presence of 0.2 μg/ml NPL001 (see FIG. 15B). Suppression of responder cell proliferation was observed following treatment with the repeat administration of 10 μg or 3 μg NexVax2 and at responder:suppressor ratio of 1:1 over a range of stimulatory peptide concentrations. This result indicates the presence of a regulatory population. Given that phenotyping demonstrated an increase in the proportion of gliadin-specific Treg cells only in mice treated with the 10 or 3 μg of NexVax2 and that Treg cells comprised between 7 and 18% of the total gliadin-specific population, the inhibition of naïve HH8-1 T cell proliferation observed is within expectations.

Cytokine Profile Following In Vitro Culture

Figure 16:
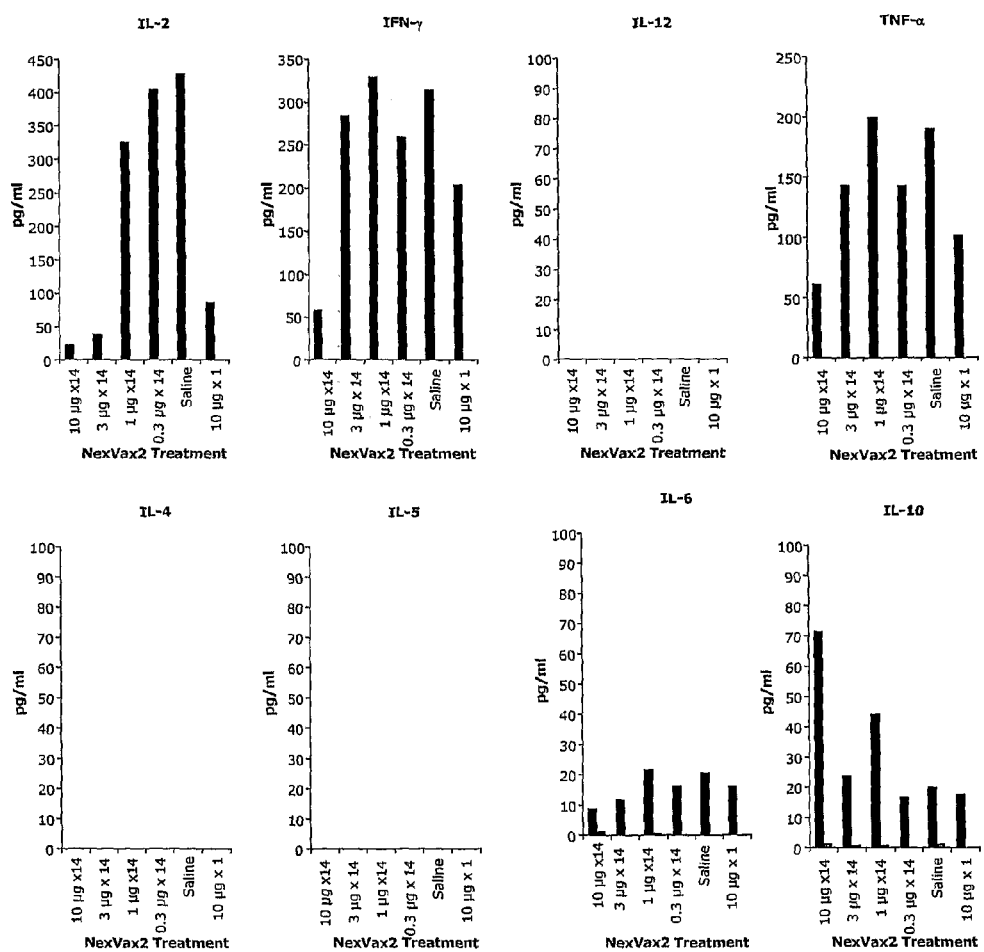
FIG. 16: shows in vitro cytokine production.

Immune modulation can alter the cytokine profile of responder cells. For example, intranasal administration of peptide has been shown to generate IL-10 secreting peptide-induced Treg cells. The profile of cytokine production by CD4+ T cells from gliadin-specific TCR transgenic mice that had been treated with repeat administration of graded amounts of NexVax2 was examined following in vitro culture in the presence or absence of 2 µg/ml NPL001 and irradiated syngeneic APC. Supernatants from day-3 of culture were collected and assessed for the production of Th1-associated cytokines (IL-2, IFNγ, IL-12 and TNFα) and Th2-associated cytokines (IL-4, IL-5, IL-6 and IL-10) (see FIG. 16). FIG. 16 shows in vitro cytokine production. CD4+ T cells were purified from the spleen of HH8-1 mice that received daily subcutaneous administration of 10, 3, 1, or 0.3 µg NexVax2 in saline or saline alone for 14 days, or a single administration of 10 µg NexVax2 on day-14. 3×104 CD4 T cells were cultured in the presence of 2 µg of NPL001 (■) or without peptide (□) and 3×100000 gamma-irradiated APC. Supernatant were harvested at 72 hours and tested by cytometric bead array for the production of Th1 cytokines (IL-2, IFNγ, IL-12, TNFα), and Th2 cytokines (IL-4, IL-5 IL-6 and IL-10). Results show the average cytokine production of the two mice in the treatment groups. No IL-12, IL-4 or IL-5 was detected in the supernatants of the cultures. A marked reduction in the production of IL-2, IFNγ, and TNFα was observed from the cultures of mice receiving repeat administration of 10 µg NexVax2. This reduction in cytokine production closely reflects the reduced proliferative response to NPL001 peptide in culture. In addition the T cells from mice receiving repeat injections of 10 µg NexVax2 produced a 3.5 fold increased amount of IL-10 following peptide stimulation in vitro, suggesting potential skewing towards an IL-10 producing Treg phenotype in these mice.

This experiment was designed to determine whether repeat administration of the therapeutic vaccine NexVax2, using a regime designed to induce immunological tolerance, is capable of modulating the gliadin-specific T cell response in a gliadin-specific T cell receptor-transgenic mouse model. NexVax2 was administered via subcutaneous injection of peptide in saline over 14 consecutive days. This treatment resulted firstly in an apparent reduction in the number of gliadin-specific T cells in the spleen. The remaining T cells showed a reduction in their proliferative response to their cognate antigen, which was reversed in the presence of IL-2 suggesting an "anergic" phenotype or the presence of a Treg population. This reduced proliferative response was accompanied by a reduction in the amount of Th1 cytokines produced in culture, and by an increase in IL-10 production. An increase in gliadin-specific IL-10 producing cells was also observed directly ex-vivo along with an increase in the total number and the proportion of FoxP3+, GITR+ Treg cells. In co-culture experiments, T cells from treated mice were capable of suppressing the proliferative response of naïve gliadin-specific T cells responding to NPL001 peptide.

The repeat administration of NexVax2 at the highest dose tested (10 µg per day, over 14 consecutive days) demonstrated the modulation of the response of gliadin-specific T cells from treated gliadin-specific T cell receptor transgenic mice.

The results provide evidence that the subcutaneous administration of NexVax2 peptide in saline is capable of modifying the T cell response to the immunodominant gliadin peptide using a biologically relevant TCR-transgenic mouse model.

Example 4

NexVax2 Vaccine for Human Celiac Disease

The NexVax2 vaccine was prepared in GMP form for administration to human patients with celiac disease.

Phase I Study to determine safety, tolerability and bioactivity of NexVax2 in HLA-DQ2+ volunteers with celiac disease following a long-term, strict gluten-free diet.

Objectives

The primary objective of this study was:
To evaluate the safety and tolerability of weekly injections of NexVax2 administered intradermally for 3 weeks.

The secondary objectives of this study were:
To determine the bioactivity of NexVax2 following 3 weekly doses in celiac disease volunteers through the measurement of T-cell response as assessed by T cell frequency and cytokine release.
To determine the bioactivity of NexVax2 following 3 weekly doses in celiac disease volunteers through the measure of symptomatic response after gluten challenge.
To measure the pharmacokinetics of NexVax2 following a single intradermal injection in celiac disease volunteers.
To measure the induction of antibodies specific for NexVax2 following 3 weekly doses in celiac disease volunteers.

Study Design

A Phase I, single-centre, placebo-controlled, dose-escalating study of the safety, tolerability and bioactivity of NexVax2 in celiac disease volunteers when administered weekly via intradermal injection.

Celiac disease patients were required to attend nine outpatient visits. This included three 8 hour visits to receive intradermal injections of NexVax2 (over 3 weeks) and three 6 hour visits to undergo a standard gluten challenge.

Volunteers remained on study for approximately 25 days from the date of the first injection.

Study Population

Individuals with a diagnosis of celiac disease according to accepted European Society of Paediatric Gastroenterology, Hepatology and Nutrition diagnostic criteria (Walker-Smith et al., 1990) following a strict gluten free diet, who possess genes encoding HLA-DQ2 (DQA1*05 and DQB1*02) but not HLA-DQ8 (DQA1*03 and DQB1*0302).

Test Formulation for NexVax2

NexVax2 for injection, contained an equimolar (0.159 µmole per 100 µl, approx. 3 mg/ml) mixture of each of NPL001, NPL002 and NPL003 in a 0.9% normal saline sterile solution supplied by Nexpep Pty Ltd Placebo Formulation Sterile normal saline 0.9% supplied by Nexpep Pty Ltd.

Study Treatments

Cohort 1: comprising 2 sentinels, 1 dosed with 9 µg NexVax2 by intradermal injection and 1 dosed with placebo and a further 6 subjects, 5 dosed with 9 µg NexVax2 and 1 dosed with placebo on days 1, 8 and 15.

Cohort 2: as per Cohort 1 but subjects dosed with 30 µg NexVax2

Cohort 3: as per Cohort 1 but subjects dosed with 90 µg NexVax2

Cohort 4: as per Cohort 1 but subjects dosed with 60 µg NexVax2

Schedule for Dosing, Meals and Blood Collection

After fasting from midnight the evening prior to study drug administration, the schedule for dose administration, meals, pharmacodynamic assessments, gluten challenge and blood collection (assuming a 0800 hour dosing time) was as shown in FIG. 17.

Assessments

Resting heart rate, semi-supine systolic/diastolic blood pressure, respiratory rate and temperature was monitored: at Screening; nominally at 0700 hours prior to receiving treatment on days-1, 8 and 15 and at 4 hours post-dose; and on days-22, 23 and 24 prior to receiving the gluten challenge and on day-25 end of study.

Blood samples for PBMC IFNγ ELISpot assay to enumerate the frequency of NexVax2 specific T cells were collected on days-1, 6, 15, 20 and 25 (End of Study).

Blood samples for Bioplex analysis to determine PBMC cyotkine release in response to NexVax2 were collected on days-1, 6, 15, 20 and 25 (End of Study).

PBMC were collected on days-1, 6, 15, 20 and 25 (End of Study) and frozen for later assay of T cell function.

Serum was collected on days-1 and 20 for assessment of antibodies specific for NexVax2.

Blood samples for pharmacokinetics sampling were collected on day-15 at pre-dose and at 15, 30, 45, 60, 75, 90 minutes, 2 hours and 3 hours post-dose.

Clinical laboratory measures (biochemistry, urinalysis and haematology) were performed: at Screening; on days-1, 8 and 15 pre-dose and 4 h post-dose; and pre-gluten challenge on days-20 and 22, and post gluten challenge and on day-25 (End of Study).

Pregnancy (urine) testing was conducted at Screening, pre-dose on day-1, 8 and 15, and pre-gluten challenge on days-20, 21 and 22 and at end of study (day-25).

Urine drugs of abuse testing was conducted at Screening and pre-dose on days-1, 8 and 15.

ECGs were performed: at Screening; nominally at 0700 hours prior to receiving treatment on days-1, 8 and 15 and at 4 hours post-dose; and on days-20, 21 and 22 prior to receiving the gluten challenge and on day-25 end of study.

Data Analysis

Screening, Compliance and Safety Data

Demographics will be tabulated and summarised. Physical examination (including height and weight) at baseline and follow up and medical/surgical history data at baseline will be listed. All clinical safety and tolerability data will be listed for each subject.

Laboratory values outside the laboratory's normal ranges will be listed separately, with comments as to their clinical significance. Associated repeat values will be listed together. Vital sign measurements (resting heart rate, semi-supine systolic/diastolic blood pressure, respiratory rate, temperature) and ECG parameters will be tabulated and summarised.

Tolerability Data

Treatment-emergent adverse events will be listed and summarised. All adverse events reported in this study will be coded using MedDRA.

Immunological Assays

The inventors consider that a single treatment of NexVax2 will increase the frequency of NexVax2-specific T cells in PBMC and will increase secretion of cytokines and chemokines by mononuclear cells.

The inventors consider that PBMC drawn after repeated (3 weekly) injection of NexVax2 will have a lower frequency of NexVax2-specific T cells than prior to treatment.

The inventors consider that compared to placebo-treated celiac disease volunteers, repeated (3 weekly) injection of NexVax2 will reduce the frequency of T cells specific for NexVax2 and cytokine secretion stimulated by NexVax2 in PBMC collected 6 days after commencing 3-day oral gluten challenge with wheat bread.

Ordinal data will be analysed by one-tailed paired Wilcoxon rank-sum test. Normally distributed data will analysed by paired t-test. A p-value <0.05 will be considered significant.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/118, 643, the entire contents of which are incorporation herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Anderson, Plant Mol. Biol. (1991) 16:335-337
Anderson et al., Nature Medicine (2000) 6:337-342
Anderson et al., Gut (2005) 54:1217-1223
Anderson et al., Gut (2006) 55:485-91
Arentz-Hansen et al., J. Exp. Med. (2000) 191:603-612
Beissbarth et al., Bioinformatics (2005) 21 Suppl. 1:i29-37
Briggs et al., Science (1986) 234:47-52
Bunce et al., Tissue Antigens (1995) 46:355-367
Chen et al., J. Immunol. (2006) 168(6):3050-6
Deshpande et al., J. Biol. Chem. (1997) 272(16):10664-10668
Li et al., Nat. Biotechnol. (1999) 17(3):241-245
Kang et al., J. Immunol. (2008) 180:5172-6
Kricka, Biolumin. Chemilumin. (1998) 13:189-93
Klein et al., Exp. Neurol. (1998) 150:183-194
Mannering et al., J. Immunol. Methods (2003) 283:173-83
Mannering et al., J. Immunol. Methods (2005) 298:83-92
Mitchell and Tjian, Science (1989) 245:371-378
Mullighan et al., Tissue Antigens (1997) 50:688-692
Nettelbeck et al., Gene Ther. (1998) 5(12)1656-1664
Oldfield et al., Lancet (2002) 360:47-53
Olerup et al., Tissue Antigens (1993) 41:119-134
Pitluk et al., J. Virol. (1991) 65:6661-6670
Stewart et al., Genomics (1996) 37(1):68-76
Vader et al., Gastroenterology (2003) 125:1105-1113
Walker-Smith et al., Arch. Dis. Child (1990) 65:909-911
  Working Group of European Society of Paediatric Gastroenterology and Nutrition (Report of), Arch. Dis. Child (1990) 65:909-11
Zolotukiin et al., J. Virol. (1996) 70(7):4646-4654

What is claimed is:

1. An agent comprising
   i) a first peptide comprising the amino acid sequence of SEQ ID NO:13,
   ii) a second peptide comprising the amino acid sequence of SEQ ID NO:14, and
   iii) a third peptide comprising the amino acid sequence of SEQ ID NO:16.

2. The agent of claim 1, wherein the second peptide comprises the amino acid sequence of SEQ ID NO:320 and/or the third peptide comprises the amino acid sequence of SEQ ID NO:321.

3. The agent of claim 1, wherein the first, second and/or third peptide comprises an N-terminal acetyl group or pyroglutamate group, and/or a C-terminal amide group.

4. The agent of claim 3, wherein the first, second and/or third peptide comprises an N-terminal pyroglutamate group and a C-terminal amide group.

5. The agent of claim 1, wherein the first, second and/or third peptide is conjugated to a compound.

6. The agent of claim 5, wherein the compound is an adjuvant or a major histocompatibility complex molecule.

7. The agent of claim 1, wherein two or three of the first, second and third peptides are on a single polypeptide chain.

8. The agent of claim 1 comprising one or more additional peptides comprising an amino acid sequence selected from the group consisting of SEQ ID NOs:47, 48, 56, 57, 58, 59, 60, 61, 62, 63, 64, 65, 66, 67, 68, 75, 76, 77, 78, 79, 80, 81, 89, 90, 91, 92, 95, 102, 103, 104, 116, 117, 118, 119, 120, 121, 122, 123, 124, 125, 126, 127, 128, 129, 130, 131, 132, 133, 136, 169, 170, 171, 172, 173, 174, 177, 178, 179, 180, 183, 184, 187, 188, 189, 190, 191, 192, 209, and 210.

9. A kit comprising the composition of claim 1, and means to detect binding of one or more peptides to T cells.

10. A vaccine comprising the composition of claim 1, and a pharmaceutically acceptable carrier.

11. The vaccine of claim 10 further comprising an adjuvant.

* * * * *